US011821026B2

(12) United States Patent
Dunaway et al.

(10) Patent No.: US 11,821,026 B2
(45) Date of Patent: *Nov. 21, 2023

(54) CHEMICAL COMPOSITIONS AND METHODS OF USING SAME

(71) Applicant: NanoString Technologies, Inc., Seattle, WA (US)

(72) Inventors: Dwayne L. Dunaway, Seattle, WA (US); Elizabeth A. Manrao, Lake Forest Park, WA (US); Joseph M. Beechem, Eugene, OR (US); Rustem Khafizov, Seattle, WA (US); Sanghamithra Korukonda, Seattle, WA (US); Yi Deng, Seattle, WA (US); Dae Kim, Bellevue, WA (US); Mark Gregory, Boise, ID (US); Margaret Hoang, Seattle, WA (US)

(73) Assignee: NanoString Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/179,684

(22) Filed: Mar. 7, 2023

(65) Prior Publication Data

US 2023/0257800 A1 Aug. 17, 2023

Related U.S. Application Data

(60) Continuation of application No. 17/699,849, filed on Mar. 21, 2022, which is a division of application No. 16/559,755, filed on Sep. 4, 2019, now Pat. No. 11,279,969, which is a continuation of application No. 15/819,151, filed on Nov. 21, 2017, now Pat. No. 10,415,080.

(60) Provisional application No. 62/536,147, filed on Jul. 24, 2017, provisional application No. 62/457,237, filed on Feb. 10, 2017, provisional application No. 62/424,887, filed on Nov. 21, 2016.

(51) Int. Cl.
*C12Q 1/6825* (2018.01)
*C12Q 1/6874* (2018.01)
*C12Q 1/6869* (2018.01)

(52) U.S. Cl.
CPC ......... *C12Q 1/6825* (2013.01); *C12Q 1/6869* (2013.01); *C12Q 1/6874* (2013.01)

(58) Field of Classification Search
CPC .. C12Q 1/6825; C12Q 1/6869; C12Q 1/6874; C12Q 1/6876; C12Q 2563/107; C12Q 2563/179; C12Q 2565/101; C12Q 2565/518

See application file for complete search history.

(56) References Cited

U.S. PATENT DOCUMENTS

| | | |
|---|---|---|
| 5,320,814 A | 6/1994 | Walt et al. |
| 5,432,272 A | 7/1995 | Benner |
| 5,543,838 A | 8/1996 | Hosier et al. |
| 5,635,352 A | 6/1997 | Urdea et al. |
| 5,665,540 A | 9/1997 | Lebo |
| 5,681,697 A | 10/1997 | Urdea et al. |
| 5,710,264 A | 1/1998 | Urdea et al. |
| 5,763,167 A | 6/1998 | Conrad |
| 5,776,688 A | 7/1998 | Bittner et al. |
| 5,780,227 A | 7/1998 | Sheridan et al. |
| 5,783,387 A | 7/1998 | Lucas et al. |
| 5,853,993 A | 12/1998 | Dellinger et al. |
| 5,871,928 A | 2/1999 | Fodor et al. |
| 5,888,778 A | 3/1999 | Shuber |
| 5,945,515 A | 8/1999 | Chomczynski |
| 5,981,180 A | 11/1999 | Chandler et al. |
| 5,985,549 A | 11/1999 | Singer et al. |
| 6,037,120 A | 3/2000 | Benner |
| 6,140,496 A | 10/2000 | Benner |
| 6,207,392 B1 | 3/2001 | Weiss et al. |
| 6,225,285 B1 | 5/2001 | Luo et al. |
| 6,238,869 B1 | 5/2001 | Kris et al. |
| 6,242,184 B1 | 6/2001 | Singer et al. |
| 6,277,569 B1 | 8/2001 | Bittner et al. |
| 6,306,643 B1 | 10/2001 | Gentalen et al. |
| 6,316,200 B1 | 11/2001 | Nadeau et al. |
| 6,365,362 B1 | 4/2002 | Terstappen et al. |
| 6,368,800 B1 | 4/2002 | Smith et al. |
| 6,379,888 B1 | 4/2002 | Nadeau et al. |
| 6,428,957 B1 | 8/2002 | Delenstarr |
| 6,429,027 B1 | 8/2002 | Chee et al. |
| 6,440,667 B1 | 8/2002 | Fodor et al. |
| 6,449,562 B1 | 9/2002 | Chandler et al. |
| 6,506,563 B1 | 1/2003 | Ward et al. |
| 6,511,824 B1 | 1/2003 | Buchman et al. |
| 6,534,266 B1 | 3/2003 | Singer |
| 6,548,259 B2 | 4/2003 | Ward et al. |
| 6,569,626 B2 | 5/2003 | Bittner et al. |
| 6,610,475 B1 | 8/2003 | Kacian et al. |
| 6,673,914 B1 | 1/2004 | Hoon |
| 6,727,356 B1 | 4/2004 | Reed et al. |

(Continued)

FOREIGN PATENT DOCUMENTS

CN 101932729 A 12/2010
CN 102439177 A 5/2012
(Continued)

OTHER PUBLICATIONS

Duowei, et al., Molecular Biology, Nanjing Normal University Press, Jul. 31, 2007, p. 149, 7 total pages (with English translation).
(Continued)

*Primary Examiner* — Narayan K Bhat
(74) *Attorney, Agent, or Firm* — COOLEY LLP; Matthew Pavao; Robert E. Powers

(57) ABSTRACT

The present disclosure relates to chemical compositions, kits, and apparatuses and methods for using these compositions, kits and apparatuses in various assays.

16 Claims, 50 Drawing Sheets
(50 of 50 Drawing Sheet(s) Filed in Color)

Specification includes a Sequence Listing.

(56) References Cited

U.S. PATENT DOCUMENTS

| | | |
|---|---|---|
| 6,750,016 B2 | 6/2004 | Mirkin et al. |
| 6,803,200 B2 | 10/2004 | Xia et al. |
| 6,942,968 B1 | 9/2005 | Dickinson et al. |
| 7,033,754 B2 | 4/2006 | Chee et al. |
| 7,033,758 B2 | 4/2006 | Kenny et al. |
| 7,052,841 B2 | 5/2006 | Delenstarr |
| 7,064,197 B1 | 6/2006 | Rabbani et al. |
| 7,250,371 B2 | 7/2007 | Kang et al. |
| 7,255,999 B2 | 8/2007 | Singh et al. |
| 7,285,384 B2 | 10/2007 | Fan et al. |
| 7,385,043 B1 | 6/2008 | Kramer |
| 7,462,475 B2 | 12/2008 | Kermekchiev et al. |
| 7,473,767 B2 | 1/2009 | Dimitrov |
| 7,524,631 B2 | 4/2009 | Patterson |
| 7,582,415 B2 | 9/2009 | Straus |
| 7,608,396 B2 | 10/2009 | Delenstarr |
| 7,615,351 B2 | 11/2009 | McMaster et al. |
| 7,709,198 B2 | 5/2010 | Luo et al. |
| 7,741,046 B2 | 6/2010 | Larsen et al. |
| 7,745,129 B1 | 6/2010 | Schatz |
| 7,763,421 B2 | 7/2010 | Farrell |
| 7,771,949 B2 | 8/2010 | Kramer |
| 7,803,541 B2 | 9/2010 | Luo et al. |
| 7,807,352 B2 | 10/2010 | Rabbani et al. |
| 7,829,278 B2 | 11/2010 | Selvin et al. |
| 7,863,012 B2 | 1/2011 | Rao et al. |
| 7,906,072 B2 | 3/2011 | Unger et al. |
| 7,919,237 B2 | 4/2011 | Dimitrov et al. |
| 7,927,798 B2 | 4/2011 | Zheng et al. |
| 7,941,279 B2 | 5/2011 | Hwang et al. |
| 7,951,539 B2 | 5/2011 | McMaster et al. |
| 7,955,794 B2 | 6/2011 | Shen et al. |
| 7,968,327 B2 | 6/2011 | McMaster et al. |
| 8,017,360 B2 | 9/2011 | Luo et al. |
| 8,048,378 B2 | 11/2011 | Unger et al. |
| 8,049,893 B2 | 11/2011 | Moon et al. |
| 8,055,034 B2 | 11/2011 | Dube et al. |
| 8,063,196 B2 | 11/2011 | Zheng et al. |
| 8,114,681 B2 | 2/2012 | Martin et al. |
| 8,148,075 B2 | 4/2012 | Farrell |
| 8,148,512 B2 | 4/2012 | Dimitrov |
| 8,173,785 B2 | 5/2012 | Stender et al. |
| 8,288,522 B2 | 10/2012 | Luo et al. |
| 8,309,306 B2 | 11/2012 | Nolan et al. |
| 8,394,944 B2 | 3/2013 | Zheng et al. |
| 8,404,444 B2 | 3/2013 | Zhang et al. |
| 8,405,970 B2 | 3/2013 | Sun |
| 8,415,102 B2 | 4/2013 | Geiss et al. |
| 8,492,094 B2 | 7/2013 | Dimitrov et al. |
| 8,501,459 B2 | 8/2013 | Chen et al. |
| 8,501,490 B2 | 8/2013 | Chen et al. |
| 8,519,115 B2 | 8/2013 | Webster et al. |
| 8,604,182 B2 | 12/2013 | Luo et al. |
| 8,628,918 B2 | 1/2014 | Luo et al. |
| 8,658,361 B2 | 2/2014 | Wu et al. |
| 8,685,646 B2 | 4/2014 | Battersby et al. |
| 8,715,926 B2 | 5/2014 | Duerksen-Hughes et al. |
| 8,741,566 B2 | 6/2014 | Winther et al. |
| 8,790,878 B2 | 7/2014 | Hayes |
| 8,865,404 B2 | 10/2014 | Wu et al. |
| 8,951,726 B2 | 2/2015 | Luo et al. |
| 9,046,477 B2 | 6/2015 | Empedocles et al. |
| 9,096,902 B2 | 8/2015 | Weier |
| 9,150,910 B2 | 10/2015 | Hu et al. |
| 9,228,948 B2 | 1/2016 | Empedocles et al. |
| 9,297,762 B2 | 3/2016 | Empedocles et al. |
| 9,304,084 B2 | 4/2016 | Empedocles et al. |
| 9,315,854 B2 | 4/2016 | Wu et al. |
| 10,138,509 B2 | 11/2018 | Church et al. |
| 10,227,639 B2 | 3/2019 | Levner et al. |
| 10,415,080 B2 | 9/2019 | Dunaway et al. |
| 10,457,980 B2 | 10/2019 | Cai et al. |
| 10,597,719 B2 | 3/2020 | Kuwahara |
| 10,844,426 B2 | 11/2020 | Daugharthy et al. |
| 11,021,737 B2 | 6/2021 | Church et al. |
| 11,098,303 B2 | 8/2021 | Zhuang et al. |
| 11,111,521 B2 | 9/2021 | Church et al. |
| 11,118,220 B2 | 9/2021 | Daugharthy et al. |
| 11,193,163 B2 | 12/2021 | Daugharthy et al. |
| 11,279,969 B2 | 3/2022 | Dunaway et al. |
| 11,293,054 B2 | 4/2022 | Levner et al. |
| 11,542,554 B2 | 1/2023 | Daugharthy et al. |
| 11,549,139 B2 * | 1/2023 | Dunaway .............. C12Q 1/6874 |
| 2001/0002315 A1 | 5/2001 | Schultz et al. |
| 2001/0007775 A1 | 7/2001 | Seul et al. |
| 2001/0023078 A1 | 9/2001 | Bawendi et al. |
| 2001/0029049 A1 | 10/2001 | Walt et al. |
| 2001/0034034 A1 | 10/2001 | Bruchez et al. |
| 2001/0053334 A1 | 12/2001 | Chen et al. |
| 2002/0028457 A1 | 3/2002 | Empedocles et al. |
| 2002/0034737 A1 | 3/2002 | Drmanac |
| 2002/0034827 A1 | 3/2002 | Singh et al. |
| 2002/0039728 A1 | 4/2002 | Kain et al. |
| 2002/0051971 A1 | 5/2002 | Stuelpnagel et al. |
| 2002/0068018 A1 | 6/2002 | Pepper et al. |
| 2002/0102574 A1 | 8/2002 | Nadeau et al. |
| 2002/0177141 A1 | 11/2002 | Chee et al. |
| 2002/0187515 A1 | 12/2002 | Chee et al. |
| 2003/0008323 A1 | 1/2003 | Ravkin et al. |
| 2003/0028981 A1 | 2/2003 | Chandler et al. |
| 2003/0148335 A1 | 8/2003 | Shen et al. |
| 2003/0186426 A1 | 10/2003 | Brewer et al. |
| 2004/0248144 A1 | 12/2004 | Mir |
| 2005/0037397 A1 | 2/2005 | Mirkin et al. |
| 2005/0048498 A1 | 3/2005 | Woudenberg et al. |
| 2005/0064435 A1 | 3/2005 | Su et al. |
| 2005/0131006 A1 | 6/2005 | Mukherjee et al. |
| 2005/0147981 A1 | 7/2005 | Yamakawa et al. |
| 2005/0170439 A1 | 8/2005 | Chan-Hui et al. |
| 2005/0233318 A1 | 10/2005 | Chee et al. |
| 2005/0239084 A1 | 10/2005 | Nadeau et al. |
| 2006/0014191 A1 | 1/2006 | Lao et al. |
| 2006/0063196 A1 | 3/2006 | Akeson et al. |
| 2006/0088872 A1 | 4/2006 | Ahmadian et al. |
| 2006/0134917 A1 | 6/2006 | Huang et al. |
| 2007/0048759 A1 | 3/2007 | Luo et al. |
| 2007/0117109 A1 | 5/2007 | Rothemund |
| 2007/0148690 A1 | 6/2007 | Shao et al. |
| 2007/0154889 A1 | 7/2007 | Wang |
| 2008/0085509 A1 | 4/2008 | Knoll et al. |
| 2008/0108073 A1 | 5/2008 | Nautiyal et al. |
| 2009/0220978 A1 | 9/2009 | Dimitrov |
| 2009/0246879 A1 | 10/2009 | Drmanac et al. |
| 2009/0299640 A1 | 12/2009 | Ellis et al. |
| 2009/0318298 A1 | 12/2009 | Kim et al. |
| 2010/0015607 A1 | 1/2010 | Geiss et al. |
| 2010/0047924 A1 | 2/2010 | Webster et al. |
| 2010/0151472 A1 | 6/2010 | Nolan et al. |
| 2010/0261026 A1 | 10/2010 | Ferree et al. |
| 2010/0268478 A1 | 10/2010 | Andregg et al. |
| 2011/0021369 A1 | 1/2011 | Mhlanga et al. |
| 2011/0086774 A1 | 4/2011 | Dunaway |
| 2011/0145176 A1 | 6/2011 | Perou et al. |
| 2011/0195864 A1 | 8/2011 | Ma |
| 2011/0201515 A1 | 8/2011 | Webster et al. |
| 2012/0003648 A1 | 1/2012 | Ma et al. |
| 2012/0004132 A1 | 1/2012 | Zhang et al. |
| 2012/0052498 A1 | 3/2012 | Nguyen et al. |
| 2012/0071343 A1 | 3/2012 | Ma et al. |
| 2012/0100540 A1 | 4/2012 | Wu et al. |
| 2012/0122712 A1 | 5/2012 | Goldstein |
| 2012/0172246 A1 | 7/2012 | Nguyen et al. |
| 2012/0178081 A1 | 7/2012 | Nguyen et al. |
| 2012/0214152 A1 | 8/2012 | Ma et al. |
| 2012/0295801 A1 | 11/2012 | Wu et al. |
| 2012/0301886 A1 | 11/2012 | Farrell et al. |
| 2012/0316082 A1 | 12/2012 | Pregibon et al. |
| 2013/0004482 A1 | 1/2013 | Perou et al. |
| 2013/0017971 A1 | 1/2013 | Geiss et al. |
| 2013/0023433 A1 | 1/2013 | Luo et al. |
| 2013/0065780 A1 | 3/2013 | He et al. |
| 2013/0171621 A1 | 7/2013 | Luo et al. |
| 2013/0178372 A1 | 7/2013 | Geiss et al. |
| 2013/0203055 A1 | 8/2013 | Aurich-Costa |

(56) References Cited

U.S. PATENT DOCUMENTS

| | | |
|---|---|---|
| 2013/0230851 A1 | 9/2013 | Geiss et al. |
| 2013/0237437 A1 | 9/2013 | Russell et al. |
| 2013/0274117 A1 | 10/2013 | Church et al. |
| 2013/0337444 A1 | 12/2013 | Ferree et al. |
| 2013/0345161 A1 | 12/2013 | Perou et al. |
| 2014/0005067 A1 | 1/2014 | Webster et al. |
| 2014/0017688 A1 | 1/2014 | Webster et al. |
| 2014/0030698 A1 | 1/2014 | Wang |
| 2014/0037620 A1 | 2/2014 | Ferree et al. |
| 2014/0087959 A1 | 3/2014 | Ellis et al. |
| 2014/0120083 A1 | 5/2014 | Stern et al. |
| 2014/0154681 A1 | 6/2014 | Wallden |
| 2014/0162251 A1 | 6/2014 | Dimitrov et al. |
| 2014/0178869 A1 | 6/2014 | Ma et al. |
| 2014/0227706 A1 | 8/2014 | Kato et al. |
| 2014/0249040 A1 | 9/2014 | Wu et al. |
| 2014/0302042 A1 | 10/2014 | Chin et al. |
| 2014/0349294 A1 | 11/2014 | Church et al. |
| 2014/0357509 A1 | 12/2014 | Ma et al. |
| 2014/0357660 A1 | 12/2014 | Mock et al. |
| 2014/0371088 A1 | 12/2014 | Webster |
| 2014/0377258 A1 | 12/2014 | Stern et al. |
| 2015/0011435 A1 | 1/2015 | Wu et al. |
| 2015/0018231 A1 | 1/2015 | Vallabhaneni |
| 2015/0038556 A1 | 2/2015 | Heartlein et al. |
| 2015/0051117 A1 | 2/2015 | Church et al. |
| 2015/0086981 A1 | 3/2015 | Cherkasov et al. |
| 2015/0105298 A1 | 4/2015 | Czaplinski |
| 2015/0110857 A1 | 4/2015 | DeRosa et al. |
| 2015/0140070 A1 | 5/2015 | Heartlein et al. |
| 2015/0232935 A1 | 8/2015 | Deshpande et al. |
| 2015/0247204 A1 | 9/2015 | Deshpande et al. |
| 2015/0247205 A1 | 9/2015 | Gandhi et al. |
| 2015/0267251 A1 | 9/2015 | Cai et al. |
| 2015/0283142 A1 | 10/2015 | Stern et al. |
| 2015/0292007 A1 | 10/2015 | Church et al. |
| 2016/0054308 A1 | 2/2016 | Guo |
| 2016/0194701 A1 | 7/2016 | Beechem et al. |
| 2017/0212986 A1 | 7/2017 | Zhuang et al. |
| 2017/0220733 A1 | 8/2017 | Zhuang et al. |
| 2017/0327876 A1 | 11/2017 | Khafizov et al. |
| 2018/0142286 A1 | 5/2018 | Dunaway et al. |
| 2019/0055594 A1 | 2/2019 | Samusik et al. |
| 2019/0119742 A1 | 4/2019 | Zhang et al. |
| 2019/0161796 A1 | 5/2019 | Hauling et al. |
| 2019/0271028 A1 | 9/2019 | Khafizov et al. |
| 2019/0345548 A1 | 11/2019 | Dunaway et al. |
| 2019/0360025 A1 | 11/2019 | Persson et al. |
| 2019/0390258 A1 | 12/2019 | Dunaway et al. |
| 2020/0010891 A1 | 1/2020 | Beechem et al. |
| 2020/0071751 A1 | 3/2020 | Daugharthy et al. |
| 2021/0164039 A1 | 6/2021 | Wang et al. |
| 2021/0403992 A1 | 12/2021 | Pinard et al. |
| 2022/0040346 A1 | 2/2022 | Phillips et al. |
| 2022/0213532 A1 | 7/2022 | Dunaway et al. |
| 2022/0243260 A1 | 8/2022 | Rothmann et al. |
| 2022/0282313 A1 | 9/2022 | Khafizov et al. |
| 2022/0298559 A1 | 9/2022 | Daugharthy et al. |
| 2022/0333186 A1 | 10/2022 | Brown |
| 2022/0356519 A1 | 11/2022 | Shen et al. |
| 2022/0364160 A1 | 11/2022 | Nolan et al. |
| 2022/0403462 A1 | 12/2022 | Meyer et al. |
| 2022/0411862 A1 | 12/2022 | Spiecker et al. |
| 2023/0039899 A1 | 2/2023 | Larman et al. |
| 2023/0160004 A1 | 5/2023 | Beechem et al. |
| 2023/0183800 A1 | 6/2023 | Beechem et al. |
| 2023/0220461 A1 | 7/2023 | Dunaway et al. |

FOREIGN PATENT DOCUMENTS

| | | |
|---|---|---|
| CN | 102858995 A | 1/2013 |
| CN | 107208144 A | 9/2017 |
| EP | 1672082 A2 | 6/2006 |
| EP | 2722388 A1 | 4/2014 |
| EP | 2766498 A2 | 8/2014 |
| EP | 2794928 A1 | 10/2014 |
| EP | 2971184 A1 | 1/2016 |
| EP | 3458601 A1 | 3/2019 |
| EP | 3472359 A1 | 4/2019 |
| EP | 4001432 A1 | 5/2022 |
| EP | 4039822 A1 | 8/2022 |
| JP | 2002537858 A | 11/2002 |
| JP | 2003517283 A | 5/2003 |
| JP | 2003523935 A | 8/2003 |
| JP | 2004298082 A | 10/2004 |
| JP | 2006129866 A | 5/2006 |
| JP | 2008512129 A | 4/2008 |
| JP | 2009519717 A | 5/2009 |
| JP | 2010539982 A | 12/2010 |
| JP | 2011525111 A | 9/2011 |
| JP | 2012500007 A | 1/2012 |
| JP | 2014531908 A | 12/2014 |
| JP | 2017535269 A | 11/2017 |
| JP | 2019522463 A | 8/2019 |
| JP | 2020500514 A | 1/2020 |
| KR | 20050044668 A | 5/2005 |
| WO | WO-9707245 A1 | 2/1997 |
| WO | WO-9714028 A2 | 4/1997 |
| WO | WO-9918434 A1 | 4/1999 |
| WO | WO-0061807 A1 | 10/2000 |
| WO | WO-0073777 A1 | 12/2000 |
| WO | WO-0100875 A2 | 1/2001 |
| WO | WO-03003810 A2 | 1/2003 |
| WO | WO-03019141 A2 | 3/2003 |
| WO | WO-03048387 A2 | 6/2003 |
| WO | WO-03054214 A2 | 7/2003 |
| WO | WO-2004067742 A1 | 8/2004 |
| WO | WO-2006031745 A2 | 3/2006 |
| WO | WO-2006084132 A2 | 8/2006 |
| WO | WO-2007121489 A2 | 10/2007 |
| WO | WO-2008039998 A2 | 4/2008 |
| WO | WO-2008069973 A2 | 6/2008 |
| WO | WO-2009046149 A1 | 4/2009 |
| WO | WO-2009076238 A2 | 6/2009 |
| WO | WO-2010019826 A1 | 2/2010 |
| WO | WO-2010080134 A1 | 7/2010 |
| WO | WO-2010081114 A2 | 7/2010 |
| WO | WO-2011032040 A1 | 3/2011 |
| WO | WO-2011047087 A2 | 4/2011 |
| WO | WO-2011106583 A2 | 9/2011 |
| WO | WO-2011156434 A2 | 12/2011 |
| WO | WO-2012049316 A1 | 4/2012 |
| WO | WO-2012058638 A2 | 5/2012 |
| WO | WO-2012150035 A1 | 11/2012 |
| WO | WO-2012157684 A1 | 11/2012 |
| WO | WO-2012173274 A1 | 12/2012 |
| WO | WO-2013053901 A1 | 4/2013 |
| WO | WO-2013055995 A2 | 4/2013 |
| WO | WO-2013096851 A1 | 6/2013 |
| WO | WO-2013102108 A2 | 7/2013 |
| WO | WO-2013184754 A2 | 12/2013 |
| WO | WO-2014152321 A1 | 9/2014 |
| WO | WO-2014153052 A2 | 9/2014 |
| WO | WO-2014163886 A1 | 10/2014 |
| WO | WO-2014165232 A1 | 10/2014 |
| WO | WO-2014182598 A1 | 11/2014 |
| WO | WO-2014186411 A1 | 11/2014 |
| WO | WO-2014201232 A2 | 12/2014 |
| WO | WO-2015031541 A1 | 3/2015 |
| WO | WO-2015089449 A2 | 6/2015 |
| WO | WO-2015095766 A2 | 6/2015 |
| WO | WO-2015100459 A2 | 7/2015 |
| WO | WO-2015108972 A1 | 7/2015 |
| WO | WO-2015124738 A1 | 8/2015 |
| WO | WO-2015127407 A1 | 8/2015 |
| WO | WO-2015136509 A1 | 9/2015 |
| WO | WO-2015143078 A1 | 9/2015 |
| WO | WO-2015148531 A1 | 10/2015 |
| WO | WO-2015148606 A2 | 10/2015 |
| WO | WO-2016081740 A1 | 5/2016 |
| WO | WO-2016168584 A1 | 10/2016 |
| WO | WO-2017201073 A1 | 11/2017 |
| WO | WO-2017222453 A1 | 12/2017 |

(56) References Cited

FOREIGN PATENT DOCUMENTS

| WO | WO-2018094385 A1 | 5/2018 |
|---|---|---|
| WO | WO-2019222178 A1 | 11/2019 |
| WO | WO-2022197801 A1 | 9/2022 |

OTHER PUBLICATIONS

Xia, et al., Spatial transcriptome profiling by MERFISH reveals subcellular RNA compartmentalization and cell cycle-dependent gene expression, PNAS, Supplementary Information, Sep. 2019, 32 pages.

Alfano, et al., Optical sensing, imaging, and manipulation for biological and biomedical applications, The International Society for Optical Engineering, Jul. 2000, 342 pages.

Bolzer, et al., Three-dimensional maps of all chromosomes in human male fibroblast nuclei and prometaphase rosettes, PloS Biol., May 2005, 17 pages.

Chen, et al., Expansion microscopy, Science, Jan. 2015, pp. 543-548.

Chen, K. H. et al., Spatially resolved, highly multiplexed RNA profiling in single cells, Science, Apr. 2015, 16 pages. doi:10.1126/science.aaa6090.

Collins M. L. et al., A branched DNA signal amplification assay for quantification of nucleic acid targets below 100 molecules/ml, Nucleic Acids Research, Aug. 1997, pp. 2979-2984.

COVID-19 SARS-CoV-2 Variant Classifications and Definitions, CDC Centers for Disease Control and Prevention, 2023, pp. 1-7.

De Capoa et al., Computer-assisted analysis of methylation status of individual interphase nuclei in human cultured cells, Cytometry, Feb. 1998, pp. 85-92.

Duose, et al., Multiplexed and reiterative fluorescence labeling via DNA circuitry, Bioconjugate chemistry, Dec. 2010, pp. 2327-2331.

Eid, et al., Real-time DNA sequencing from single polymerase molecules, Science, Jan. 2009, pp. 133-138.

Emanuel, et al., Using MERSCOPE to generate a cell atlas of the mouse brain that includes lowly expressed genes, Microscopy Today, Nov. 2021, pp. 16-19.

Fang, et al., Conservation and divergence in cortical cellular organization between human and mouse revealed by single-cell transcriptome imaging, bioRxiv, Nov. 2021, pp. 2021-11.

Femino, et al., Visualization of single RNA transcripts in situ, Science, Apr. 1998, pp. 585-590.

Ferguson, et al., High-density fiber-optic DNA random microsphere array, Analytical Chemistry, Nov. 2000, pp. 5618-5624.

Geiss et al., Direct multiplexed measurement of gene expression with color-coded probe pairs, Nat. Biotechnol., Mar. 2008, pp. 317-325.

Göransson, et al., A single molecule array for digital targeted molecular analyses, Nucleic Acids Research, Jan. 2009, 9 pages.

Gunderson, et al., Decoding Randomly Ordered DNA Arrays, Genome Res, May 2004, pp. 870-877.

Hauser et al Utilising the left-helical conformation of L-DNA for analysing different marker types on a single universal microarray platform, Nucleic Acids Research, Sep. 2006, pp. 5101-5111.

Itzkovitz, et al., Validating transcripts with probes and imaging technology, Nature Methods Supplement, Apr. 2011, pp. S12-S19.

Jungmann, et al., Multiplexed 3D cellular super-resolution imaging with DNA-PAINT and Exchange-PAINT, Nat Methods, Mar. 2014, pp. 313-318.

Ke, et al., In situ sequencing for RNA analysis in preserved tissue and cells, Nature methods, Sep. 2013, pp. 857-860.

Kosman et al., Multiplex detection of RNA expression in *Drosophila* embryos, Science, Aug. 2004, p. 846.

Kosman, et al., Multiplex detection of RNA expression in *Drosophila* embryos, Science, Aug. 2004, Supporting Online Material, 13 pages.

Lee, et al., Fluorescent in situ sequencing (FISSEQ) of RNA for gene expression profiling in intact cells and tissues, Nature protocols, Mar. 2015, pp. 442-458.

Lee, et al., Highly multiplexed subcellular RNA sequencing in situ, Science, Mar. 2014, pp. 1360-1363.

Levsky et al., Single-Cell Gene Expression Profiling, Science, Aug. 2002, pp. 836-840.

Lin, et al., Submicrometre geometrically encoded fluorescent barcodes self-assembled from DNA, Nature chemistry, Oct. 2012, pp. 832-839.

Liu, et al., Comparative analysis of MERFISH spatial transcriptomics with bulk and single-cell RNA sequencing, bioRxiv. Mar. 7, 2022, 48 pages.

Lu, et al., Spatial transcriptome profiling by MERFISH reveals fetal liver hematopoietic stem cell niche architecture, Cell Discovery, Jun. 2021, 17 pages.

Lubeck, et al., Single-cell in situ RNA profiling by sequential hybridization, Nature methods, Apr. 2014, pp. 360-361.

Lubeck, et al., Single-cell systems biology by super-resolution imaging and combinatorial labeling, Nature methods, Jul. 2012, pp. 743-748.

Marbleston, et al., Rosetta Brains: A Strategy for Molecularly-Annotated Connectomics, Apr. 2014, 18 pages.

McElwain, et al., NanoString: Single-molecule long read sequencing using Hyb & Seq™, Chemistry, Feb. 13, 2017, 1 page.

Merscope™ Instrument User Guide, Document No. 91600001, Document Revision: Rev B, Revision Date Oct. 2021, 39 pages.

Merscope™ User Guide, Fresh and Fixed Frozen Tissue Sample Preparation, Document No. 91600002, Document Revision Rev B, Revision Date Oct. 2021, 28 pages.

Müller, et al., Towards unlimited colors for fluorescence in-situ hybridization (FISH), Chromosome Research, Mar. 2002, pp. 223-232.

Moffitt, et al., RNA imaging with multiplexed error-robust fluorescence in situ hybridization (MERFISH), Methods in Enzymology, Jan. 2016, pp. 1-49 pages.

Moffitt, et al., High-throughput single-cell gene-expression profiling with multiplexed error-robust fluorescence in situ hybridization, PNAS, Sep. 2016, pp. 11046-11051.

Olejnik, et al., Photocleavable aminotag phosphoramidites for 5'-termini DNA/RNA labeling, Nucleic Acids Research, Aug. 1998, pp. 3572-3576.

Player, et al., Single-copy gene detection using branched DNA (bDNA) in situ hybridization, The Journal of Histochemistry & Cytochemistry, May 2001, pp. 603-611.

Press Release, Wyss Institute Launches New Company to Provide Inexpensive Access to Super-Resolution Microscopy, published online Oct. 13, 2015, 6 pages.

Raj, et al., Imaging individual mRNA molecules using multiple singly labeled probes, Nature Methods, Oct. 2008, pp. 877-879.

Söderberg, et al., Characterizing proteins and their interactions in cells and tissues using the in situ proximity ligation assay, Methods, Jul. 2008, pp. 227-232.

Söderberg, et al., Direct observation of individual endogenous protein complexes in situ by proximity ligation, Nature Methods, Dec. 2006, pp. 995-1000.

Seelig, et al., Catalyzed relaxation of a metastable DNA fuel, J. Am. Chem. Soc. Sep. 2006, pp. 12211-12220.

Seo, et al., Four-color DNA sequencing by synthesis on a chip using photocleavable fluorescent nucleotides, PNAS, Apr. 2005, pp. 5926-5931.

Shendure, et al., Accurate multiplex polony sequencing of an evolved bacterial genome Science, 2005, pp. 1728-1732.

Shendure, et al., Accurate Multiplex Polony Sequencing of an Evolved Bacterial Genome, Supporting Online Material, Science, 2005, pp. 1728-1732.

Sinnamon, et al., RNA detection in situ with FISH-STICs, RNA, Feb. 2014, pp. 260-266.

Steemers et al., Screening unlabeled DNA targets with randomly ordered fiber-optic gene arrays, Nat. Biotechnol. 2000. 18:91-94.

Sweeney, et al., Quantitative multiplexed quantum dot immunohistochemistry, Biochemical and biophysical research communications, Sep. 2008, pp. 181-186.

Swoboda, et al., Enzymatic oxygen scavenging for photostability without pH drop in single-molecule experiments, ACS nano, Jul. 2012, pp. 6364-6369.

(56) References Cited

OTHER PUBLICATIONS

Voelkerding, et al., Next-Generation Sequencing: From Basic Research to Diagnostics, Clinical Chemistry, Apr. 2009, pp. 641-658.

Wang, et al., NAscope: a novel in situ RNA analysis platform for formalin-fixed, paraffin-embedded tissues, The Journal of Molecular Diagnostics, Jan. 2012, pp. 22-29.

Wang, et al., Multiplexed imaging of high-density libraries of RNAs with MERFISH and expansion microscopy, Scientific Reports, Mar. 2018, 13 pages.

Wang, et al., Spatial organization of the transcriptome in individual neurons, bioRxiv, Dec. 2020, pp. 2020-12.

Wei, et al., Complex shapes self-assembled from single-stranded DNA tiles, Nature, May 2012, pp. 623-626.

Werner, et al., Current status of DNA sequencing by single molecule detection, Advances in Fluorescence Sensing Technology IV, May 1999, pp. 355-366.

Wikipedia, ABI Solid Sequencing, downloaded on Feb. 23, 2023, 3 pages.

Xia, et al., Multiplexed detection of RNA using MERFISH and branched DNA amplification, Scientific reports, May 2019, 13 pages.

Xia, et al., Spatial transcriptome profiling by MERFISH reveals subcellular RNA compartmentalization and cell cycle-dependent gene expression, Proceedings of the National Academy of Sciences, Sep. 2019, pp. 19490-19499.

\* cited by examiner

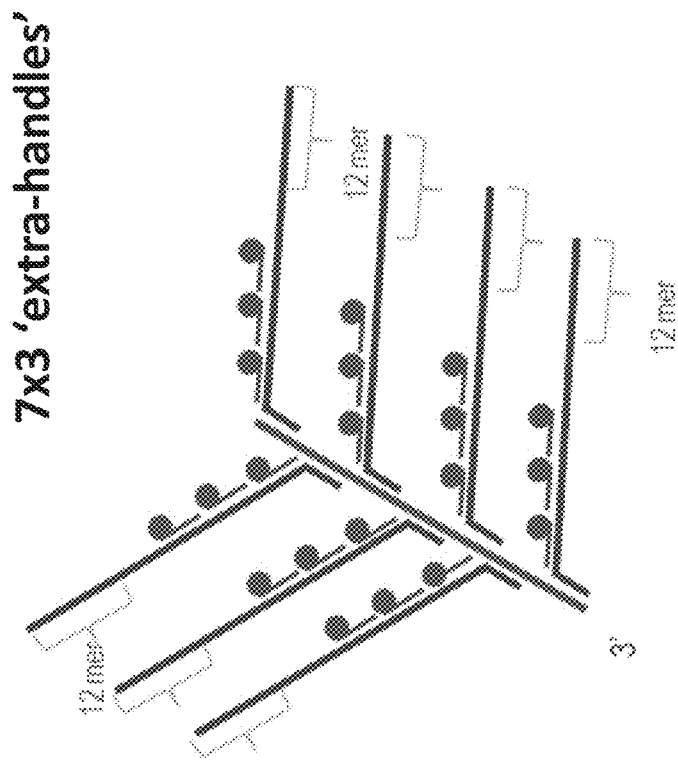
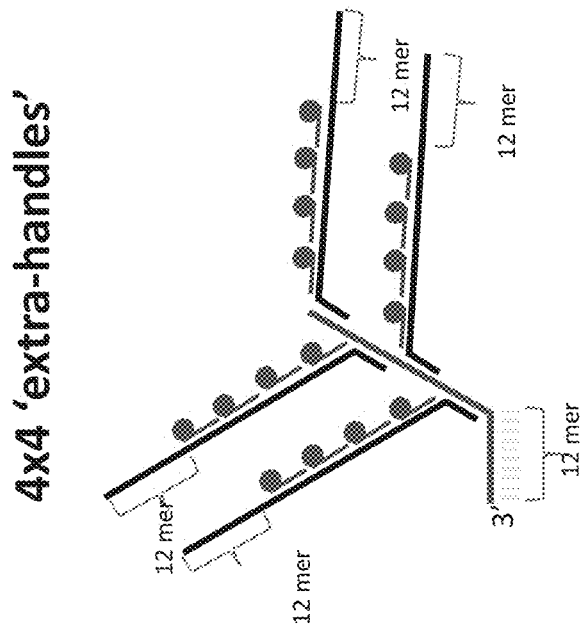
FIG. 6

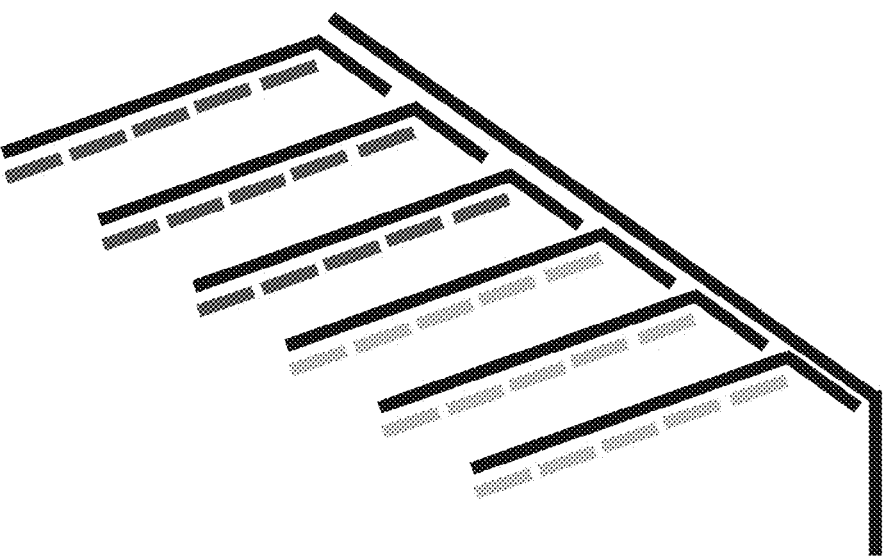
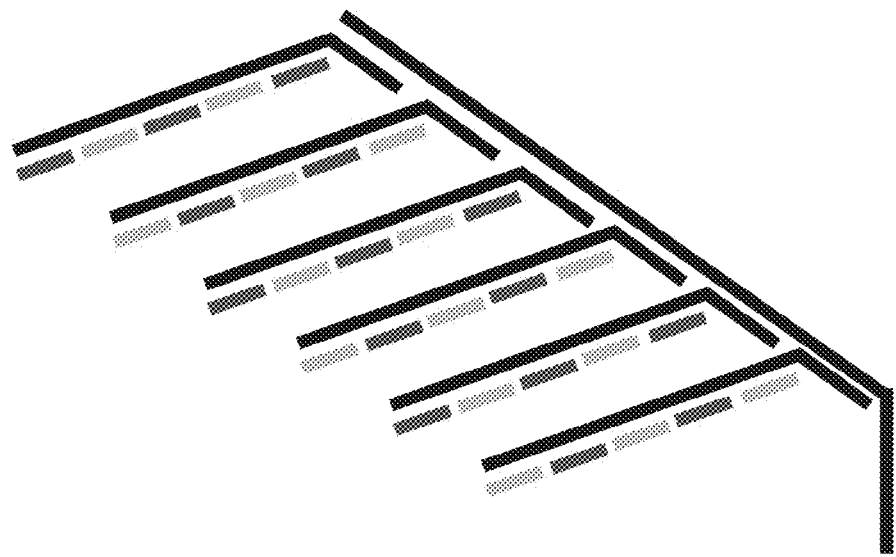
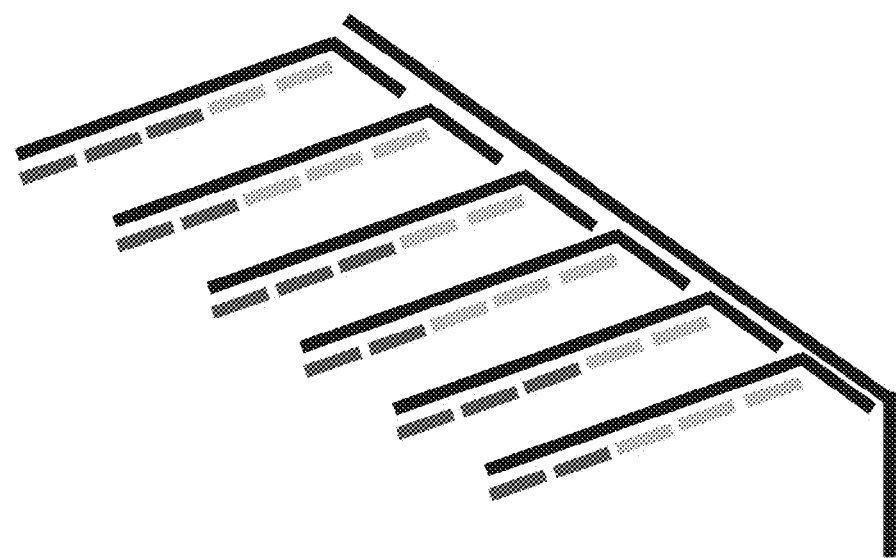
FIG. 7

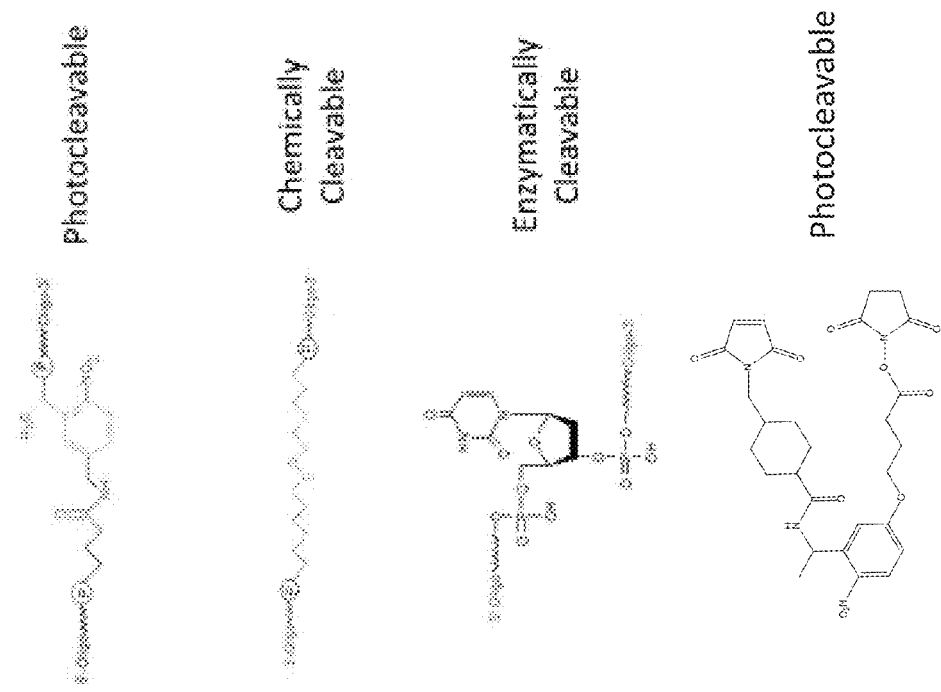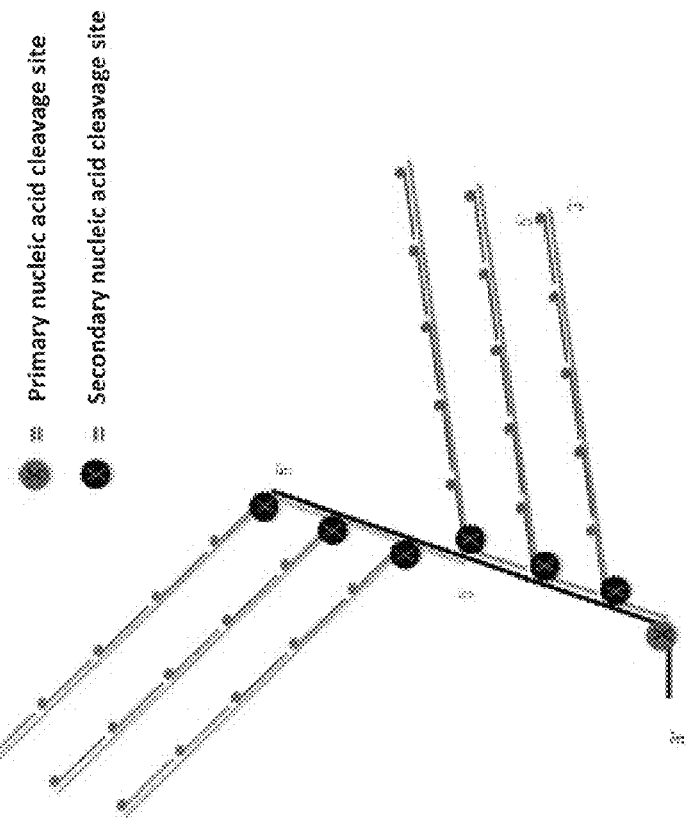
FIG. 10

*As disclosed in US 2016-0194701, which is incorporated herein by reference in its entirety

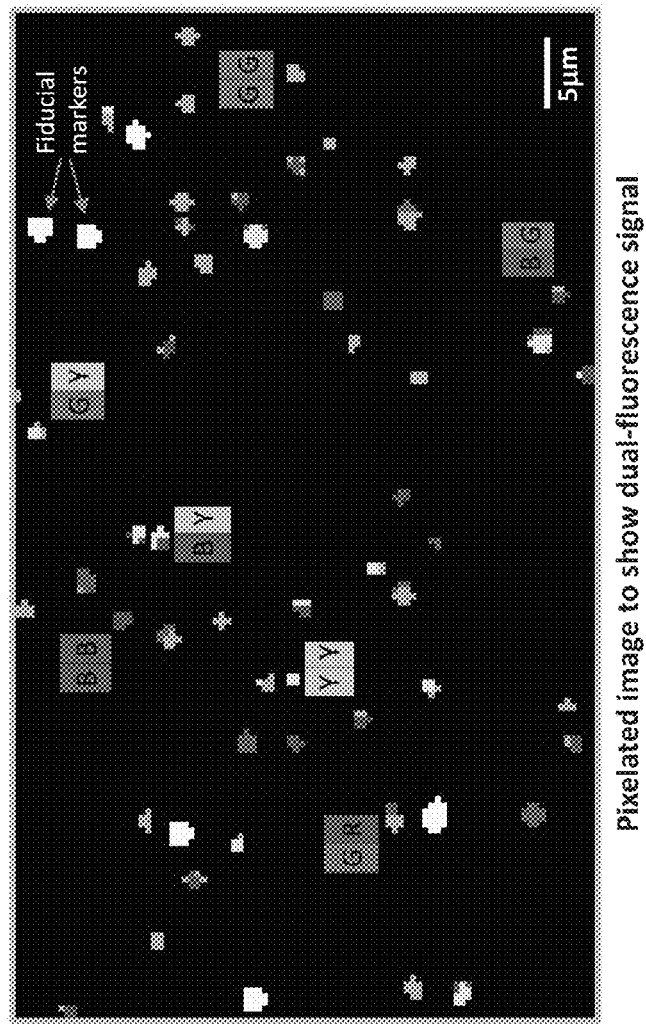
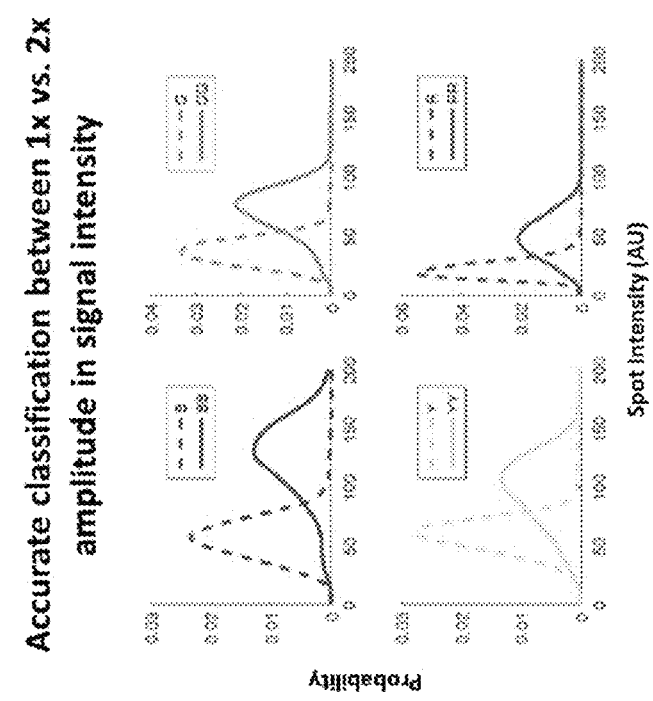
FIG. 21

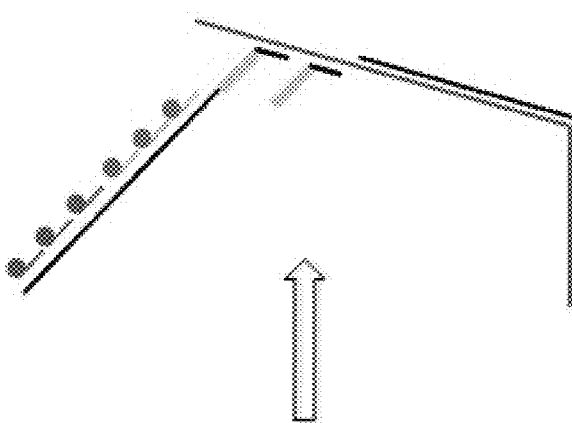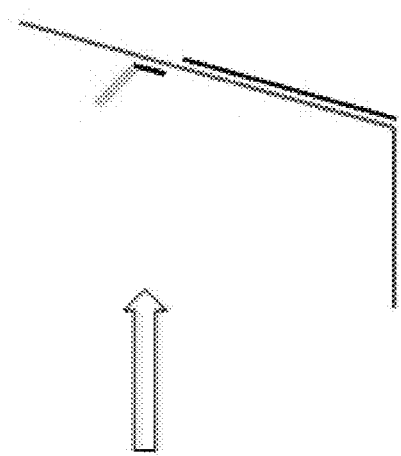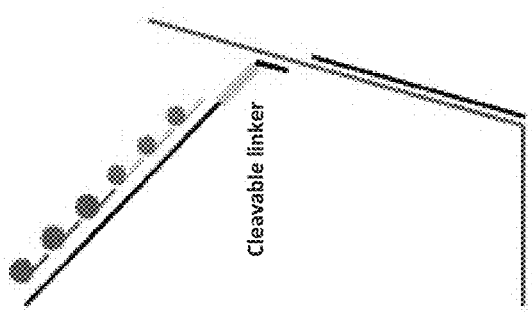
FIG. 22

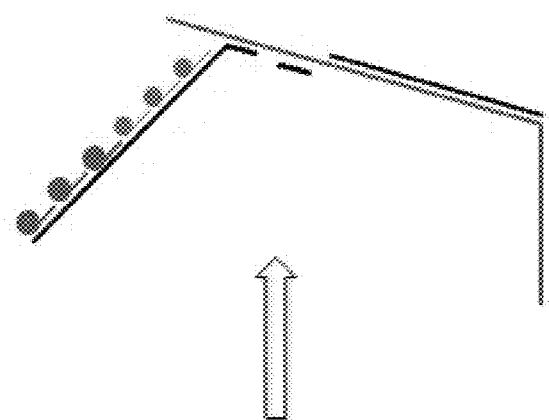
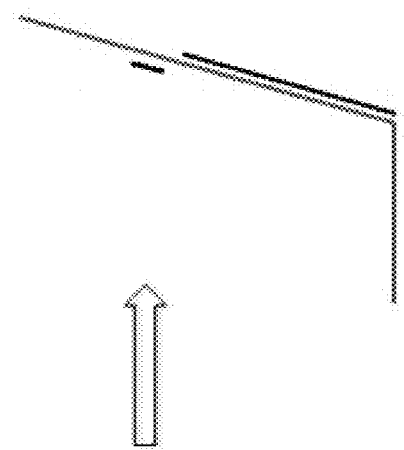
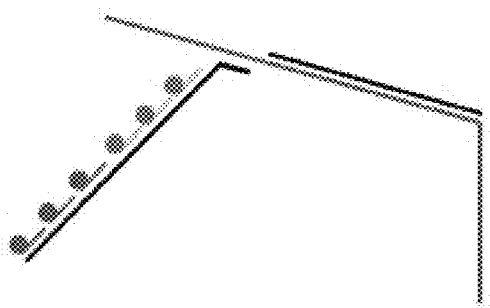
FIG. 23

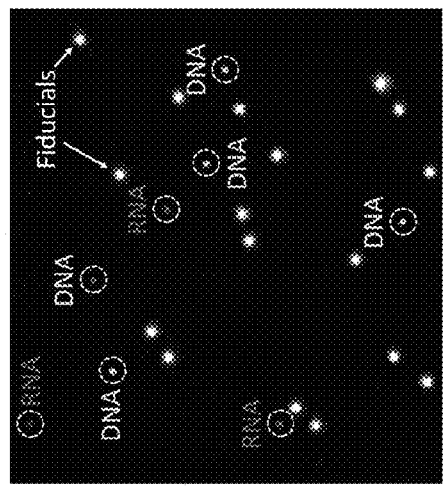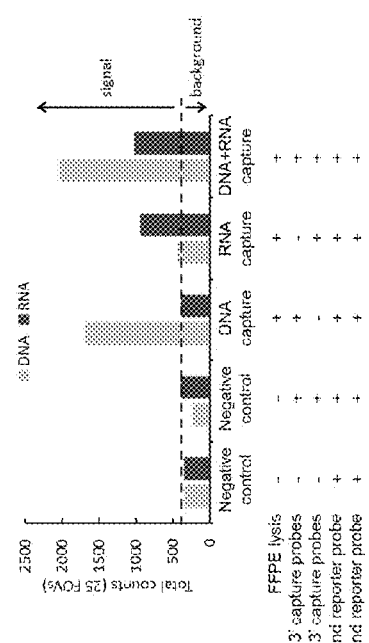
FIG. 24

```
      CACCT        Four calls of C
      CACCT        Two different probes observed
AACAC C            Voting High Quality Call
AACAC C
3'-AACACCACCT-5' consensus
   (SEQ ID NO: 2)

ACACCT       Six calls of C from two different
      CCACCT       probes
      CCACCT       One Call of A
    AACACC         Two different probes observed
    AACACC         calling C
    AACACC         Voting High Quality Call
    AACAAC
3'-AACACCACCT-5' consensus
   (SEQ ID NO: 2)

CCACCT       Three calls of C from two different Probes
      ACACCT       Two Calls of A from a single probe
      ACACCT       Voting Medium Quality Call
      CCACCT
    AACACC
3'-AACACCACCT-5' consensus
   (SEQ ID NO: 2)
```

FIG. 26

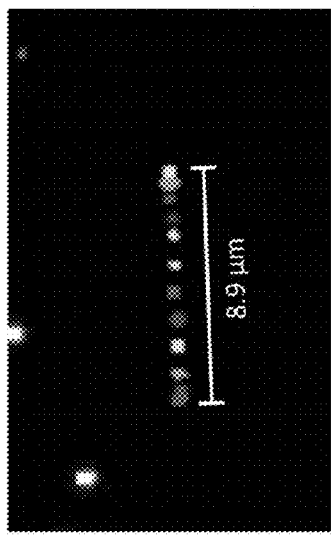
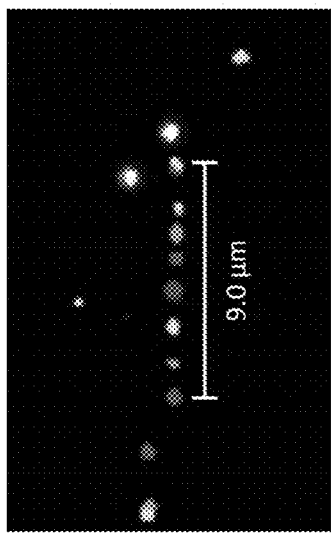
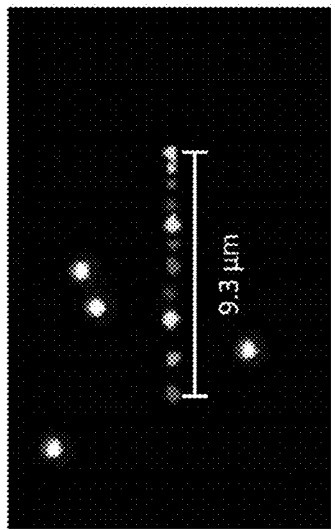
FIG. 27

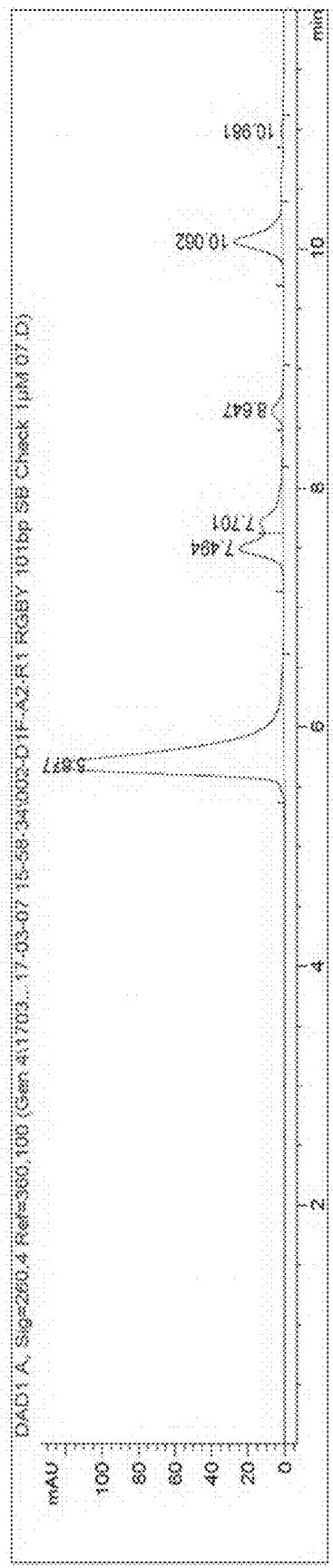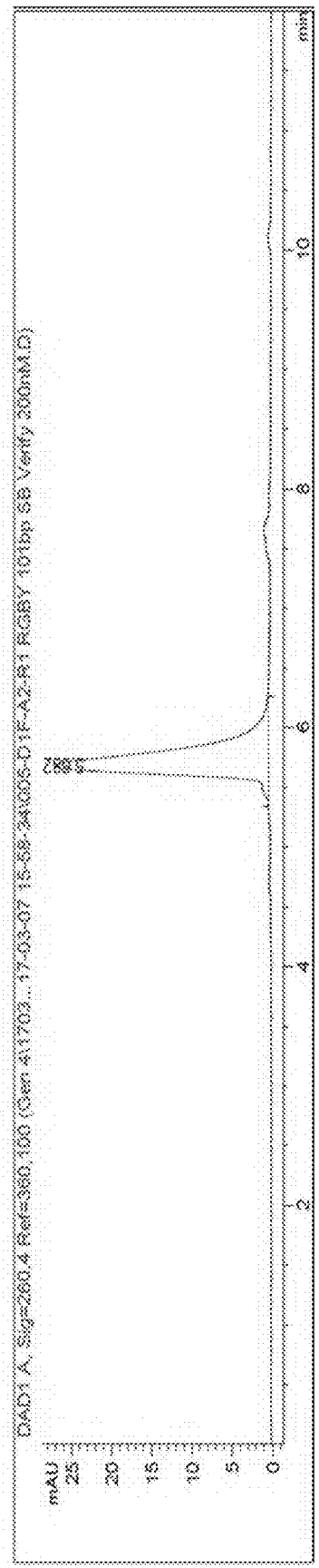
FIG. 39

CHEMICAL COMPOSITIONS AND METHODS OF USING SAME

CROSS-REFERENCE TO RELATED APPLICATIONS

This application is a continuation of U.S. patent application Ser. No. 17/699,849, filed Mar. 21, 2022, which is a divisional of U.S. patent application Ser. No. 16/559,755, filed Sep. 4, 2019, now U.S. Pat. No. 11,279,969, issued on Mar. 22, 2022, which is a continuation of U.S. patent application Ser. No. 15/819,151, filed Nov. 21, 2017, now U.S. Pat. No. 10,415,080, issued on Sep. 17, 2019, which claims priority to, and the benefit of, U.S. Provisional Application No. 62/424,887, filed Nov. 21, 2016; U.S. Provisional Application No. 62/457,237, filed Feb. 10, 2017; and U.S. Provisional Application No. 62/536,147, filed Jul. 24, 2017. The contents of each of the aforementioned patent applications are incorporated herein by reference in their entireties.

SEQUENCE LISTING

The Sequence Listing XML associated with this application is provided electronically in XML file format and is hereby incorporated by reference into the specification. The name of the XML file containing the Sequence Listing XML is "NATE-033_C02US_SeqList.xml". The XML file is 119,667 bytes, created on Mar. 7, 2023, and is being submitted electronically via USPTO Patent Center.

BACKGROUND OF THE INVENTION

There are currently a variety of methods for nucleic acid sequencing, i.e., the process of determining the precise order of nucleotides within a nucleic acid molecule. Current methods require amplifying a nucleic acid enzymatically, e.g., PCR, and/or by cloning. Further enzymatic polymerizations are required to produce a detectable signal by a light detection means. Such amplification and polymerization steps are costly and/or time-consuming. Thus, there is a need in the art for a method of nucleic acid sequencing that is rapid and amplification- and enzyme-free. The present disclosure addresses these needs.

SUMMARY OF THE INVENTION

The present disclosure provides sequencing probes, methods, kits, and apparatuses that provide rapid enzyme-free, amplification-free, and library-free nucleic acid sequencing that has long-read-lengths and with low error rate. The sequencing probes described herein include barcode domains in which each position in the barcode domain corresponds to at least two nucleotides in the target binding domain. Moreover, the methods, kits, and apparatuses have rapid sample-to-answer capability. These features are particularly useful for sequencing in a clinical setting. The present disclosure is an improvement of the disclosure disclosed in Patent Publication No. U.S. 2016/0194701, the contents of which are herein incorporated by reference is their entirety.

The present disclosure provides a complex comprising a) a composition comprising a target binding domain and a barcode domain, wherein the target binding domain comprises at least eight nucleotides and is capable of binding a target nucleic acid, wherein at least six nucleotides in the target binding domain are capable of identifying a corresponding nucleotide in the target nucleic acid molecule and wherein at least two nucleotides in the target binding domain do not identify a corresponding nucleotide in the target nucleic acid molecule; wherein at least two nucleotides of the at least six nucleotides in the target binding domain are modified nucleotides or nucleotide analogues; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein the nucleic acid sequence of the at least three attachment positions determines the position and identity of the at least six nucleotides in the target nucleic acid that is bound by the target binding domain, and wherein each of the at least three attachment positions have a different nucleic acid sequence; and a first complementary primary nucleic acid molecule hybridized to a first attachment position of the at least three attachment positions, wherein the first primary complementary nucleic acid molecule comprises at least two domains and a linker modification, wherein the first domain is hybridized to the first attachment position of the barcode domain and the second domain capable of hybridizing to at least one complementary secondary nucleic acid molecule, and wherein the linker modification is

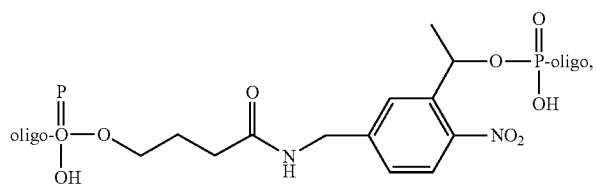

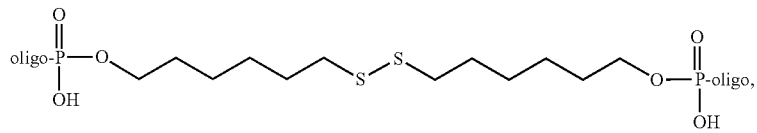

-continued

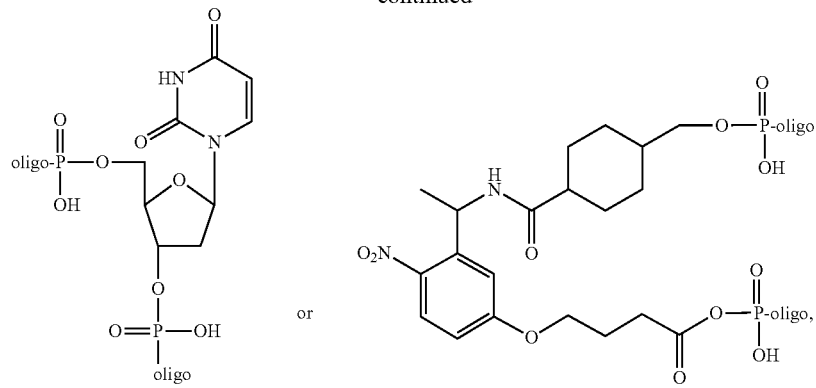

or and wherein the linker modification is located between the first and second domains.

The present disclosure provides a complex comprising a) a composition comprising a target binding domain and a barcode domain, wherein the target binding domain comprises at least eight nucleotides and is capable of binding a target nucleic acid, wherein at least six nucleotides in the target binding domain are capable of identifying a corresponding nucleotide in the target nucleic acid molecule and wherein at least two nucleotides in the target binding domain do not identify a corresponding nucleotide in the target nucleic acid molecule; wherein at least two nucleotides of the at least six nucleotides in the target binding domain are modified nucleotides or nucleotide analogues; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein the nucleic acid sequence of the at least three attachment positions determines the position and identity of the at least six nucleotides in the target nucleic acid that is bound by the target binding domain, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain; and a first complementary primary nucleic acid molecule hybridized to a first attachment position of the at least three attachment positions, wherein the first primary complementary nucleic acid molecule comprises at least two domains and a linker modification, wherein the first domain is hybridized to the first attachment position of the barcode domain and the second domain capable of hybridizing to at least one complementary secondary nucleic acid molecule, and wherein the linker modification is

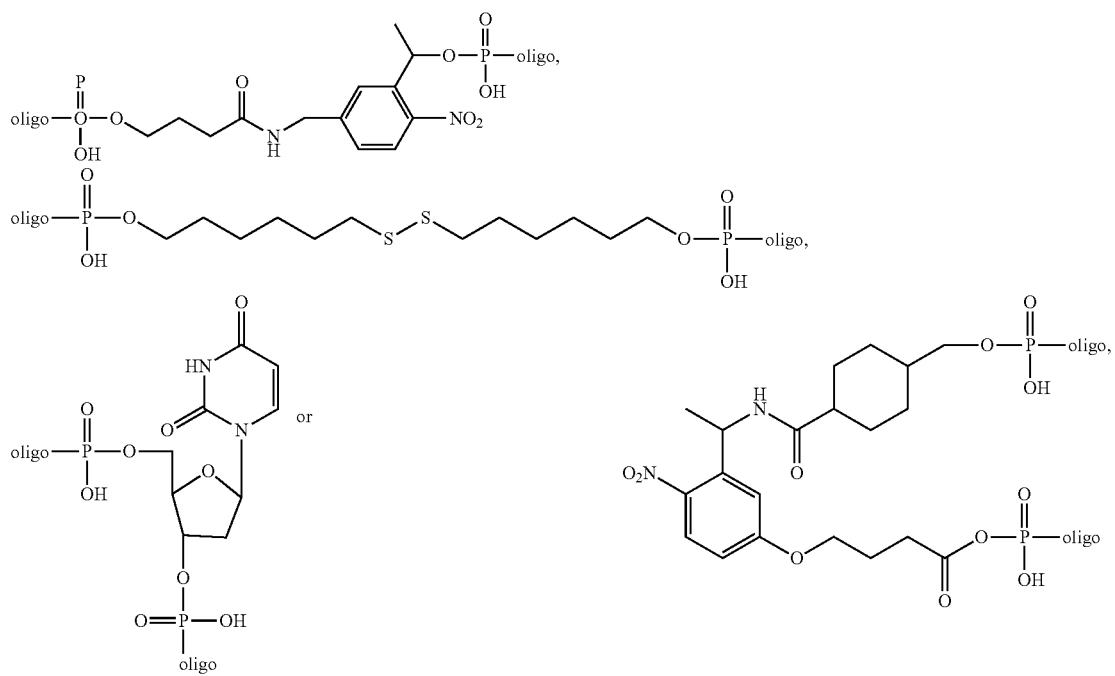

or and wherein the linker modification is located between the first and second domains.

The present disclosure provides a sequencing probe comprising a target binding domain and a barcode domain; wherein the target binding domain comprises at least eight nucleotides and is capable of binding a target nucleic acid, wherein at least six nucleotides in the target binding domain are capable of identifying a corresponding nucleotide in the target nucleic acid molecule and wherein at least two nucleotides in the target binding domain do not identify a corresponding nucleotide in the target nucleic acid molecule; wherein at least two nucleotides of the at least six nucleotides in the target binding domain are modified nucleotides or nucleotide analogues; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein the nucleic acid sequence of the at least three attachment positions determines the position and identity of the at least six nucleotides in the target nucleic acid that is bound by the target binding domain, and wherein each of the at least three attachment positions have a different nucleic acid sequence.

The present disclosure provides a sequencing probe comprising a target binding domain and a barcode domain; wherein the target binding domain comprises at least eight nucleotides and is capable of binding a target nucleic acid, wherein at least six nucleotides in the target binding domain are capable of identifying a corresponding nucleotide in the target nucleic acid molecule and wherein at least two nucleotides in the target binding domain do not identify a corresponding nucleotide in the target nucleic acid molecule; wherein at least two nucleotides of the at least six nucleotides in the target binding domain are modified nucleotides or nucleotide analogues; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

The present disclosure provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein the nucleic acid sequence of the at least three attachment positions determines the position and identity of the at least six nucleotides in the target nucleic acid that is bound by the target binding domain, and wherein each of the at least three attachment positions have a different nucleic acid sequence.

The present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

The synthetic backbone can comprise a polysaccharide, a polynucleotide, a peptide, a peptide nucleic acid, or a polypeptide. The synthetic backbone can comprise DNA. The synthetic backbone comprises a single-stranded DNA. The sequencing probe can comprise a single-stranded DNA synthetic backbone and a double-stranded DNA spacer between the target binding domain and the barcode domain. The double-stranded DNA spacer can be from about 1 nucleotide to about 100 nucleotides in length; from about 2 nucleotides to about 50 nucleotides in length; or from 20 nucleotides to 40 nucleotides in length. The double-stranded DNA spacer is about 36 nucleotides in length. The sequencing probe can comprise a single-stranded DNA synthetic backbone and a polymer-based spacer between the target binding domain and the barcode domain, wherein the polymer-based spacer provides similar mechanical properties as a double-stranded DNA spacer.

The number of nucleotides in the target binding domain can be the same as, less than, or greater than, the number of attachment positions in the barcode domain. Preferably, the number of nucleotides in the target binding domain is greater than the number of attachment positions in the barcode domain. The number of nucleotides in the target binding domain can be at least three more, at least four more, at least five more, at least six more, at least seven more, at least eight more, at least nine more or at least ten more than the number of attachment positions in the barcode domain. Preferably, the target binding domain comprises eight nucleotides and the barcode domain comprises three attachment positions.

At least three, at least four, at least five, or at least six nucleotides in the target binding domain capable of identifying a corresponding nucleotide in the target nucleic acid molecule can be modified nucleotides or nucleotide analogues. The modified nucleotide or nucleic acid analogue can be locked nucleic acids (LNA), bridged nucleic acids (BNA), propyne-modified nucleic acids, zip nucleic acids (ZNA®), isoguanine, isocytosine, or any combination thereof. Preferably, the modified nucleotide or nucleic acid analogue is a locked nucleic acid (LNA).

The at least two nucleotides in the target binding domain that do not identify a corresponding nucleotide can precede the at least six nucleotides in the target binding domain. The at least two nucleotides in the target binding domain that do not identify a corresponding nucleotide can follow the at least six nucleotides in the target binding domain. The at least one of the at least two nucleotides in the target binding domain that do not identify a corresponding nucleotide precedes the at least six nucleotides in the target binding domain and wherein at least one of the at least two nucleotides in the target binding domain that do not identify a corresponding nucleotide follows the at least six nucleotides in the target binding domain. That is, the at least two nucleotides in the target binding domain that do not identify a corresponding nucleotide flank the at least six nucleotides in the target binding domain.

The at least two nucleotides in the target binding domain that do not identify a corresponding nucleotide in the target nucleic acid molecule can be universal bases, degenerate bases, or a combination thereof. At least two of the at least four nucleotides in the target binding domain that do not identify a corresponding nucleotide in the target nucleic acid molecule can be universal bases, degenerate bases, or a combination thereof.

Each attachment position in the barcode domain can comprise one attachment region. Each attachment position in the barcode domain can comprise more than one attachment region.

Each attachment position in the barcode domain can comprise the same number of attachment regions. Each attachment position in the barcode domain can comprise a different number of attachment regions. At least one of the at least three attachment positions in the barcode domain can comprise a different number of attachment regions than the other two. When the attachment position in the barcode domain comprises more than one attachment region, the attachment regions can be the same. When the attachment position in the barcode domain comprises more than one attachment region, the attachment regions can comprise the same nucleic acid sequence. When the attachment position in the barcode domain comprises more than one attachment region, the attachment regions can be different. When the attachment position in the barcode domain comprises more than one attachment region, the attachment regions can comprise a different nucleic acid sequence.

Each nucleic acid sequence comprising each attachment region in the barcode domain is from about 8 nucleotides to about 20 nucleotides in length. Each nucleic acid sequence comprising each attachment region in the barcode domain is about 12 nucleotides in length. Each nucleic acid sequence comprising each attachment region in the barcode domain is about 14 nucleotides in length.

At least one, at least two, or at least three of the at least three attachment positions in the barcode domain can be adjacent to at least one flanking single-stranded polynucleotide. Each of the at least three attachment positions in the barcode domain can be adjacent to at least one flanking single stranded polynucleotide.

At least one, at least two, or at least three attachment regions in at least one attachment position can be integral to the synthetic backbone. Each attachment region in each of the at least three attachment positions can be integral to the synthetic backbone. At least one, at least two, or at least three attachment regions in at least one attachment position can branch from the synthetic backbone. Each attachment region in each of the at least three attachment positions can branch from the synthetic backbone.

The complementary nucleic acid molecule capable of binding, directly or indirectly, to at least one nucleic acid sequence within at least one attachment region within each attachment position can be RNA, DNA or PNA. Preferably, the complementary nucleic acid molecule is DNA.

The complementary nucleic acid molecule can be a primary nucleic acid molecule, wherein a primary nucleic acid molecule directly binds to at least one attachment region within at least one attachment position of the barcode domain.

The primary nucleic acid molecule can comprise at least two domains, a first domain capable of binding to at least one attachment region within at least one attachment position of the barcode domain and a second domain capable of binding to at least one complementary secondary nucleic acid molecule. The primary nucleic acid molecule can comprise at least two domains, a first domain capable of binding to at least one attachment region within at least one attachment position of the barcode domain and a second domain comprising comprises a first detectable label and an at least second detectable label.

The primary nucleic molecule can be hybridized to at least one attachment region within at least one attachment position of the barcode domain and be hybridized to at least one, at least two, at least three, at least four, at least five, or more secondary nucleic acid molecules. Preferably the primary nucleic molecule is hybridized to four secondary nucleic acid molecules. The primary nucleic molecule can be hybridized to at least one attachment region within at least one attachment position of the barcode domain and can be hybridized to a first detectable label and an at least second detectable label. The first and at least second detectable labels can have the same emission spectrum or can have different emission spectra The primary nucleic acid molecule can comprise a cleavable linker. Preferably, the cleavable linker is located between the first domain and the second domain. The cleavable linker can be a photo-cleavable linker (e.g., UV-light cleavable linker), a reducing agent cleavable linker, or an enzymatically cleavable linker. Preferably, the linker is a photo-cleavable linker.

A secondary nucleic acid molecule can comprise at least two domains, a first domain capable of binding to complementary sequence in at least one primary nucleic acid molecule; and a second domain capable of binding to (a) a first detectable label and an at least second detectable label, (b) to at least one complementary tertiary nucleic acid molecule, or (c) a combination thereof.

The secondary nucleic molecule can be hybridized to at least one primary nucleic acid molecule and be hybridized to at least one, at least two, at least three, at least four, at least five, at least six, at least seven or more tertiary nucleic acid molecules. Preferably the secondary nucleic molecule is hybridized to one tertiary nucleic acid molecule. The secondary nucleic molecule can be hybridized to at least one primary nucleic acid molecule and can comprise a first detectable label and an at least second detectable label. The secondary nucleic molecule can be hybridized to at least one primary nucleic acid molecule, at least one tertiary nucleic acid molecule and to a first detectable label and an at least second detectable label. The first and at least second detectable labels can have the same emission spectrum or can have different emission spectra. When the secondary nucleic molecule is hybridized to at least one primary nucleic acid molecule, at least one tertiary nucleic acid molecule comprising a first detectable label and an at least second detectable label, and to a first detectable label and an at least second detectable label, the at least first and second detectable labels located on the secondary nucleic acid molecule can have the same emission spectra and the at least first and second detectable labels located on the tertiary nucleic acid molecule can have the same emission spectra, and wherein the emission spectra of the detectable labels on the secondary nucleic acid molecule can be different than the emission spectra of the detectable labels on the tertiary nucleic acid molecule.

The secondary nucleic acid molecule can comprise a cleavable linker. Preferably, the cleavable linker is located between the first domain and the second domain. The cleavable linker can be a photo-cleavable linker (e.g., UV-light cleavable linker), a reducing agent cleavable linker, or an enzymatically cleavable linker. Preferably, the linker is a photo-cleavable linker.

A tertiary nucleic acid molecule can comprise at least two domains, a first domain capable of binding to complementary sequence in at least one secondary nucleic acid molecule; and a second domain capable of binding to a first detectable label and an at least second detectable label.

The tertiary nucleic molecule can be hybridized to at least one secondary nucleic acid molecule and can comprise a first detectable label and an at least second detectable label. The first and at least second detectable labels can have the same emission spectrum or can have different emission spectra.

The tertiary nucleic acid molecule can comprise a cleavable linker. Preferably, the cleavable linker is located between the first domain and the second domain. The cleavable linker can be a photo-cleavable linker (e.g., UV-light cleavable linker), a reducing agent cleavable linker, or an enzymatically cleavable linker. Preferably, the linker is a photo-cleavable linker.

The present disclosure also provides a population of the sequencing probes comprising a plurality of the sequencing probes disclosed herein. Preferably, each sequencing probe within the plurality of sequencing probes comprises a different target binding domain and binds a different region within a target nucleic acid.

The present disclosure also provides a method for sequencing a nucleic acid comprising (1) hybridizing a sequencing probe described herein to a target nucleic acid that is optionally immobilized to a substrate at one or more positions; (2) binding a first complementary nucleic acid molecule comprising a first detectable label and an at least second detectable label to a first attachment position of the at least three attachment positions of the barcode domain; (3) detecting the first and at least second detectable label of the bound first complementary nucleic acid molecule; (4) identifying the position and identity of at least two nucleotides in the immobilized target nucleic acid; (5) binding to the first attachment position a first hybridizing nucleic acid molecule lacking a detectable label, thereby unbinding the first complementary nucleic acid molecule comprising the detectable labels, or contacting the first complementary nucleic acid molecule comprising the detectable labels with a force sufficient to release the first detectable label and at least second detectable label; (6) binding a second complementary nucleic acid molecule comprising a third detectable label and an at least fourth detectable label to a second attachment position of the at least three attachment positions of the barcode domain; (7) detecting the third and at least fourth detectable label of the bound second complementary nucleic acid molecule; (8) identifying the position and identity of at least two nucleotides in the optionally immobilized target nucleic acid; (9) repeating steps (5) to (8) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a first region of the optionally immobilized target nucleic acid that was hybridized to the target binding domain of the sequencing probe; and (10) removing the sequencing probe from the optionally immobilized target nucleic acid.

The method can further comprise (11) hybridizing a second sequencing probe to a target nucleic acid that is optionally immobilized to a substrate at one or more positions, and wherein the target binding domain of the first sequencing probe and the second sequencing probe are different; (12) binding a first complementary nucleic acid molecule comprising a first detectable label and an at least second detectable label to a first attachment position of the at least three attachment positions of the barcode domain; (13) detecting the first and at least second detectable label of the bound first complementary nucleic acid molecule; (14) identifying the position and identity of at least two nucleotides in the optionally immobilized target nucleic acid; (15) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (16) binding a second complementary nucleic acid molecule comprising a third detectable label and an at least fourth detectable label to a second attachment position of the at least three attachment positions of the barcode domain; (17) detecting the third and at least fourth detectable label of the bound second complementary nucleic acid molecule; (18) identifying the position and identity of at least two nucleotides in the optionally immobilized target nucleic acid; (19) repeating steps (15) to (18) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a second region of the optionally immobilized target nucleic acid that was hybridized by the target binding domain of the sequencing probe; and (20) removing the second sequencing probe from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (5) and (6) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photo-cleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The present disclosure also provides a method for sequencing a nucleic acid comprising (1) hybridizing at least one first population of first sequencing probes comprising a plurality of the sequencing probes described herein to a target nucleic acid that is optionally immobilized to a substrate at one or more positions; (2) binding a first complementary nucleic acid molecule comprising a first detectable label and an at least second detectable label to a first attachment position of the at least three attachment positions of the barcode domain; (3) detecting the first and at least second detectable label of the bound first complementary nucleic acid molecule; (4) identifying the position and identity of at least two nucleotides in the optionally immobilized target nucleic acid; (5) binding to the first attachment position a first hybridizing nucleic acid molecule lacking a detectable label, thereby unbinding the first complementary nucleic acid molecule comprising the detectable labels, or contacting the first complementary nucleic acid molecule comprising the detectable labels with a force sufficient to release the first detectable label and at least second detectable label; (6) binding a second complementary nucleic acid molecule comprising a third detectable label and an at least fourth detectable to a second attachment position of the at least three attachment positions of the barcode domain; (7) detecting the third and at least fourth detectable label of the bound second complementary nucleic acid molecule; (8) identifying the position and identity of at least two nucleotides in the optionally immobilized target nucleic acid; (9) repeating steps (5) to (8) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a first region of the optionally immobilized target nucleic acid that was hybridized by the target binding domain of the sequencing probe; and (10) removing the at least one first population of first sequencing probes from the optionally immobilized target nucleic acid.

The method can further comprise (11) hybridizing at least one second population of second sequencing probes comprising a plurality of the sequencing probes disclosed herein to a target nucleic acid that is optionally immobilized to a substrate at one or more positions, and wherein the target binding domain of the first sequencing probe and the second sequencing probe are different; (12) binding a first complementary nucleic acid molecule comprising a first detectable label and an at least second detectable label to a first attachment position of the at least three attachment positions of the barcode domain; (13) detecting the first and at least second detectable label of the bound first complementary nucleic acid molecule; (14) identifying the position and identity of at least two nucleotides in the optionally immobilized target nucleic acid; (15) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (16) binding a second complementary nucleic acid molecule comprising a third detectable label and an at least fourth detectable label to a second attachment position of the at least three attachment positions of the barcode domain; (17) detecting the third and at least fourth detectable label of the bound second complementary nucleic acid molecule; (18) identifying the position and identity of at least two nucleotides in the optionally immobilized target nucleic acid; (19) repeating steps (15) to (18) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a second region of the optionally immobilized target nucleic acid that was hybridized by the target binding domain of the sequencing probe; and (20) removing the at least one second population of second sequencing probes from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (5) and (6) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photocleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The present disclosure also provides a method for determining a nucleotide sequence of a nucleic acid comprising (1) hybridizing a first sequencing probe as disclosed herein to a target nucleic acid that is optionally immobilized to a substrate at one or more positions; (2) hybridizing a first complementary nucleic acid molecule comprising a first detectable label and a second detectable label to a first attachment position of the at least three attachment positions of the barcode domain; (3) identifying the first and the second detectable label of the first complementary nucleic acid molecule hybridized to the first attachment position; (4) removing the first and the second detectable label hybridized to the first attachment position; (5) hybridizing a second complementary nucleic acid molecule comprising a third detectable label and a fourth detectable label to a second attachment position of the at least three attachment positions of the barcode domain; (6) identifying the third and the fourth detectable label of the second complementary nucleic acid molecule hybridized to the second attachment position; (7) removing the third and fourth detectable label hybridized to the second attachment position; (8) hybridizing a third complementary nucleic acid molecule comprising a fifth detectable label and a sixth detectable label to a third attachment position of the at least three attachment positions of the barcode domain; (9) identifying the fifth and the sixth detectable label of the third complementary nucleic acid molecule hybridized to the third attachment position; and (10) identifying the linear order of at least six nucleotides of the optionally immobilized target nucleic acid hybridized to the target binding domain of the sequencing probe based on the identity of the first detectable label, second detectable label, third detectable label, fourth detectable label, fifth detectable label and sixth detectable label.

The method can further comprise (11) removing the at least first sequencing probe from the first region of the optionally immobilized target nucleic acid; (12) hybridizing at least a second sequencing probe as disclosed herein to a second region of the target nucleic acid that is optionally immobilized to a substrate at one or more positions, and wherein the target binding domain of the first sequencing probe and the at least second sequencing probe are different; (13) hybridizing a first complementary nucleic acid molecule comprising a first detectable label and a second detectable label to a first attachment position of the at least three attachment positions of the barcode domain; (14) detecting the first and the second detectable label of the first complementary nucleic acid molecule hybridized to the first attachment position; (15) hybridizing a second complementary nucleic acid molecule comprising a third detectable label and a fourth detectable label to a second attachment position of the at least three attachment positions of the barcode domain; (16) detecting the third and the fourth detectable label of the second complementary nucleic acid molecule hybridized to the second attachment position; (17) removing the third and fourth detectable label hybridized to the second attachment position; (18) hybridizing a third complementary nucleic acid molecule comprising a fifth detectable label and a sixth detectable label to a third attachment position of the at least three attachment positions of the barcode domain; (19) identifying the fifth and the sixth detectable label of the third complementary nucleic acid molecule hybridized to the third attachment position; and (20) identifying the linear order of at least six nucleotides in the second region of the optionally immobilized target nucleic acid hybridized to the target binding domain of the at least second sequencing probe based on the identity of the first detectable label, second detectable label, third detectable label, fourth detectable label, fifth detectable label and sixth detectable label.

The method can further comprise assembling each identified linear order of nucleotides in the at least first region and at least second region of the immobilized target nucleic acid, thereby identifying a sequence for the immobilized target nucleic acid.

Steps (4) and (5) can occur sequentially or concurrently. The first and at least second detectable labels can have the same emission spectrum or can have different emission spectra. The third and at least fourth detectable labels can have the same emission spectrum or can have different emission spectra. The fifth and at least sixth detectable labels can have the same emission spectrum or can have different emission spectra.

The first complementary nucleic acid molecule can comprise a cleavable linker. The second complementary nucleic acid molecule can comprise a cleavable linker. The third complementary nucleic acid molecule can comprise a cleavable linker. The first complementary nucleic acid molecule, the second complementary nucleic acid molecule and the at least third complementary nucleic molecule can each comprise a cleavable linker. Preferably, the cleavable linker is photo-cleavable. A method of removing any one of the first complementary nucleic acid molecule, the second complementary nucleic acid molecule and the at least third complementary nucleic molecule can comprise contact with light. Preferably, UV light. The light can be provided by a light source selected from the group consisting of an arc-lamp, a laser, a focused UV light source, and light emitting diode.

The present disclosure also provides a method for determining the nucleotide sequence of a nucleic acid comprising (1) hybridizing a first sequencing probe as disclosed herein to a first region of a target nucleic acid obtained from a predetermine gene, wherein the target nucleic acid is optionally immobilized to a substrate at one or more positions; (2) hybridizing a first complementary nucleic acid molecule comprising a first detectable label and a second detectable label to a first attachment position of the at least three attachment positions of the barcode domain; (3) detecting the first and the second detectable label of the first complementary nucleic acid molecule hybridized to the first attachment position; (4) removing the first and the second detectable label hybridized to the first attachment position; (5) hybridizing a second complementary nucleic acid molecule comprising a third detectable label and a fourth detectable label to a second attachment position of the at least three attachment positions of the barcode domain; (6) detecting the third and and fourth detectable label of the second complementary nucleic acid molecule hybridized to the second attachment position; (7) removing the third and the fourth detectable label hybridized to the second attachment position; (8) hybridizing a third complementary nucleic acid molecule comprising a fifth detectable label and a sixth detectable label to a third attachment position of the at least three attachment positions of the barcode domain; (9) identifying the fifth and the sixth detectable label of the third complementary nucleic acid molecule hybridized to the third attachment position; and (10) identifying the linear order of the at least six nucleotides in the first region of the optionally immobilized target nucleic acid hybridized to the target binding domain of the first sequencing probe based on the identity of the first detectable label, second detectable label, third detectable label, fourth detectable label, fifth detectable label and sixth detectable label.

The method can further comprise (11) removing the at least first sequencing probe from the first region of the optionally immobilized target nucleic acid; (12) hybridizing at least a second sequencing probe as disclosed herein to a second region of the target nucleic acid that is optionally immobilized to a substrate at one or more positions, and wherein the target binding domain of the first sequencing probe and the at least second sequencing probe are different; (13) hybridizing a first complementary nucleic acid molecule comprising a first detectable label and a second detectable label to a first attachment position of the at least three attachment positions of the barcode domain; (14) detecting the first and the second detectable label of the first complementary nucleic acid molecule hybridized to the first attachment position; (15) hybridizing a second complementary nucleic acid molecule comprising a third detectable label and a fourth detectable label to a second attachment position of the at least three attachment positions of the barcode domain; (16) detecting the third and the fourth detectable label of the second complementary nucleic acid molecule hybridized to the second attachment position; (17) removing the third and fourth detectable label hybridized to the second attachment position; (18) hybridizing a third complementary nucleic acid molecule comprising a fifth detectable label and a sixth detectable label to a third attachment position of the at least three attachment positions of the barcode domain; (19) identifying the fifth and the sixth detectable label of the third complementary nucleic acid molecule hybridized to the third attachment position; and (20) identifying the linear order of at least six nucleotides in the second region of the optionally immobilized target nucleic acid hybridized to the target binding domain of the at least second sequencing probe based on the identity of the first detectable label, second detectable label, third detectable label, fourth detectable label, fifth detectable label and sixth detectable label.

The method can further comprise assembling each identified linear order of nucleotides in the at least first region and at least second region of the immobilized target nucleic acid, thereby identifying a sequence for the immobilized target nucleic acid.

Steps (4) and (5) can occur sequentially or concurrently. The first and at least second detectable labels can have the same emission spectrum or can have different emission spectra. The third and at least fourth detectable labels can have the same emission spectrum or can have different emission spectra. The fifth and at least sixth detectable labels can have the same emission spectrum or can have different emission spectra.

The first complementary nucleic acid molecule can comprise a cleavable linker. The second complementary nucleic acid molecule can comprise a cleavable linker. The third complementary nucleic acid molecule can comprise a cleavable linker. The first complementary nucleic acid molecule, the second complementary nucleic acid molecule and the at least third complementary nucleic molecule can each comprise a cleavable linker. Preferably, the cleavable linker is photo-cleavable. A method of removing any one of the first complementary nucleic acid molecule, the second complementary nucleic acid molecule and the at least third complementary nucleic molecule can comprise contact with light. Preferably, UV light. The light can be provided by a light source selected from the group consisting of an arc-lamp, a laser, a focused UV light source, and light emitting diode.

The present disclosure also provides an apparatus for performing any of the methods disclosed herein.

The present disclosure also provides one or more kits comprising a substrate, a population of sequencing probes disclosed herein, at least three complementary nucleic acid molecules comprising a first detectable label and at least two second detectable labels, and instructions for use. The one or more kits can further comprise at least one capture probe. The one or more kits can further comprise at least two capture probes.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and further features will be more clearly appreciated from the following detailed description when taken in conjunction with the accompanying drawings.

FIG. 6 is a schematic illustration of exemplary reporter probes of the present disclosure comprising "extra-handles".

FIG. 7 is a schematic illustration of several exemplary reporter probes of the present disclosure comprising different arrangements of tertiary nucleic acids.

FIG. 10 shows possible positions for cleavable linker modifications within an exemplary reporter probe of the present disclosure.

FIG. 21 shows exemplary imaging data recorded during a sequencing cycle of the present disclosure and the fluorescence signal intensity profiles of reporter probes of the present disclosure.

FIG. 22 is a schematic illustration of a sequencing cycle of the present disclosure in which a cleavable linker modification is used to darken a barcode position.

FIG. 23 is an illustrative example of an exemplary sequencing cycle of the present disclosure in which a position within a barcode domain is darkened by displacement of the primary nucleic acids.

FIG. 24 shows an example of integrated capture of RNA and DNA from a FFPE sample.

FIG. 26 shows how multiple base calls for a specific nucleotide position on the target nucleic acid, recorded from one or more sequencing probes, can be combined to create a consensus sequence, thereby increasing the accuracy of the final base call.

FIG. 27 shows recorded fluorescence images of the sequencing method of the present disclosure after the capture, stretching, and detection of 33 kilobase DNA fragments.

FIG. 39 shows the HLPC purification of an exemplary reporter complex of the present disclosure.

DETAILED DESCRIPTION OF THE INVENTION

Figure 1:
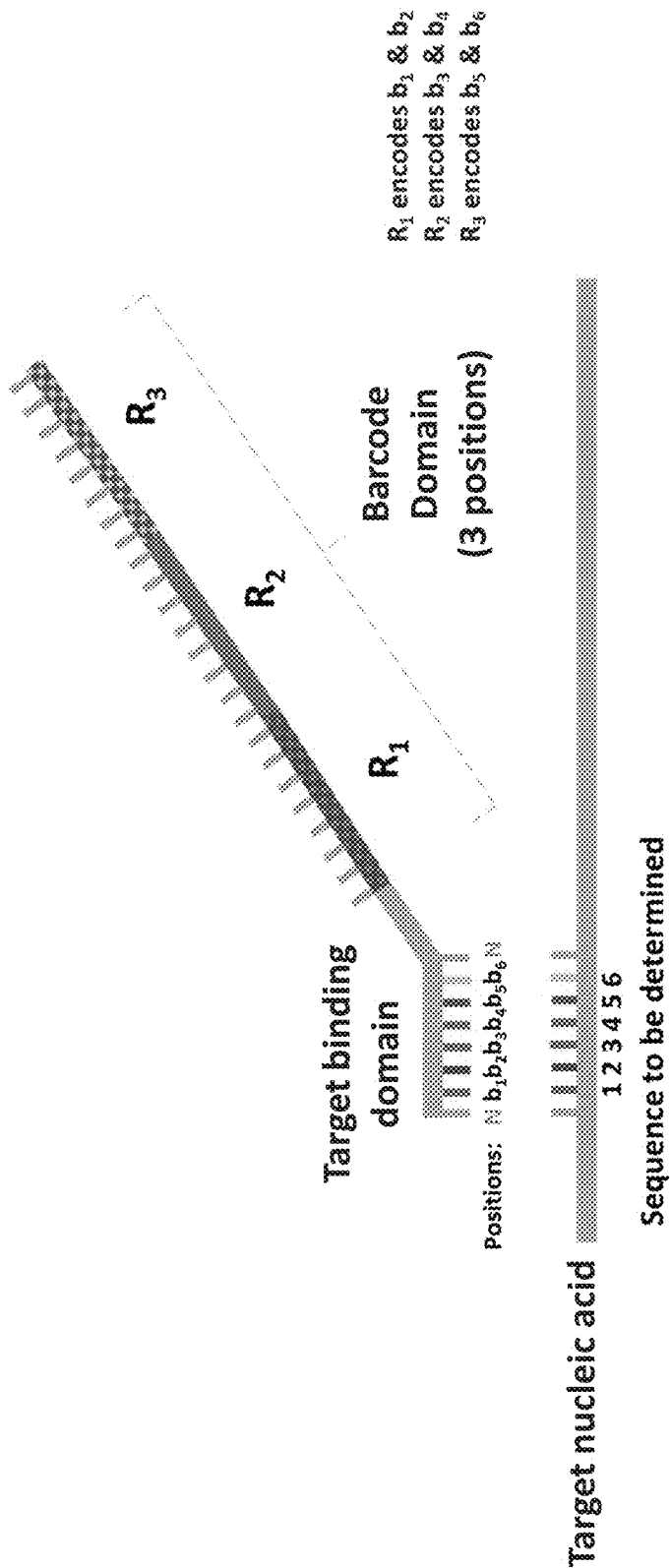
FIG. 1 is an illustration of one exemplary sequencing probe of the present disclosure.

The present disclosure provides sequencing probes, reporter probes, methods, kits, and apparatuses that provide rapid, enzyme-free, amplification-free, and library-free nucleic acid sequencing that has long-read-lengths and with low error rate.

Compositions of the Present Disclosure

The present disclosure provides a sequencing probe comprising a target binding domain and a barcode domain; wherein the target binding domain comprises at least eight nucleotides and is capable of binding a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein at least one, or at least two nucleotides, of the at least six nucleotides in the target binding domain are modified nucleotides or nucleotide analogues and wherein the at least one, or at least two nucleotides in the target binding domain are universal or degenerate bases; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

The present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

The present disclosure also provides a population of sequencing probes comprising a plurality of any of the sequencing probes disclosed herein.

The target binding domain, barcode domain, and backbone of the disclosed sequencing probes, as well as, the complementary nucleic acid molecule (e.g., reporter molecules or reporter complexes) are described in more detail below.

A sequencing probe of the present disclosure comprises a target binding domain and a barcode domain. FIG. 1 is a schematic illustration of an exemplary sequencing probe of the present disclosure. FIG. 1 shows that the target binding domain is capable of binding a target nucleic acid. A target nucleic acid can be any nucleic acid to which the sequencing probe of the present disclosure can hybridize. The target nucleic acid can be DNA or RNA. The target nucleic acid can be obtained from a biological sample from a subject. The terms "target binding domain" and "sequencing domain" are used interchangeably herein.

The target binding domain can comprise a series of nucleotides (e.g. is a polynucleotide). The target binding domain can comprise DNA, RNA, or a combination thereof. In the case when the target binding domain is a polynucleotide, the target binding domain binds to a target nucleic acid by hybridizing to a portion of the target nucleic acid that is complementary to the target binding domain of the sequencing probe, as shown in FIG. 1.

The target binding domain of the sequencing probe can be designed to control the likelihood of sequencing probe hybridization and/or de-hybridization and the rates at which these occur. Generally, the lower a probe's Tm, the faster and more likely that the probe will de-hybridize to/from a target nucleic acid. Thus, use of lower Tm probes will decrease the number of probes bound to a target nucleic acid.

The length of a target binding domain, in part, affects the likelihood of a probe hybridizing and remaining hybridized to a target nucleic acid. Generally, the longer (greater number of nucleotides) a target binding domain is, the less likely that a complementary sequence will be present in the target nucleotide. Conversely, the shorter a target binding domain is, the more likely that a complementary sequence will be present in the target nucleotide. For example, there is a 1/256 chance that a four-mer sequence will be located in a target nucleic acid versus a 1/4096 chance that a six-mer sequence will be located in the target nucleic acid. Consequently, a collection of shorter probes will likely bind in more locations for a given stretch of a nucleic acid when compared to a collection of longer probes.

In circumstances, it is preferable to have probes having shorter target binding domains to increase the number of reads in the given stretch of the nucleic acid, thereby enriching coverage of a target nucleic acid or a portion of the target nucleic acid, especially a portion of particular interest, e.g., when detecting a mutation or SNP allele.

The target binding domain can be any amount or number of nucleotides in length. The target binding domain can be at least 12 nucleotides in length, at least 10 nucleotides in length, at least 8 nucleotides in length, at least 6 nucleotides in length or at least three nucleotides in length.

Each nucleotide in the target binding domain can identify (or code for) a complementary nucleotide of the target molecule. Alternatively, some nucleotides in the target binding domain identify (or code for) a complementary nucleotide of the target molecule and some nucleotides in the target binding domain do not identify (or code for) a complementary nucleotide of the target molecule.

The target binding domain can comprise at least one natural base. The target binding domain can comprise no natural bases. The target binding domain can comprise at least one modified nucleotide or nucleic acid analog. The target binding domain can comprise no modified nucleotides or nucleic acid analogs. The target binding domain can comprise at least one universal base. The target binding domain can comprise no universal bases. The target binding domain can comprise at least one degenerate base. The target binding domain can comprise no degenerate bases.

The target domain can comprise any combination natural bases (e.g. 0, 1, 2, 3, 4, 5, 6, 7, 8, 9, 10, or more natural bases), modified nucleotides or nucleic acid analogs (e.g. 0, 1, 2, 3, 4, 5, 6, 7, 8, 9, 10, or more modified or analog nucleotides), universal bases (e.g. 0, 1, 2, 3, 4, 5, 6, 7, 8, 9, 10, or more universal bases), or degenerate bases (e.g. 0, 1, 2, 3, 4, 5, 6, 7, 8, 9, 10, or more degenerative bases). When present in a combination, the natural bases, modified nucleotides or nucleic acid analogs, universal bases and degenerate bases of a particular target binding domain can be arranged in any order.

The terms "modified nucleotides" or "nucleic acid analogues" include, but are not limited to, locked nucleic acids (LNA), bridged nucleic acids (BNA), propyne-modified nucleic acids, zip nucleic acids (ZNA®), isoguanine and isocytosine. The target binding domain can include zero to six (e.g. 0, 1, 2, 3, 4, 5 or 6) modified nucleotides or nucleic acid analogues. Preferably, the modified nucleotides or nucleic acid analogues are locked nucleic acids (LNAs).

The term "locked nucleic acids (LNA)" as used herein includes, but is not limited to, a modified RNA nucleotide in which the ribose moiety comprises a methylene bridge connecting the 2' oxygen and the 4' carbon. This methylene bridge locks the ribose in the 3'-endo confirmation, also known as the north confirmation, that is found in A-form RNA duplexes. The term inaccessible RNA can be used interchangeably with LNA. The term "bridged nucleic acids (BNA)" as used herein includes, but is not limited to, modified RNA molecules that comprise a five-membered or six-membered bridged structure with a fixed 3'-endo confirmation, also known as the north confirmation. The bridged structure connects the 2' oxygen of the ribose to the 4' carbon of the ribose. Various different bridge structures are possible containing carbon, nitrogen, and hydrogen atoms. The term "propyne-modified nucleic acids" as used herein includes, but is not limited to, pyrimidines, namely cytosine and thymine/uracil, that comprise a propyne modification at the C5 position of the nucleic acid base. The term "zip nucleic acids (ZNA®)" as used herein includes, but is not limited to, oligonucleotides that are conjugated with cationic spermine moieties.

The term "universal base" as used herein includes, but is not limited to, a nucleotide base does not follow Watson-Crick base pair rules but rather can bind to any of the four canonical bases (A, T/U, C, G) located on the target nucleic acid. The term "degenerate base" as used herein includes, but is not limited to, a nucleotide base that does not follow Watson-Crick base pair rules but rather can bind to at least two of the four canonical bases A, T/U, C, G), but not all four. A degenerate base can also be termed a Wobble base; these terms are used interchangeably herein.

The exemplary sequencing probe depicted in FIG. 1 illustrates a target binding domain that comprises a six nucleotide long (6-mer) sequence $(b_1-b_2-b_3-b_4-b_5-b_6)$ that hybridizes specifically to complementary nucleotides 1-6 of the target nucleic acid that is to be sequenced. This 6-mer portion of the target binding domain $(b_1-b_2-b_3-b_4-b_5-b_6)$ identifies (or codes for) the complementary nucleotides in the target sequence (1-2-3-4-5-6). This 6-mer sequence is flanked on either side by a base (N). The bases indicated by (N) may independently be a universal or degenerate base. Typically, the bases indicated by (N) are independently one of the canonical bases. The bases indicated by (N) do not identify (or code for) the complementary nucleotide it binds in the target sequence and are independent of the nucleic acid sequence of the (6-mer) sequence $(b_1-b_2-b_3-b_4-b_5-b_6)$.

The sequencing probe depicted in FIG. 1 can be used in conjugation with the sequencing methods of the present disclosure to sequence target nucleic acids using only hybridization reactions, no covalent chemistry, enzymes or amplification is needed. To sequence all possible 6-mer sequences in a target nucleic acid molecule, a total of 4096 sequencing probes are needed (4^6=4096).

FIG. 1 is exemplary for one configuration of a target binding domain of the sequence probe of the present disclosure. Table 1 provides several other configurations of target binding domains of the present disclosure. One preferred target binding domain, called the "6 LNA" target binding domain, comprises 6 LNAs at positions b1 to b6 of the target binding domain. These 6 LNAs are flanked on either side by a base (N). As used herein, an (N) base can be a universal/degenerate base or a canonical base that is independent of the nucleic acid sequence of the (6-mer) sequence $(b_1-b_2-b_3-b_4-b_5-b_6)$. In other words, while the bases $b_1-b_2-b_3-b_4-b_5-b_6$ may be specific to any given target sequence, the (N) bases can be a universal/degenerate base or composed of any of the four canonical bases that is not specific to the target dictated by bases $b_1$-b2-$b_3$-$b_4$-$b_5$-$b_6$. For example, if the target sequence to be interrogated is CAGG-CATA bases $b_1$-b2-$b_3$-$b_4$-$b_5$-$b_6$ of the target binding domain would be TCCGTA while each of the (N) bases of the target binding domain could independently be A, C, T or G such that a resulting target binding domain could have the sequence ATCCGTAG, TTCCGTAC, GTCCGTAG or any of the other 16 possible iterations. Alternatively, the two (N) bases could proceed the 6 LNAs. Alternatively still, the two (N) bases could follow the 6 LNAs.

TABLE 1

| Target Binding Domain | | B1 | B2 | B3 | B4 | B5 | B6 | | |
|---|---|---|---|---|---|---|---|---|---|
| "6 LNA" | | N | + | + | + | + | + | + | N |
| "10mer" | b | b | b | b | b | b | b | b | b | b |
| "Natural I" | N | N | b | b | b | b | b | b | N | N |
| "Natural II" | | N | b | b | b | b | b | b | N |
| "2 LNA" | | N | b | b | + | + | b | b | N |
| | | N | b | + | b | b | + | b | N |
| | | N | + | b | b | b | b | + | N |
| "4 LNA" | | N | + | + | b | b | + | + | N |
| | | N | + | b | + | + | b | + | N |
| | | N | b | + | + | + | + | b | N |

B = natural base;
+ = modified nucleotide or nucleotide analog (e.g. LNA);
N = natural, universal or degenerate base Table 1 also describes a "10 mer" target binding domain that comprises 10 natural, target-specific bases.

Table 1 further describes the "Natural I" target binding domain that comprises 6 natural bases at positions b1 to b6. These 6 natural bases are flanked on either side by 2 (N) bases. Alternatively, all four (N) bases could proceed the 6 natural bases. Alternatively still, all four (N) bases could follow the 6 natural bases. Any number of the four (N) bases (i.e. 1, 2, 3 or 4) could proceed the 6 natural bases while the remaining (N) bases would follow the 6 natural bases.

Table 1 further describes the "Natural II" target binding domain that comprises 6 natural bases at positions b1 to b6. These 6 natural bases are flanked on either side by an (N) base. Alternatively, both (N) bases could proceed the 6 natural bases. Alternatively still, both (N) bases could follow the 6 natural bases.

Table 1 also describes a "2 LNA" target binding domain that comprises a combination of 2 LNAs and 4 natural bases at positions b1 to b6 of the target binding domain. The 2 LNAs and 4 natural bases can occur in any order. For example, the positions b3 and b4 can be LNAs while positions b1, b2, b5 and b6 are natural bases. Bases b1 to b6 are flanked on either side by a (N) base. Alternatively, bases b1 to b6 can be proceeded by two (N) bases. Alternatively still, bases b1 to b6 can be followed by two (N) bases.

Table 1 further describes a "4 LNA" target binding domain that comprises a combination of 4 LNAs and 2 natural bases at positions b1 to b6 of the target binding domain. The 4 LNAs and 2 natural bases can occur in any order. For example, the positions b2 to b5 can be LNAs while positions b1 and b6 are natural bases. Bases b1 to b6 are flanked on either side by a (N) base. Alternatively, bases b1 to b6 can be proceeded by two (N) bases. Alternatively still, bases b1 to b6 can be followed by two (N) bases.

The sequencing probe of the present disclosure comprises a synthetic backbone. The target binding domain and the barcode domain are operably linked. The target binding domain and barcode domain can be covalently attached, as part of one synthetic backbone. The target binding domain and barcode domain can be attached via a linker (e.g., nucleic acid linker, chemical linker). The synthetic backbone can comprise any material, e.g., polysaccharide, polynucleotide, polymer, plastic, fiber, peptide, peptide nucleic acid, or polypeptide. Preferably, the synthetic backbone is rigid. The synthetic backbone can comprise a single-stranded DNA molecule. The backbone can comprise "DNA origami" of six DNA double helices (See, e.g., Lin et al, "Submicrometre geometrically encoded fluorescent barcodes self-assembled from DNA." *Nature Chemistry;* 2012 October; 4(10): 832-9). A barcode can be made of DNA origami tiles (Jungmann et al, "Multiplexed 3D cellular super-resolution imaging with DNA-PAINT and Exchange-PAINT", *Nature Methods*, Vol. 11, No. 3, 2014).

The sequencing probe of the present disclosure can comprise a partially double-stranded synthetic backbone. The sequencing probe can comprise a single-stranded DNA synthetic backbone and a double-stranded DNA spacer between the target binding domain and the barcode domain. The sequencing probe can comprise a single-stranded DNA synthetic backbone and a polymer-based spacer, with similar mechanical properties as double-stranded DNA, between the target binding domain and the barcode domain. Typical polymer-based spacers include polyethylene glycol (PEG) type polymers.

The double-stranded DNA spacer can be from about 1 nucleotide to about 100 nucleotides in length; from about 2 nucleotides to about 50 nucleotides in length; from about 20 nucleotides to about 40 nucleotides in length. Preferably, the double-stranded DNA spacer is about 36 nucleotides in length.

Figure 2:
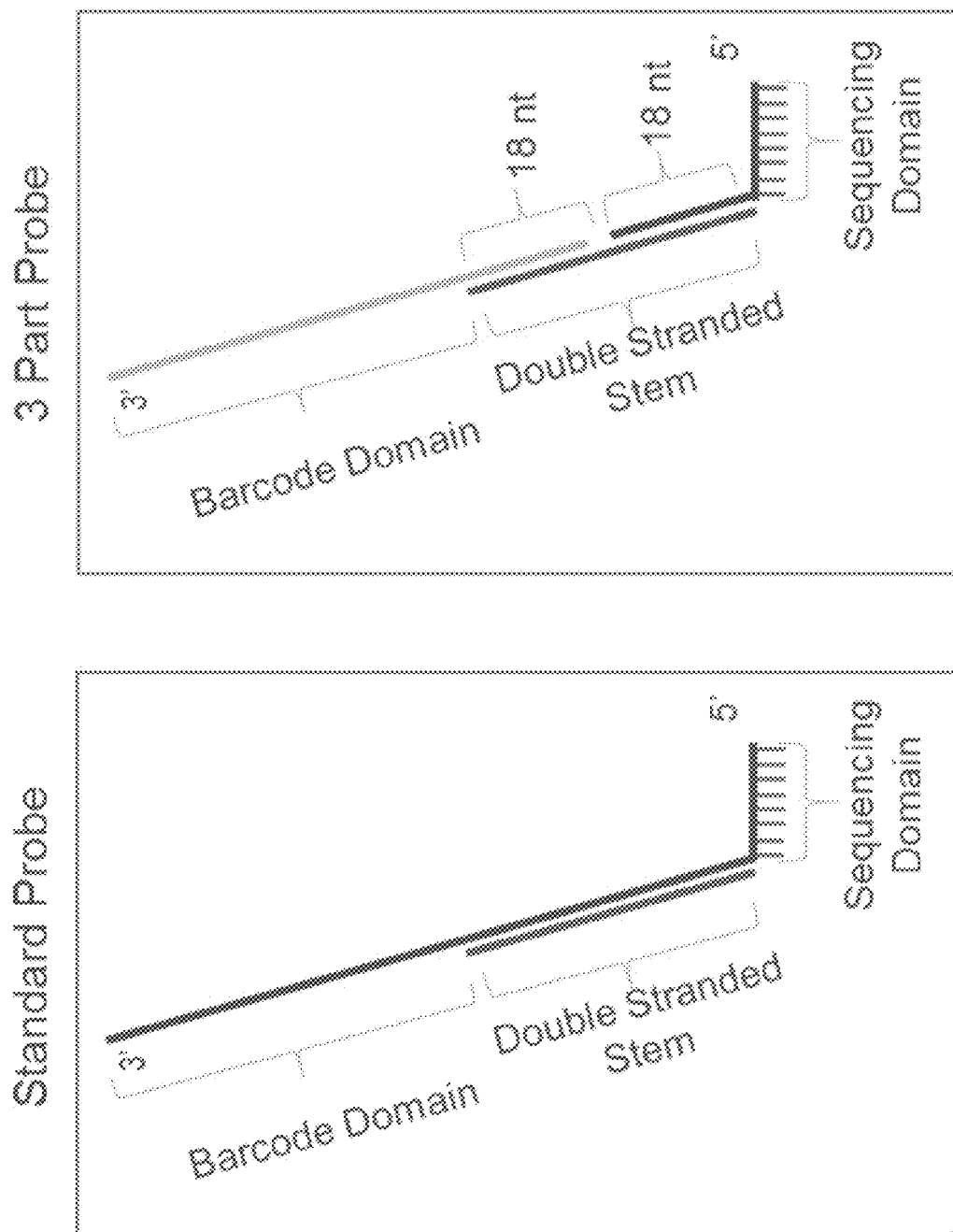
FIG. 2 shows the design of standard and three-part sequencing probes of the present disclosure.

One sequencing probe of the present disclosure, termed a "standard probe" is illustrated in the left panel of FIG. 2. The standard probe of FIG. 2 comprises a barcode domain covalently attached to the target binding domain, such that the target binding and barcode domains are present within the same single stranded oligonucleotide. In FIG. 2, left panel, a single stranded oligonucleotide binds to a stem oligonucleotide to create a 36 nucleotide long double-stranded spacer region called the stem. Using this architecture, each sequencing probe in a pool of probes can hybridize to the same stem sequence.

Another sequencing probe of the present disclosure, termed a "3 Part Probe" is illustrated in the right panel of FIG. 2. The 3 Part Probe of FIG. 2 comprises a barcode domain that is attached to the target binding domain via a linker. In this example, the linker is a single stranded stem oligonucleotide that hybridizes to the single stranded oligonucleotide that contains the target binding domain and the single stranded oligonucleotide that contains the barcode domain, creating a 36 nucleotide long double stranded spacer region that bridges the barcode domain (18 nucleotides) and target binding domain (18 nucleotides). Using this exemplary probe configuration, in order to prevent the exchange of barcode domains, each barcode can be designed such that it hybridizes to a unique stem sequence. Furthermore, each barcode domain can also be hybridized to its corresponding stem oligonucleotide prior to pooling together different sequencing probes.

The barcode domain comprises a plurality of attachment positions, e.g., one, two, three, four, five, six, seven, eight, nine, ten, or more attachment positions. The number of attachment positions can be less than, equal to, or more than the number of nucleotides in the target binding domain. The target binding domain can comprise more nucleotides than number of attachment positions in the backbone domain, e.g., one, two, three, four, five, six, seven, eight, nine, ten, or more nucleotides. The target binding domain can comprise eight nucleotides and the barcode domain comprises three attachment positions. The target binding domain can comprise ten nucleotides and the barcode domain comprises three attachment positions The length of the barcode domain is not limited as long as there is sufficient space for at least three attachment positions, as described below. The terms "attachment positions," "positions" and "spots," are used interchangeably herein. The terms "barcode domain" and "reporting domain," are used interchangeably herein.

Each attachment position in the barcode domain corresponds to two nucleotides (a dinucleotide) in the target binding domain and, thus, to the complementary dinucleotide in the target nucleic acid that is hybridized to the dinucleotide in the target binding domain. As a non-limiting example, the first attachment position in the barcode domain corresponds to the first and second nucleotides in the target binding domain (e.g., FIG. 1 where R1 is the first attachment position in the barcode domain and R1 corresponds to dinucleotide b1 and b2 in the target binding domain—which in turn identifies dinucleotides 1 and 2 of the target nucleic acid); the second attachment position in the barcode domain corresponds to the third and fourth nucleotides in the target binding domain (e.g., FIG. 1 where R2 is the second attachment position in the barcode domain and R2 corresponds to dinucleotide b3 and b4 in the target binding domain—which in turn identifies dinucleotides 3 and 4 of the target nucleic acid); and the third attachment position in the barcode domain corresponds to the fifth and sixth nucleotides in the target binding domain (e.g., FIG. 1 where R3 is the third attachment position in the barcode domain and R3 corresponds to dinucleotide b5 and b6 in the target binding domain—which in turn identifies dinucleotides 5 and 6 of the target nucleic acid).

Each attachment position in the barcode domain comprises at least one attachment region, e.g., one to 50, or more, attachment regions. Certain positions in a barcode domain can have more attachment regions than other positions (e.g., a first attachment position can have three attachment regions whereas a second attachment position can have two attachment positions); alternately, each position in a barcode domain has the same number of attachment regions. Each attachment position in the barcode domain can comprise one attachment region. Each attachment position in the barcode domain can comprise more than one attachment region. At least one of the at least three attachment positions in the barcode domain can comprise a different number of attachment regions than the other two attachments positions in the barcode domain.

Each attachment region comprises at least one (i.e., one to fifty, e.g., ten to thirty) copies of a nucleic acid sequence(s) capable of being reversibly bound by a complementary nucleic acid molecule (e.g., DNA or RNA). The nucleic acid sequences of attachment regions at a single attachment position can be identical; thus, the complementary nucleic acid molecules that bind those attachment regions are identical. Alternatively, the nucleic acid sequences of attachment regions at a position are not identical; thus, the complementary nucleic acid molecules that bind those attachment regions are not identical.

The nucleic acid sequence comprising each attachment region in a barcode domain can be about 8 nucleotides to about 20 nucleotides in length. The nucleic acid sequence comprising each attachment region in a barcode domain can be about 12 or is about 14 nucleotides in length. Preferably, the nucleic acid sequence comprising each attachment region in a barcode domain is about 14 nucleotides in length.

Each of the nucleic acids comprising each attachment region in a barcode domain can independently be a canonical base or a modified nucleotide or nucleic acid analogue. At least one, at least two, at least three, at least four, at least five, or at least six nucleotides in the attachment region in a barcode domain can be modified nucleotides or nucleotide analogues. Typical ratios of modified nucleotides or nucleotide analogues to canonical bases in a barcode domain are 1:2 to 1:8. Typical modified nucleotides or nucleic acid analogues useful in the attachment region in a barcode domain are isoguanine and isocytosine. The use of modified nucleotides or nucleotide analogues such as isoguanine and isocytosine, for example, can improve binding efficiency and accuracy of the reporter to the appropriate attachment region in a barcode domain while minimizing binding elsewhere, including to the target.

One or more attachment regions can be integral to a polynucleotide backbone; that is, the backbone is a single polynucleotide and the attachment regions are parts of the single polynucleotide's sequence. One or more attachment regions can be linked to a modified monomer (e.g., modified nucleotide) in the synthetic backbone such that the attachment region branches from the synthetic backbone. An attachment position can comprise more than one attachment region, in which some attachment regions branch from the synthetic backbone and some attachment regions are integral to the synthetic backbone. At least one attachment region in at least one attachment position can be integral to the synthetic backbone. Each attachment region in each of the at least three attachment positions can be integral to the synthetic backbone. At least one attachment region in at least one attachment position can branch from the synthetic backbone. Each attachment region in each of the at least three attachment positions can branch from the synthetic backbone.

Each attachment position within a barcode domain corresponds to one of sixteen dinucleotides i.e., either adenine-adenine, adenine-thymine/uracil, adenine-cytosine, adenine-guanine, thymine/uracil-adenine, thymine/uracil-thymine/uracil, thymine/uracil-cytosine, thymine/uracil-guanine, cytosine-adenine, cytosine-thymine/uracil, cytosine-cytosine, cytosine-guanine, guanine-adenine, guanine-thymine/uracil, guanine-cytosine or guanine-guanine. Thus, the one or more attachment regions located in a single attachment position of a barcode domain correspond to one of sixteen dinucleotides and comprise a nucleic acid sequence that is specific to the dinucleotide to which the attachment region corresponds. Attachment regions located in different attachment positions of a barcode domain contain unique nucleic acid sequences even if these positions within the barcode domain correspond to the same dinucleotide. For example, given a sequencing probe of the present disclosure that contains a target binding domain with a hexamer that encodes the sequence A-G-A-G-A-C, the barcode domain of this sequencing probe would contain three positions, with the first attachment position corresponding to an adenine-guanine dinucleotide, the second attachment position corresponding to an adenine-guanine dinucleotide and the third attachment position corresponding to an adenine-cytosine dinucleotide. The attachment regions located in position one of this example probe would comprise a nucleic acid sequence that is unique from the nucleic acid sequence of the attachment regions located in position two, even though both attachment position one and attachment position two correspond to the dinucleotide adenine-guanine. The sequences of specific attachment positions are designed and tested such that the complementary nucleic acid of a particular attachment position will not interact with a different attachment position. Additionally, the nucleotide sequence of a complementary nucleic acid is not limited; preferably it lacks substantial homology (e.g., 50% to 99.9%) with a known nucleotide sequence; this limits undesirable hybridization of a complementary nucleic acid and a target nucleic acid.

FIG. 1 shows an illustration of one exemplary sequencing probe of the present disclosure comprising an exemplary barcode domain. The exemplary barcode domain depicted in FIG. 1 comprises three attachment positions, $R_1$, $R_2$, and $R_3$. Each attachment position corresponds to a specific dinucleotide present within the 6-mer sequence ($b_1$ thru $b_6$) of the target binding domain. In this example, $R_1$ corresponds to positions $b_1$ and $b_2$, $R_2$ corresponds to positions $b_3$ and $b_4$, and $R_3$ corresponds to positions $b_5$ and $b_6$. Thus, each position decodes a particular dinucleotide present in the 6-mer sequence of the target binding domain, allowing for the identification of the particular two bases (A, C, G or T) present in each particular dinucleotide.

In the exemplary barcode domain depicted in FIG. 1, each attachment position comprises a single attachment region that is integral to the synthetic backbone. Each attachment region of the three attachment positions contains a specific nucleotide sequence that corresponds to the particular dinucleotide that is encoded by each attachment position. For example, attachment position $R_1$ comprises an attachment region that has a specific sequence that corresponds to the identity of the dinucleotide $b_1$-$b_2$.

The barcode domain can further comprise one or more binding regions. The barcode domain can comprise at least one single-stranded nucleic acid sequence adjacent or flanking at least one attachment position. The barcode domain can comprise at least two single-stranded nucleic acid sequences adjacent or flanking at least two attachment positions. The barcode domain can comprise at least three single-stranded nucleic acid sequences adjacent or flanking at least three attachment positions. These flanking portions are known as "Toe-Holds," which can be used to accelerate the rate of exchange of oligonucleotides hybridized adjacent to the Toe-Holds by providing additional binding sites for single-stranded oligonucleotides (e.g., "Toe-Hold" Probes; see, e.g., Seeling et al., "Catalyzed Relaxation of a Metastable DNA Fuel"; *J. Am. Chem. Soc.* 2006, 128(37), pp 12211-12220).

Sequencing probes of the present disclosure can have overall lengths (including target binding domain, barcode domain, and any optional domains) of about 20 nanometers to about 50 nanometers. The sequencing probe's backbone can be a polynucleotide molecule comprising about 120 nucleotides.

A sequencing probe can comprise a cleavable linker modification. Any cleavable linker modification known to one of skill in the art can be utilized. Non-limiting examples of cleavable linker modifications include, but are not limited to, UV-light cleavable linkers, reducing agent cleavable linkers and enzymatically cleavable linkers. An example of an enzymatically cleavable linker is the insertion of uracil for cleavage by the USER™ enzyme. The cleavable linker modification can be located anywhere along the length of the sequencing probe, including, but not limited to, a region between the target binding domain and the barcode domain. The right panel of FIG. 10 depicts exemplary cleavable linker modifications that can be incorporated into the probes of the present disclosure.

Reporter Probes

A nucleic acid molecule that binds (e.g., hybridizes) to a complementary nucleic acid sequence within at least one attachment region within at least one attachment position of a barcode domain of a sequencing probe of the present disclosure and comprises (directly or indirectly) a detectable label is referred to herein as a "reporter probe" or "reporter probe complex," these terms are used interchangeably herein. The reporter probe can be DNA, RNA or PNA. Preferably, the reporter probe is DNA.

Figure 3:
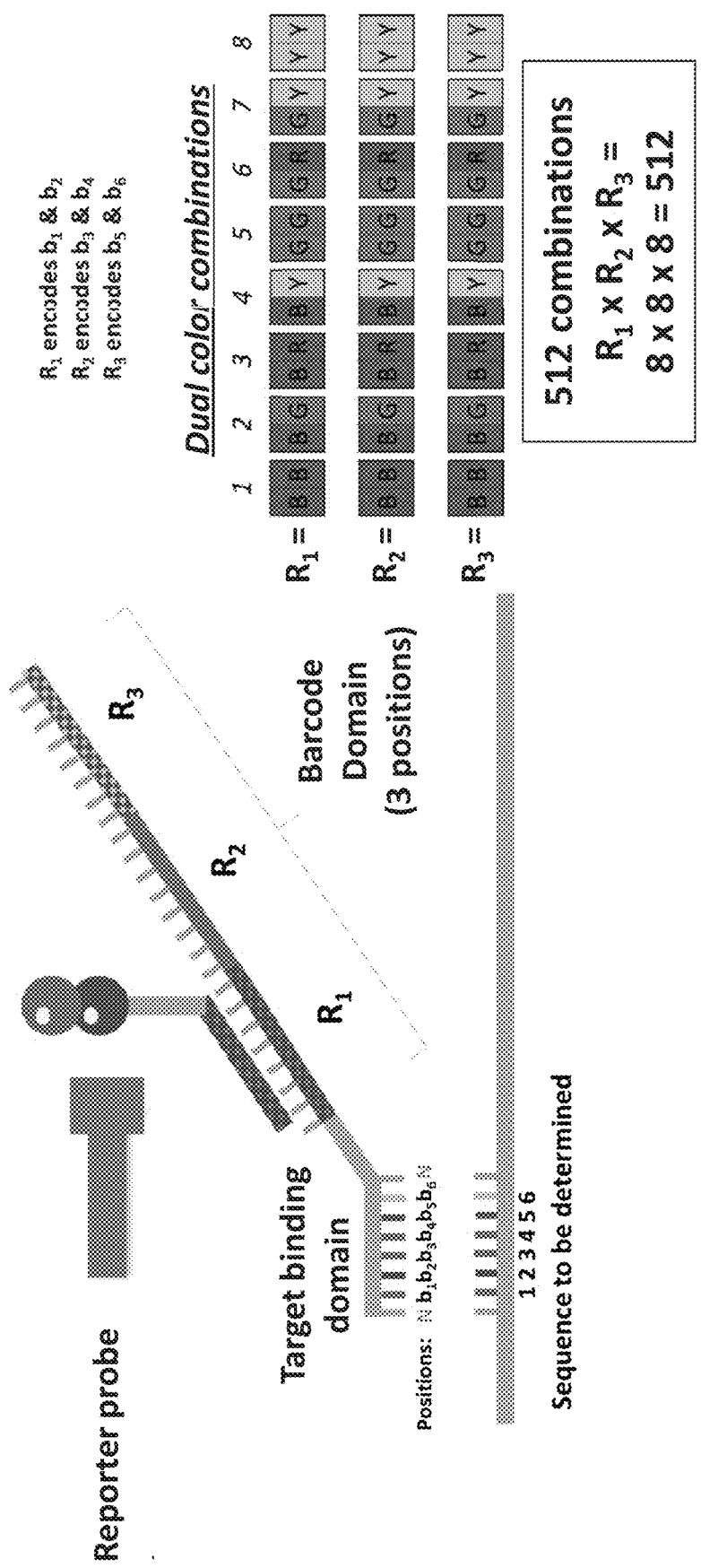
FIG. 3 is an illustration of an exemplary reporter complex of the present disclosure hybridized to an exemplary sequencing probe of the present disclosure.

A reporter probe can comprise at least two domains, a first domain capable of binding at least one first complementary nucleic acid molecule and a second domain capable of binding a first detectable label and at least a second detectable label. FIG. 3 shows a schematic of an exemplary reporter probe of the present disclosure bound to the first attachment position of a barcode domain of an exemplary sequencing probe. In FIG. 3, the first domain of the reporter probe (shown in hatched maroon) binds a complementary nucleic acid sequence within attachment position $R_1$ of the barcode domain and the second domain of the reporter probe (shown in gray) is bound to two detectable labels (one green label, one red label).

Alternatively, the reporter probe can comprise at least two domains, a first domain capable of binding at least one first complementary nucleic acid molecule and a second domain capable of binding at least one second complementary nucleic acid molecule. The at least one first and at least one second complementary nucleic acid molecules can be different (have different nucleic acid sequences).

A "primary nucleic acid molecule" is a reporter probe comprising at least two domains, a first domain capable of binding (e.g. hybridizing) to a complementary nucleic acid sequence within at least one attachment region within at least one attachment position of a barcode domain of a sequencing probe and a second domain capable of binding (e.g. hybridizing) to at least one additional complementary nucleic acid. A primary nucleic acid molecule can directly bind the complementary nucleic acid sequence within the at least one attachment region within the at least one attachment position of a barcode domain of a sequencing probe. A primary nucleic acid molecule can indirectly bind the complementary nucleic acid sequence within the at least one attachment region within the at least one attachment position of a barcode domain of a sequencing probe via a nucleic acid linker. The primary nucleic acid molecule can comprise a cleavable linker. The cleavable linker can be located between the first domain and the second domain. Preferably, the cleavable linker is photo-cleavable.

Each of the nucleic acids comprising the first domain of a primary nucleic acid molecule can independently be a canonical base or a modified nucleotide or nucleic acid analogue. At least one, two, at least three, at least four, at least five, or at least six nucleotides in the first domain of a primary nucleic acid molecule can be modified nucleotides or nucleotide analogues. Typical ratios of modified nucleotides or nucleotide analogues to canonical bases in a barcode domain are 1:2 to 1:8. Typical modified nucleotides or nucleic acid analogues useful in the first domain of a primary nucleic acid molecule are isoguanine and isocytosine. The use of modified nucleotides or nucleotide analogues such as isoguanine and isocytosine, for example, can improve binding efficiency and accuracy of the first domain of a primary nucleic acid molecule to the appropriate complementary nucleic acid sequence within at least one attachment region within at least one attachment position of a barcode domain of a sequencing probe while minimizing binding elsewhere, including to the target.

The at least one additional complementary nucleic acid that binds the primary nucleic acid molecule is referred to herein as a "secondary nucleic molecule." The primary nucleic acid molecule can bind (e.g., hybridize) to at least one, at least two, at least three, at least four, at least five, or more secondary nucleic acid molecules. Preferably, the primary nucleic acid molecule binds (e.g., hybridizes) to four secondary nucleic acid molecules.

A secondary nucleic acid molecule comprises at least two domains, a first domain capable of binding (e.g. hybridizing) to at least one complementary sequence in at least one primary nucleic acid molecule and a second domain capable of binding (e.g. hybridizing) to (a) a first detectable label and an at least second detectable label; (b) to at least one additional complementary nucleic acid; or (c) a combination thereof. The secondary nucleic acid molecule can comprise a cleavable linker. The cleavable linker can be located between the first domain and the second domain. Preferably, the cleavable linker is photo-cleavable.

Each of the nucleic acids comprising the first domain of a secondary nucleic acid molecule can independently be a canonical base or a modified nucleotide or nucleic acid analogue. At least one, two, at least three, at least four, at least five, or at least six nucleotides in the first domain of a secondary nucleic acid molecule can be modified nucleotides or nucleotide analogues. Typical ratios of modified nucleotides or nucleotide analogues to canonical bases in a barcode domain are 1:2 to 1:8. Typical modified nucleotides or nucleic acid analogues useful in the first domain of a secondary nucleic acid molecule are isoguanine and isocytosine. The use of modified nucleotides or nucleotide analogues such as isoguanine and isocytosine, for example, can improve binding efficiency and accuracy of the first domain of a secondary nucleic acid molecule to the appropriate complementary nucleic acid sequence within the second domain of a primary nucleic acid molecule while minimizing binding elsewhere.

The at least one additional complementary nucleic acid that binds the secondary nucleic acid molecule is referred to herein as a "tertiary nucleic molecule." The secondary nucleic acid molecule can bind (e.g., hybridize) to at least one, at least two, at least three, at least four, at least five, at least six, at least seven, or more tertiary nucleic acid molecules. Preferably, the at least one secondary nucleic acid molecule binds (e.g., hybridizes) to one tertiary nucleic acid molecule.

A tertiary nucleic acid molecule comprises at least two domains, a first domain capable of binding (e.g. hybridizing) to at least one complementary sequence in at least one secondary nucleic acid molecule and a second domain capable of binding (e.g. hybridizing) to a first detectable label and an at least second detectable label. Alternatively, the second domain can include the first detectable label and an at least second detectable label via direct or indirect attachment of the labels during oligonucleotide synthesis using, for example, phosphoroamidite or NHS chemistry. The tertiary nucleic acid molecule can comprise a cleavable linker. The cleavable linker can be located between the first domain and the second domain. Preferably, the cleavable linker is photo-cleavable.

Each of the nucleic acids comprising the first domain of a tertiary nucleic acid molecule can independently be a canonical base or a modified nucleotide or nucleic acid analogue. At least one, two, at least three, at least four, at least five, or at least six nucleotides in the first domain of a tertiary nucleic acid can be modified nucleotides or nucleotide analogues. Typical ratios of modified nucleotides or nucleotide analogues to canonical bases in a first domain of a tertiary nucleic acid molecule are 1:2 to 1:8. Typical modified nucleotides or nucleic acid analogues useful in the first domain of a tertiary nucleic acid molecule are isoguanine and isocytosine. The use of modified nucleotides or nucleotide analogues such as isoguanine and isocytosine, for example, can improve binding efficiency and accuracy of the first domain of a tertiary nucleic acid molecule to the appropriate complementary nucleic acid sequence within the second domain of a second nucleic acid molecule while minimizing binding elsewhere.

Reporter probes are bound to a first detectable label and an at least second detectable label to create a dual color combination. This dual combination of fluorescent dyes can include a duplicity of a single color, e.g. blue-blue. As used herein, the term "label" includes a single moiety capable to producing a detectable signal or multiple moieties capable of producing the same or substantially the same detectable signal. For example, a label includes a single yellow fluorescent dye such as ALEXA FLUOR™ 532 or multiple yellow fluorescent dyes such as ALEXA FLUOR™ 532.

The reporter probes can bind to a first detectable label and an at least second detectable label, in which each detectable label is one of four fluorescent dyes: blue (B); green (G); yellow (Y); and red (R). The use of these four dyes creates 10 possible dual color combinations BB; BG; BR; BY; GG; GR; GY; RR; RY; or YY. In some aspects, reporter probes of the present disclosure are labeled with one of 8 possible color combinations: BB; BG; BR; BY; GG; GR; GY; or YY as depicted in FIG. 3. The detectable label and an at least second detectable label can have the same emission spectrum or can have a different emission spectra.

In aspects comprising a sequencing probe and a primary nucleic acid molecule, the present disclosure provides a sequencing probe comprising a target binding domain and a barcode domain; wherein the target binding domain comprises at least eight nucleotides and is capable of binding a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein at least one, or at least two nucleotides, of the at least six nucleotides in the target binding domain are modified nucleotides or nucleotide analogues; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule comprises a first detectable label and at least a second detectable label, wherein each attachment position of the at least three attachment positions corresponds to two nucleotides of the at least six nucleotides in the target binding domain and each of the at least three attachment positions have a different nucleic acid sequence, and wherein the at least first detectable label and at least second detectable label of each complementary primary nucleic acid molecule bound to each position of the at least three attachment positions determines the position and identity of the corresponding two nucleotides of the at least six nucleotides in the target nucleic acid that is bound by the target binding domain. The at least two nucleotides in the target binding domain that do not identify a corresponding nucleotide in the target nucleic acid molecule can be any of the four canonical bases that is not specific to the target dictated by the at least six nucleotides in the target binding domain or universal or degenerate bases.

In aspects comprising a sequencing probe and a primary nucleic acid molecule, the present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule comprises at first detectable label and at least a second detectable label, wherein each attachment position of the at least three attachment positions corresponds to two nucleotides of the at least six nucleotides in the target binding domain and each of the at least three attachment positions have a different nucleic acid sequence, wherein the at least first detectable label and at least second detectable label of each complementary primary nucleic acid molecule bound to each position of the at least three attachment positions determines the position and identity of the corresponding two nucleotides of the at least six nucleotides in the target nucleic acid that is bound by the target binding domain.

In aspects comprising a sequencing probe, a primary nucleic acid molecule and a secondary nucleic acid molecule, the present disclosure provides a sequencing probe comprising a target binding domain and a barcode domain; wherein the target binding domain comprises at least eight nucleotides and is capable of binding a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein at least one, or at least two nucleotides, of the at least six nucleotides in the target binding domain are modified nucleotides or nucleotide analogues and wherein the at least one, or at least two nucleotides in the target binding domain are any of the four canonical bases that is not specific to the target dictated by the other bases in the target binding domain or universal or degenerate bases; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, and wherein the at least first detectable label and at least second detectable label of each complementary secondary nucleic acid molecule bound to each position of the at least three attachment positions determines the position and identity of the corresponding two nucleotides of the at least six nucleotides in the target nucleic acid that is bound by the target binding domain.

In aspects comprising a sequencing probe, a primary nucleic acid molecule and a secondary nucleic acid molecule, the present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, wherein the at least first detectable label and at least second detectable label of each complementary secondary nucleic acid molecule bound to each position of the at least three attachment positions determines the position and identity of the corresponding two nucleotides of the at least six nucleotides in the target nucleic acid that is bound by the target binding domain.

In aspects comprising a sequencing probe, a primary nucleic acid molecule, a secondary nucleic acid molecule and a tertiary nucleic acid molecule, the present disclosure provides a sequencing probe comprising a target binding domain and a barcode domain; wherein the target binding domain comprises at least eight nucleotides and is capable of binding a target nucleic acid, wherein at least six nucleotides in the target binding domain are capable of identifying a corresponding (complementary) nucleotide in the target nucleic acid molecule and wherein at least two nucleotides in the target binding domain do not identify a corresponding nucleotide in the target nucleic acid molecule; wherein at least one, or at least two nucleotides, of the at least six nucleotides in the target binding domain are modified nucleotides or nucleotide analogues and wherein the least two nucleotides in the target binding domain that do not identify a corresponding nucleotide in the target nucleic acid molecule can be any of the four canonical bases that is not specific to the target dictated by the at least six nucleotides in the target binding domain or universal or universal or degenerate bases; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule, and wherein the at least one complementary secondary nucleic acid molecule is further bound by at least one complementary tertiary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, and wherein the at least first detectable label and at least second detectable label of each complementary tertiary nucleic acid molecule bound to each position of the at least three attachment positions determines the position and identity of the corresponding two nucleotides of the at least six nucleotides in the target nucleic acid that is bound by the target binding domain.

In aspects comprising a sequencing probe, a primary nucleic acid molecule, a secondary nucleic acid molecule and a tertiary nucleic acid molecule, the present disclosure also provides a sequencing probe comprising a target binding domain and a barcode domain; wherein the target binding domain comprises at least ten nucleotides and is capable of binding a target nucleic acid, wherein at least six nucleotides in the target binding domain are capable of identifying a corresponding (complementary) nucleotide in the target nucleic acid molecule and wherein at least four nucleotides in the target binding domain do not identify a corresponding nucleotide in the target nucleic acid molecule; wherein the barcode domain comprises a synthetic backbone, the barcode domain comprising at least three attachment positions, each attachment position comprising at least one attachment region comprising at least one nucleic acid sequence bound by at least one complementary primary nucleic acid molecule, wherein the complementary primary nucleic acid molecule is further bound by at least one complementary secondary nucleic acid molecule, and wherein the at least one complementary secondary nucleic acid molecule is further bound by at least one complementary tertiary nucleic acid molecule comprising at first detectable label and at least a second detectable label, wherein each attachment position of the at least three attachment positions corresponds to two nucleotides of the at least six nucleotides in the target binding domain and each of the at least three attachment positions have a different nucleic acid sequence, wherein the at least first detectable label and at least second detectable label of each complementary tertiary nucleic acid molecule bound to each position of the at least three attachment positions determines the position and identity of the corresponding two nucleotides of the at least six nucleotides in the target nucleic acid that is bound by the target binding domain.

The present disclosure also provides sequencing probes and reporter probes having detectable labels on both a secondary nucleic acid molecule and a tertiary nucleic acid molecule. For example, a secondary nucleic acid molecule can bind a primary nucleic acid molecule and the secondary nucleic acid molecule can comprise both a first detectable label and an at least second detectable label and also be bound to at least one tertiary molecule comprising a first detectable label and an at least second detectable label. The first and at least second detectable labels located on the secondary nucleic acid molecule can have the same emission spectra or can have different emission spectra. The first and at least second detectable labels located on the tertiary nucleic acid molecule can have the same emission spectra or can have different emission spectra. The emission spectra of the detectable labels on the secondary nucleic acid molecule can be the same or can be different than the emission spectra of the detectable labels on the tertiary nucleic acid molecule.

Figure 4:
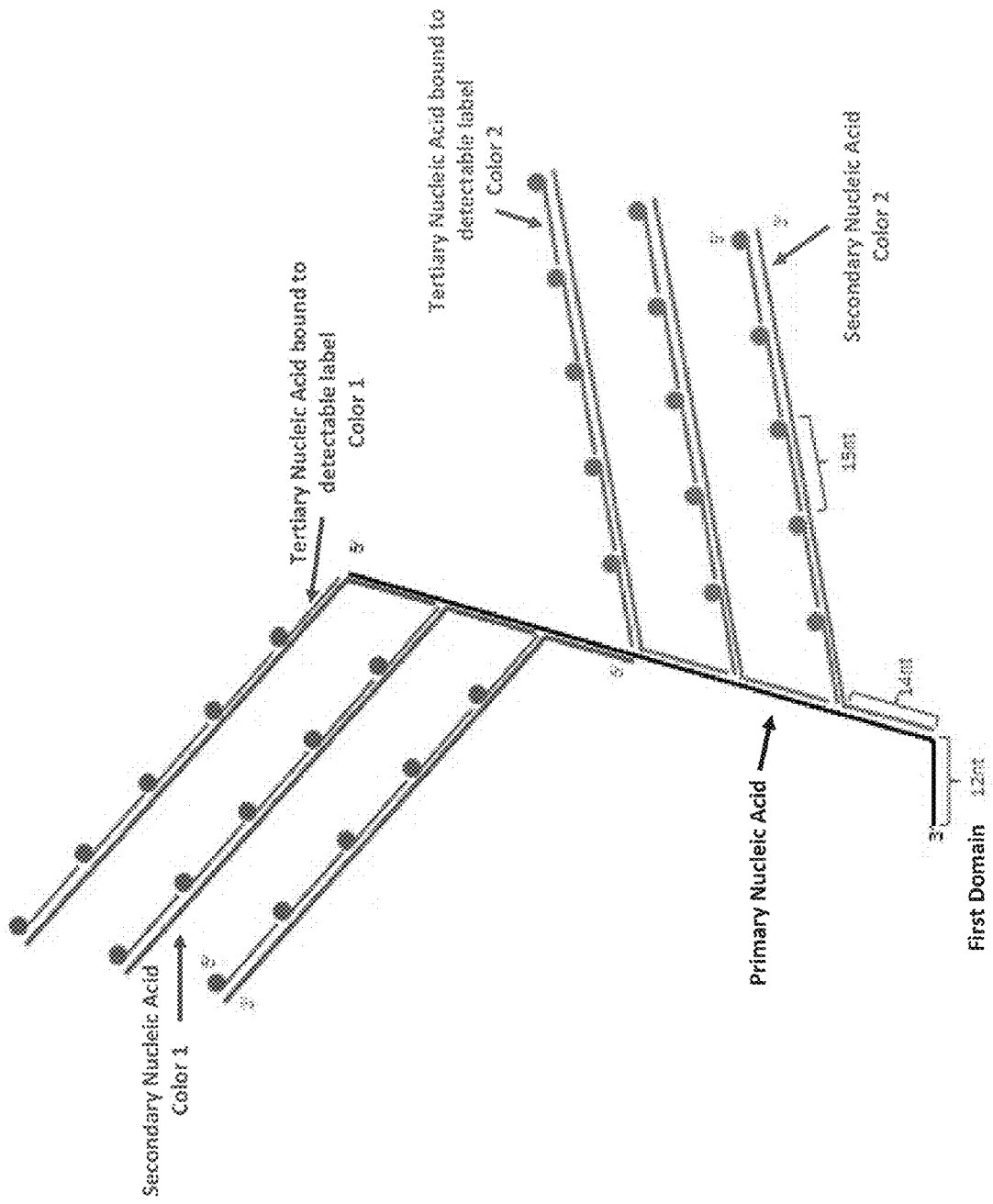
FIG. 4 shows a schematic illustration of an exemplary reporter probe of the present disclosure.

FIG. 4 is an illustrative schematic of an exemplary reporter probe of the present disclosure that comprises an exemplary primary nucleic acid molecule, secondary nucleic acid molecule and tertiary nucleic acid molecule. At the 3' end, the primary nucleic acid comprises a first domain, wherein the first domain comprises a twelve nucleotide sequence that hybridizes to a complementary attachment region within an attachment position of a sequencing probe barcode domain. At the 5' end is a second domain that is hybridized to six secondary nucleic acid molecules. The exemplary secondary nucleic acid molecules depicted in turn comprise a first domain in the 5' end that hybridizes to the primary nucleic acid molecule and a domain that in the 3' portion that hybridizes to five tertiary nucleic acid molecules.

A tertiary nucleic acid molecule comprises at least two domains. The first domain is capable of binding to a secondary nucleic acid molecule. The second domain of a tertiary nucleic acid is capable of binding to a first detectable label and at least second detectable label. The second domain of a tertiary nucleic acid can be bound to the first detectable label and at least second detectable label by the direct incorporation of one or more fluorescently-labeled nucleotide monomers into the sequence of the second domain of the tertiary nucleic acid. The second domain of the secondary nucleic acid molecule can be bound by the first detectable label and at least second detectable label by hybridizing short polynucleotides that are labeled to the second domain of the secondary nucleic acid. These short polynucleotides, called "labeled-oligos," can be labeled by direct incorporation of fluorescently-labeled nucleotide monomers or by other methods of labeling nucleic acids that are known to one of skill in that art. The exemplary tertiary nucleic acid molecules depicted in FIG. 4, which may be considered "labeled oligos" comprise a first domain that hybridizes to a secondary nucleic acid molecule and a second domain that is fluorescently labeled by indirect attachment of the labels during oligonucleotide synthesis using, for example, NHS chemistry or incorporation of one or more fluorescently-labeled nucleotide monomers during the synthesis of the tertiary nucleic acid molecule. The labeled-oligos can be DNA, RNA or PNA.

In alternative aspects, the second domain of a secondary nucleic acid is capable of binding to a first detectable label and at least second detectable label. The second domain of the secondary nucleic acid can be bound to the first detectable label and at least second detectable label by the direct incorporation of one or more fluorescently-labeled nucleotide monomers into the sequence of the second domain of the secondary nucleic acid. The second domain of the secondary nucleic acid molecule can be bound by the first detectable label and at least second detectable label by hybridizing short polynucleotides that are labeled to the second domain of the secondary nucleic acid. These short polynucleotides, called labeled-oligos, can be labeled by direct incorporation of fluorescently-labeled nucleotide monomers or by other methods of labeling nucleic acids that are known to one of skill in that art.

A primary nucleic acid molecule can comprise about 100, about 95, about 90, about 85, about 80 or about 75 nucleotides. A primary nucleic acid molecule can comprise about 100 to about 80 nucleotides. A primary nucleic acid molecule can comprise about 90 nucleotides. A secondary nucleic acid molecule can comprise about 90, about 85, about 80, about 75 or about 70 nucleotides. A secondary nucleic acid molecule can comprise about 90 to about 80 nucleotides. A secondary nucleic acid molecule can comprise about 87 nucleotides. A secondary nucleic acid molecule can comprise about 25, about 20, about 15, or about 10 nucleotides. A tertiary nucleic acid molecule can comprise about 20 to about 10 nucleotides. A tertiary nucleic acid molecule can comprise about 15 nucleotides.

Reporter probes of the present disclosure can be of various designs. For example, a primary nucleic acid molecule can be hybridized to at least one (e.g., 1, 2, 3, 4, 5, 6, 7, 8, 9, 10, or more) secondary nucleic acid molecules. Each secondary nucleic acid molecule can be hybridized to at least one (e.g., 1, 2, 3, 4, 5, 6, 7, 8, 9, 10, or more) tertiary nucleic acid molecules. To create a reporter probe that is labeled with a particular dual color combination, the reporter probe is designed such that the probe comprises secondary nucleic acid molecules, tertiary nucleic acid molecules, labeled-oligos or any combination of secondary nucleic acid molecules, tertiary nucleic acid molecules and labeled-oligos that are labeled with each color of the particular dual color combination. For example, FIG. 4 depicts a reporter probe of the present disclosure that comprises 30 total dyes, with 15 dyes for color 1 and 15 dyes for color 2. To prevent color-swapping or cross hybridization between different fluorescent dyes, each tertiary nucleic acid or labeled-oligo that is bound to a specific label or fluorescent dye comprises a unique nucleotide sequence.

Figure 5:
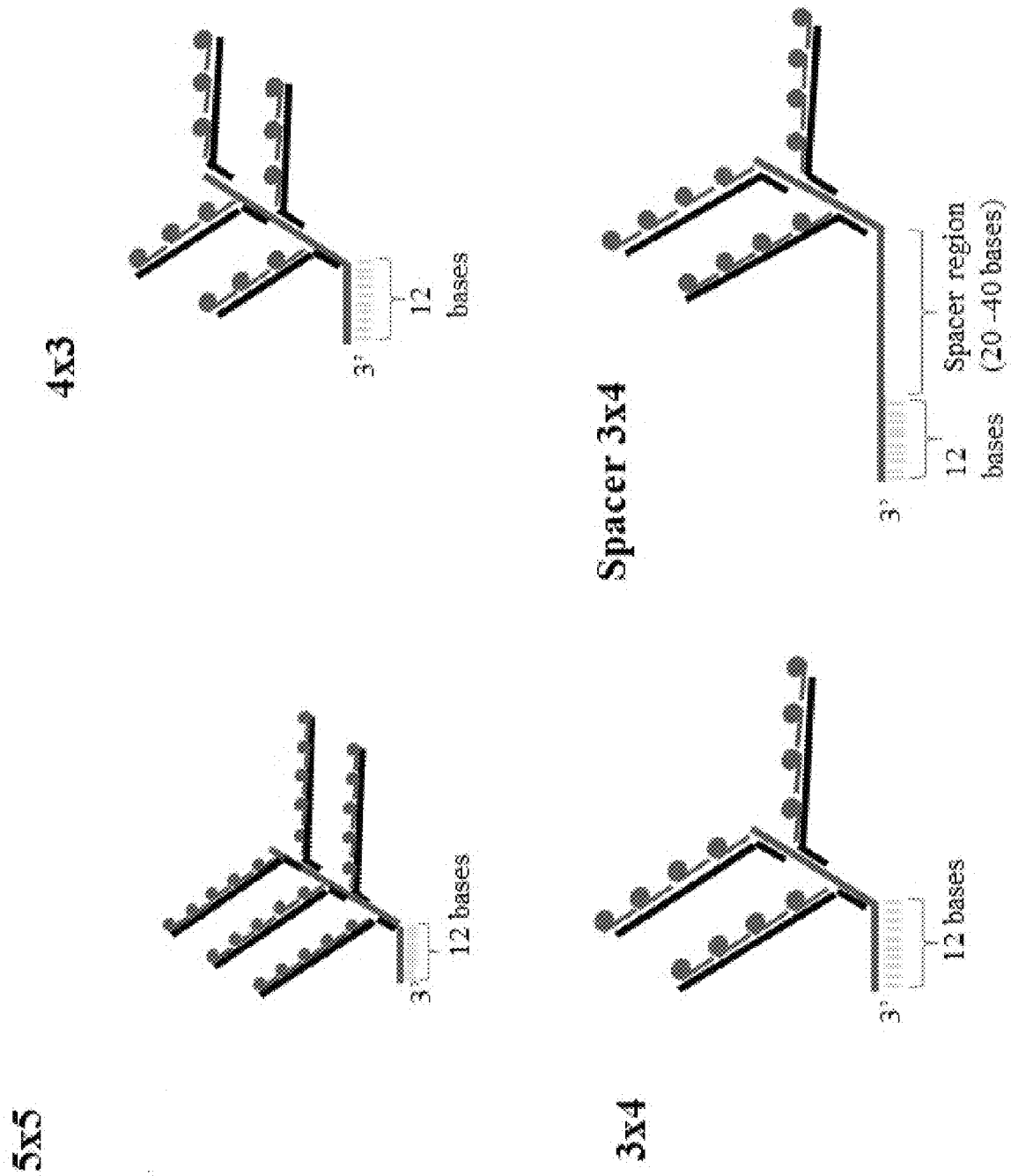
FIG. 5 is a schematic illustration of several exemplary reporter probes of the present disclosure.

FIG. 5 depicts four exemplary reporter probe designs of the present disclosure. The top left panel of FIG. 5 depicts a 5×5 reporter probe. A 5×5 reporter probe comprises a primary nucleic acid, wherein the primary nucleic acid comprises a first domain of 12 nucleotides. The primary nucleic acid also comprises a second domain, wherein the second domain comprises a nucleotide sequence that can be hybridized to 5 secondary nucleic acid molecules. Each secondary nucleic acid comprises a nucleotide sequence such that 5 tertiary nucleic acids that are bound by detectable labels can hybridize to each secondary nucleic acid.

The top right panel of FIG. 5 depicts a 4×3 reporter probe. A 4×3 reporter probe comprises a primary nucleic acid, wherein the primary nucleic acid comprises a first domain of 12 nucleotides. The primary nucleic acid also comprises a second domain, wherein the second domain comprises a nucleotide sequence that can be hybridized to 4 secondary nucleic acid molecules. Each secondary nucleic acid comprises a nucleotide sequence such that 3 tertiary nucleic acids that are bound to detectable labels can hybridize to each secondary nucleic acid.

The bottom left panel of FIG. 5 depicts a 3×4 reporter probe. A 3×4 reporter probe comprises a primary nucleic acid, wherein the primary nucleic acid comprises a first domain of 12 nucleotides. The primary nucleic acid also comprises a second domain, wherein the second domain comprises a nucleotide sequence that can be hybridized to 3 secondary nucleic acid molecules. Each secondary nucleic acid comprises a nucleotide sequence such that 4 tertiary nucleic acids that are bound to detectable labels can hybridize to each secondary nucleic acid.

The bottom right panel of FIG. 5 depicts a Spacer 3×4 reporter probe. A Spacer 3×4 reporter probe comprises a primary nucleic acid, wherein the primary nucleic acid comprises a first domain of 12 nucleotides. Located between the first domain and second domain of the primary nucleic acid is a spacer region consisting of 20 to 40 nucleotides. The spacer is identified as 20 to 40 nucleotides long; however, the length of a spacer is non-limiting and it can be shorter than 20 nucleotides or longer than 40 nucleotides. The second domain of the primary nucleic acid comprises a nucleotide sequence that can hybridize to 3 secondary nucleic acid molecules. Each secondary nucleic acid comprises a nucleotide sequence such that 4 tertiary nucleic acids that are bound to detectable labels can hybridize to each secondary nucleic acid.

In FIG. 5, each primary nucleic acid comprises a first domain that is 12 nucleotides long. However, the length of the first domain of a primary nucleic acid is non-limited and can be less than 12 or more than 12 nucleotides. Preferably, the first domain of a primary nucleic acid is 14 nucleotides.

Any of the features of a specific reporter probe design depicted in a particular panel of FIG. 5 can be combined with any of the features of a reporter probe design depicted in a different panel of FIG. 5 or described elsewhere herein. For example, a 5×5 reporter probe can be modified to contain a spacer region of approximately 20 to 40 nucleotides between the complementary nucleic and the primary nucleic acid. In another example, a 4×3 reporter probe can be modified such that the 4 secondary nucleic acids comprise a nucleotide sequence that allows 5 tertiary nucleic acids that are bound to detectable labels to hybridize to each secondary nucleic acid, thereby creating a 4×5 reporter probe.

Referring to FIG. 5, a 5×5 reporter contains more fluorescent labels (25) than a 4×3 reporter (12) and therefore the fluorescent intensity of the 5×5 reporter will be greater. The fluorescence detected in any given field of view FOV is a function a variety of variable including the fluorescent intensity of the given reporter probes and the number of optionally bound target molecules within that FOV. The number of optionally bound target molecules per field of view (FOV) can be from 1 to 2.5 million targets per FOV. Typical numbers of bound target molecules per FOV are 20,000 to 40,000, 220,000 to 440,000 or 1 million to 2 million target molecules. Typical FOVs are 0.05 mm$^2$ to 1 mm$^2$. Further examples of typical FOVs are 0.05 mm$^2$ to 0.65 mm$^2$.

FIG. 6 shows reporter probe designs in which the secondary nucleic acid molecules comprise "extra-handles" that are not hybridized to a tertiary nucleic acid molecule and are distal to the primary nucleic acid molecule. In FIG. 6, each "extra-handle" is 12 nucleotides long ("12 mer"); however, their lengths are non-limited and can be less than 12 or more than 12 nucleotides. The "extra-handles" can each comprise the nucleotide sequence of the first domain of the primary nucleic acid molecule to which the secondary nucleic acid molecule is hybridized. Thus, when a reporter probe comprises "extra-handles", the reporter probe can hybridize to a sequencing probe either via the first domain of the primary nucleic acid molecule or via an "extra-handle." Accordingly, the likelihood that a reporter probe binds to a sequencing probe is increased. The "extra-handle" design can also improve hybridization kinetics. Without being bound by any theory, the "extra-handles" can increase the effective concentration of the reporter probe's complementary nucleic acid. A 5×4 "extra-handles" reporter probe is expected to yield approximately 4750 fluorescent counts per standard FOV. A 5×3 "extra-handles" reporter probe, a 4×4 "extra-handles" reporter probe, a 4×3 "extra-handles" reporter probe and a 3×4 "extra-handles" reporter probe are all expected to yield approximately 6000 fluorescent counts per standard FOV. The exemplary reporter probe designs depicted in FIG. 5 can also be modified to include "extra-handles".

Individual secondary nucleic acid molecules of a reporter probe can hybridize to tertiary nucleic acid molecules that are all labeled with the same detectable label. For example, the left panel of FIG. 7 depicts a "5×6" reporter probe. A 5×6 reporter probe comprises one primary nucleic acid that comprises a second domain, wherein the second domain comprises a nucleotide sequence hybridized to 6 secondary nucleic acid molecules. Each secondary nucleic acid comprises a nucleotide sequence such that 5 tertiary nucleic acid molecules that are bound to detectable labels hybridized to each secondary nucleic acid. Each of the 5 tertiary nucleic acid molecules that bind to a particular secondary nucleic acid molecule are labeled with the same detectable label. Three of the secondary nucleic acid molecules bind to tertiary nucleic acid molecules labeled with a yellow fluorescent dye and the other three secondary nucleic acid bind to tertiary nucleic acid molecules labeled with a red fluorescent dye, for example.

Individual secondary nucleic acid molecules of a reporter probe can hybridize to tertiary nucleic acid molecules that are labeled with different detectable labels. For example, the middle panel of FIG. 7 depicts a "3×2×6" reporter probe design. A "3×2×6" reporter probe comprises one primary nucleic acid that comprises a second domain, wherein the second domain comprises a nucleotide sequence hybridized to 6 secondary nucleic acid molecules. Each secondary nucleic acid comprises a nucleotide sequence such that 5 tertiary nucleic acids that are bound to detectable labels hybridized to each secondary nucleic acid. Each secondary nucleic acid binds to both tertiary nucleic acid molecules labeled with a yellow fluorescent dye and to tertiary nucleic acid molecules labeled with a red fluorescent dye. In this specific example, three secondary nucleic acid molecules bind two red and three yellow tertiary nucleic acid molecules, while the other three secondary nucleic acid molecules bind two red and three yellow tertiary nucleic acid molecules. Each secondary nucleic acid molecule can bind to any number of tertiary nucleic acid molecules bound by different detectable labels. In the middle panel of FIG. 7, the tertiary nucleic acid molecules bound to an individual secondary nucleic acid molecule are arranged such that the colors of the label alternate (i.e. red-yellow-red-yellow-red or yellow-red-yellow-red-yellow).

In any of the described reporter probe designs, tertiary nucleic acids labeled with different detectable labels can be arranged in any order along the secondary nucleic acid. For example, the right panel of FIG. 7 depicts a "Fret resistant 3×2×6" reporter probe that is similar to the 3×2×6 reporter probe design except in the arrangement (e.g., linear order or grouping) of red and yellow tertiary nucleic acid molecules along each secondary nucleic acid molecule.

Figure 8:
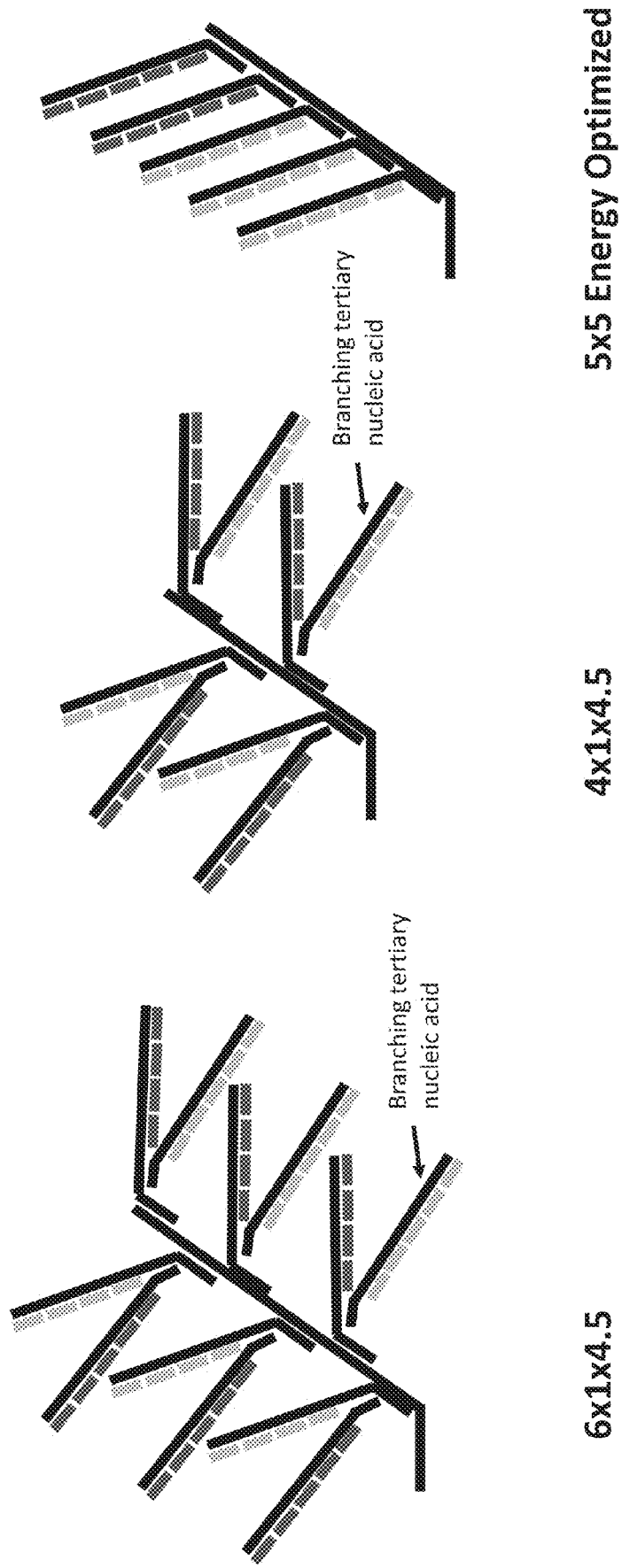
FIG. 8 is a schematic illustration of several exemplary reporter probes of the present disclosure comprising branching tertiary nucleic acids.

FIG. 8 depicts more exemplary reporter probe designs of the present disclosure that include individual secondary nucleic acid molecules that bind to varying tertiary nucleic acid molecules. The left panel depicts a "6×1×4.5" reporter probe that comprises one primary nucleic acid molecule, wherein the primary nucleic acid molecule comprises a second domain, wherein the second domain comprises a nucleotide sequence hybridized to six secondary nucleic acid molecules. Each secondary nucleic acid molecule is hybridized to five tertiary nucleic acid molecules. Four of the five tertiary nucleic acid molecules that hybridize to each secondary nucleic acid molecule are directly labeled with the same color detectable label. The fifth tertiary nucleic acid, denoted as the branching tertiary nucleic acid, is bound to 5 labeled-oligos of the other color of the dual color combination. Of the six secondary nucleic acids, three of them bind to a branching tertiary nucleic acid labeled with one color of the dual color combination (in this example red), while the other three secondary nucleic acids bind to a branching tertiary nucleic acid labeled with the other color of the dual color combination (in this example yellow). In total, the 6×1×4.5 reporter probe is labeled with 54 total dyes, 27 dyes for each color. The middle panel of FIG. 8 depicts a "4×1×4.5" reporter probe that shares the same overall architecture as the 6×1×4.5 reporter probe, except that the primary nucleic acid of the 4×1×4.5 reporter probe binds only 4 secondary nucleic acids, such that there are a total of 36 dyes, 18 for each color.

A reporter probe can comprise the same number of dyes for each color of the dual color combination. A reporter probe can comprise a different number of dyes for each color of the dual color combination. The selection as to which color has more dyes within a reporter probe can be made on the basis of the energy level of light that the two dyes absorb. For example, the right panel of FIG. 8 depicts a "5×5 energy optimized" reporter probe design. This reporter probe design comprises 15 yellow dyes (which are higher energy) and 10 red dyes (which are lower energy). In this example, the 15 yellow dyes can constitute a first label and the 10 red dyes can constitute a second label.

A detectable moiety, label or reporter can be bound to a secondary nucleic acid molecule, a tertiary nucleic acid molecule or to a labeled-oligo in a variety of ways, including the direct or indirect attachment of a detectable moiety such as a fluorescent moiety, colorimetric moiety and the like. One of skill in the art can consult references directed to labeling nucleic acids. Examples of fluorescent moieties include, but are not limited to, yellow fluorescent protein (YFP), green fluorescent protein (GFP), cyan fluorescent protein (CFP), red fluorescent protein (RFP), umbelliferone, fluorescein, fluorescein isothiocyanate, rhodamine, dichlorotriazinylamine fluorescein, cyanines, dansyl chloride, phycocyanin, phycoerythrin and the like.

Fluorescent labels and their attachment to nucleotides and/or oligonucleotides are described in many reviews, including Haugland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). Particular methodologies applicable to the disclosure are disclosed in the following sample of references: U.S. Pat. Nos. 4,757,141; and 5,091,519. One or more fluorescent dyes can be used as labels for labeled target sequences, e.g., as disclosed by U.S. Pat. No. 5,188,934 (4,7-dichlorofluorescein dyes); (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); Lee et al. (xanthine dyes); U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 6,207,392; 2002/0045045; and 2003/0017264. As used herein, the term "fluorescent label" comprises a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, NJ), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY TM 630/650-14-dUTP, BODIPY TM 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY TM FL-14-UTP, BODIPY TMR-14-UTP, BODIPYTM TR-14-UTP, RHODAMINE GREEN™-5-UTP, ALEXA FLUOR™ 488-5-UTP, LEXA FLUOR™ 546-14-UTP (Molecular Probes, Inc. Eugene, OR) and the like. Alternatively, the above fluorophores and those mentioned herein can be added during oligonucleotide synthesis using for example phosphoroamidite or NHS chemistry. Protocols are known in the art for custom synthesis of nucleotides having other fluorophores (See, Henegariu et al. (2000) Nature Biotechnol. 18:345). 2-Aminopurine is a fluorescent base that can be incorporated directly in the oligonucleotide sequence during its synthesis. Nucleic acid could also be stained, a priori, with an intercalating dye such as DAPI, YOYO-1, ethidium bromide, cyanine dyes (e.g., SYBR Green) and the like.

Other fluorophores available for post-synthetic attachment include, but are not limited to, ALEXA FLUOR™ 350, ALEXA FLUOR™ 405, ALEXA FLUOR™ 430, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, Pacific Orange, rhodamine 6G, rhodamine green, rhodamine red, tetramethyl rhodamine, Texas Red (available from Molecular Probes, Inc., Eugene, OR), Cy2, Cy3, Cy3.5, Cy5, Cy5.5, Cy7 (Amersham Biosciences, Piscataway, NJ) and the like. FRET tandem fluorophores can also be used, including, but not limited to, PerCP-Cy5.5, PE-Cy5, PE-Cy5.5, PE-Cy7, PE-Texas Red, APC-Cy7, PE-Alexa dyes (610, 647, and 680), APC-Alexa dyes and the like.

Metallic silver or gold particles can be used to enhance signal from fluorescently labeled nucleotide and/or oligonucleotide sequences (Lakowicz et al. (2003) BioTechniques 34:62).

Other suitable labels for an oligonucleotide sequence can include fluorescein (FAM, FITC), digoxigenin, dinitrophenol (DNP), dansyl, biotin, bromodeoxyuridine (BrdU), hexahistidine (6×His), phosphor-amino acids (e.g., P-tyr, P-ser, P-thr) and the like. The following hapten/antibody pairs can be used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

Detectable labels described herein are spectrally resolvable. "Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218; or the like, or in Wheeless et al., pgs. 21-76, in Flow Cytometry: Instrumentation and Data Analysis (Academic Press, New York, 1985). Spectrally resolvable organic dyes, such as fluorescein, rhodamine, and the like, means that wavelength emission maxima are spaced at least 20 nm apart, and in another aspect, at least 40 nm apart. For chelated lanthanide compounds, quantum dots, and the like, spectrally resolvable means that wavelength emission maxima are spaced at least 10 nm apart, or at least 15 nm apart.

Figure 9:
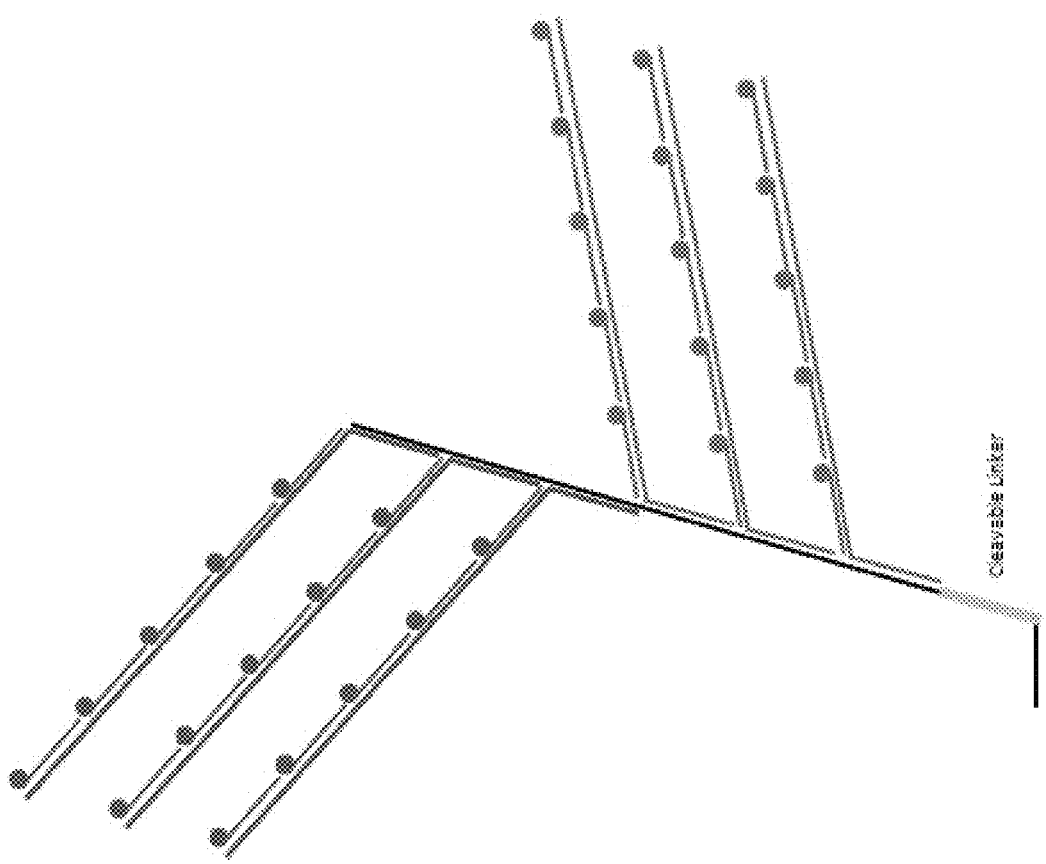
FIG. 9 is an illustration of one exemplary reporter probe of the present disclosure comprising a cleavable linker modification.

A reporter probe can comprise one or more cleavable linker modifications. The one or more cleavable linker modifications can be positioned anywhere in the reporter probe. A cleavable linker modification can be located between the first and second domains of a primary nucleic acid molecule of a reporter probe. FIG. 9 depicts an exemplary reporter probe of the present disclosure comprising a cleavable linker modification between the first and second domains of the primary nucleic acid molecule. A cleavable linker modification can be present between the first and second domains of the secondary nucleic acid molecules of a reporter probe. A cleavable linker modification can be present between the first and second domains of the primary nucleic acid molecule and secondary nucleic acid molecules of a reporter probe. The left panel of FIG. 10 depicts an exemplary reporter probe of the present disclosure comprising cleavable linker modification between the first and second domains of the primary nucleic acid and between the first and second domains of the secondary nucleic acids.

A cleavable linker modification can be a compound of the Formula (I):

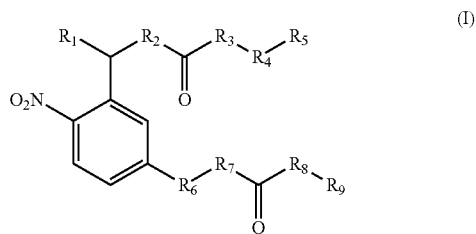

or a stereoisomer or salt thereof, wherein: $R_1$ is hydrogen, halogen, $C_{1-6}$alkyl, $C_{2-6}$alkenyl, $C_{2-6}$alkynyl, wherein said $C_{1-6}$alkyl, $C_{2-6}$alkenyl, $C_{2-6}$alkynl are each independently optionally substituted with at least one substituent $R_{10}$; $R_2$ is O, NH, or N($C_{1-6}$alkyl); $R_3$ is cycloalkyl, heterocycloalkyl, aryl, or heteroaryl, each optionally substituted with at least one substituent $R_{10}$; each $R_4$ and $R_7$ are independently $C_{1-6}$alkyl, $C_{2-6}$alkenyl, $C_{2-6}$alkynyl, wherein said $C_{1-6}$alkyl, $C_{2-6}$ alkenyl, $C_{2-6}$alkynl are each independently optionally substituted with at least one substituent $R_{10}$; $R_5$ and $R_9$ are each independently cycloalkyl, heterocycloalkyl, aryl, or heteroaryl, each optionally substituted with at least one substituent $R_{10}$; $R_6$ is O, NH or N($C_{1-6}$alkyl); $R_8$ is O, NH, or N($C_{1-6}$alkyl); each $R_{10}$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —NO₂, oxo, —OR$_{11}$, —SO₂R$_{11}$, —SO₃⁻, —COR$_{11}$, —CO₂R$_{11}$, —CONR$_{11}$R$_{12}$, —C(=NR$_{11}$)NR$_{12}$R$_{13}$, —NR$_{11}$R$_{12}$, —NR$_{12}$COR$_{12}$, —NR$_{11}$CONR$_{12}$R$_{13}$, —NR$_{11}$CO₂R$_{12}$, —NR$_{11}$SONR$_{12}$R$_{13}$, —NR$_{11}$SO₂NR$_{12}$R$_{13}$, or —NR$_{11}$SO₂R$_{12}$; and $R_{11}$, $R_{12}$, and $R_{13}$; which may be the same or different, are each independently hydrogen, —$C_{1-6}$alkyl, —$C_{2-6}$alkenyl, —$C_{2-6}$alkynyl, halo$C_{1-6}$alkyl, halo$C_{2-6}$ alkenyl, halo$C_{2-6}$alkynyl, $C_{1-6}$alkyloxy$C_{1-6}$alkyl-, cycloalkyl, heterocyclyl, aryl, or heteroaryl.

In one aspect, $R_1$ is $C_{1-6}$alkyl, preferably $C_{1-3}$alkyl such as methyl, ethyl, propyl or isopropyl; $R_2$ is NH or N($C_{1-6}$alkyl); $R_3$ is a 5- to 6-membered cycloalkyl, preferably cyclohexyl; $R_4$ is $C_{1-6}$alkyl, preferably $C_{1-3}$alkylene such as methylene, ethylene, propylene, or isopropylene; $R_5$ is a 5- to 6-membered heterocyclyl comprising one nitrogen atom and 0 or 1 additional heteroatoms selected from N, O and S, wherein said heterocyclyl is optionally substituted with one or two $R_{10}$; $R_6$ is O; $R_7$ is $C_{1-6}$alkyl, preferably $C_{1-3}$alkylene such as methylene, ethylene, propylene, or isopropylene; $R_8$ is O; $R_9$ is a 5- to 6-membered heterocyclyl comprising one nitrogen atom and 0 or 1 additional heteroatoms selected from N, O and S, wherein said heterocyclyl is optionally substituted with one or two $R_{10}$; and each $R_{10}$ is independently halogen, $C_{1-6}$alkyl, halo$C_{1-6}$alkyl, oxo, —SO₂H, or —SO₃⁻.

In one aspect, $R_3$ is cyclohexyl, $R_4$ is methylene, $R_5$ is 1H-pyrrole-2,5-dione, and $R_9$ is pyrrolidine-2,5-dione, optionally substituted with SO₃⁻.

41
The linker compound can be
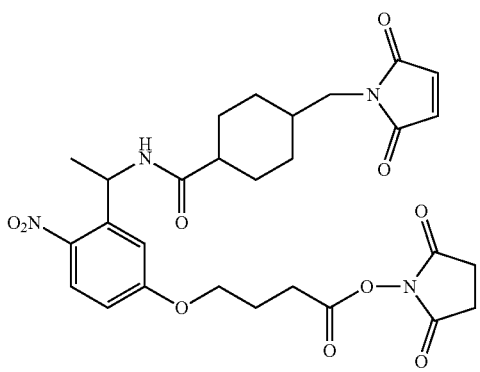 [SMILES: CC(NC(=O)C1CCC(CN2C(=O)C=CC2=O)CC1)c1cc(OCCCC(=O)ON2C(=O)CCC2=O)ccc1[N+](=O)[O-]]
or a stereoisomer or salt thereof
The linker compound can be
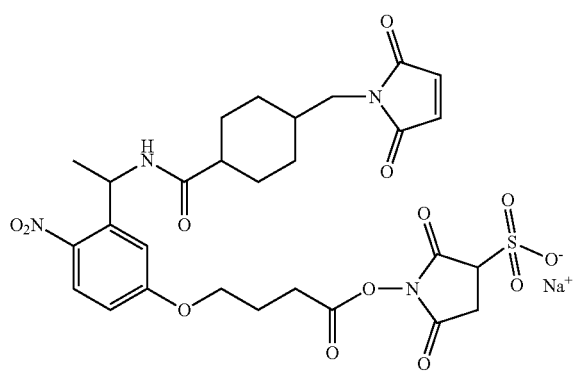 [SMILES: CC(NC(=O)C1CCC(CN2C(=O)C=CC2=O)CC1)c1cc(OCCCC(=O)ON2C(=O)CC(S(=O)(=O)[O-])C2=O)ccc1[N+](=O)[O-] ; [Na+]]
or a stereoisomer or salt thereof.
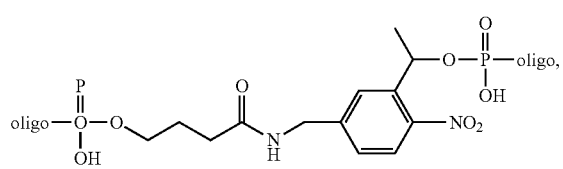
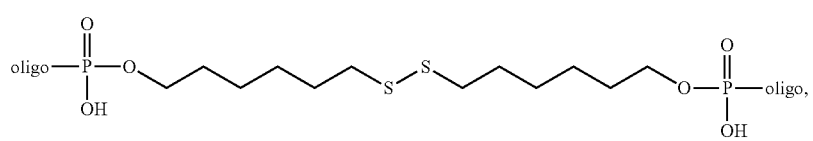
42
The linker compound or linker modification can be
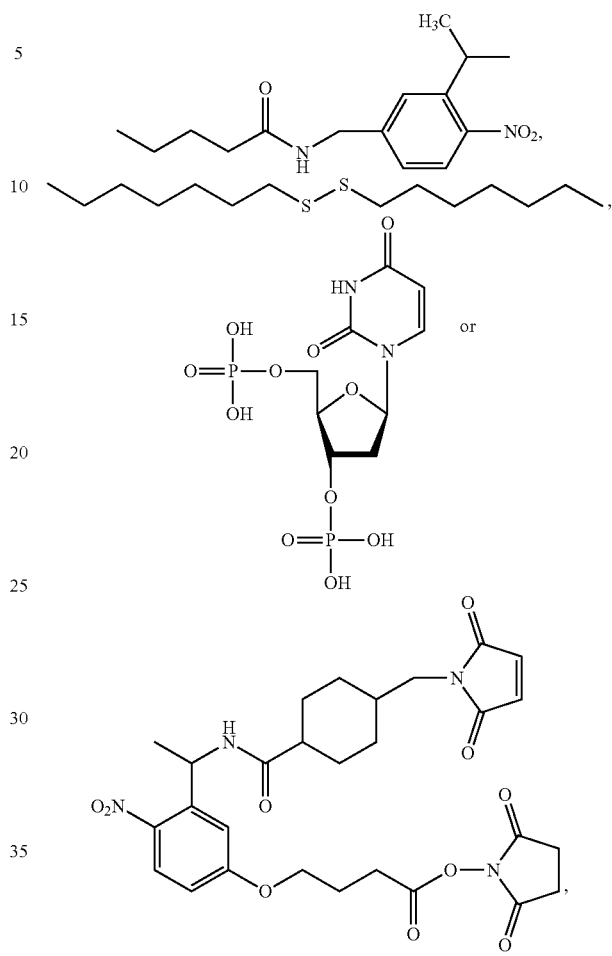
The linker compound or linker modification can be

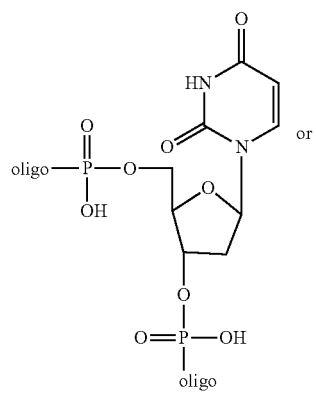
or
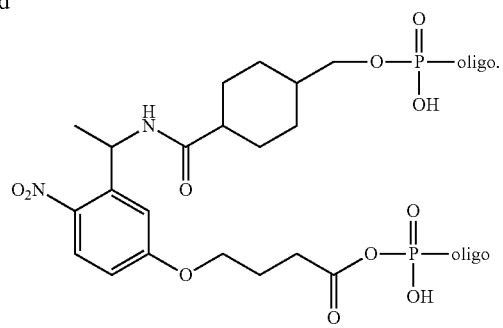

Reporter probes can be assembled by mixing together three stock solutions together with water. One stock solution contains primary nucleic acid molecules, one stock solution contains secondary nucleic acid molecules and the final stock solution contains the tertiary nucleic acid molecules. Table 2 depicts exemplary amounts of each stock solution that can be mixed to assemble particular reporter probe designs.

TABLE 2

| Reporter probe Design | Volume (μl) of primary nucleic acid molecules (10 μM stock) | Volume (μl) of secondary nucleic acid molecules (10 μM stock) | Volume (μl) of tertiary nucleic acid molecules (10 μM stock) | Volume (μl) of Water |
|---|---|---|---|---|
| 5 × 4 | 1 | 4.5 | 2.25 | 92.25 |
| 5 × 3 | 1 | 4.5 | 1.8 | 92.7 |
| 4 × 4 | 1.28 | 4.5 | 2.25 | 91.97 |
| 4 × 3 | 1.28 | 4.5 | 1.8 | 92.42 |
| 3 × 4 | 1.8 | 4.5 | 2.25 | 91.45 |

Target Nucleic Acid

The present disclosure provides methods for sequencing a nucleic acid using the sequencing probes disclosed herein. The nucleic acid that is to be sequenced using the method of the present disclosure is herein referred to as a "target nucleic acid". The term "target nucleic acid" shall mean a nucleic acid molecule (DNA, RNA, or PNA) whose sequence is to be determined by the probes, methods, and apparatuses of the disclosure. In general, the terms "target nucleic acid", "target nucleic acid molecule,", "target nucleic acid sequence," "target nucleic acid fragment," "target oligonucleotide" and "target polynucleotide" are used interchangeably and are intended to include, but not limited to, a polymeric form of nucleotides that can have various lengths, either deoxyribonucleotides or ribonucleotides, or analogs thereof. Non-limiting examples of nucleic acids include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), non-coding RNA (ncRNA), cDNA, recombinant polynucleotides, branched polynucleotides, plasmids, vectors, isolated DNA of a sequence, isolated RNA of a sequence, nucleic acid probes, and primers. Prior to sequencing using the methods of the present disclosure, the identity and/or sequence of the target nucleic is known. Alternatively, the identity and/or sequence is unknown. It is also possible that a portion of the sequence of a target nucleic acid is known prior to sequencing using the methods of the present disclosure. For example, the method can be directed at determining a point mutation in a known target nucleic acid molecule.

The present methods directly sequence a nucleic acid molecule obtained from a sample, e.g., a sample from an organism, and, preferably, without a conversion (or amplification) step. As an example, for direct RNA-based sequencing, the present methods do not require conversion of an RNA molecule to a DNA molecule (i.e., via synthesis of cDNA) before a sequence can be obtained. Since no amplification or conversion is required, a nucleic acid sequenced in the present disclosure will retain any unique base and/or epigenetic marker present in the nucleic acid when the nucleic acid is in the sample or when it was obtained from the sample. Such unique bases and/or epigenetic markers are lost in sequencing methods known in the art.

The present methods can be used to sequence at single molecule resolution. In other words, the present methods allow the user to generate a final sequence based on data collected from a single target nucleic acid molecule, rather than having to combine data from different target nucleic acid molecules, preserving any unique features of that particular target.

The target nucleic acid can be obtained from any sample or source of nucleic acid, e.g., any cell, tissue, or organism, in vitro, chemical synthesizer, and so forth. The target nucleic acid can be obtained by any art-recognized method. The nucleic acid can be obtained from a blood sample of a clinical subject. The nucleic acid can be extracted, isolated, or purified from the source or samples using methods and kits well known in the art.

A target nucleic acid can be fragmented by any means known in the art. Preferably, the fragmenting is performed by an enzymatic or a mechanical means. The mechanical means can be sonication or physical shearing. The enzymatic means can be performed by digestion with nucleases (e.g., Deoxyribonuclease I (DNase I)) or one or more restriction endonucleases.

When a nucleic acid molecule comprising the target nucleic acid is an intact chromosome, steps should be taken to avoid fragmenting the chromosome.

The target nucleic acid can include natural or non-natural nucleotides, comprising modified nucleotides or nucleic acid analogues, as well-known in the art.

The target nucleic acid molecule can include DNA, RNA, and PNA molecules up to hundreds of kilobases in length (e.g. 1, 2, 3, 4, 5, 10, 20, 30, 40, 50, 100, 200, 500, or more kilobases).

Capture Probes

The target nucleic acid can be immobilized (e.g., at one, two, three, four, five, six, seven, eight, nine, ten, or more positions) to a substrate.

Exemplary useful substrates include those that comprise a binding moiety selected from the group consisting of ligands, antigens, carbohydrates, nucleic acids, receptors, lectins, and antibodies. The capture probe comprises a substrate binding moiety capable of binding with the binding moiety of the substrate. Exemplary useful substrates comprising reactive moieties include, but are not limited to, surfaces comprising epoxy, aldehyde, gold, hydrazide, sulfhydryl, NETS-ester, amine, alkyne, azide, thiol, carboxylate, maleimide, hydroxymethyl phosphine, imidoester, isocyanate, hydroxyl, pentafluorophenyl-ester, psoralen, pyridyl disulfide or vinyl sulfone, polyethylene glycol (PEG), hydrogel, or mixtures thereof. Such surfaces can be obtained from commercial sources or prepared according to standard techniques. Exemplary useful substrates comprising reactive moieties include, but are not limited to, OptArray-DNA NHS group (Acclr8), Nexterion Slide AL (Schott) and Nexterion Slide E (Schott).

The substrate can be any solid support known in the art, e.g., a coated slide and a microfluidic device, which is capable of immobilizing a target nucleic acid. The substrate can be a surface, membrane, bead, porous material, electrode or array. The substrate can be a polymeric material, a metal, silicon, glass or quartz for example. The target nucleic acid can be immobilized onto any substrate apparent to those of skill in the art.

When the substrate is an array, the substrate can comprise wells, the size and spacing of which is varied depending on the target nucleic acid molecule to be attached. In one example, the substrate is constructed so that an ultra-dense ordered array of target nucleic acids is attached. Examples of the density of the array of target nucleic acids on a substrate include from 500,000 to 10,000,000 target nucleic acid molecules per $mm^2$, from 1,000,000 to 4,000,000 target nucleic acid molecules per $mm^2$ or from 850,000 to 3,500,000 target nucleic acid molecules per $mm^2$.

The wells in the substrate are locations for attachment of a target nucleic acid molecule. The surface of the wells can be functionalized with reactive moieties described above to attract and bind specific chemical groups existing on the on the target nucleic acid molecules or capture probes bound to the target nucleic acid molecules to attract, immobilize and bind the target nucleic acid molecule. These functional groups are well known to be able to specifically attract and bind biomolecules through various conjugation chemistries.

For single nucleic acid molecule sequencing on a substrate such as an array, a universal capture probe or universal sequence complementary to the substrate binding moiety of a capture probe is attached to each well. A single target nucleic acid molecule is then bound to the universal capture probe or universal sequence complementary to the substrate binding moiety of a capture probe bound to the capture probe and sequencing can commence.

The target nucleic acid can be bound by one or more capture probes (i.e. two, three, four, five, six, seven, eight, nine, ten or more capture probes). A capture probe comprises a domain that is complementary to a portion of the target nucleic acid and a domain that comprises a substrate binding moiety. The portion of the target nucleic acid to which a capture probe is complementary can be an end of the target nucleic acid or not towards an end.

The substrate binding moiety of the capture probe can be biotin and the substrate can be avidin (e.g., streptavidin). Useful substrates comprising avidin are commercially available including TB0200 (Accelr8), SAD6, SAD20, SAD100, SAD500, SAD2000 (Xantec), SuperAvidin (Array-It), streptavidin slide (catalog #MPC 000, Xenopore) and STREPTAVIDINnslide (catalog #439003, Greiner Bio-one). The substrate binding moiety of the capture probe can be avidin (e.g., streptavidin) and the substrate can be biotin. Useful substrates comprising biotin that are commercially available include, but are not limited to, Optiarray-biotin (Accler8), BD6, BD20, BD100, BD500 and BD2000 (Xantec).

The substrate binding moiety of the capture probe can be a reactive moiety that is capable of being bound to the substrate by photoactivation. The substrate can comprise the photoreactive moiety, or the first portion of the nanoreporter can comprise the photoreactive moiety. Some examples of photoreactive moieties include aryl azides, such as N((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromo-deoxyuridine.

The substrate binding moiety of a capture probe can be a nucleic acid that can hybridize to a binding moiety of a substrate that is complementary. Each of the nucleic acids comprising a substrate binding moiety of a capture probe can independently be a canonical base or a modified nucleotide or nucleic acid analogue. At least one, at least two, at least three, at least four, at least five, or at least six nucleotides in the substrate binding moiety of a capture probe can be modified nucleotides or nucleotide analogues. Typical ratios of modified nucleotides or nucleotide analogues to canonical bases in a substrate binding moiety of a capture probe are 1:2 to 1:8. Typical modified nucleotides or nucleic acid analogues useful in a substrate binding moiety of a capture probe are isoguanine and isocytosine.

The substrate binding moiety of the capture probe can be immobilized to the substrate via other binding pairs apparent to those of skill in the art. After binding to the substrate, the target nucleic acid can be elongated by applying a force (e.g., gravity, hydrodynamic force, electromagnetic force "electrostretching", flow-stretching, a receding meniscus technique, and combinations thereof) sufficient to extend the target nucleic acid. A capture probe can comprise or be associated with a detectable label, i.e., a fiducial spot.

The target nucleic acid can be bound by a second capture probe which comprises a domain that is complementary to a second portion of the target nucleic acid. The second portion of the target nucleic acid bound by the second capture probe is different than the first portion of the target nucleic acid bound by the first capture probe. The portion can be an end of the target nucleic acid or not towards an end. Binding of a second capture probe can occur after or during elongation of the target nucleic acid or to a target nucleic acid that has not been elongated. The second capture probe can have a binding as described above.

The target nucleic acid can be bound by a third, fourth, fifth, sixth, seventh, eighth, ninth or tenth capture probe which comprises a domain that is complementary to a third, fourth, fifth, sixth, seventh, eighth, ninth or tenth portion of the target nucleic acid. The portion can be an end of the target nucleic acid or not towards an end. Binding of a third, fourth, fifth, sixth, seventh, eighth, ninth or tenth capture probe can occur after or during elongation of the target nucleic acid or to a target nucleic acid that has not been elongated. The third, fourth, fifth, sixth, seventh, eighth, ninth or tenth capture probe can have a binding as described above.

The capture probe is capable of isolating a target nucleic acid from a sample. Here, a capture probe is added to a sample comprising the target nucleic acid. The capture probe binds the target nucleic acid via the region of the capture probe that his complementary to a region of the target nucleic acid. When the target nucleic acid contacts a substrate comprising a moiety that binds the capture probe's substrate binding moiety, the nucleic acid becomes immobilized onto the substrate.

Figure 11:
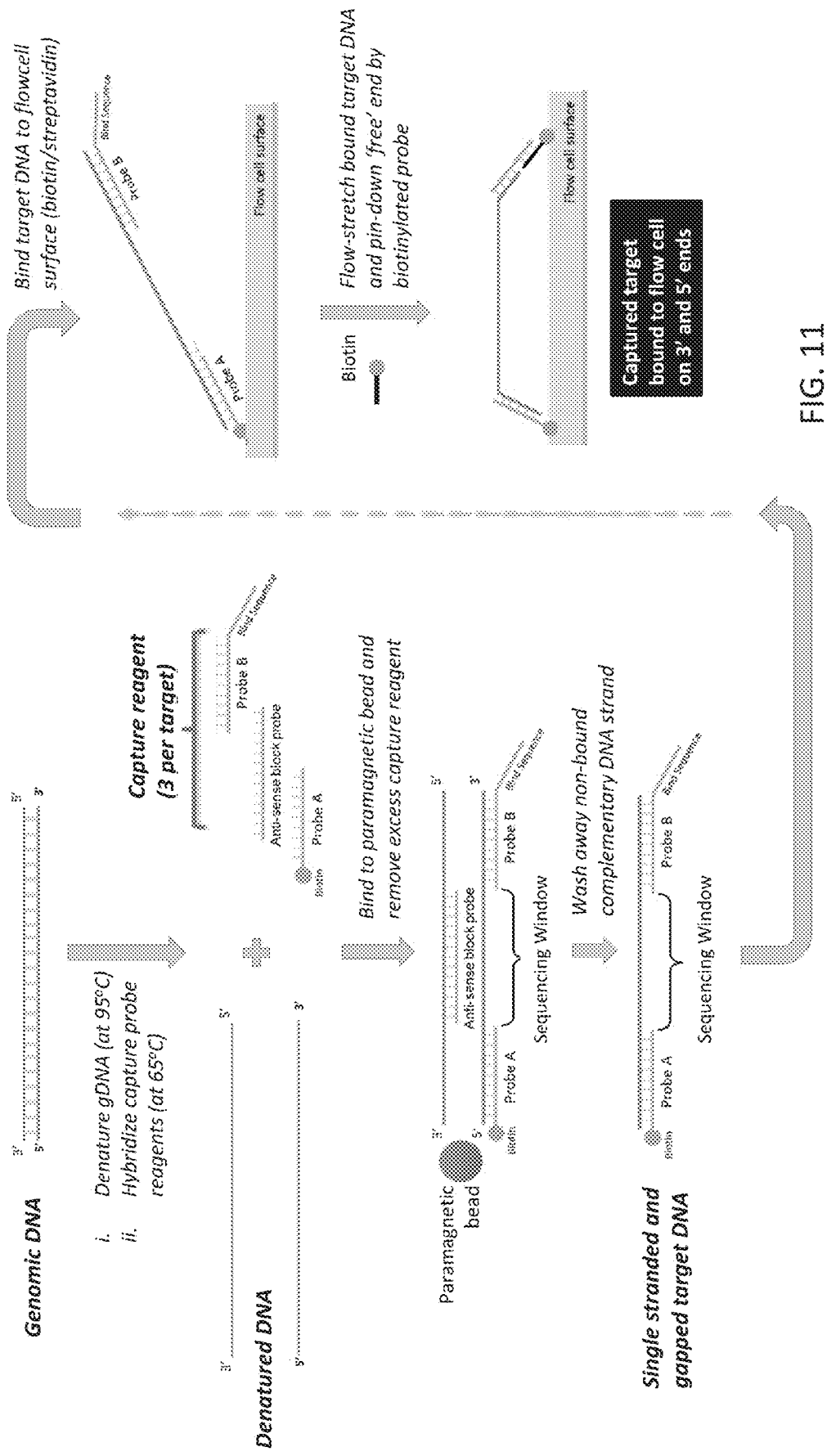
FIG. 11 is a schematic illustration of the capture of a target nucleic acid using the two capture probe system of the present disclosure.

FIG. 11 shows the capture of a target nucleic acid using a two capture probe system of the present disclosure. Genomic DNA is denatured at 95° C. and hybridized to a pool of capture reagents. This pool of capture reagents comprise the oligonucleotides Probe A, Probe B, and anti-sense block probes. Probe A comprises a biotin moiety at the 3' end of the probe and a sequence that is complementary to the 5' end of the target nucleic acid. Probe B comprises a purification binding sequence that can be bound by paramagnetic beads at the 5' end of the probe and a nucleotide sequence that is complementary to the 3' end of the target nucleic acid. The anti-sense block probe comprises a nucleotide sequence that is complementary to the anti-sense strand of the portion of the target nucleic acid that is to be sequenced. After hybridization with the capture reagents, a sequencing window is created on the target nucleic acid between the hybridized Probe A and Probe B. The target nucleic acid is purified using paramagnetic beads that bind to the 5' sequence of Probe B. Any excess capture reagents or complementary anti-sense DNA strands are washed away, resulting in the purification of the intended target nucleic acid. The purified target nucleic acid is then flowed through a flow chamber that includes a surface that can bind to the biotin moiety on the hybridized Probe A, such as streptavidin. This results in the tethering of one end of the target nucleic acid to the surface of the flow cell. To capture the other end, the target nucleic acid is flow-stretched and a biotinylated probe complementary to the purification binding sequence of Probe B is added. Upon hybridizing to the purification binding sequence of Probe B, the biotinylated probe can bind to the surface of the flow cell, resulting in a captured target nucleic acid molecule that is elongated and bound to the flow cell surface at both ends.

To ensure that a user "captures" as many target nucleic acid molecules as possible from high fragmented samples, it is helpful to include a plurality of capture probes, each complementary to a different region of the target nucleic acid. For example, there can be three pools of capture probes, with a first pool complementary to regions of the target nucleic acid near its 5' end, a second pool complementary to regions in the middle of the target nucleic acid, and a third pool near its 3' end. This can be generalized to "n-regions-of-interest" per target nucleic acid. In this example, each individual pool of fragmented target nucleic acid bound to a capture probe comprising or bound to a biotin tag. 1/nth of input sample (where n=the number of distinct regions in target nucleic acid) is isolated for each pool chamber. The capture probe binds the target nucleic acid of interest. Then the target nucleic acid is immobilized, via the capture probe's biotin, to an avidin molecule adhered to the substrate. Optionally, the target nucleic acid is stretched, e.g., via flow or electrostatic force. All n-pools can be stretched-and-bound simultaneously, or, in order to maximize the number of fully stretched molecules, pool 1 (which captures most 5' region) can be stretched and bound first; then pool 2, (which captures the middle-of-target region) is then can be stretched and bound; finally, pool 3 is can be stretched and bound.

Figure 12:
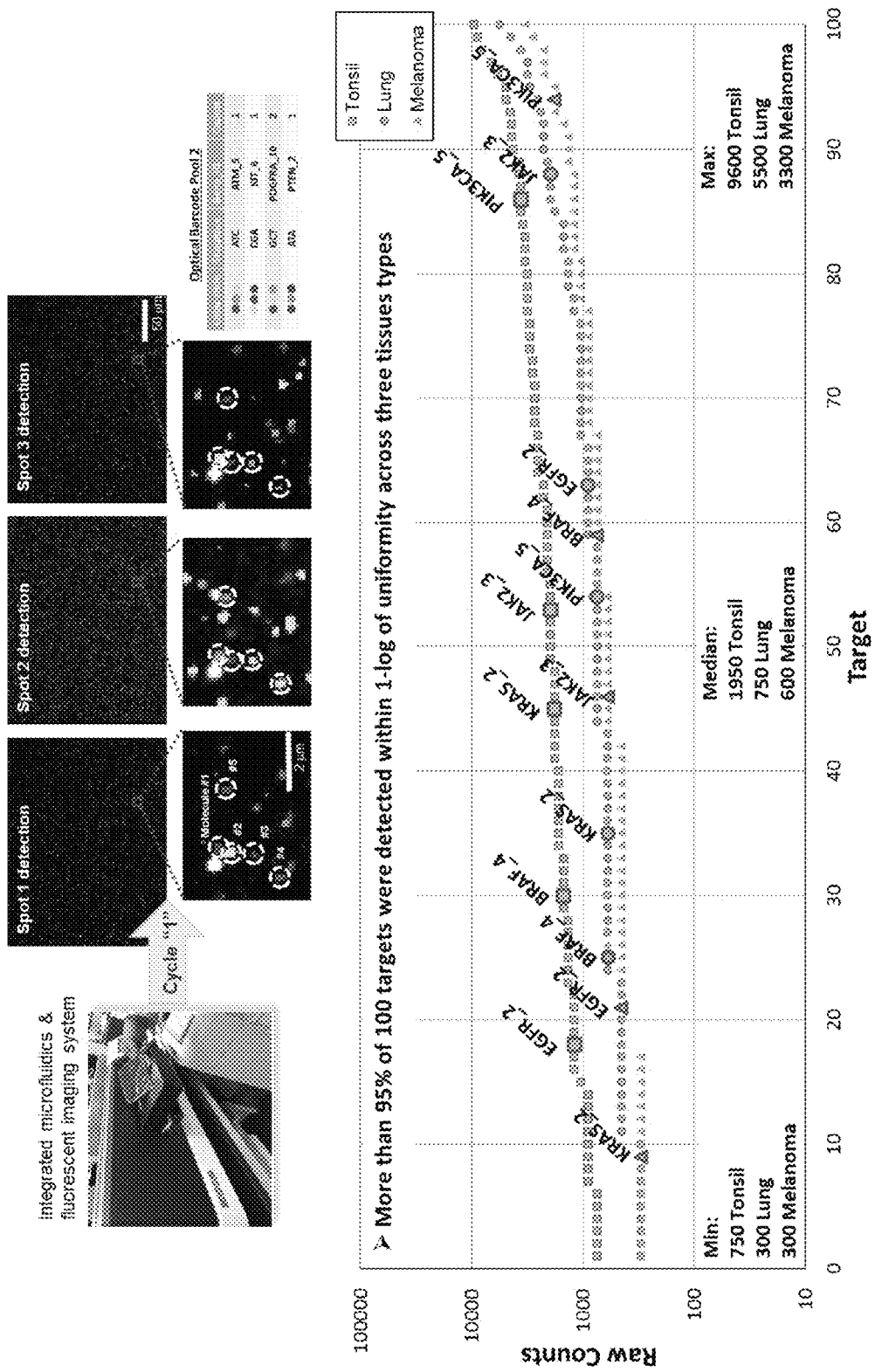
FIG. 12 shows the results from an experiment using the present methods to capture and detect a multiplex cancer panel, composed of 100 targets, using a FFPE sample.

The present disclosure also allows a user to capture and concurrently sequence a plurality of target nucleic acids, a plurality of capture probes can be hybridized to a mixed sample of target nucleic acids. A plurality of target nucleic acids can include a group of more than one nucleic acid, in which each nucleic acid contains the same sequence, or a group of more than one nucleic acid, in which each nucleic acid does not necessarily contain the same sequence. Likewise, the plurality of capture probes can include either a group of more than one capture probe that are identical in sequence, or a group of more than one capture probe that are not necessarily identical in sequence. For example, using a plurality of capture probes that all contain the same sequence can allow the user to capture a plurality of target nucleic acids that all contain the same sequence. By sequencing this plurality of target nucleic acids containing the same sequence, a higher level of sequencing accuracy can be achieved due to data redundancy. In another example, two or more specific genes of interest can be captured and sequenced concurrently using a group of capture probes that includes capture probes complementary to each gene of interest. This allows the user to perform multiplexed sequencing of specific genes. FIG. 12 shows the results from an experiment using the present methods to capture and detect a multiplex cancer panel, composed of 100 targets, using a FFPE sample.

When complete sequencing coverage is desired, the number of distinct capture probes required is inversely related to the size of target nucleic acid fragment. In other word, more capture probes will be required for a highly-fragmented target nucleic acid. For sample types with highly fragmented and degraded target nucleic acids (e.g., Formalin-Fixed Paraffin Embedded Tissue) it can be useful to include multiple pools of capture probes. On the other hand, for samples with long target nucleic acid fragments, e.g., in vitro obtained isolated nucleic acids, a single capture probe at a 5' end can be sufficient.

The region of the target nucleic acid between two capture probes or after one capture probe and before a terminus of the target nucleic acid is referred herein as a "sequencing window". The sequencing window created when two capture probes are used to capture a target nucleic acid is labeled in FIG. 11. The sequencing window is a portion of the target nucleic acid that is available to be bound by a sequencing probe. The minimum sequencing window is a target binding domain length (e.g., 4 to 10 nucleotides) and a maximum sequencing window is the majority of a whole chromosome.

Figure 13:
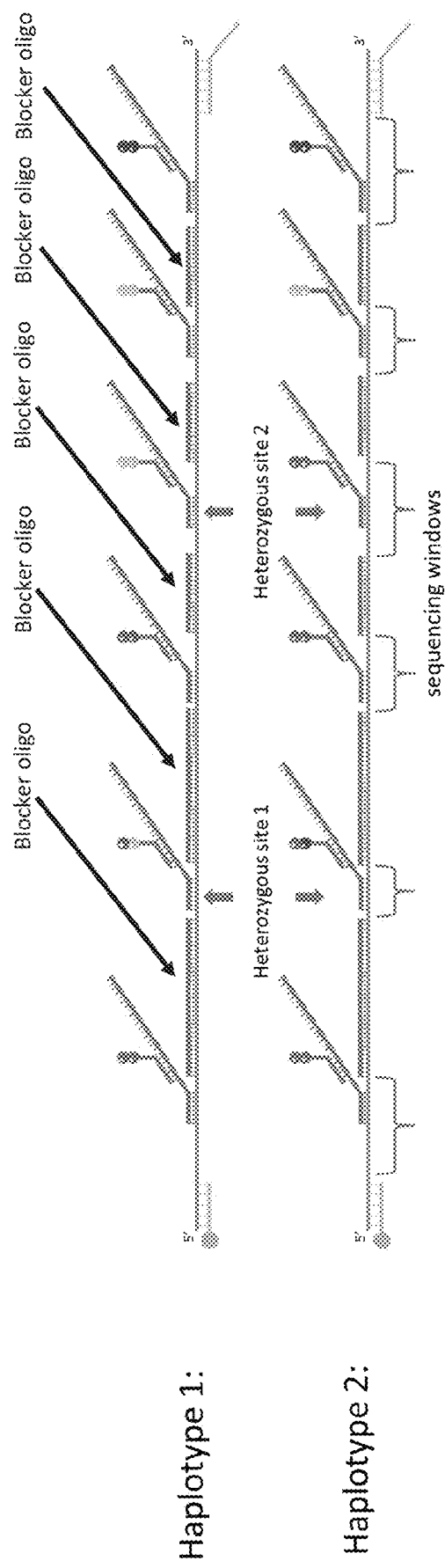
FIG. 13 shows a schematic illustration of two captured target DNA molecules hybridized to capture probes, blocker oligos, and sequencing probes for targeted sequencing of large target nucleic acid molecules.

When large target nucleic acid molecules are sequenced using the present methods, a "blocker oligo" or a plurality of blocker oligos can be hybridized along the length of the target nucleic acid to control the size of the sequencing window. Blocker oligos hybridize to the target nucleic acid at specific locations, thereby preventing the binding of sequencing probes at those locations, creating smaller sequencing windows of interest. FIG. 13 shows a schematic of two captured target DNA molecules hybridized to capture probes, blocker oligos, and sequencing probes. By creating smaller sequencing windows, the sequencing reactions is confined to specific regions of interest on the target DNA molecule, increasing the speed and accuracy of sequencing. The use of blocker oligos is particularly useful when sequencing particular mutations at known locations within a target nucleic acid, as the entire target nucleic acid does not need to be sequenced. The example in FIG. 13 shows the targeted sequencing of two heterozygous sites to distinguish between two different haplotypes.

Methods of the Present Disclosure

The sequencing method of the present disclosure comprises reversibly hybridizing at least one sequencing probe disclosed herein to a target nucleic acid.

A method for sequencing a nucleic acid can comprise (1) hybridizing a sequencing probe described herein to a target nucleic acid. The target nucleic acid can optionally be immobilized to a substrate at one or more positions. An exemplary sequencing probe can comprise a target binding domain and a barcode domain; wherein the target binding domain comprises at least eight nucleotides hybridized to the target nucleic acid, wherein at least six nucleotides in the target binding domain can identify a corresponding nucleotide in the target nucleic acid molecule (for example, when the target binding domain sequence is exactly six nucleotides, those six nucleotides identify the complementary six nucleotides with the target molecule to which it is hybridized) and wherein at least two nucleotides in the target binding domain do not identify a corresponding nucleotide in the target nucleic acid molecule (for example, those at least two nucleotides do not identify the complementary two nucleotides with the target molecule to which it is hybridized); wherein at least two nucleotides of the at least six nucleotides in the target binding domain are modified nucleotides or nucleotide analogues; wherein the barcode domain comprises a synthetic backbone, the barcode domain comprising at least three attachment positions, each attachment position comprising at least one attachment region comprising at least one nucleic acid sequence capable of being bound by a complementary nucleic acid molecule, wherein each attachment position of the at least three attachment positions corresponds to two nucleotides of the at least six nucleotides in the target binding domain and each of the at least three attachment positions have a different nucleic acid sequence, and wherein the nucleic acid sequence of each position of the at least three attachment positions determines the position and identity of the corresponding two nucleotides of the at least six nucleotides in the target nucleic acid that is bound by the target binding domain.

Following hybridizing of a sequencing probe to the target nucleic acid, the method comprises (2) binding a first complementary nucleic acid molecule comprising a first detectable label and an at least second detectable label to a first attachment position of the at least three attachment positions of the barcode domain; (3) detecting the first and at least second detectable label of the bound first complementary nucleic acid molecule; (4) identifying the position and identity of at least two nucleotides in the immobilized target nucleic acid. For example, when the first complementary nucleic acid molecule comprises two detectable labels, the two detectable labels identify the at least two nucleotides in the immobilized target nucleic acid.

Following detection of the at least two detectable labels, removing the at least two detectable labels from the first complementary nucleic acid molecule. Thus, the method further comprises (5) binding to the first attachment position a first hybridizing nucleic acid molecule lacking a detectable label, thereby unbinding the first complementary nucleic acid molecule comprising the detectable labels, or contacting the first complementary nucleic acid molecule comprising the detectable labels with a force sufficient to release the first detectable label and at least second detectable label. Thus, following step (5) no detectable labels are bound to the first attachment positions. The method further comprises (6) binding a second complementary nucleic acid molecule comprising a third detectable label and an at least fourth detectable to a second attachment position of the at least three attachment positions of the barcode domain; (7) detecting the third and at least fourth detectable label of the bound second complementary nucleic acid molecule; (8) identifying the position and identity of at least two nucleotides in the optionally immobilized target nucleic acid; (9) repeating steps (5) to (8) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a first region of the immobilized target nucleic acid that was hybridized by the target binding domain of the sequencing probe; and (10) removing the sequencing probe from the optionally immobilized target nucleic acid.

The method can further comprise (11) hybridizing a second sequencing probe to a target nucleic acid that is optionally immobilized to a substrate at one or more positions, and wherein the target binding domain of the first sequencing probe and the second sequencing probe are different; (12) binding a first complementary nucleic acid molecule comprising a first detectable label and an at least second detectable label to a first attachment position of the at least three attachment positions of the barcode domain; (13) detecting the first and at least second detectable label of the bound first complementary nucleic acid molecule; (14) identifying the position and identity of at least two nucleotides in the optionally immobilized target nucleic acid; (15) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (16) binding a second complementary nucleic acid molecule comprising a third detectable label and an at least fourth detectable label to a second attachment position of the at least three attachment positions of the barcode domain; (17) detecting the third and at least fourth detectable label of the bound second complementary nucleic acid molecule; (18) identifying the position and identity of at least two nucleotides in the immobilized target nucleic acid; (19) repeating steps (15) to (18) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a second region of the immobilized target nucleic acid that was hybridized by the target binding domain of the sequencing probe; and (20) removing the second sequencing probe from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (5) and (6) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photocleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. For example, the first hybridizing nucleic acid molecule lacking a detectable label can comprise the same nucleic acid sequence as that portion of the first complementary nucleic acid molecule that binds to a first attachment position of the at least three attachment positions of the barcode domain. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The present invention further provides methods of sequencing a nucleic acid utilizing a plurality of sequencing probes disclosed herein. For example, the target nucleic acid is hybridized to more than one sequencing probe and each probe can sequence the portion of the target nucleic acid to which it is hybridized.

The present disclosure also provides a method for sequencing a nucleic acid comprising (1) hybridizing at least one first population of first sequencing probes comprising a plurality of the sequencing probes described herein to a target nucleic acid that is optionally immobilized to a substrate at one or more positions; (2) binding a first complementary nucleic acid molecule comprising a first detectable label and an at least second detectable label to a first attachment position of the at least three attachment positions of the barcode domain; (3) detecting the first and at least second detectable label of the bound first complementary nucleic acid molecule; (4) identifying the position and identity of at least two nucleotides in the immobilized target nucleic acid; (5) binding to the first attachment position a first hybridizing nucleic acid molecule lacking a detectable label, thereby unbinding the first complementary nucleic acid molecule comprising the detectable labels, or contacting the first complementary nucleic acid molecule comprising the detectable labels with a force sufficient to release the first detectable label and at least second detectable label; (6) binding a second complementary nucleic acid molecule comprising a third detectable label and an at least fourth detectable to a second attachment position of the at least three attachment positions of the barcode domain; (7) detecting the third and at least fourth detectable label of the bound second complementary nucleic acid molecule; (8) identifying the position and identity of at least two nucleotides in the optionally immobilized target nucleic acid; (9) repeating steps (5) to (8) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a first region of the immobilized target nucleic acid that was hybridized by the target binding domain of the sequencing probe; and (10) removing the at least one first population of first sequencing probes from the optionally immobilized target nucleic acid.

The method can further comprise (11) hybridizing at least one second population of second sequencing probes comprising a plurality of the sequencing probes disclosed herein to a target nucleic acid that is optionally immobilized to a substrate at one or more positions, and wherein the target binding domain of the first sequencing probe and the second sequencing probe are different; (12) binding a first complementary nucleic acid molecule comprising a first detectable label and an at least second detectable label to a first attachment position of the at least three attachment positions of the barcode domain; (13) detecting the first and at least second detectable label of the bound first complementary nucleic acid molecule; (14) identifying the position and identity of at least two nucleotides in the optionally immobilized target nucleic acid; (15) binding to the first attachment position a first hybridizing nucleic acid molecule lacking a detectable label, thereby unbinding the first complementary nucleic acid molecule or complex comprising the detectable labels, or contacting the first complementary nucleic acid molecule or complex comprising the detectable labels with a force sufficient to release the first detectable label and at least second detectable label; (16) binding a second complementary nucleic acid molecule comprising a third detectable label and an at least fourth detectable label to a second attachment position of the at least three attachment positions of the barcode domain; (17) detecting the third and at least fourth detectable label of the bound second complementary nucleic acid molecule; (18) identifying the position and identity of at least two nucleotides in the immobilized target nucleic acid; (19) repeating steps (15) to (18) until each attachment position of the at least three attachment positions in the barcode domain have been bound by a complementary nucleic acid molecule comprising two detectable labels, and the two detectable labels of the bound complementary nucleic acid molecule has been detected, thereby identifying the linear order of at least six nucleotides for at least a second region of the immobilized target nucleic acid that was hybridized by the target binding domain of the sequencing probe; and (20) removing the at least one second population of second sequencing probes from the optionally immobilized target nucleic acid.

The method can further comprise assembling each identified linear order of nucleotides in the at least first region and at least second region of the immobilized target nucleic acid, thereby identifying a sequence for the immobilized target nucleic acid.

Steps (5) and (6) can occur sequentially or concurrently. The first and at least second detectable labels can have the same emission spectrum or can have different emission spectra. The third and at least fourth detectable labels can have the same emission spectrum or can have different emission spectra.

The first complementary nucleic acid molecule can comprise a cleavable linker. The second complementary nucleic acid molecule can comprise a cleavable linker. The first complementary nucleic acid molecule and the second complementary nucleic acid molecule can each comprise a cleavable linker. Preferably, the cleavable linker is photocleavable. The release force can be light. Preferably, UV light. The light can be provided by a light source selected from the group consisting of an arc-lamp, a laser, a focused UV light source, and light emitting diode.

The first complementary nucleic acid molecule and the first hybridizing nucleic acid molecule lacking a detectable label can comprise the same nucleic acid sequence. The first hybridizing nucleic acid molecule lacking a detectable label can comprise a nucleic acid sequence complementary to a flanking single-stranded polynucleotide adjacent to the first attachment position in the barcode domain.

The second complementary nucleic acid molecule and the second hybridizing nucleic acid molecule lacking a detectable label can comprise the same nucleic acid sequence. The second hybridizing nucleic acid molecule lacking a detectable label can comprise a nucleic acid sequence complementary to a flanking single-stranded polynucleotide adjacent to the second attachment position in the barcode domain.

The sequencing methods are further described herein.

Figure 14:
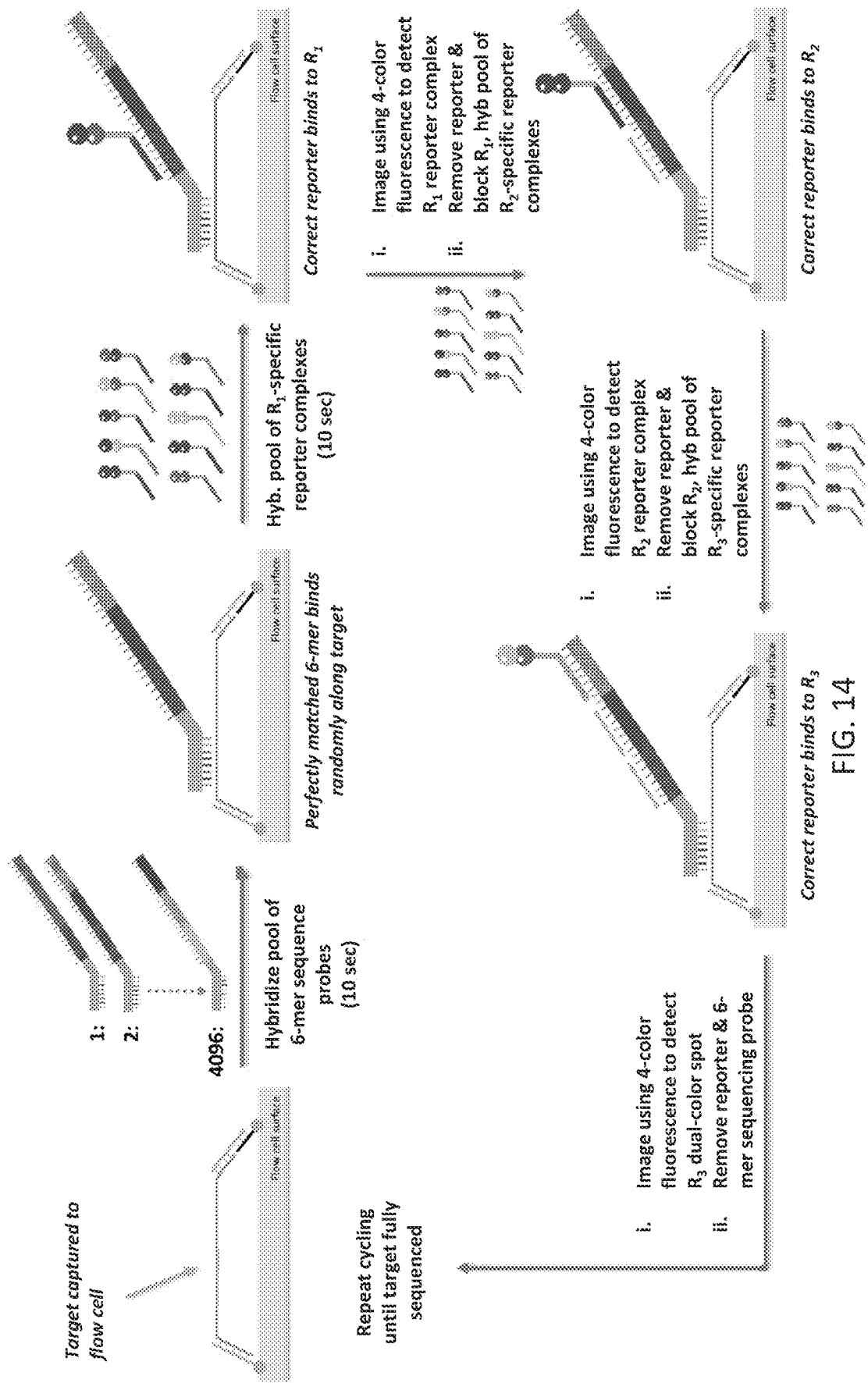
FIG. 14 is a schematic illustration of a single cycle of the sequencing method of the present disclosure.

FIG. 14 shows a schematic overview of a single exemplary sequencing cycle of the present disclosure. Although immobilizing a target nucleic acid prior to sequencing is not required for the instant methods, in this example, the method begins with a target nucleic acid that has been captured using capture probes and bound to a flow cell surface as shown in the left upper-most panel. A pool of sequencing probes is then flowed into the flow cell to allow sequencing probes to hybridize to the target nucleic acid. In this example, the sequencing probes are those depicted in FIG. 1. These sequencing probes comprise a 6-mer sequence within the target binding domain that hybridizes to the target nucleic acid. The 6-mer is flanked on either side by (N) bases which can be a universal/degenerate base or composed of any of the four canonical bases that is not specific to the target dictated by bases $b_1$-$b_2$-$b_3$-$b_4$-$b_5$-$b_6$. Using 6-mer sequences, a set of 4096 (4^6) sequencing probes enables the sequencing of any target nucleic acid. For this example, the set of 4096 sequencing probes are hybridized to the target nucleic acid in 8 pools of 512 sequencing probes each. The 6-mer sequences in the target binding domain of the sequencing probes will hybridize along the length of the target nucleic acid at positions where there is a perfect complementary match between the 6-mer and the target nucleic acid, as shown in upper middle panel of FIG. 14. In this example, a single sequencing probe hybridizes to the target nucleic acid. Any unbound sequencing probes are washed out of the flow cell.

These sequencing probes also comprise a barcode domain with three attachment positions $R_1$, $R_2$ and $R_3$, as described above. The attachment regions within attachment position $R_1$ comprise one or more nucleotide sequences that correspond to the first dinucleotide of the 6-mer of the sequencing probe. Thus, only reporter probes comprising complementary nucleic acids that correspond to the identity of the first dinucleotide present in the target binding domain of the sequencing probe will hybridize to attachment position $R_1$. Likewise, the attachment regions within attachment position $R_2$ of the sequencing probe correspond to the second dinucleotide present in the target binding domain and the attachment regions within attachment position $R_3$ of the sequencing probe correspond to the second dinucleotide present in the target binding domain The method continues in the right upper-most panel of FIG. 14. A pool of reporter probes is flowed into the flow cell. Each reporter probe in the reporter probe pool comprises a detectable label, in the form of a dual color combination, and a complementary nucleic acid that can hybridize to a corresponding attachment region within the attachment position $R_1$ of a sequencing probe. The dual color combination and the complementary nucleic acid of a particular reporter probe correspond to one of 16 possible dinucleotides, as described above. Each pool of reporter probes is designed such that the dual color combination that corresponds to a specific dinucleotide is established before sequencing. For example, in the sequencing experiment depicted in FIG. 14, for the first pool of reporter probes that is hybridized to attachment position $R_1$, the dual color combination Yellow-Red can correspond to the dinucleotide Adenine-Thymine. After hybridization of the reporter probe to attachment position $R_1$, as shown in the upper right panel of FIG. 14, any unbound reporter probes are then washed out of the flow cell and the detectable label of the bound reporter probe is recorded to determine the identity of the first dinucleotide of the 6-mer.

The detectable label attributed to the reporter probe hybridized to attachment position $R_1$ is removed. To remove the detectable label, the reporter probe can include a cleavable linker and the addition of the appropriate cleaving agent can be added. Alternatively, a complementary nucleic acid lacking a detectable label is hybridized to attachment position $R_1$ of the sequencing probe and displaces the reporter probe with the detectable label. Irrespective of the method of removing the detectable label, the attachment position $R_1$ no longer emits a detectable signal. The process by which an attachment position of a barcode domain that was previously emitting a detectable signal is rendered no longer able to emit a detectable signal is referred to herein as "darkening".

A second pool of reporter probes is flowed into the flow cell. Each reporter probe in the reporter probe pool comprises a detectable label, in the form of a dual color combination, and a complementary nucleic acid that can hybridize to a corresponding attachment region within attachment position $R_2$ of a sequencing probe. The dual color combination and the complementary nucleic acid of a particular reporter probe correspond to one of 16 possible dinucleotides. It is possible that a particular dual color combination corresponds to one dinucleotide in the context of the first pool of reporter probes, and a different dinucleotide in the context of the second pool of reporter probes. After hybridization of the reporter probes to attachment position $R_2$, as shown in the bottom right panel of FIG. 14, any unbound reporter probes are then washed out of the flow cell and the detectable label is recorded to determine the identity of the second dinucleotide of the 6-mer present in the sequencing probe.

To remove the detectable label at position $R_2$, the reporter probe can include a cleavable linker and the addition of the appropriate cleaving agent can be added. Alternatively, a complementary nucleic acid lacking a detectable label is hybridized to attachment position $R_2$ of the sequencing probe and displaces the reporter probe with the detectable label. Irrespective of the method of removing the detectable label, the attachment position $R_2$ no longer emits a detectable signal.

A third pool of reporter probes is then flowed into the flow cell. Each reporter probe in the third reporter probe pool comprises a detectable label, in the form of a dual color combination, and a complementary nucleic acid that can hybridize to a corresponding attachment region within attachment position $R_3$ of a reporter probe. The dual color combination and the complementary nucleic acid of a particular reporter probe correspond to one of 16 possible dinucleotides. After hybridization of the reporter probes to position $R_3$, as shown in the bottom middle panel of FIG. 14, any unbound reporter probes are then washed out of the flow cell and the detectable label is recorded to determine the identity of the third dinucleotide of the 6-mer present in the sequencing probe. In this way, all three dinucleotides of the target binding domain are identified and can be assembled together to reveal the sequence of the target binding domain and therefore the sequence of the target nucleic acid.

To continue to sequence the target nucleic acid, any bound sequencing probes can be removed from the target nucleic acid. The sequencing probe can be removed from the target nucleic acid even if a reporter probe is still hybridized to position $R_3$ of the barcode domain. Alternatively, the reporter probe hybridized to position $R_3$ can be removed from the barcode domain prior to the removal of the sequencing probe from the target binding domain, for example, by using the darkening procedures as described above for reporters at positions $R_1$ and $R_2$.

The sequencing cycle depicted in FIG. 14 can be repeated any number of times, beginning each sequencing cycle either with the hybridization of the same pool of sequencing probes to the target nucleic acid molecule or with the hybridization of a different pool of sequencing probes to the target nucleic acid. It is possible that the second pool of sequencing probes bind to the target nucleic acid at a position that overlaps the position at which the first sequencing probe or pool of sequencing probes were bound during the first sequencing cycle. Thereby certain nucleotides within the target nucleic acid can be sequenced more than once and using more than one sequencing probe.

Figure 15:
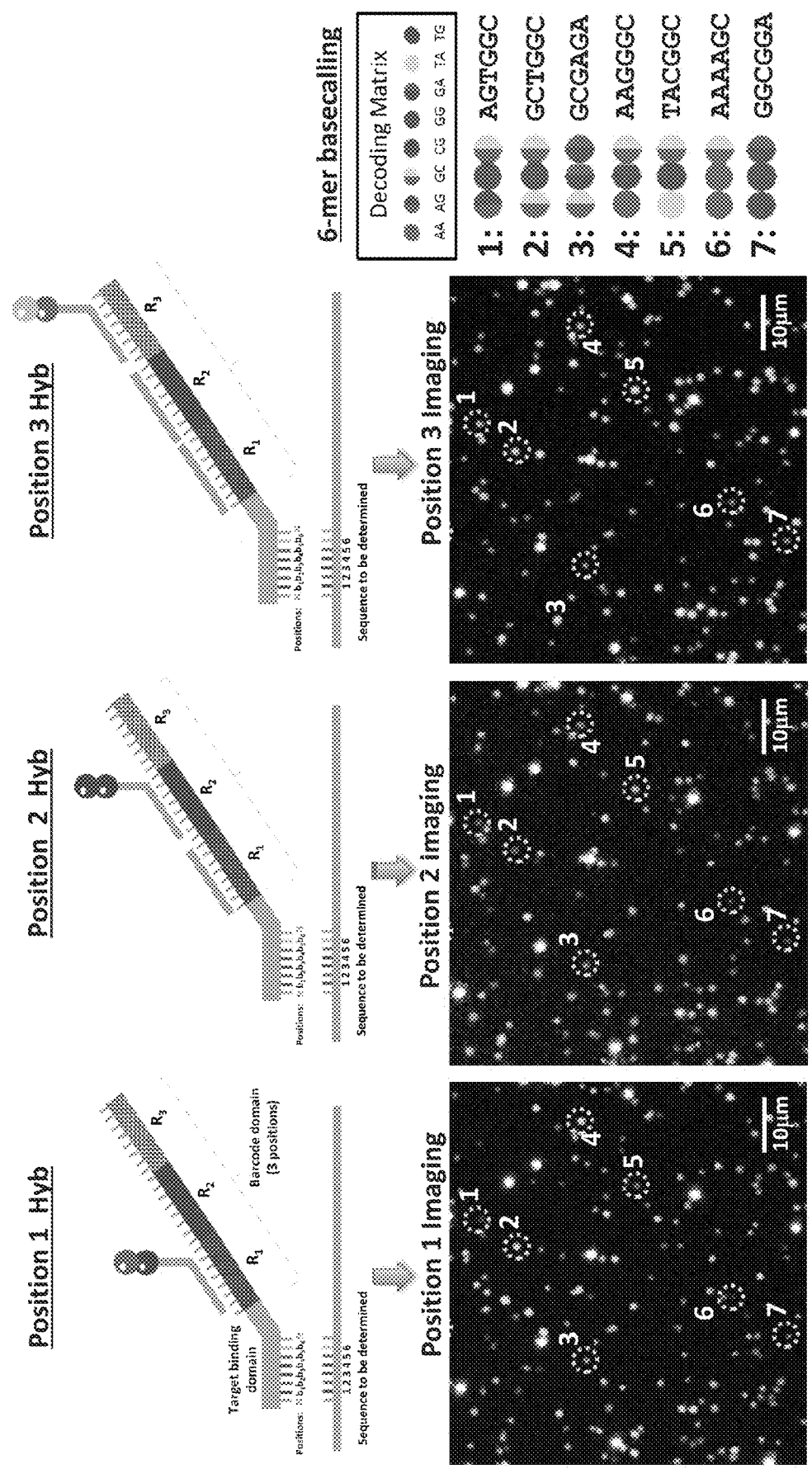
FIG. 15 is a schematic illustration of one cycle of the sequencing method of the present disclosure and the corresponding imaging data collected during this cycle.

FIG. 15 depicts a schematic of one full cycle of the sequencing method of the present disclosure and the corresponding imaging data collected during this cycle. In this example, the sequencing probe used are those depicted in FIG. 1 and the sequencing steps are the same as those depicted in FIG. 14 and described above. After the sequencing domain of the sequencing probe is hybridized to the target nucleic acid, a reporter probe is hybridized to the first attachment position ($R_1$) of the sequencing probe. The first reporter probe is then imaged to record color dots. In FIG. 15, the color dots are labeled with dotted circles. The color dots correspond to a single sequencing probe that is being recorded during the full cycle. In this example, 7 sequencing probes are recorded (1 to 7). The first attachment position of the barcode domain is then darkened and a dual fluorescence reporter probe is hybridized to the second attachment position ($R_2$) of the sequencing probe. The second reporter probe is then imaged to record color dots. The second attachment position of the barcode domain is then darkened and a dual fluorescence reporter is hybridized to the third attachment position ($R_3$) of the sequencing probe. The third reporter probe is then imaged to record color dots. The three color dots from each sequencing probe 1 to 7 are then arranged in order. Each color spot is then mapped to a specific dinucleotide using the decoding matrix to reveal the sequence of the target binding domain of sequencing probes 1 to 7.

During a single sequencing cycle, the number of reporter probe pools needed to determine the sequence of the target binding domain of any sequencing probes bound to a target nucleic acid is identical to the number of attachment positions in the barcode domain. Thus, for a barcode domain having three positions, three reporter probe pools will be cycled over the sequencing probes.

A pool of sequencing probes can comprise a plurality of sequencing probes that are all identical in sequence or a plurality of sequencing probes that are not all identical in sequence. When a pool of sequencing probes include a plurality of sequencing probes that are not all identical in sequence, each different sequencing probe can be present in the same number, or different sequencing probes can be present in different numbers.

Figure 16:
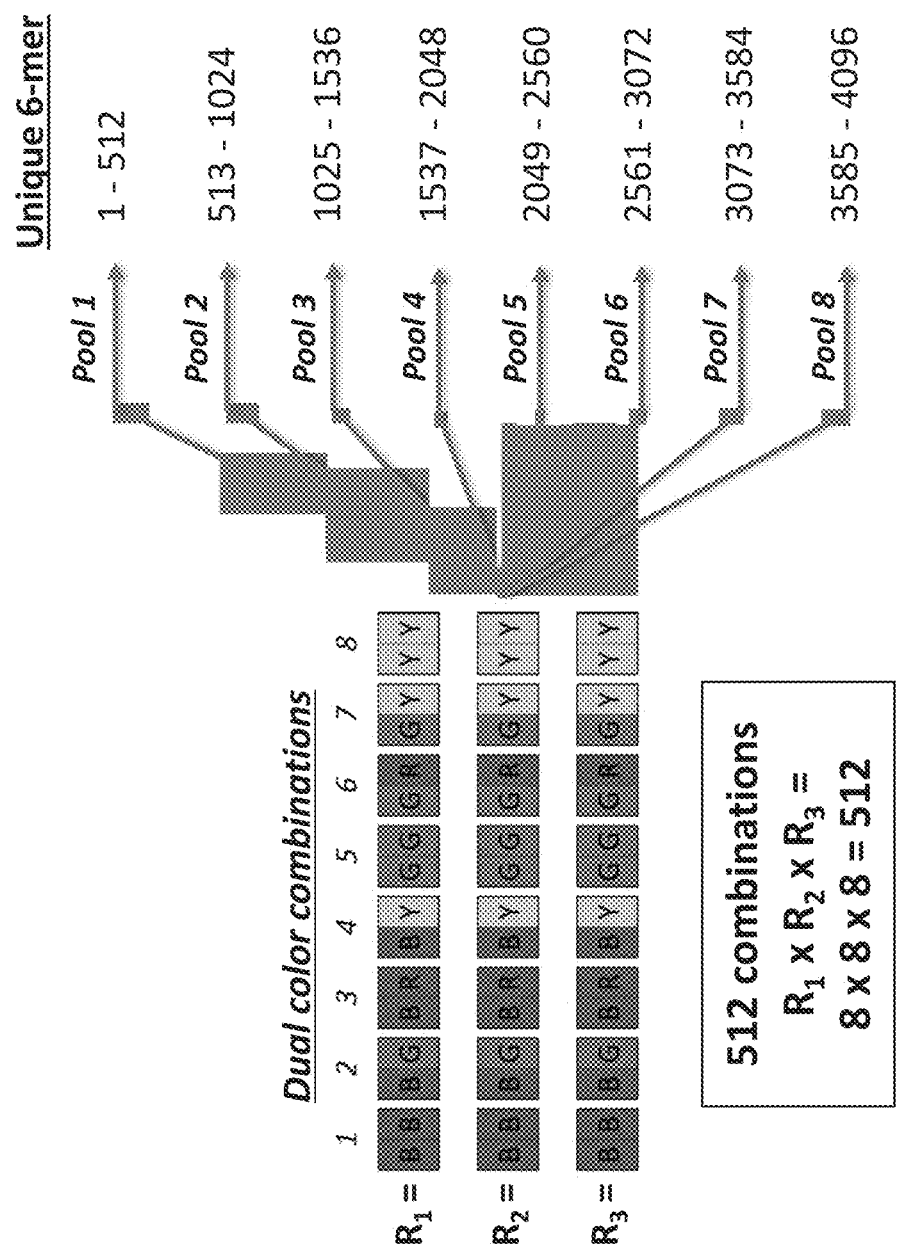
FIG. 16 illustrates an exemplary sequencing probe pool configuration of the present disclosure in which the eight color combinations are used to design eight different pools of sequencing probes.

FIG. 16 shows an exemplary sequencing probe pool configuration of the present disclosure in which the eight color combinations specified above are used to design eight different pools of sequencing probes when the sequencing probe contains: (a) a target binding domain that has 6 nucleotides (6-mer) that specifically binds to the target nucleic acid and (b) three attachment positions ($R_1$, $R_2$ and $R_3$) in the barcode domain. There are a possible 4096 unique 6-mer sequences (4×4×4×4×4×4=4096). Given that each of the three attachment positions in the barcode domain can be hybridized to a complementary nucleic acid bound by one of eight different color combinations, there are 512 unique sets of 3 color combinations possible (8*8*8=512). For example, a probe where $R_1$ hybridizes to a complementary nucleic acid bound to the color combination GG, $R_2$ hybridizes to a complementary nucleic acid bound to the color combination BG, and $R_3$ hybridizes to a complementary nucleic acid bound to the color combination YR, the set of 3 color combinations is accordingly GG-BG-YR. Within a pool of sequencing probes, each unique set of three color combinations will correspond to a unique 6 mer within the target binding domain. Given each pool contains 512 unique 6 mers, and there are a total of 4096 possible 6 mers, eight pools are needed to sequence all possible 6 mers (4096/512=8). The specific sequencing probes that are placed in each of the 8 pools is determined to ensure optimal hybridization of each sequencing probe to the target nucleic acid. To ensure optimal hybridization several precautions are taken including: (a) separating perfect 6 mer complements into different pools; (b) separating 6 mers with a high Tm and a low Tm into different pools; and (c) separating 6 mers into different pools based on empirically-learned hybridization patterns.

Figure 17:
FIG. 17 compares the barcode domain design disclosed in U.S. 2016/019470 with the barcode domain design of the present disclosure.

FIG. 17 shows the difference between the sequencing probes described in US Patent Publication No. 20160194701 and the sequencing probes of the present disclosure. As depicted on the left panel of FIG. 17, US Patent Publication No. 20160194701 describes a sequencing probe with a barcode domain that comprises six attachment positions that are hybridized to complementary nucleic acids. Each complementary nucleic acids is bound to one of four different fluorescent dyes. In this configuration, each color (red, blue, green, yellow) corresponds to one nucleotide (A, T, C, or G) in the target binding domain. This probe design creates 4096 unique probes (4^6). As depicted in the right panel of FIG. 17, in one example of the present disclosure, the barcode domain of each sequencing probe comprises 3 attachment positions that are hybridized to complementary nucleic acids, as depicted in the right panel of FIG. 17. Unlike US Patent Publication No. 20160194701, these complementary nucleic acids are bound by 1 of 8 different color combinations (GG, RR, GY, RY, YY, RG, BB, and RB). Each color combination corresponds to a specific dinucleotide in the target binding domain. This configuration creates 512 unique probes (8^3). To cover all possible hexamer combinations within a target binding domain (4096), 8 separate pools of these 512 unique probes are needed to sequence an entire target nucleic acid. Since 8 color combinations are used to label the complementary nucleic acid, but there are 16 possible dinucleotides, certain color combinations will correspond to different dinucleotides depending on which pool of sequencing probes is being used. For example, in FIG. 17, in the $1^{st}$, $2^{nd}$, $3^{rd}$ and $4^{th}$ pools of sequencing probes, the color combination BB corresponds to the dinucleotide AA and the color combination GG corresponds to the dinucleotide AT. In the $5^{th}$, $6^{th}$, $7^{th}$, and $8^{th}$ pools of sequencing probes, the color combination BB corresponds to the dinucleotide CA and the color combination CT corresponds to the dinucleotide AT.

A plurality of sequencing probes (i.e. more than one sequencing probe) can be hybridized within the sequencing window. During sequencing, the identity and spatial position of the detectable labels bound to each sequencing probe in the plurality of hybridized sequencing probes is recorded. This allows for subsequent identification of both the position and identity of a plurality of dinucleotides. In other words, by hybridizing a plurality of sequencing probes simultaneously to a single target nucleic acid molecule, multiple positions along the target nucleic acid can be sequenced concurrently, increasing the speed of sequencing.

Figure 18:
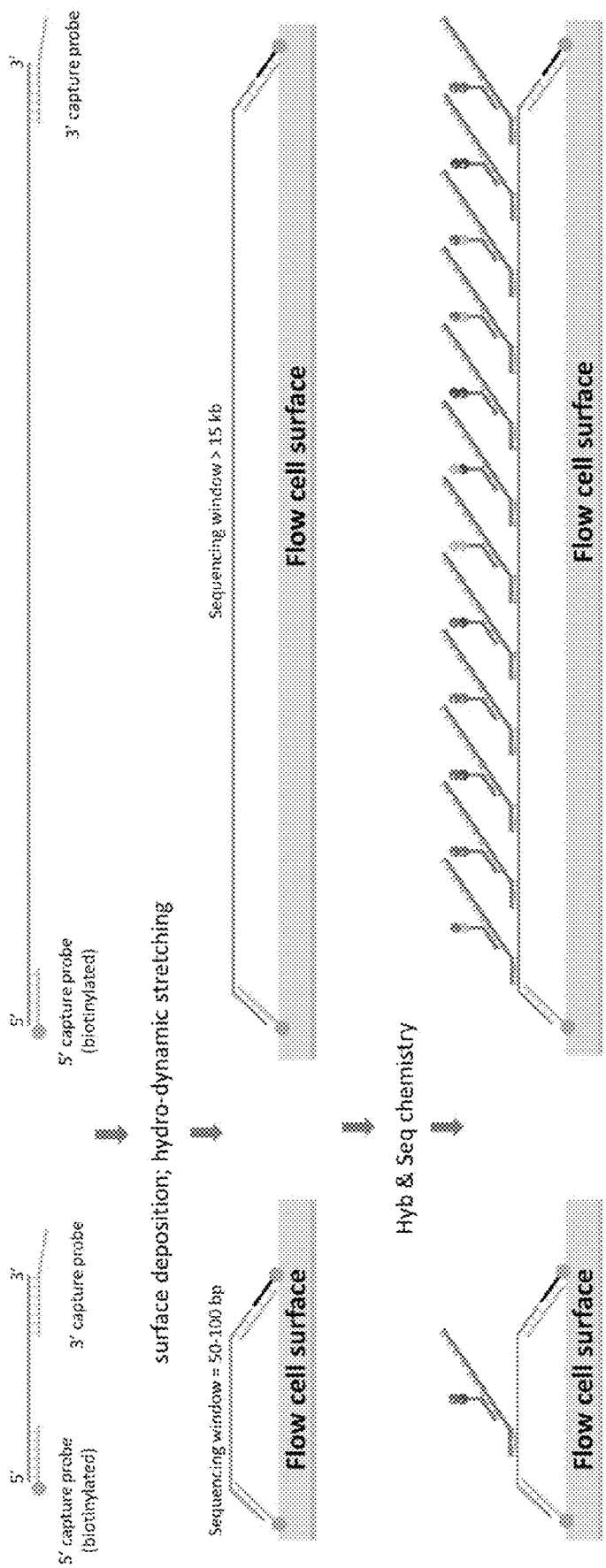
FIG. 18 is a schematic illustration of a single sequencing probe or a plurality of sequencing probes of the present disclosure hybridized to a captured target nucleic acid molecule.
Figure 19:
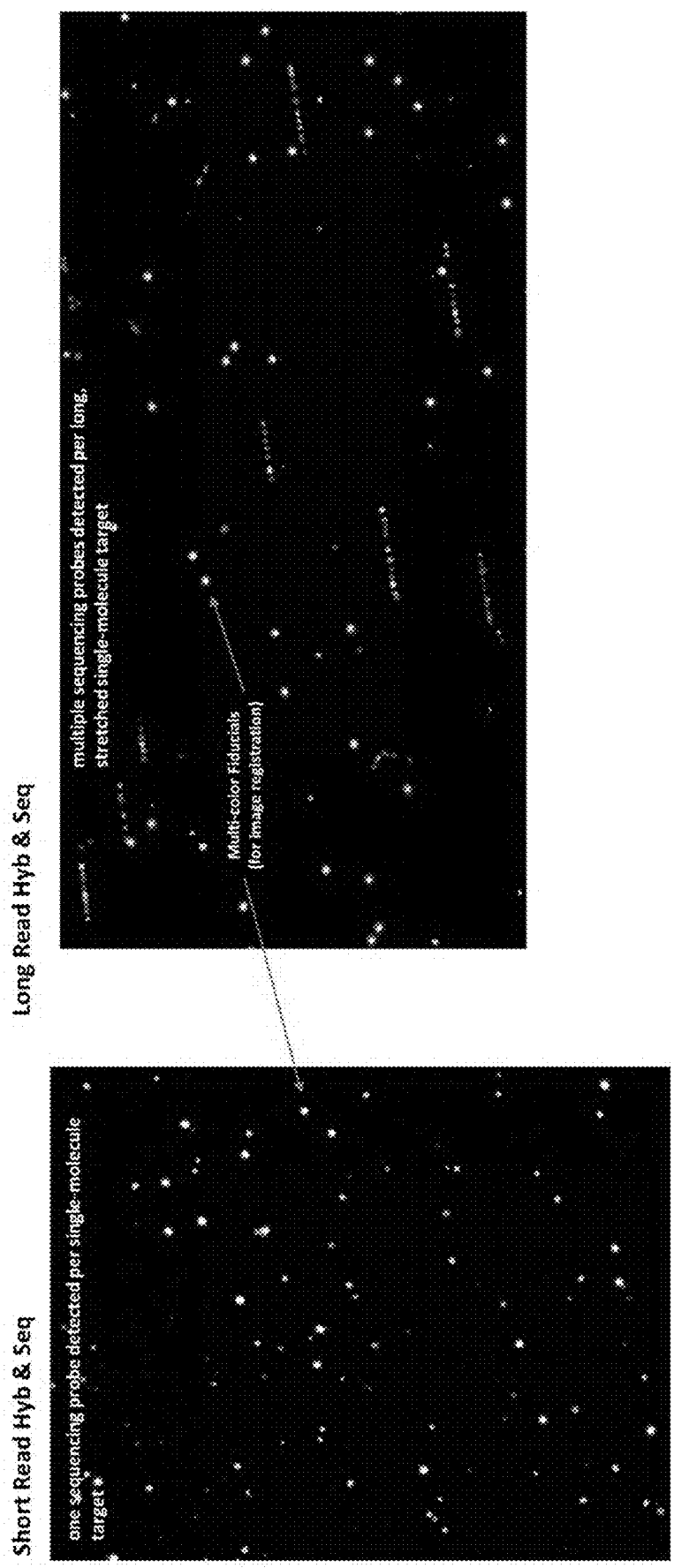
FIG. 19 shows fluorescence images recorded during the sequencing method of the present disclosure when a single sequencing probe or a plurality of sequencing probes are hybridized to a target nucleic acid.

FIG. 18 shows a schematic of a single sequencing probe and a plurality of sequencing probes hybridized to a captured target nucleic acid molecule. The sequencing window between the two hybridized 5' and 3' capture probes allows for the hybridization of a single sequencing probe (left panel) or a plurality of sequencing probes (right panel) along the length of the target nucleic acid molecule. By hybridizing a plurality of sequencing probes along the length of the target nucleic acid molecule, more than one location on the target nucleic acid molecule can be sequence concurrently, increasing the speed of sequencing. FIG. 19 shows fluorescence images recorded during the sequencing method of the present disclosure when a single probe (left panel) or a plurality of probes (right panel) are hybridized to a captured target nucleic acid. The right panel of FIG. 19 shows that the fluorescence signal from individual probes of a plurality of probes bound along the length of a target nucleic acid can be spatially resolved.

Figure 20:
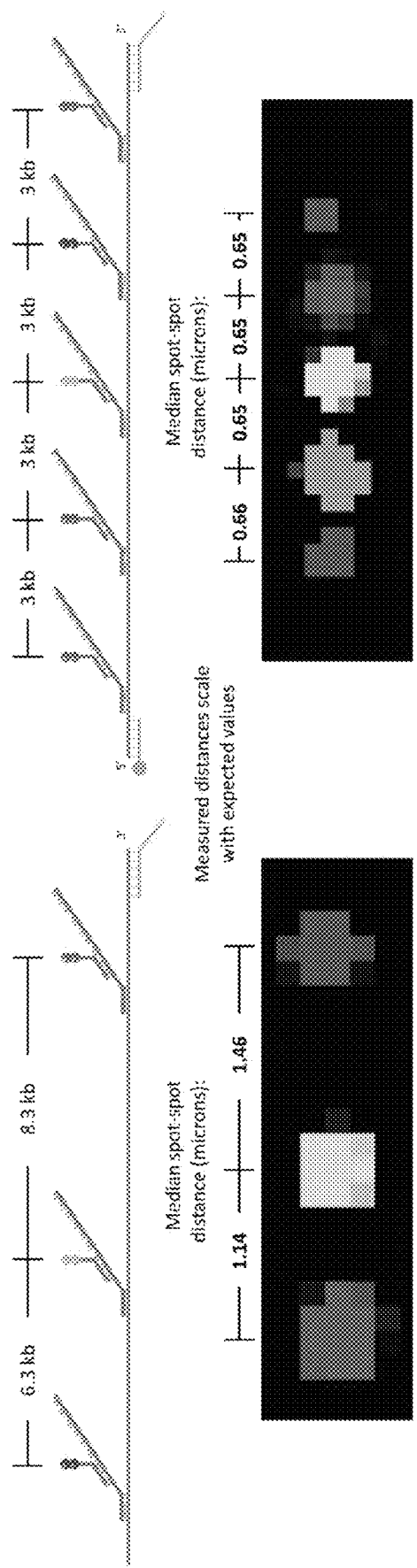
FIG. 20 is a schematic illustration of a plurality of sequencing probes of the present disclosure bound along the length of a target nucleic acid and the corresponding recorded fluorescence images.

FIG. 20 shows a schematic of a plurality of sequencing probes of the present disclosure bound along the length of a target nucleic acid that is 15 kilobases in length and the corresponding recorded fluorescence images. Sequencing probes can bind at even intervals along the length of target nucleic acid, as shown in the right panel of FIG. 20. Sequencing probes need not bind at even intervals along the length of a target nucleic acid, as shown in the left panel of FIG. 20. The fluorescence images shown in FIG. 20 demonstrate the signals from a plurality of sequencing probes bound along the length of a target nucleic acid can be spatially resolved to obtain sequencing information at multiple locations of a target nucleic acid concurrently.

The distribution of probes along a length of target nucleic acid is critical for resolution of detectable signal. There are occasions when too many probes in a region can cause overlap of their detectable label, thereby preventing resolution of two nearby probes. This is explained as follows. Given that one nucleotide is 0.34 nm in length and given that the lateral (x-y) spatial resolution of a sequencing apparatus is about 200 nm, a sequencing apparatus's resolution limit is about 588 base pair (i.e., a 1 nucleotide/0.34 nm×200 nm). That is to say, the sequencing apparatus mentioned above would be unable to resolve signals from two probes hybridized to a target nucleic acid when the two probes are within about 588 base pair of each other. Thus, two probes, depending on the resolution of the sequencing apparatus, will need be spaced approximately 600 bp's apart before their detectable label can be resolved as distinct "spots". So, at optimal spacing, there should be a single probe per 600 bp of target nucleic-acid. Preferably, each sequencing probe in a population of probes will bind no closer than 600 nucleotides from each other. A variety of software approaches (e.g., utilize fluorescence intensity values and wavelength dependent ratios) can be used to monitor, limit, and potentially deconvolve the number of probes hybridizing inside a resolvable region of a target nucleic acid and to design probe populations accordingly. Moreover, detectable labels (e.g., fluorescent labels) can be selected that provide more discrete signals. Furthermore, methods in the literature (e.g., Small and Parthasarthy: "Superresolution localization methods." *Annu. Rev. Phys Chem.*, 2014; 65:107-25) describe structured-illumination and a variety of super-resolution approaches which decrease the resolution limit of a sequencing microscope up to 10's-of-nanometers. Use of higher resolution sequencing apparatuses allow for use of probes with shorter target binding domains.

As mentioned above, designing the Tm of probes can affect the number of probes hybridized to a target nucleic acid. Alternately or additionally, the concentration of sequencing probes in a population can be increased to increase coverage of probes in a specific region of a target nucleic acid. The concentration of sequencing probes can be reduced to decrease coverage of probes in a specific region of a target nucleic acid, e.g., to above the resolution limit of the sequencing apparatus.

While the resolution limit for two detectable labels is about 600 nucleotides, this does not hinder the powerful sequencing methods of the present disclosure. In certain aspects, a plurality of the sequencing probes in any population will not be separated by 600 nucleotides on a target nucleic acid. However, statistically (following a Poisson distribution), there will be target nucleic acids that only have one sequencing probe bound to it, and that sequencing probe is the one optically resolvable. For target nucleic acids that have multiple probes bound within 600 nucleotides (and thus are not optically resolvable), the data for these unresolvable sequencing probes may be discarded. Importantly, the methods of the present disclosure provide multiple rounds of binding and detecting pluralities of sequencing probes. Thus, it is possible in some rounds the signal from all the sequencing probes are detected, in some rounds the signal from only a portion of the sequencing probes are detected and in some rounds the signal from none of the sequencing probes is detected. In some aspects, the distribution of the sequencing probes bound to the target nucleic acid can be manipulated (e.g., by controlling concentration or dilution) such that only one sequencing probe binds per target nucleic acid.

Randomly, but in part depending on the length of the target binding domain, the Tm of the probes, and concentration of probes applied, it is possible for two distinct sequencing probes in a population to bind within 600 nucleotides of each other.

Alternately or additionally, the concentration of sequencing probes in a population can be reduced to decrease coverage of probes in a specific region of a target nucleic acid, e.g., to above the resolution limit of the sequencing apparatus, thereby producing a single read from a resolution-limited spot.

If the sequence, or part of the sequence, of a target nucleic acid is known prior to sequencing the target nucleic acid using the methods of the present disclosure, the sequencing probes can be designed and chosen such that no two sequencing probes will bind to the target nucleic acid within 600 nucleotides of each other.

Prior to hybridizing sequencing probes to a target nucleic acid, one or more complementary nucleic acid molecules can be bound by a first detectable label and an at least second detectable label can be hybridized to one or more of the attachment positions within the barcode domain of the sequencing probes. For example, prior to hybridization to a target nucleic acid, one or more complementary nucleic acid molecules bound by a first detectable label and an at least second detectable label can be hybridized to the first attachment position of each sequencing probe. Thus, when contacted with its target nucleic acid, the sequencing probes are capable of emitting a detectable signal from the first attachment position and it is unnecessary to provide a first pool of complementary nucleic acids or reporter probes that are directed to the first position on the barcode domain. In another example, one or more complementary nucleic acid molecules bound by a first detectable label and an at least second detectable label can be hybridized to all of the attachment positions within the barcode domain of the sequencing probes. Thus, in this example, a six nucleotide sequence can be read without needing to sequentially replace complementary nucleic acids. Use of this pre-hybridized sequencing probe-reporter probe complex would reduce the time to obtain sequence information since many steps of the described method are omitted. However, this probe would benefit from detectable labels that are non-overlapping, e.g., fluorophores are excited by non-overlapping wavelengths of light or the fluorophores emit non-overlapping wavelengths of light During sequencing, the signal intensity from a recorded color dot can be used to more accurately sequence a target nucleic acid. FIG. 21 shows exemplary imaging data recorded during a sequencing cycle of the present disclosure. The right panel of FIG. 21 shows the fluorescence microscopy image recorded after a reporter probe is hybridized to the first attachment position of a sequencing probe. Particular color dots are highlighted and the specific color combinations recorded are noted, demonstrating that dual-fluorescence signals are clearly detectable and distinguishable. Bright signals from fiducial makers are denoted by arrows. The left panel of FIG. 21 shows that that the spot intensity of a particular color within a color dot can be used to determine the probability that a specific color dot corresponds to color combinations that are the duplicity of one color (i.e. BB, GG, YY, or RR).

The darkening of a position within a barcode domain can be accomplished by strand cleavage at a cleavable linker modification present within the reporter probes that are hybridized to that position. FIG. 22 depicts the use of a cleavable linker modification to darken a barcode position during a sequencing cycle. The first step, depicted on the furthest left panel of FIG. 22, comprises hybridizing a primary nucleic acid of a reporter probe to the first attachment position of a sequencing probe. The primary nucleic acid hybridizes to a specific, complementary sequence within an attachment region of the first position of the barcode domain. The first and second domains of the primary nucleic acid are covalently linked by a cleavable linker modification. In the second step, the detectable labels are then recorded to determine the identity and position of a specific dinucleotide in the target binding domain of the sequencing probe. In the third step, the first position of the barcode domain is darkened by cleaving the reporter probe at the cleavable linker modification. This releases the second domain of the primary nucleic acid, thereby releasing the detectable labels. The first domain of the primary nucleic acid molecule, now lacking any detectable label, is left hybridized to the first attachment position of the barcode domain, thereby the first position of the barcode domain no longer emits a detectable signal and will not be able to hybridize to any other reporter probe in subsequent sequencing steps. In the final step, depicted in the furthest right panel of FIG. 22, a reporter probe is hybridized to the second position of the barcode domain to continue sequencing.

An attachment position of a barcode domain can be darkened by displacing any secondary or tertiary nucleic acid in the reporter probe that is bound by a detectable label while still allowing the primary nucleic acid molecule of the reporter probe to remain hybridized to the sequencing probe. This displacement can be accomplished by hybridizing to the primary nucleic acid secondary or tertiary nucleic acids that are not bound by a detectable label. FIG. 23 is an illustrative example of an exemplary sequencing cycle of the present disclosure in which a position within a barcode domain is darkened by displacement of labeled secondary nucleic acids. The far left panel of FIG. 23 depicts the start of a sequencing cycle in which a primary nucleic acid molecule of a reporter probe is hybridized to the first attachment position of a barcode domain of a sequencing probe. Secondary nucleic acid molecules bound to a detectable label are then hybridized to the primary nucleic acid molecule and the detectable label is recorded. To darken the first position of the barcode domain, the secondary nucleic acid molecules bound to a detectable label are displaced by secondary nucleic acid molecules that lack a detectable label. In the next step of the sequencing cycle, a reporter probe comprising detectable labels is hybridized to the second position of the barcode domain.

An attachment position of a barcode domain can be darkened by displacing any primary nucleic acid molecule of the reporter probe by hybridizing to the sequencing probe at the corresponding barcode domain attachment position nucleic acids that are not bound by a detectable label. In those instances where a barcode domain comprises at least one single-stranded nucleic acid sequence adjacent or flanking at least one attachment position, the nucleic acid not bound by a detectable label can displace a primary nucleic acid molecule by hybridizing to the flanking sequence and a portion of the barcode domain occupied by the primary nucleic acid molecule. If needed, the rate of detectable label exchange can be accelerated by incorporating small single-stranded oligonucleotides that accelerate the rate of exchange of detectable labels (e.g., "Toe-Hold" Probes; see, e.g., Seeling et al., "Catalyzed Relaxation of a Metastable DNA Fuel"; *J. Am. Chem. Soc.* 2006, 128(37), pp 12211-12220).

The complementary nucleic acids comprising a detectable label or reporter probes can be removed from the attachment region but not replaced with a hybridizing nucleic acid lacking a detectable label. This can occur, for example, by adding a chaotropic agent, increasing the temperature, changing salt concentration, adjusting pH, and/or applying a hydrodynamic force. In these examples, fewer reagents (i.e., hybridizing nucleic acids lacking detectable labels) are needed.

The methods of the present disclosure can be used to concurrently capture and sequence RNA and DNA molecules, including mRNA and gDNA, from the same sample. The capture and sequencing of both RNA and DNA molecules from the same sample can be performed in the same flow cell. The left panel of FIG. 24 is an illustrative schematic of how the methods of the present disclosure can be used to concurrently capture, detect, and sequence both gDNA and mRNA from a FFPE sample.

The sequencing method of the present disclosure further comprise steps of assembling each identified linear order of nucleotides for each region of an immobilized target nucleic acid, thereby identifying a sequence for the immobilized target nucleic acid. The steps of assembling uses a non-transitory computer-readable storage medium with an executable program stored thereon. The program instructs a microprocessor to arrange each identified linear order of nucleotides for each region of the target nucleic acid, thereby obtaining the sequence of the nucleic acid. Assembling can occur in "real time", i.e., while data is being collected from sequencing probes rather than after all data has been collected or post complete data acquisition.

Figure 25:
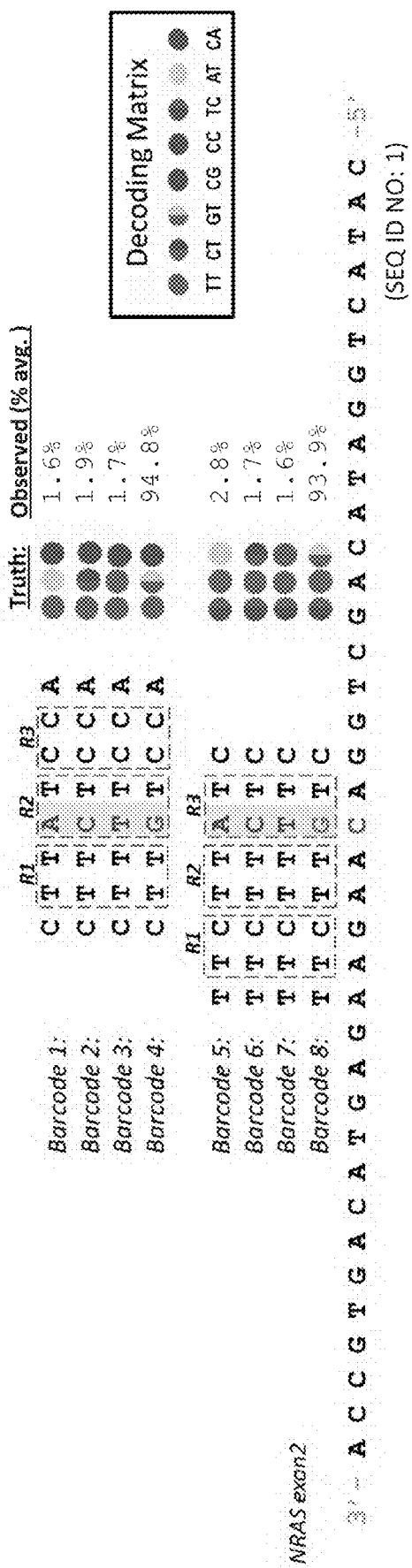
FIG. 25 is schematic illustration of how the sequencing method of the present disclosure allows for the sequencing of the same base of a target nucleic acid with different sequencing probes.

The raw specificity of the sequencing method of the present disclosure is approximately 94%. The accuracy of the sequencing method of the present disclosure can be increased to approximately 99% by sequencing the same base in a target nucleic acid with more than one sequencing probe. FIG. 25 depicts how the sequencing method of the present disclosure allows for the sequencing of the same base of a target nucleic acid with different sequencing probes. The target nucleic acid in this example is a fragment of NRAS exon2 (SEQ ID NO: 1). The particular base of interest is a cytosine (C) that is highlighted in the target nucleic acid. The base of interest will be hybridized to two different sequencing probes, each with a distinct footprint of hybridization to the target nucleic acid. In this example, sequencing probes 1 to 4 (barcode 1 to 4) bind three nucleotides to the left of the base of interest, while sequencing probes 5 to 8 (barcodes 5 to 8) bind 5 nucleotides to the left of the base of interest. Thereby, the base of interest will be sequenced by two different probes, thereby increasing the amount of base calls for that specific position, and thereby increasing overall accuracy at that specific position. FIG. 26 shows how multiple different base calls for a specific nucleotide position on the target nucleotide, recorded from one or more sequencing probes, can be combined to create a consensus sequence (SEQ ID NO: 2), thereby increasing the accuracy of the final base call.

The terms "Hyb & Seq chemistry," "Hyb & Seq sequencing," and "Hyb & Seq" refer to the methods of the present disclosure described above.

Any of the above aspects can be combined with any other aspect as disclosed herein.

Definitions

The terms "annealing" and "hybridization," as used herein, are used interchangeably to mean the formation of a stable duplex. In one aspect, stable duplex means that a duplex structure is not destroyed by a stringent wash under conditions such as a temperature of either about 5° C. below or about 5° C. above the Tm of a strand of the duplex and low monovalent salt concentration, e.g., less than 0.2 M, or less than 0.1 M or salt concentrations known to those of skill in the art. The term "perfectly matched," when used in reference to a duplex means that the polynucleotide and/or oligonucleotide strands making up the duplex form a double stranded structure with one another such that every nucleotide in each strand undergoes Watson-Crick base pairing with a nucleotide in the other strand. The term "duplex" comprises, but is not limited to, the pairing of nucleoside analogs, such as deoxyinosine, nucleosides with 2-aminopurine bases, PNAs, and the like, that can be employed. A "mismatch" in a duplex between two oligonucleotides means that a pair of nucleotides in the duplex fails to undergo Watson-Crick bonding.

As used herein, the term "hybridization conditions," will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, e.g., conditions under which a probe will specifically hybridize to its target subsequence. Stringent conditions are sequence-dependent and are different in different circumstances. Longer fragments can require higher hybridization temperatures for specific hybridization. As other factors can affect the stringency of hybridization, including base composition and length of the complementary strands, presence of organic solvents and extent of base mismatching, the combination of parameters is more important than the absolute measure of any one alone.

Generally, stringent conditions are selected to be about 5° C. lower than the Tm for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, "Molecular Cloning A Laboratory Manual, 2nd Ed." Cold Spring Harbor Press (1989) and Anderson Nucleic Acid Hybridization, 1st Ed., BIOS Scientific Publishers Limited (1999). As used herein, the terms "hybridizing specifically to" or "specifically hybridizing to" or similar terms refer to the binding, duplexing, or hybridizing of a molecule substantially to a particular nucleotide sequence or sequences under stringent conditions.

Detectable labels associated with a particular position of a probe can be "readout" (e.g., its fluorescence detected) once or multiple times; a "readout" can be synonymous with the term "basecall". Multiple reads improve accuracy. A target nucleic acid sequence is "read" when a contiguous stretch of sequence information derived from a single original target molecule is detected; typically, this is generated via multi-pass consensus (as defined below). As used herein, the term "coverage" or "depth of coverage" refers to the number of times a region of target has been sequenced (via discrete reads) and aligned to a reference sequence. Read coverage is the total number of reads that map to a specific reference target sequence; base coverage is the total number of basecalls made at a specific genomic position.

A "read" is a unit of sequencer output. A contiguous stretch of sequence information derived from a single original target molecule. Each read has a quality metric that associates the confidence level of the base calls within the read. A unit of sequencer output. A contiguous stretch of sequence information derived from a single original target molecule. In Hyb & Seq, all reads are generated via multi-pass consensus.

The "readlength" is a metric describing length of sequence (in bp) from each read. This metric is determined by the sequencing technology.

As used in herein, a "Hyb & Seq cycle" refers to all steps required to detect each attachment region on a particular probe or population of probes. For example, for a probe capable of detecting six positions on a target nucleic acid, one "Hyb & Seq cycle" will include, at least, hybridizing the probe to the target nucleic acid, hybridizing complementary nucleic acids/reporter probes to attachment region at each of the six positions on the probe's barcode domain, and detecting the detectable labels associated with each of the six positions.

The term "k-mer probe" is synonymous with a sequencing probe of the present disclosure. The k-mer readout is the fundamental unit of Hyb & Seq's data. A single k-mer readout is obtained from a single target molecule per single Hyb & Seq cycle. Multiple Hyb & Seq cycles are performed to generate enough discrete k-mer readouts from a single target molecule to enable an unambiguous alignment of discrete k-mers into a contiguous stretch of sequence When two or more sequences from discrete reads are aligned, the overlapping portions can be combined to create a single consensus sequence. In positions where overlapping portions have the same base (a single column of the alignment), those bases become the consensus. Various rules can be used to generate the consensus for positions where there are disagreements among overlapping sequences. A simple majority rule uses the most common base in the column as the consensus. A "multi-pass consensus" is an alignment of all discrete probe readouts from a single target molecule. Depending on the total number of cycles of probe populations/polls applied, each base position within a single target molecules can be queried with different levels of redundancy or overlap; generally, redundancy increases the confidence level of a basecall.

A "consensus" is when two or more DNA sequences from discrete reads are aligned, the overlapping portions can be combined to create a single consensus sequence. In positions where overlapping portions have the same base (a single column of the alignment), those bases become the consensus. Various rules can be used to generate the consensus for positions where there are disagreements among overlapping sequences. A simple majority rule uses the most common base in the column as the consensus.

The "Raw Accuracy" is a measure of system's inherent ability to correctly identify a base. Raw accuracy is dependent on sequencing technology. "Consensus Accuracy" is a measure of system's ability to correctly identify a base with the use of additional reads and statistical power. "Specificity" refers to the percentage of reads that map to the intended targets out of total reads per run. "Uniformity" refers to the variability in sequence coverage across target regions; high uniformity correlates with low variability. This feature is commonly reported as the fraction of targeted regions covered by ≥20% of the average coverage depth across all targeted regions. Stochastic errors (i.e., intrinsic sequencing chemistry errors) can be readily corrected with 'multi-pass' sequencing of same target nucleic acid; given a sufficient number of passes, substantially 'perfect consensus' or 'error-free' sequencing can be achieved.

The methods described herein can be implemented and/or the results recorded using any device capable of implementing the methods and/or recording the results. Examples of devices that can be used include but are not limited to electronic computational devices, including computers of all types. When the methods described herein are implemented and/or recorded in a computer, the computer program that can be used to configure the computer to carry out the steps of the methods can be contained in any computer readable medium capable of containing the computer program. Examples of computer readable medium that can be used include but are not limited to diskettes, CD-ROMs, DVDs, ROM, RAM, non-transitory computer-readable media, and other memory and computer storage devices. The computer program that can be used to configure the computer to carry out the steps of the methods, assemble sequence information, and/or record the results can also be provided over an electronic network, for example, over the internet, an intranet, or other network.

A "Consumable Sequencing Card" can be incorporated into a fluorescence imaging device known in the art. Any fluorescence microscope with a number of varying features is capable of performing this sequencing readout. For instance: wide-field lamp, laser, LED, multi-photon, confocal or total-internal reflection illumination can be used for excitation and/or detection. Camera (single or multiple) and/or Photomultiplier tube (single or multiple) with either filter-based or grating-based spectral resolution (one or more spectrally resolved emission wavelengths) are possible on the emission-detection channel of the fluorescence microscope. Standard computers can control both the Consumable Sequencing Card, the reagents flowing through the Card, and detection by the fluorescence microscope.

The sequencing data can be analyzed by any number of standard next-generation-sequencing assemblers (see, e.g., Wajid and Serpedin, "Review of general algorithmic features for genome assemblers for next generation sequencers" *Genomics, proteomics & bioinformatics,* (2), 58-73, 2012). The sequencing data obtained within a single diffraction limited region of the microscope is "locally-assembled" to generate a consensus sequence from the multiple reads within a diffraction spot. The multiple diffraction spot assembled reads are then mapped together to generate contiguous sequences representing the entire targeted gene set, or a de-novo assembly of entire genome(s).

Additional teachings relevant to the present disclosure are described in one or more of the following: U.S. Pat. Nos. 8,148,512, 7,473,767, 7,919,237, 7,941,279, 8,415,102, 8,492,094, 8,519,115, U.S. 2009/0220978, U.S. 2009/0299640, U.S. 2010/0015607, U.S. 2010/0261026, U.S. 2011/0086774, U.S. 2011/0145176, U.S. 2011/0201515, U.S. 2011/0229888, U.S. 2013/0004482, U.S. 2013/0017971, U.S. 2013/0178372, U.S. 2013/0230851, U.S. 2013/0337444, U.S. 2013/0345161, U.S. 2014/0005067, U.S. 2014/0017688, U.S. 2014/0037620, U.S. 2014/0087959, U.S. 2014/0154681, U.S. 2014/0162251, and U.S. 2016/0194701 each of which is incorporated herein by reference in their entireties.

EXAMPLES

Example 1—Single-Molecule Long Reads Using Hyb & Seq Chemistry

The presently disclosed sequencing probes and methods of utilizing the sequencing probes is conveniently termed, Hyb & Seq. This term is utilized throughout the specification to describe the disclosed sequencing probes and methods. Hyb & Seq is a library-free, amplification-free, single-molecule sequencing technique that uses nucleic acid hybridization cycles of fluorescent molecular barcodes onto native targets.

Long reads using Hyb & Seq are demonstrated on a single molecule DNA target 33 kilobases (kb) long with the following key steps: (1) long DNA molecules are captured and hydro-dynamically stretched onto the sequencing flow-cell; (2) multiple perfectly matched sequencing probes hybridize across the long single molecule target; (3) fluorescent reporters hybridize to the barcode region in the sequencing probes to identify all the bound sequences; and/or (4) relative positions of sequences within a single molecule target are determined using spatially-resolved fluorescence data.

Key advantages of long reads using Hyb & Seq, include but are not limited to: read lengths determined by molecule length, not limited by chemistry; simple, limited sample preparation results in less fragmentation; positional information associated with sequencing probes aids assembly; and/or capability to phase variants into long-range haplotypes.

Hyb & Seq Chemistry Design—Sequencing Probes comprise a target binding domain that base-pairs with a single molecule target and a barcode domain having at least three positions ($R_1$, $R_2$, and $R_3$) that correspond to the hexamer sequence present in the target binding domain. A set of 4096 sequencing probes enables sequencing of any target sequence. Reporter Probes: Three reporter probes bind sequentially to the positions of the barcode domain. Each reporter complex corresponds to a specific dinucleotide. Hybridization drives the functionality.

Long read and short read sequencing methods of the present disclosure use the same simple probe hybridization workflow for targeted capture of nucleic acids as shown in FIGS. 18 and 19. A plurality of sequencing probes can hybridize to a target nucleic acid concurrently, as shown in the right panel of FIG. 18, and optical resolution allows several spots per long target to be individually distinguished, as shown in the right panel of FIG. 19. By hybridizing and recording a plurality of sequencing probes concurrently, the information content of a single read is increased. Long-range haplotypes are inherent in single-molecule analysis and can be assembled by actual physical location rather than computational reconstruction. Long sequencing reads up to hundreds of kilobases are feasible using the sequencing methods of the present disclosure.

Pools of specific sequencing probes hybridize to 15 kilobase targets in expected patterns as shown in FIG. 20. Sequencing probes hybridize to stretched targets (preferably hydro-dynamically stretched targets) at expected sequence-specific positions and relative physical distances. The sequencing methods of the present disclosure have increased information content compared to short-read technologies, allowing more bases to be read out each cycle. The sequencing methods of the present disclosure also record the relative position of sequencing readouts, which aids in assembly of long reads. Using the sequencing methods of the present disclosure, read length=consensus sequence length=length of captured target molecule.

FIG. 27 shows the results of an experiment in which 33 kilobase DNA fragments were captured, stretched, hybridized to sequencing probes and reporter probes, and detected. The sequencing methods of the present disclosure are compatible with DNA fragments up to 33 kilobases and beyond. Read length is limited only by initial length of the target nucleic acid fragment, not enzymes or sequencing chemistry.

FIG. 13 shows additional capabilities of the sequencing method of the present disclosure with respect to targeted phased long reads. Long-range phased haplotypes are inherent in data and easily identified for phasing of variants. Sequencing of the entire long target molecule is not necessary as "blocker oligos" can be used to limit sequence cycling to sequencing windows of interest.

The results of Example 1 show that the sequencing method of the present disclosure is capable of single molecule sequencing with long read lengths. In particular, the results show: successful capture and hydro-dynamic stretching of a 15 kilobase and 33 kilobase single-stranded DNA molecule; spatially-resolved fluorescence data accurately corresponds to the actual relative positions across the long single molecule; and simultaneous readout of 10+ base sequences per sequencing cycle.

Example 2—ShortStack™ Technology: Accurate, Reference-Guided Assembly of Hyb & Seq Reads for Targeted Sequencing to Resolve Short Nucleotide Variants and InDels ShortStack is an open source algorithm designed to perform assembly of Hyb & Seq's unique hexamer readouts (hexamer spectra). The algorithm is a statistical approach to target identification utilizing hexamer reads from each imaged feature and to perform assembly of hexamer readouts into a consensus sequence on a single molecule basis with error-correction.

Single molecule sequencing using Hyb & Seq chemistry and ShortStack was performed as follows: hexamer readout of the single molecule target was generated after each cycle of hybridization using Hyb & Seq chemistry; after many cycles of hybridization, hexamer spectra that cover each single molecule target regions were produced; and hexamer spectra are used with a reference sequence of each of the target nucleic acid molecules to derive the consensus sequence of each single-molecule target.

Figure 28:
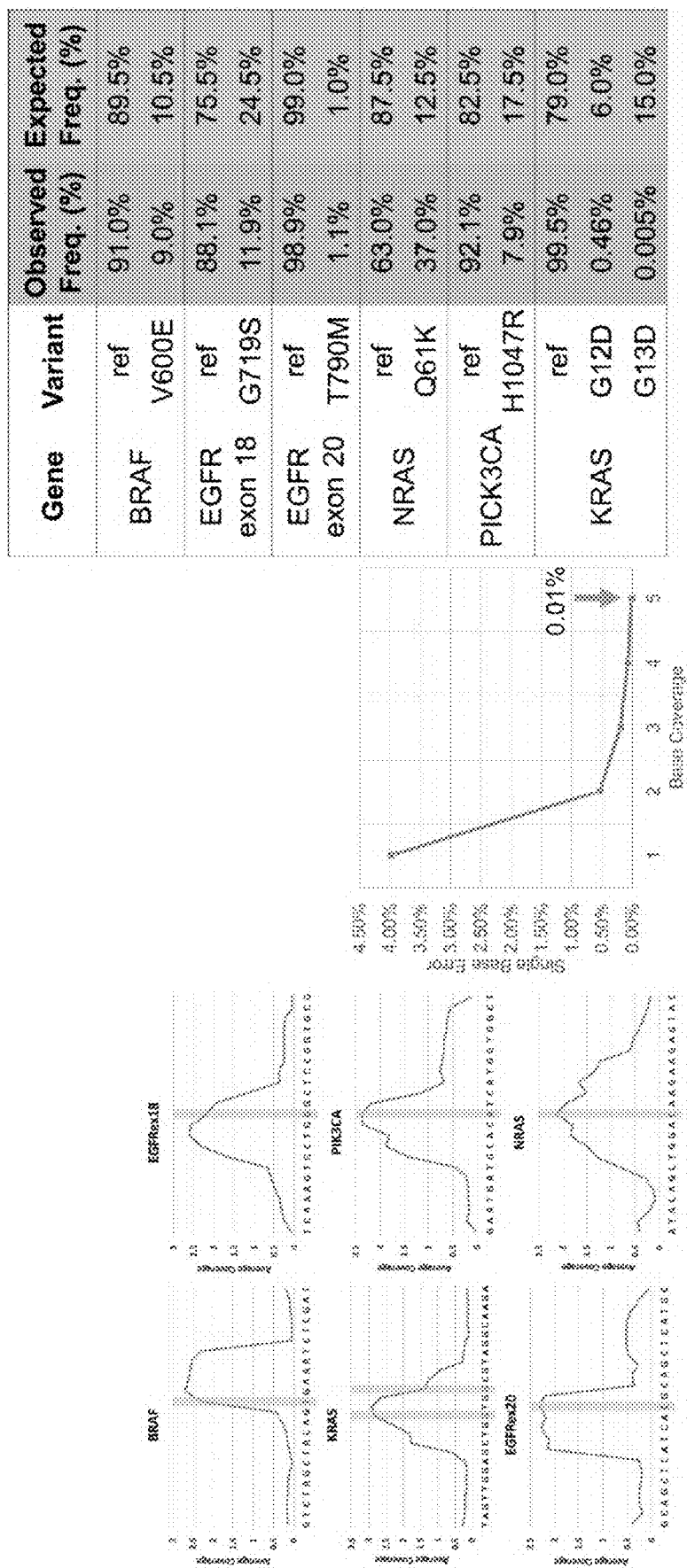
FIG. 28 shows the results from a sequencing experiment obtained using the sequencing method of the present disclosure and analyzed using the ShortStack™ algorithm. For plots on the left panel, starting at the top left plot proceeding clockwise, sequences shown correspond to SEQ ID NOs: 3, 4, 6, 8, 7 and 5. For the table on the right, starting at the top moving down, sequences correspond to SEQ ID NOs: 3, 4, 7, 8, 6 and 5.

The results of target sequencing using Hyb & Seq technology with ShortStack show: single molecule target identification algorithm using the hexamer spectra had 100% success rate; reference guided assembly algorithm produced single molecule consensus accuracy of >99% (~QV 32) at 5× coverage; concordant somatic variant detection ($R^{2\,[<]}$ BEGINITALm90%) was demonstrated using a pre-characterized reference gDNA sample; and/or in silico experiments using all hexamers and ShortStack confirmed average QV>90 across larger target panels The ShortStack algorithm can accurately assemble Hyb & Seq data. FIG. 28 shows the results from a sequencing experiment obtained using the sequencing method of the present disclosure and analyzed using the ShortStack algorithm. In this experiment, the target nucleic acids that were sequenced included fragments of the genes BRAF (SEQ ID NO: 3), EGFRex18 (SEQ ID NO: 4), KRAS (SEQ ID NO: 5), PIK3CA (SEQ ID NO: 6), EGFRex20 (SEQ ID NO: 7) and NRAS (SEQ ID NO: 8). FIG. 28 shows both the base coverage and variant calling. The coverage plots show coverage of bases in FFPE (formalin-fixed paraffin-embedded) gDNA. The results show that most bases across a variety of targets are covered by available sequencing probes. The error plots show error rate vs coverage at queried position in FFPE gDNA samples across a variety of targets. The results show that at 8× coverage, error rates are <1%. The frequency plot shows the correlation between expected and known frequency of variants in sequenced Horizon gDNA samples. The table provides sequenced Horizon Genomic Reference gDNA and shows that the fraction of variant molecules is consistent with known frequency of reference sample.

The results in Example 2 show that ShortStack is an accurate algorithm for sub-assembly of hexamer spectra obtained using the sequencing method of the present disclosure. In particular the results show: 100% accuracy in target identification and average per-base quality values >30 using simulated data; at 5× coverage, >99% accuracy in base calling in experimental Hyb & Seq data; detection of variants from genomic DNA at frequencies consistent with known values ($R^{2\,[<]BEGINITALm}90\%$); and computational performance is efficient and scales linearly with the number of hexamers assembled, capable of assembling 69 k molecules in ~15 min on a personal computer.

Example 3—Library-Free, Targeted Sequencing of Native gDNA from FFPE Samples Using Hyb & Seq™ Technology—the Hybridization Based Single Molecule Sequencing System A targeted cancer panel sequencing of native gDNA from FFPE samples using the sequencing method of the present disclosure (Hyb & Seq) was performed to demonstrate: targeted single-molecule sequencing of oncogene targets with accurate base-calling; accurate detection of known oncogenic Single Nucleotide Variants (SNVs) and Insertions/Deletions (InDels); multiplexed capture of oncogene targets from FFPE-extracted gDNA (median DNA fragment size 200 bases); and/or end-to-end automated sequencing performed on an advanced prototype instrument.

Hyb & Seq chemistry and workflow were demonstrated as follows: genomic targets of interest are directly captured onto the sequencing flow cell; a pool containing hundreds of hexamer sequencing probes is flowed into the sequencing chamber; fluorescent reporter probes sequentially hybridize to the barcode region of the sequencing probe to identify the hexamer bases over 3 reporter exchange cycles; once the bases are identified, the sequencing probe is washed away; and the cycle is repeated with a new pool of sequencing probes until the target regions have been read to sufficient depth Key Advantages of Hyb & Seq: simple and rapid FFPE workflow—Clinical specimen to start of sequencing within 60 minutes; no enzymes or amplification/No library construction; 15 minutes of total hands-on-time; high accuracy–Low chemistry error rate+intrinsic error correction; and/or both long & short reads–Read length defined by input sample, not limited by chemistry.

Hyb & Seq Chemistry Design is as described in Example 1. Hyb & Seq sample preparation for processing FFPE tissues consists of three simple steps: (1) Single-tube deparaffinization and lysis; (2) Removal of particulates using a syringe filter; and (3) Optional DNA fragmentation and target capture. The process requires one to three 10 micron FFPE curls used per sample. The entire process is completed within 60 minutes and it needs only common lab equipment: heat block, pipette, filter and reagents.

Figure 29:
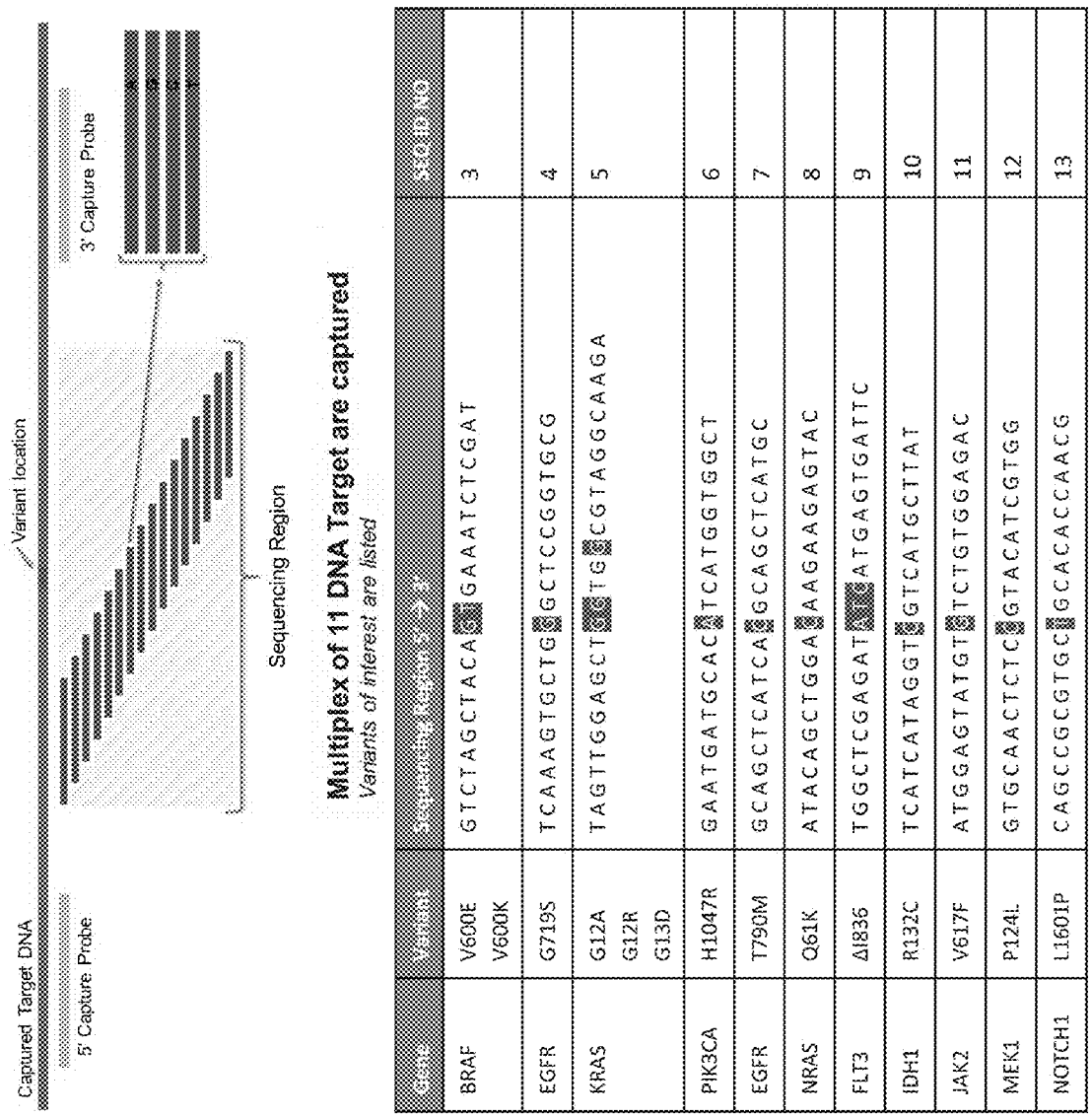
FIG. 29 shows a schematic illustration of the experimental design for the multiplexed capture and sequencing of oncogene targets from a FFPE sample.

FIG. 29 shows a schematic illustration of the experimental design for the multiplexed capture and sequencing of oncogene targets from a FFPE sample. A total of 425 sequencing probes were designed and constructed to sequence portions of 11 oncogenic gene targets (SEQ ID NOs: 3-13). The loci of known variant for each gene target was covered with many sequencing probes (perfect match+single mismatch). Base coverage and base by base accuracy was measured across these regions. Using a pre-characterized reference sample, accuracy of variant detection was obtained. The top panel of FIG. 29 shows that sequencing Probes (blue) align to a target sequence (grey) surrounding a known variant location (red). For each variant location (red), 4 probe sequences were included with each (A, G, C, T) base variant. During Sequencing, single target DNA molecules were tracked for 800 barcode exchange cycles, providing multiple hexamer reads which are reassembled by the ShortStack™ algorithm, as described in Example 2.

FIG. 28 shows the sequencing results including the average coverage of each target, the single base error rate, and the observed vs. expected variant frequencies. The results in Example 3 show that Hyb & Seq sequencing can be used to perform multiplexed sequencing of 11 target regions in FFPE and reference gDNA samples with Single nucleotide variations detected with low error.

Example 4—Direct Single-Molecule RNA Sequencing without cDNA Conversion Using Hyb & Seq™ Chemistry Direct single-molecule RNA sequencing using Hyb & Seq chemistry was demonstrated as follows: native RNA molecules were captured directly without cDNA conversion and immobilized onto sequencing flow cell; a pool containing hundreds of hexamer sequencing probes was flowed into the sequencing flow cell; a perfectly matched sequencing probe was hybridized randomly on a single molecule RNA target; fluorescent reporter probes were sequentially hybridized to barcode region of sequencing probe to identify hexamer bases; and bases were identified and then sequencing probes washed away; cycle was repeated until target had been read to sufficient depth.

Key results: targeted single-molecule RNA was sequenced showing similar coverage profiles to DNA; RNA molecules were stably maintained on the flow cell throughout more than 200 Hyb & Seq cycles; mRNA and genomic DNA were simultaneously captured and quantitated from a single FFPE slice; and/or eight transcripts were multiplex captured and quantitated using as little as 10 ng of total RNA.

Figure 30:
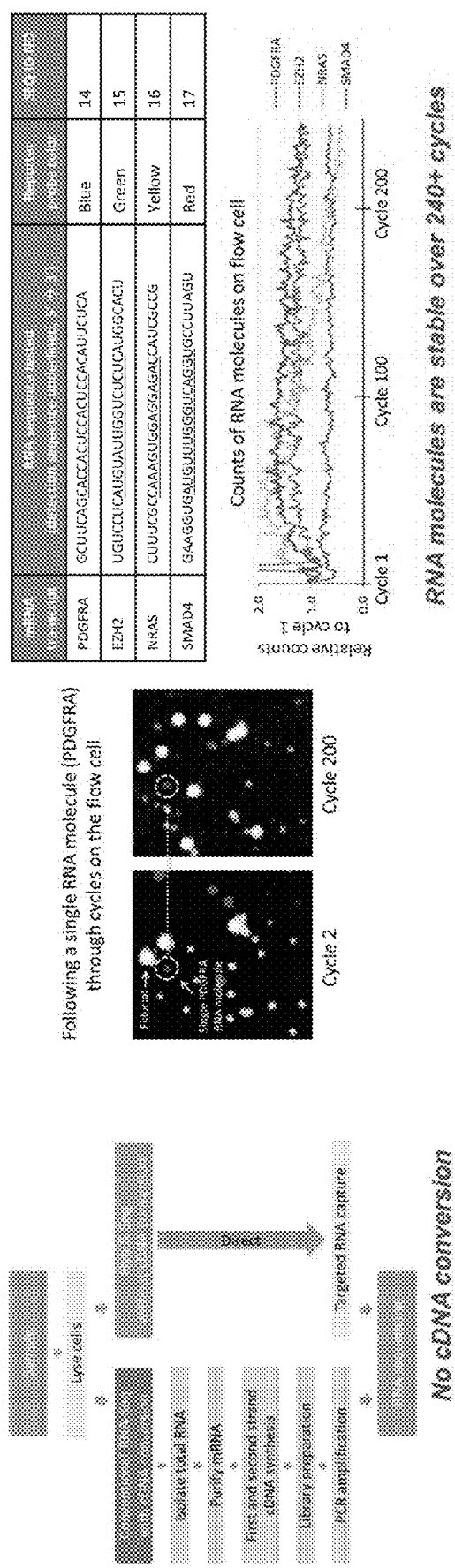
FIG. 30 shows an illustrative schematic of direct RNA sequencing and the results from experiments to test the compatibility of RNA molecules with the sequencing method of the present disclosure.

Hyb & Seq Chemistry Design is as described in Example 1. The left panel of FIG. 30 shows an illustrative schematic of the experimental steps associated with direct RNA sequencing compared to the steps associated with conventional RNA sequencing performed using cDNA conversion. The middle and left panels of FIG. 30 show results from experiments to test the compatibility of RNA molecules with the sequencing method of the present disclosure. In the experiment, 4 target RNA molecules were sequenced (SEQ ID NOs: 14-17). The results show that RNA molecules can be captured and detected for at least 200 sequencing cycles, demonstrating the compatibility of the sequencing methods of the present disclosure and RNA molecules.

Figure 31:
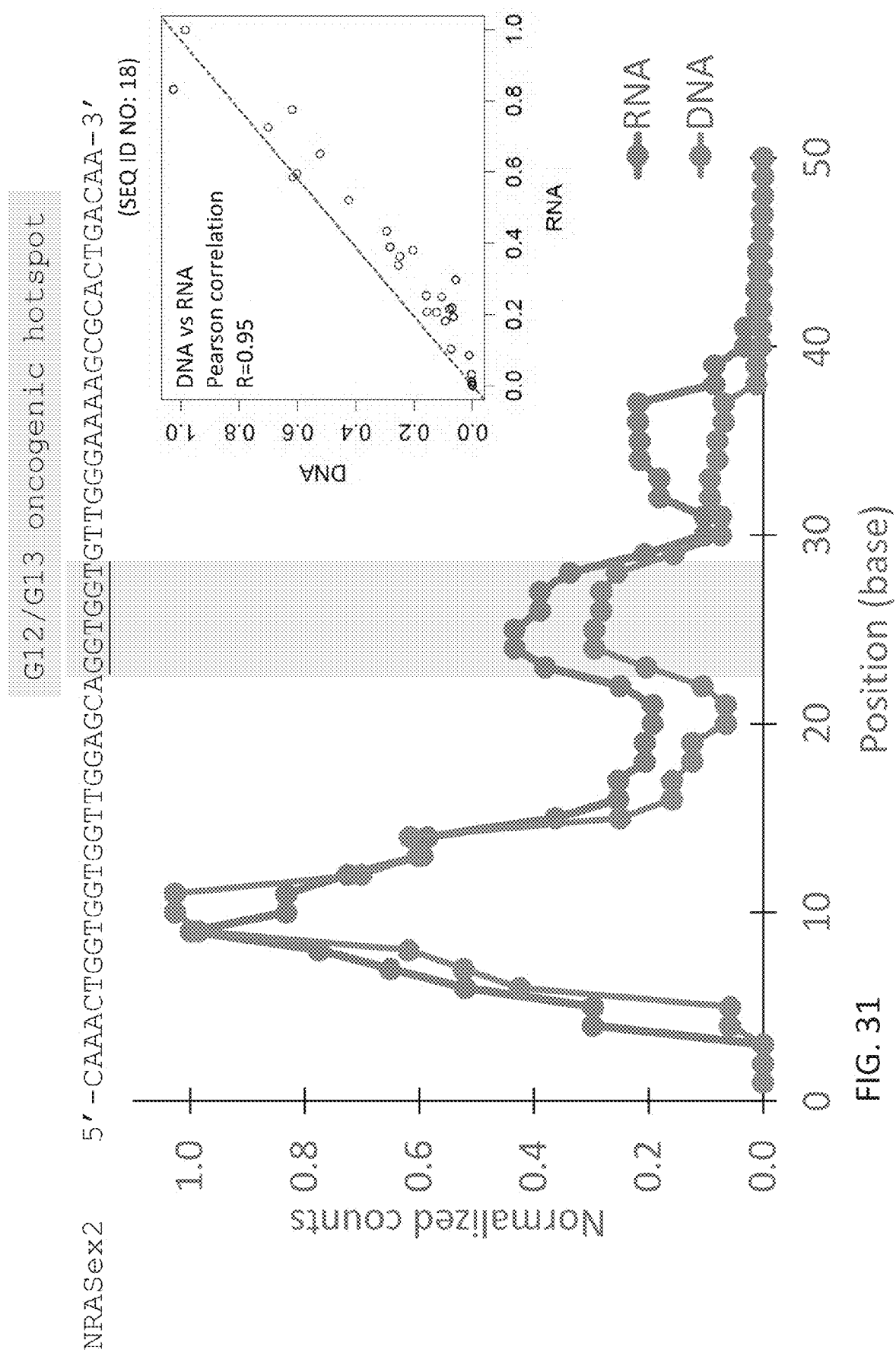
FIG. 31 shows the sequencing of a RNA molecule and a DNA molecule that have the same nucleotide sequence using the sequencing method of the present disclosure.

FIG. 31 shows the results from an experiment to validate direct single-molecule RNA sequencing using the sequencing method of the present disclosure. Native RNA molecules encoding a fragment of NRASex2 (SEQ ID NO: 18) were captured directly without cDNA conversion and immobilized onto a sequencing flow cell and sequenced using the present methods. The experiment was also repeated using captured DNA molecules instead of RNA. FIG. 31 shows that sequencing coverage for DNA and RNA was comparable, demonstrating that RNA can be directly sequenced without conversion to cDNA using the sequencing method of the present disclosure.

FIG. 24 shows an example of integrated capture of RNA and DNA from a FFPE sample. The left panel of FIG. 24 is an illustrative schematic of how the methods of the present disclosure can be used to concurrently capture, detect, and sequence both gDNA and mRNA from a FFPE sample. Sample are prepared using the same FFPE workflow described in Example 3. The same capture protocol is used, but with RNA- and DNA-specific capture probes. The DNA and RNA molecules are concurrently sequenced in the same flow cell with the same sequencing probes. The right panel of FIG. 24 shows the results from an experiment to concurrently capture and detect NRAS RNA and DNA from a tonsil FPPE sample. The fluorescence image shows that both RNA and DNA can be captured and detected. The bar graph demonstrates that specific RNA and DNA capture probes are required to concurrently capture RNA and DNA.

Figure 32:
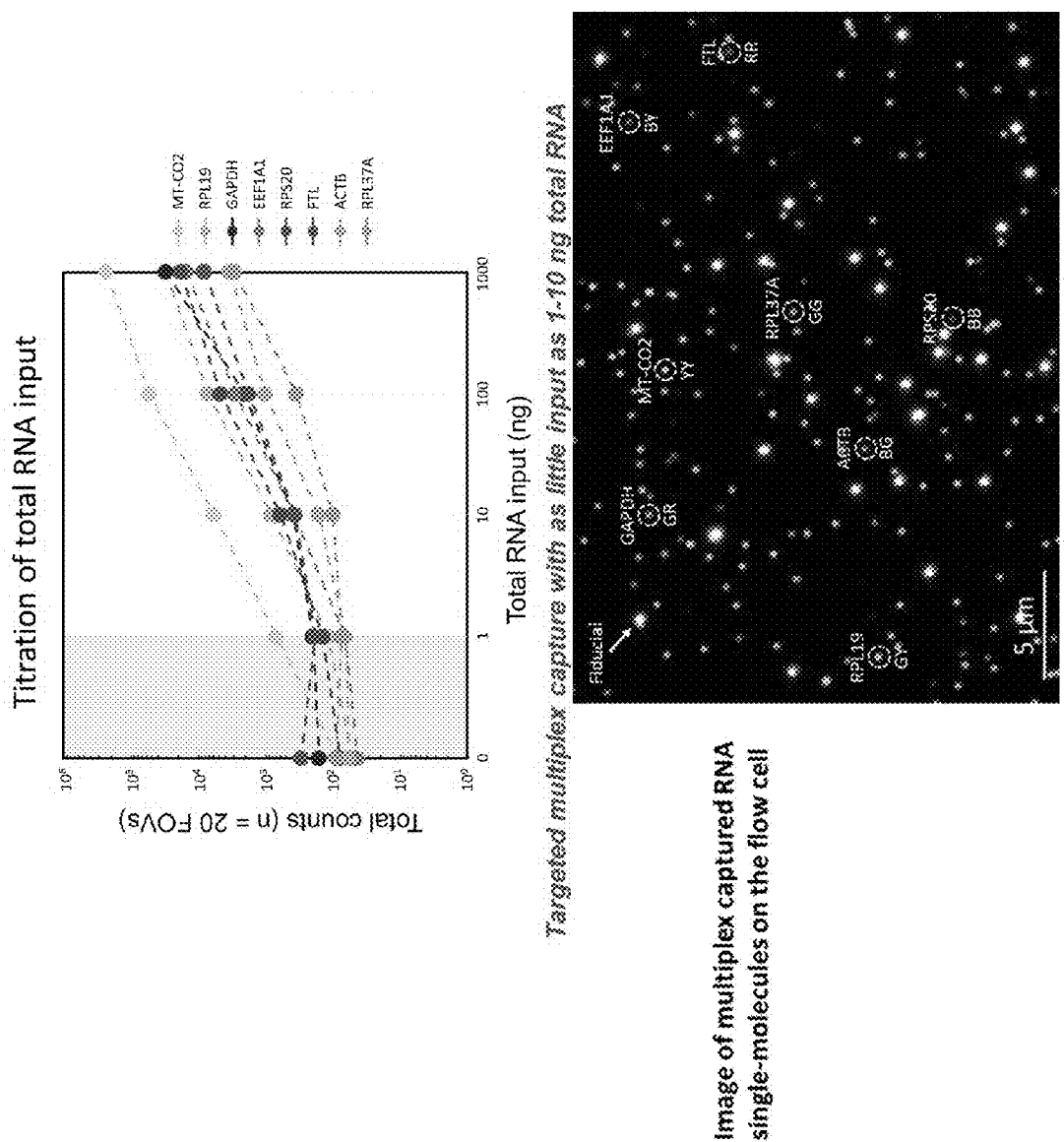
FIG. 32 shows the results of a multiplex target capture of an RNA panel.

FIG. 32 shows the results of a multiplex target capture of an RNA panel. Multiplex capture of 8 mid-to-high expressing transcripts on Human Universal Reference RNA with various input amounts of total RNA (0 ng, 1 ng, 10 ng, 100 ng, 1000 ng) was performed. Multiplexed captured RNA molecules were immobilized onto a flow cell and specific sequencing probes and reporter probes were hybridized to the immobilized RNA molecules for quantitation. The bottom panel of FIG. 32 shows a fluorescence image from 100 ng input capture. One example of each RNA is circled with transcript name and corresponding reporter complex color combination used for identification. The top panel of FIG. 32 shows the quantitation of counts for each specific RNA target.

The results in Example 4 show that single-molecule RNA sequencing is achieved with Hyb & Seq chemistry. In particular, the results demonstrate: (1) direct RNA sequencing without cDNA conversion; (2) RNA molecules are stable throughout the Hyb & Seq cycling process; (3) both RNA and DNA molecules can be captured and sequenced in one Hyb & Seq workflow; and (4) target capture of mRNA panel can be performed with as little as 10 ng of total RNA input.

Figure 33:
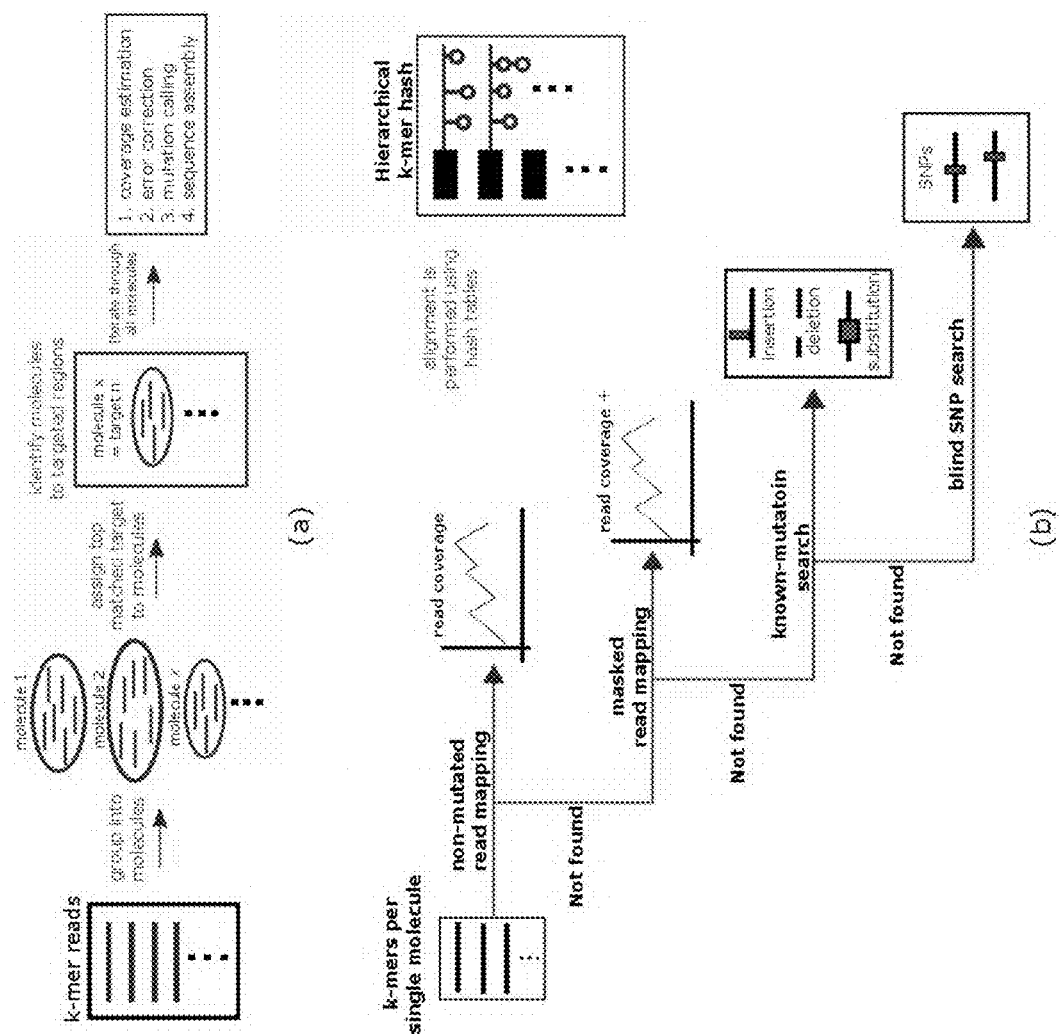
FIG. 33 shows a schematic overview of the steps of the ShortStack™ software pipeline.

Example 5—Integrative Bioinformatics Algorithm for High Throughput Molecule-Level Short-Reads Generated from Hyb & Seq Sequencing Platform The ShortStack™ software is designed to perform standard sequencing-based bioinformatics analysis tasks such as alignment, error-correction, mutation-calling, and read assembly. FIG. 33 shows a schematic overview of the steps of the ShortStack™ software pipeline, including: alignment of hexamers and coverage estimation; mutated sequence identification; graph data structure construction; and/or molecule level sequence reconstruction and error correction.

All algorithms were performed strictly within the information obtained from a single molecule, ensuring that the final mutation call results were not biased by the mutation frequency of the sample. Hexamers were grouped into different molecules according to the panel binding position. To assign molecules to targets, the hexamers were aligned per molecule to all different target regions and the top matched gene target was selected.

A statistical metric was measured to assess the quality of the molecule identification. The alignment against N different target regions produces a distribution of N summed coverage values for each target. The top summed coverage score match was selected as the correct match. Z-score statistics of the selected top match score against the score distribution of all N different targets were measured. Low confidence molecule identifications (under z-score of 2.5 sigma) were filtered out.

Key Advantages of ShortStack™ algorithm include: accurately handles possible sequence ambiguities by implementing a hierarchical hash index design; and/or advanced algorithm design structure assures the mapping quality by prioritization and prevents the overestimation of mutations.

In addition, the mutation graph data structure enables computational modeling of various types of mutations (substitution, insertion, and deletion) and produces output for sequence reconstruction and variant calling: substitution variants are represented as additional nodes in the graph of same length with the original sequence; insertions can be modeled by adding any length of connected nodes; deletions are modeled as adding an artificial node in the graph with empty base pair string; in a blind mutation search (i.e. a search for mutation tolerant sequence alignments), hamming distances are measured from every reference sequence position and new nodes are added to the graph representing searched mutations; and/or coverage estimation for mutated hexamers is performed using the hierarchical hash table.

The constructed graph data structure enables molecule level sequence reconstruction and instrument error correction. In the constructed graph, the dynamic programming algorithm was applied to find the best scoring path where the score was defined as the normalized base coverages. The best scoring path of the graph represented the molecule level sequence reconstruction. The correct mutated sequences were included, while the instrument errors in hexamers were discarded.

Figure 34:
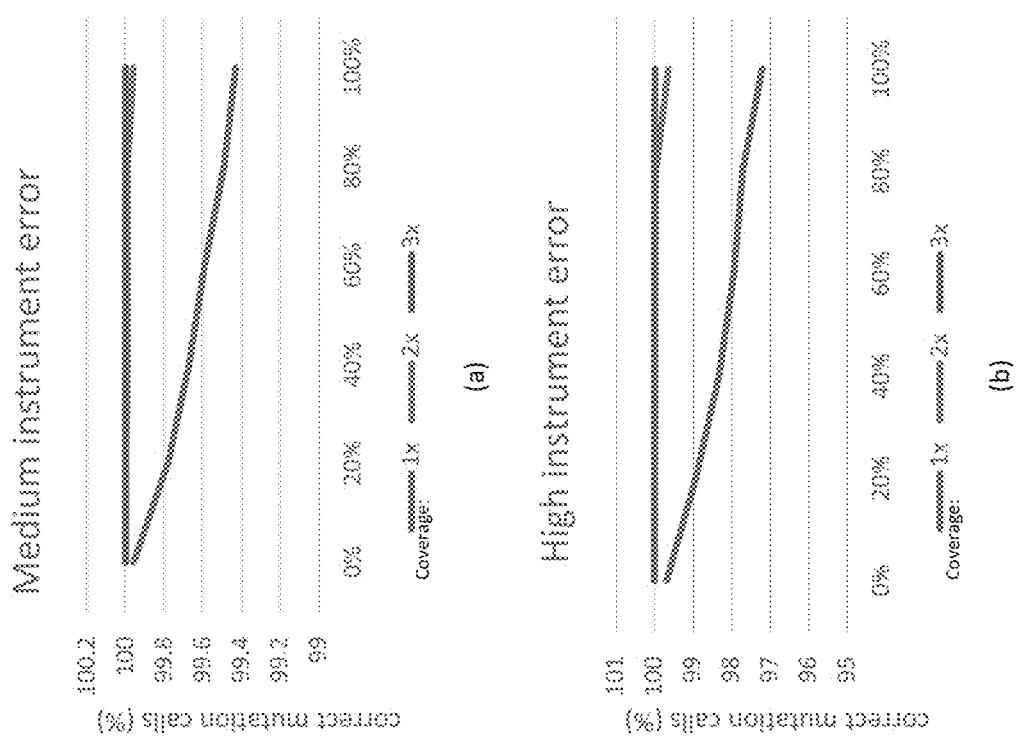
FIG. 34 shows the results of mutational analysis of simulated data sets using the ShortStack™ software pipeline.

Simulated data sets confirmed that the software was able deliver highly accurate molecule level sequence assembly and mutation calling results. FIG. 34 shows the results of mutational analysis of simulated data sets using the ShortStack™ software pipeline. These results show the mutation calling accuracy for 10 random mutations. In medium instrument error datasets, the accuracy showed 99.39% (targeted search) and 98.02% (blind search) on average. Under the elevated instrument error simulations, the performance showed 97.19% (targeted search) and 93.53% (blind search) on average. When the molecule level base coverage threshold was increased to 2×, results improved to 99.5% (2× coverage) and 99.9% (3× coverage).

Figure 35:
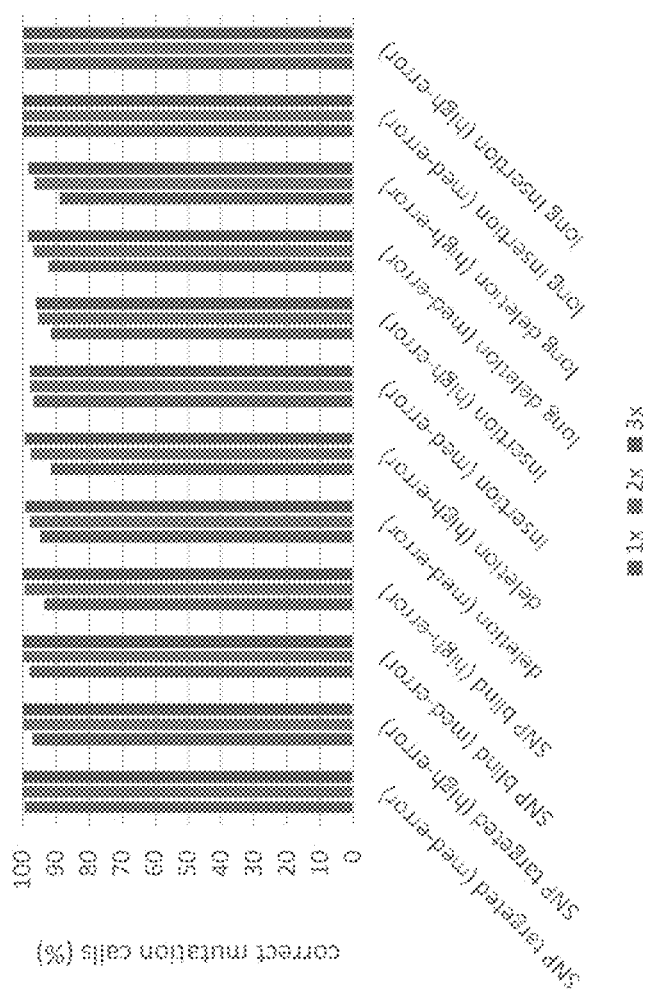
FIG. 35 shows the overall mutation calling accuracy of the ShortStack™ software pipeline for various types of mutations.

The ShortStack™ software can process a broad scope of various mutations. FIG. 35 shows the overall mutation calling accuracy, where each bar represents averaged value from 10 different mutated targets across various types of mutations. The length of insertions and deletions is selected between 1 bp and 15 bp. These results show that the mutation calling accuracy was 94.4% (1× coverage), 97.7% (2× coverage), to 98.5% (3× coverage).

Example 6—Sample Preparation for Processing FFPE Tissue for Hyb & Seq

Formalin-fixed paraffin embedded (FFPE) tissue is a challenging sample input type for traditional sequencing platforms. Hyb & Seq's sample preparation methods successfully process FFPE tissue inputs for downstream sequencing. First, the nucleic acid(s) to be sequenced is extracted from formalin-fixed, paraffin embedded (FFPE) tissue in a single-step process. One or more 10 µm thick FFPE curl is heated in an aqueous-based nucleic acid extraction buffer to simultaneously melt the paraffin wax, decompose the tissue, and release nucleic acid from the cells. Suitable extraction buffers are known in the art and typically include proteinases, detergents such as Triton™-100, chelating agents such as EDTA, and ammonium ions. The FFPE curl and extraction buffer are incubated at 56° C. for 30 minutes to separate the paraffin from the tissue and allow the Proteinase K to digest the tissue structure and expose the embedded cells to the detergent to enable cell lysis. The solution is inverted three times at 8 minute intervals to assist in mixing of the reagents during the tissue deparaffinization and digestion process. Following this step, the solution is heated to 98° C. to facilitate the reversal of the formaldehyde cross-links to further assist in the extraction of nucleic acids.

Once the nucleic acids have been extracted from the FFPE tissue, the solution is filtered using a glass fiber filter with 2.7 µm pore size (Whatman) to remove tissue debris and congealed paraffin. The resulting solution is a homogenous, semi-opaque solution containing nucleic acids which are highly fragmented due to the formalin-fixation process and storage conditions. If further fragmentation is required, the DNA can be mechanically sheered using a Covaris focusedultrasonicator. Due to buffer conditions, extended sonication is required to shear the nucleic acids. Sonicating using the standard settings of 50 W peak incident power, 20% duty factor, 200 cycles/burst were used for 600 seconds to achieve the maximal increase in targets captured. To achieve shorter fragment length, emulsified paraffin can be precipitated out of the filtered solution by centrifuging at 21,000 g and 4° C. for 15 minutes. This allows the DNA to be sheared down to about 225 bp, Next, target capture is performed by binding pairs of capture probes to target nucleic acid molecules during a rapid hybridization step. The 5' capture probe contains a 3' oligo composed of the same sequence as the sequencing window to hybridize to targets' antisense strand and prevent reannealing. The solution containing the capture probes is heated to 98° C. for 3 minutes to denature the genomic DNA, followed by a 15-minute incubation at 65° C. The concentration of NaCl in the range of 400 mM to 600 mM is used for this hybridization reaction. A panel of over 100 targets that have been experimentally validated is listed in the Table 3, detailing the gene and exon of the targeted DNA region.

TABLE 3

| Gene and Exon of targeted DNA regions | | | | | |
|---|---|---|---|---|---|
| Gene | Target | Gene | Target | Gene | Target |
| ABL1 | ABL1_ex4 | EZH2 | EZH2_ex8 | NOTCH1 | NOTCH1_ex26 |
|  | ABL1_ex6 |  | EZH2_ex11 | NRAS | NRAS_ex2 |
|  | ABL1_ex7 |  | EZH2_ex15 |  | NRAS_ex3 |
| AKT1 | AKT1_ex6 | FBXW7 | FBXW7_ex2 |  | NRAS_ex3 |
| ALK | ALK_ex26 |  | FBXW7_ex5 |  | NRAS_ex4 |
| APC | APC_ex5 |  | FBXW7_ex7 | PDGFRA | PDGFRA_ex1 |
|  | APC_ex16 |  | FBXW7_ex8 |  | PDGFRA_ex4 |
|  | APC_ex17 |  | FBXW7_ex9 |  | PDGFRA_ex7 |
|  | APC_ex17 |  | FBXW7_ex10 |  | PDGFRA_ex10 |
|  | APC_ex17 | FGFR1 | FGFR1_ex6 |  | PDGFRA_ex11 |
|  | APC_ex17 | FGFR2 | FGFR2_ex7 |  | PDGFRA_ex14 |
|  | APC_ex17 | FLT3 | FLT3_ex11 |  | PDGFRA_ex15 |
| ATM | ATM_ex8 |  | FLT3_ex12 |  | PDGFRA_ex16 |
|  | ATM_ex9 |  | FLT3_ex21 |  | PDGFRA_ex18 |
|  | ATM_ex11 | GNAQ | GNAQ_ex5 |  | PDGFRA_ex23 |
|  | ATM_ex26 | IDH1 | IDH1_ex4 | PIK3CA | PIK3CA_ex2 |
|  | ATM_ex34 |  | IDH1_ex10 |  | PIK3CA_ex3 |
|  | ATM_ex39 | IDH2 | IDH2_ex4 |  | PIK3CA_ex7 |
|  | ATM_ex49 | JAK2 | JAK2_ex3 |  | PIK3CA_ex10 |
|  | ATM_ex49 |  | JAK2_ex7 |  | PIK3CA_ex14 |
|  | ATM_ex55 |  | JAK2_ex14 |  | PIK3CA_ex21 |
|  | ATM_ex59 |  | JAK2_ex20 |  | PIK3CA_ex21 |
| BRAF | BRAF_ex8 | KDR | KDR_ex7 | PTEN | PTEN_ex5 |
|  | BRAF_ex11 |  | KDR_ex7 |  | PTEN_ex7 |
|  | BRAF_ex13 |  | KDR_ex9 |  | PTEN_ex8 |
|  | BRAF_ex15 |  | KDR_ex11 | PTENP1 | PTENP1_ex1 |
| CDH1 | CDH1_ex9 |  | KDR_ex27 | RB1 | RB1_ex10 |
| CSF1R | CSF1R_ex3 |  | KDR_ex30 |  | RB1_ex17 |
|  | CSFIR_ex22 | KIT | KIT_ex5 |  | RB1_ex17 |
| CTNNB1 | CTNNB1_ex3 |  | KIT_ex9 |  | RB1_ex20 |
|  | CTNNB1_ex6 |  | KIT_ex14 |  | RB1_ex22 |
|  | CTNNB1_ex16 |  | KIT_ex14 | RET | RET_ex12 |
| EGFR | EGFR_ex3 |  | KIT_ex17 |  | RET_ex15 |
|  | EGFR_ex10 |  | KIT_ex18 | SMAD4 | SMAD4_ex3 |
|  | EGFR_ex15 | KRAS | KRAS_ex2 |  | SMAD4_ex8 |
|  | EGFR_ex18 |  | KRAS_ex3 |  | SMAD4_ex9 |
|  | EGFR_ex20 |  | KRAS_ex4 |  | SMAD4_ex10 |
|  | EGFR_ex21 | MEK | MEK_ex3 |  | SMAD4_ex11 |
| ERBB2 | ERBB2_ex7 | MET | MET_ex2 | SMARCB1 | SMARCB1_ex5 |
| ERBB4 | ERBB4_ex4 |  | MET_ex3 | TP53 | TP53_ex4 |
|  | ERBB4_ex5 |  | MET_ex11 |  | TP53_ex6 |
|  | ERBB4_ex7 |  | MET_ex14 |  |  |
|  | ERBB4_ex8 |  | MET_ex16 |  |  |
|  | ERBB4_ex23 |  | MET_ex19 |  |  |
|  | ERBB4_ex25 | MLH1 | MLH1_ex12 |  |  |
|  |  |  | MLH1_ex16 |  |  | biotin moiety, which allows the target to bind to a streptavidin-coated flow cell surface during the target deposition process. The 3' capture probe contains a 5' tag sequence (G-sequence) that enables binding to beads during the purification process. The reaction rate is driven by the capture probe concentration which are added in the low nanomolar range to maximize the reaction rate. The capture probes hybridize to the target in a manner that flanks to region of interest in order to generate a sequencing window. For each DNA target, the capture probe set also includes an After the targeted DNA regions are bound with capture probes, they are purified from the rest of the genomic DNA to create an enriched solution of the targets. Beads coated with the anti-sense oligo (anti G-sequence) to the 3' capture probes' binding sequence are incubated with the capture reaction mix for 15 minutes at room temperature. After the binding step, the beads are washed three times with 0.1× SSPE to remove non-target DNA and the biotin-containing 5' capture probes. Following the washes, the beads are re-suspended in 14 μL of 0.1×SSPE then heated at 45° C. for 10 minutes to elute the purified DNA targets from the beads. After elution, 1 µL of 5 M NaCl is added to ensure the capture probes remain bound to the DNA targets.

The final step of the sample preparation process is the deposition of the DNA targets onto the flow cell surface, where they can be analyzed using the probes of the present disclosure as disclosed herein. A syringe pump is utilized to control the rate at which the targets are loaded into the flow cell fluidic channel, such that all targets have time to diffuse across the height of the channel and bind to the streptavidin surface. This method of loading generates a density gradient of targets, where the highest number of molecules per unit area is greatest at the fluidic channel inlet and decreases along the channel length in the direction of the fluidic flow towards the outlet. A flow rate of 0.35 µL/second achieves a quantitative capture within a channel length of about 10 mm for a channel width of 1.6 mm and height of 40 µm. Once the targets are bound to the surface by the biotinylated 5' capture probe, a solution of biotinylated oligo (G-hooks) that are the reverse complement of the 3' capture probes' bind sequence are injected to pin down the free end of the targets to create a bridged structure, where the ssDNA region in the middle is the sequencing window of interest. Next, a solution of G-sequence oligos are added to hybridize to the excess G-hooks on the surface to reduce the amount of ssDNA on the surface. FIG. 11 shows the capture of a target nucleic acid using a two capture probe system of the present disclosure.

Example 7—Multi-Color Reporter Image Processing for Hyb & Seq

The image processing pipeline includes the following steps background subtraction, registration, feature detection, and classification. In background subtraction, the mean background of any given channel is a function of shot noise and exposure. In our system, the blue channel has the highest background levels coupled with greater variance. A simple tophat filter with a circular structuring element of radius 7 pixels is applied to perform localized background subtraction. For registration, it is imperative that the features of interest as perfectly aligned for multi-color and multi-cycle feature analysis. This system requires two forms of registration. For the first form, a local affine transformation is applied to all image channels within a single acquisition stack. This transformation is a function of the optical system and hence is consistent for a given instrument. This function is computed in advance for every run and is applied to every image acquired. For the second form, a global transformation in the form of a rigid shift is computed using normalized cross-correlation to capture drift of the mechanical gantry during the run. The next step is feature detection.

Once all the images are registered, features are detected using a matched filter via a LoG (Laplace of Gaussian) filter. The filter is applied with a fixed kernel size (matched to the diffraction limit of the features) and a varying standard deviation (matched to the wavelength of the corresponding channel) to match to enhance spot response. Local maxima are used to identify potential reporter locations. The associated intensity values for each identified feature are retrieved for classification. The final step is classification. The multi-color reporter intensities are classified using the Gaussian naïve-Bayes model. The model assumes that the reporter intensities are independent and follow a normal distribution. The model then calculates the probability that a specific feature $\hat{y}$ (specified by intensities in all channels $\hat{x}_i$) belongs to a certain class ($C_k$) using a maximum a posteriori or MAP rule:

$$\hat{y} = \mathrm{argmax}_{\{k \in \{1, \ldots K\}\}} \, p(C_k) \prod_{i=1}^{n} P(x_i \mid C_k)$$

Figure 36:
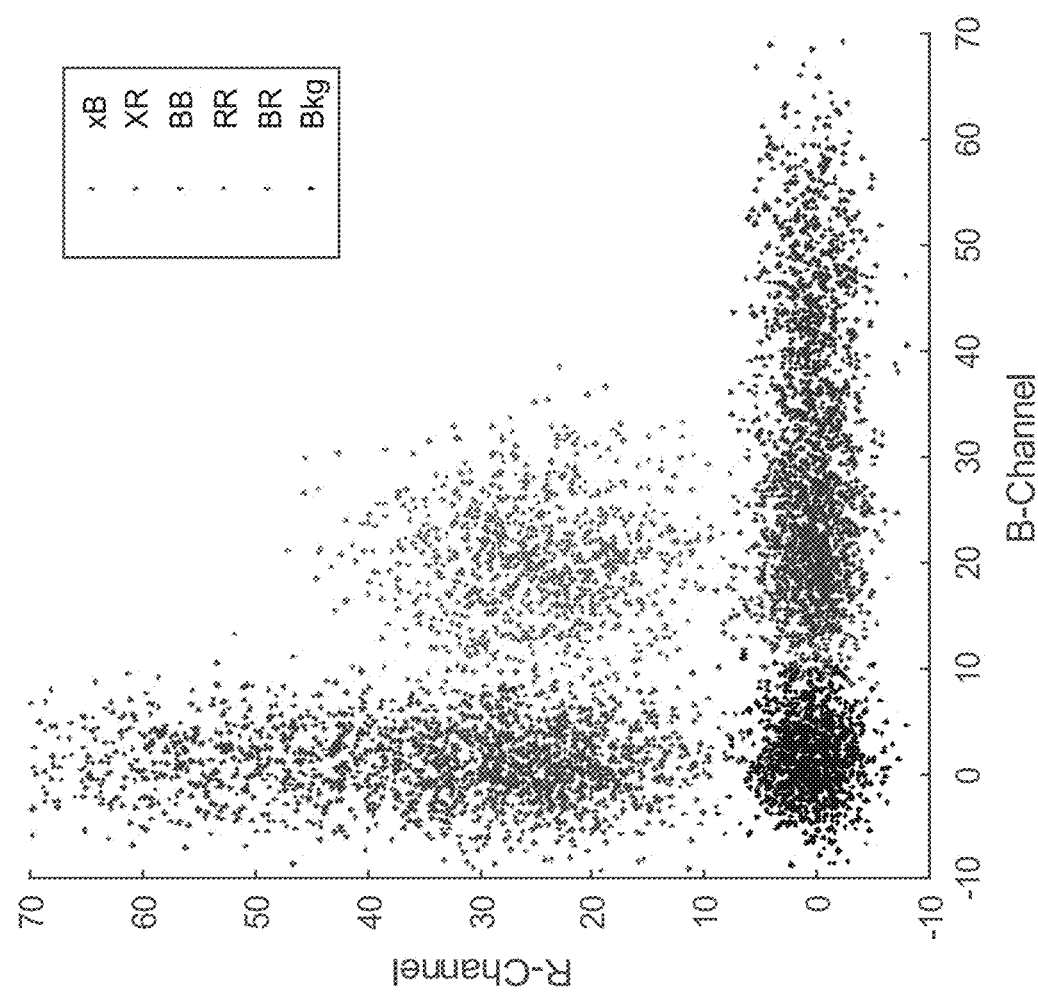
FIG. 36 the intensity distributions for a reporter complex labeled with particular color combinations.

The intensity distributions for a reporter complex labeled with a particular color combinations is shown in FIG. 36. FIG. 36 illustrates the coding scheme using 2 dyes: blue and red. There are six classes (including background) possible in a 2-color coding scenario. In the implemented system, the choice of four colors results in 14 potential classes. Note that there is some overlap between the single half dye vs full dye distributions. Consequently, classification between these classes presents a higher error rate, with a maximum miss-classification rate of 11.8% between 'xG' and 'GG'. The miss-classification rates for the 10 Class model is less than 0.2%. Since each reporter requires a maximum of eight classes, it is simple to choose the ones with least classification error. The detected color code is translated into an identified base pair based on a look up table. Using the probes of the present disclosure as disclosed herein, a feature is tracked across multi-cycles.

Example 8—Target Nucleic Acid Purification and Deposition Using Capture Probes

To capture target nucleic acid molecules, a two capture probe system is used for highly specific enrichment. Capture probes are designed to bind to the target nucleic acid at positions flanking the targeted region of interest, creating a "sequencing window". The 5' capture probe, referred to as CapB, contains a 3' biotin moiety. The 3' capture probe, referred to as CapA, contains a 5' affinity tag sequence, referred to as the G-sequence. On average, capture probes are approximately 40 nucleotides in length and designed based on Tm and sequence context. Sequencing windows are around 70 nucleotides in length and are easily adjusted. FIG. 11 shows a schematic of the two capture probe system.

The biotin moiety on CapB tethers the target nucleic acid to a streptavidin-coated flow cell surface for sequencing. The affinity tag on CapA allows for the reversible binding of target nucleic acid molecules to magnetic beads during purification. The use of CapA and CapB allows for highly stringent target enrichment since both probes remain bound to a single target nucleic acid molecule in order for that target to survive both the magnetic bead purification and the surface deposition process. Multiplexed capture has been demonstrated with up to 100 targets at once. In order to achieve an efficient capture within a short period of time, capture probes are added at the concentration range of 1 nM to 10 nM.

In experimental tests, a panel of ~10 target nucleic acid molecules were purified using G-beads and the two probe capture system. CapA and CapB probes were first hybridized to target nucleic acids. The G-sequence portion of the bound CapA probes were then hybridized to the G-hooks on the G-beads, thereby linking the target nucleic acid molecule to the G-beads. A series of stringent washes using 0.1×SSPE was performed to remove non-targeted DNA and unbound CapB. To release the target nucleic acid molecules from the G-beads, a low-salt, 45° C. elution was performed to denature the G-sequence while still permitting CapA and CapB to remain hybridized to the target nucleic acid.

Tests show that when purifying a panel of ~100 target nucleic acid molecules, the non-specific/background signal increases significantly. This increase in background could be due to several factors including: (1) increased interactions between CapA and CapB probe species, which leads to increased amounts of free CapB probe carried through purification; and (2) increased interaction between CapB probes and the G-hooks or the G-beads, which leads to the purification of unwanted target nucleic acids. Furthermore, as the size of the panel increases, the possible interactions between CapB species, CapA species, and sequencing probes increase exponentially. These interactions can interfere with the ability to densely deposit targets and lead to wasted sequencing reads.

To reduce non-specific and background signal due to the purification of free probe species and unwanted target nucleic acid molecules, several modifications to the purification procedure can be made. First, the inclusion of formamide at a concentration of 30% v/v in the buffer used during the binding of target nucleic acid molecules to G-beads decreases background counts by two-fold (as measured by counts in controls lacking target molecules), likely through interfering with imperfect hybridizations of free capture probe with G-hooks, allowing excess probes to be washed away. Secondly, the inclusion of four iso-dG bases in the G-hook on the G-beads (iso-G-hooks) and the complementary iso-dC bases in the CapA G-sequence decreases background counts by three-fold (as measured by counts in controls lacking target molecules). Iso-dC and iso-dG are isomer variants of the natural dC and dG bases. Since, iso bases will base-pair with other iso bases but not natural bases, imperfect hybridization between capture probes and iso-G-hooks can only exist between the non-iso bases of the G-sequence and iso-G-hooks. These imperfect interactions are more easily disrupted during stringent washes. Finally, subsequent purification of the iso-G-bead eluates with Ampure® XP (Agencourt Biosciences Company) beads further decreases background counts by at least 20-fold (as measured by counts in controls lacking target molecules). During, Ampure® XP bead purification, a DNA sample is mixed with a suspension of carboxylated magnetic beads in a solution of polyethylene glycol (PEG) and NaCl. The concentration of PEG and NaCl can be titrated such that only molecules above a molecular weight threshold precipitate and bind to the beads. Hyb & Seq targets hybridized to capture probes are on the order of 81 kDa, while free probes are on the order of 17 kDa or less. By mixing the Ampure® XP bead suspension with iso-G-bead eluate at a volume ratio of 1.8:1, hybridized targets are bound to the beads and a significant portion of free probes can be washed away before the final elution.

Thus, a model purification workflow consists of the following steps: (1) Hybridization of capture probe-target nucleic acid assemblies to iso-G-beads in 5×SSPE/30% formamide; (2) Washing of the iso-G-beads with 0.1×SSPE; (3) Elution of capture probe-target nucleic acid assemblies at 45° C. in 0.1×SSPE; (4) Binding of iso-G bead eluates to a 1.8× volume of Ampure® XP beads; (5) Washing of Ampure® XP beads with 75% ethanol; and (6) Elution of capture probe-target nucleic acid assemblies in 0.1×SSPE, such that the targets are eluted in 7.5 µL, followed by the addition of 0.5 µL of 5 M NaCl.

Figure 37:
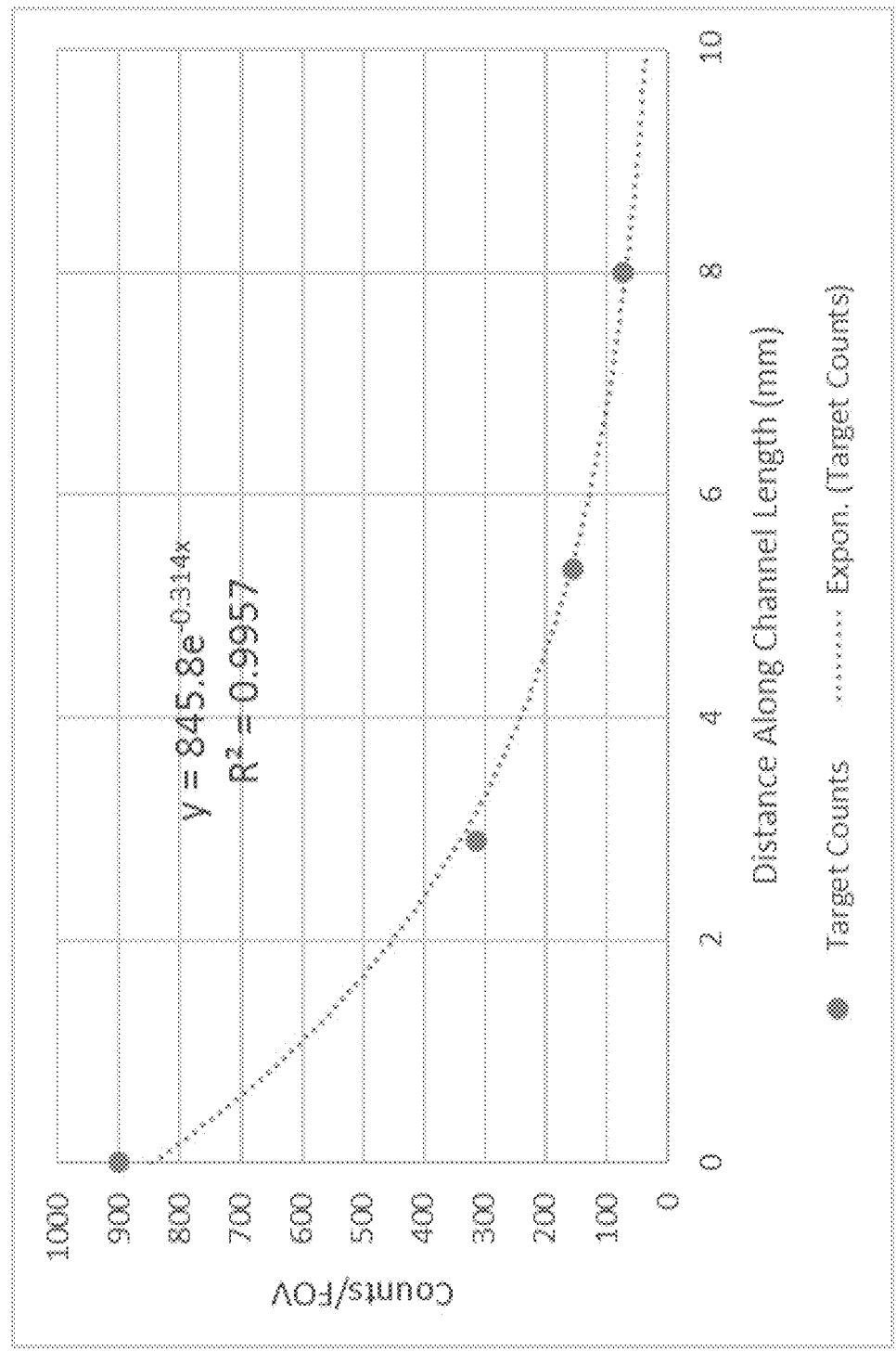
FIG. 37 shows a typical deposition gradient of the present disclosure.

After purification, capture probe-target nucleic acid assemblies are deposited onto the sequencing surface using an infusion syringe pump to slowly inject the purified targets through the flow cell. To determine the deposition gradient, the flow cell is imaged at various positions along the channel length. A typical deposition gradient is shown in FIG. 37. For a channel height of 20 µm, loading the sample at a flow rate of 0.167 µL/min will concentrate the targets such that 80% of all targets bind within 5.1 mm along the channel length, which represents ~240 FOVs for the Gen2 imager with a FOV of 0.0357 mm$^2$ and flow cell channel width of 1.7 mm. The gradient can be modulated by adjusting the flow rate during deposition.

Figure 38:
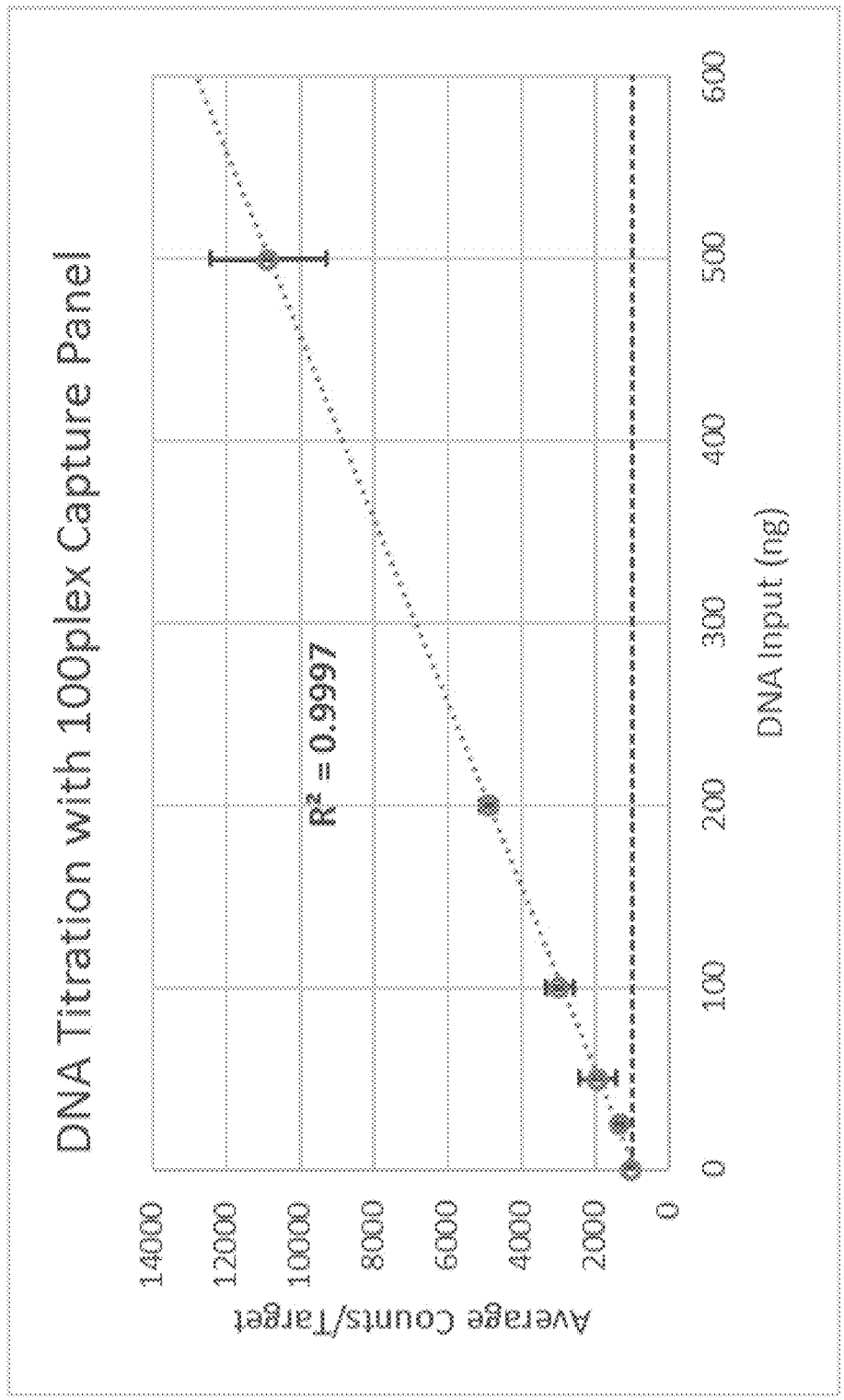
FIG. 38 shows the capture efficiency of the present disclosure during a titration of DNA mass inputs between 25 ng to 500 ng.

The procedures described above were used to test the purification and deposition of a 100 plex target nucleic acid panel with genomic DNA sheared to a size of ~300 base pairs. A series of experiments was performed in triplicate with a range of DNA input between 25 ng and 500 ng. The total number of targets on the flow cell was extrapolated by imaging the deposition gradient to obtain the number of average counts, as shown in FIG. 38. The capture efficiency was 6.6% and was consistent over the range of DNA mass inputs.

Example 9—Design and Features of Sequencing Probes

Sequencing probes hybridize to a target nucleic acid molecule via a target binding domain. In the present example, the target binding domain is 8 nucleotides long and contains a locked nucleic acid (LNA) hexamer that is flanked by (N) bases that can be a universal/degenerate base or a canonical base ($N_1$-$B_1$-$B_2$-$B_3$-$B_4$-$B_5$-$B_6$-$N_2$, where $B_1$ to $B_6$ are LNAs and $N_1$ and $N_2$ are universal/degenerate bases or a canonical base that is independent of the nucleic acid sequence of the (6-mer) sequence $B_1$-$B_2$-$B_3$-$B_4$-$B_5$-$B_6$). A complete set of 4,096 sequencing probes encodes all possible hexamers and enables sequencing of any target nucleic acid. Each sequencing probe also includes a barcode domain that encodes for the hexamer sequence present in the target binding domain. Each barcode domain contains three positions (R1, R2, and R3). Each position in the barcode domain corresponds to a specific dinucleotide in the hexamer of the target binding domain and contains a unique sequence that can bind to a specific labeled reporter complex. A schematic overview of sequencing probes are shown in FIG. 1. Each position in the barcode domain encodes eight "color combinations", created using four fluorescent dyes: blue (B); green (G); yellow (Y); and red (R). During each cycle of sequencing, a reporter complex is bound to one of the three positions in the barcode domain, indicating the identity of the corresponding dinucleotide in the hexamer of the target binding domain. During three sequential sequencing cycles, three "color combinations" are recorded, one for each position in the barcode domain, allowing for the identification of the entire hexamer of the target binding domain. The 4,096 sequencing probes are split into 8 pools and each is associated with one of 512 possible barcodes.

Example 10—Reporter Complex Design, Purification, and Binding Conditions

In this example, each reporter complex is a 37 DNA oligomer branched structure designed to hold a total of 30 fluorescent dyes, with 15 dyes for each color of the color combination. The 37 DNA oligomers that make up the reporter complex can be classified by their size. The largest oligomer, called the primary nucleic acid, is covalently attached to a complementary nucleic acid that is either 12 or 14 nucleotides in length. The primary nucleic acid is 96 nucleotides long. The primary complementary nucleic acid binds to positions R1, R2, or R3 on the barcode domain of the sequencing probe. The next largest DNA oligomers are 89 nucleotides long and are called secondary nucleic acids. There are six secondary nucleic acids per reporter complex, with three secondary nucleic acids per for each color of the color combination. Each secondary nucleic acid comprises a 14 nucleotide long sequences that allows the secondary nucleic acids to hybridize to the primary nucleic acid. The smallest DNA oligomers are 15 nucleotides long and are called the tertiary nucleic acids. There are 30 tertiary nucleic acids per two color probe, with 15 tertiary nucleic acids per color. Five tertiary nucleic acids bind to each secondary nucleic acid. A schematic of the 37 DNA oligomer branched structure is shown in FIG. 4.

The tertiary nucleic acids include a detectable label in the form of a fluorescent dye. There are four fluorescent dyes: blue (B); green (G); yellow (Y); and red (R). Combining dyes together in a reporter complex results in ten possible two-color combinations (BB, BG, BR, BY, GG, GR, GY, RR, YR, YY). To prevent color-swapping or cross hybridization between different fluorescent dyes, each secondary and tertiary nucleic acid that correspond to a specific fluorescent dye contains a unique sequence. For example, each tertiary nucleic acid labeled with the Alexa 488 fluorophore, or blue color, comprises a complementary sequences only to the blue secondary nucleic acid. The blue secondary nucleic acid further has a distinct sequence that is complementary only to the primary nucleic acid molecules that correspond to a color combination that includes blue.

Each complementary nucleic acid contains a sequence that is distinct between positions R1, R2, and R3 of the barcode domain of the sequencing probe. Thus, even if positions R1 and R2 of the same barcode domain encode for the same dinucleotide, the binding of the complementary nucleic acid molecule that identifies that dinucleotide at position R1 will not bind to position R2. Likewise, the complementary nucleic acid molecule that identifies that dinucleotide at position R2 will not bind to position R1. Complementary nucleic acids are designed such that they can be unbound from the sequencing probe efficiently using competitive toe-hold exchange (for complementary nucleic acids 12 nucleotides in length) or UV cleavage (for complementary nucleic acids 14 nucleotides in length).

Preparation of the reporter complex occurs in two sequential hybridization steps: (1) tertiary nucleic acids to secondary nucleic acids and then (2) tertiary nucleic acids+secondary nucleic acids to the primary nucleic acid. Four separate tertiary nucleic acid-to-secondary nucleic acid reactions are prepared by combining 100 uM of secondary nucleic acids and 600 uM of tertiary nucleic acids in 4.2×SSPE buffer at room temperature for 30 minutes. Twenty-four reporter probes are then prepared separately using 2 uM of primary nucleic acid, 7.2 uM of secondary nucleic acid+Dye #1 tertiary nucleic acid, and 7.2 uM secondary nucleic acid+ Dye #2 tertiary nucleic acid in 4.8×SSPE. These reactions are heated at 45 C for 5 minutes and then cooled at room temperature for 30 minutes. The 24 reactions are then pooled into three different pools corresponding to the barcode domain (i.e. $R_1$, $R_2$, and $R_3$). For example, eight different reporter probes (2 uM each) binding to the $R_1$ barcode domain are pooled together, diluting ten-fold to a final working concentration of 200 nM each reporter complex. The reporter complex can be purified using high pressure liquid chromatography (HPLC). FIG. 39 shows that HPLC purification can remove free oligomers and malformed probes to yield reporter probes.

Following reporter complex preparation is standard testing for quality assurance. Each of the three pools of reporter probes are tested for binding to its corresponding barcode region ($R_1$, $R_2$, or $R_3$) in three separate flow cells. Testing is performed on a modified sequencing probe construct, with only the barcode domain present and immobilized on the flow cell. All eight 12-mers representing each color is multiplexed and all eight reporter probes are expected to be identified with high color counts.

Figure 40:
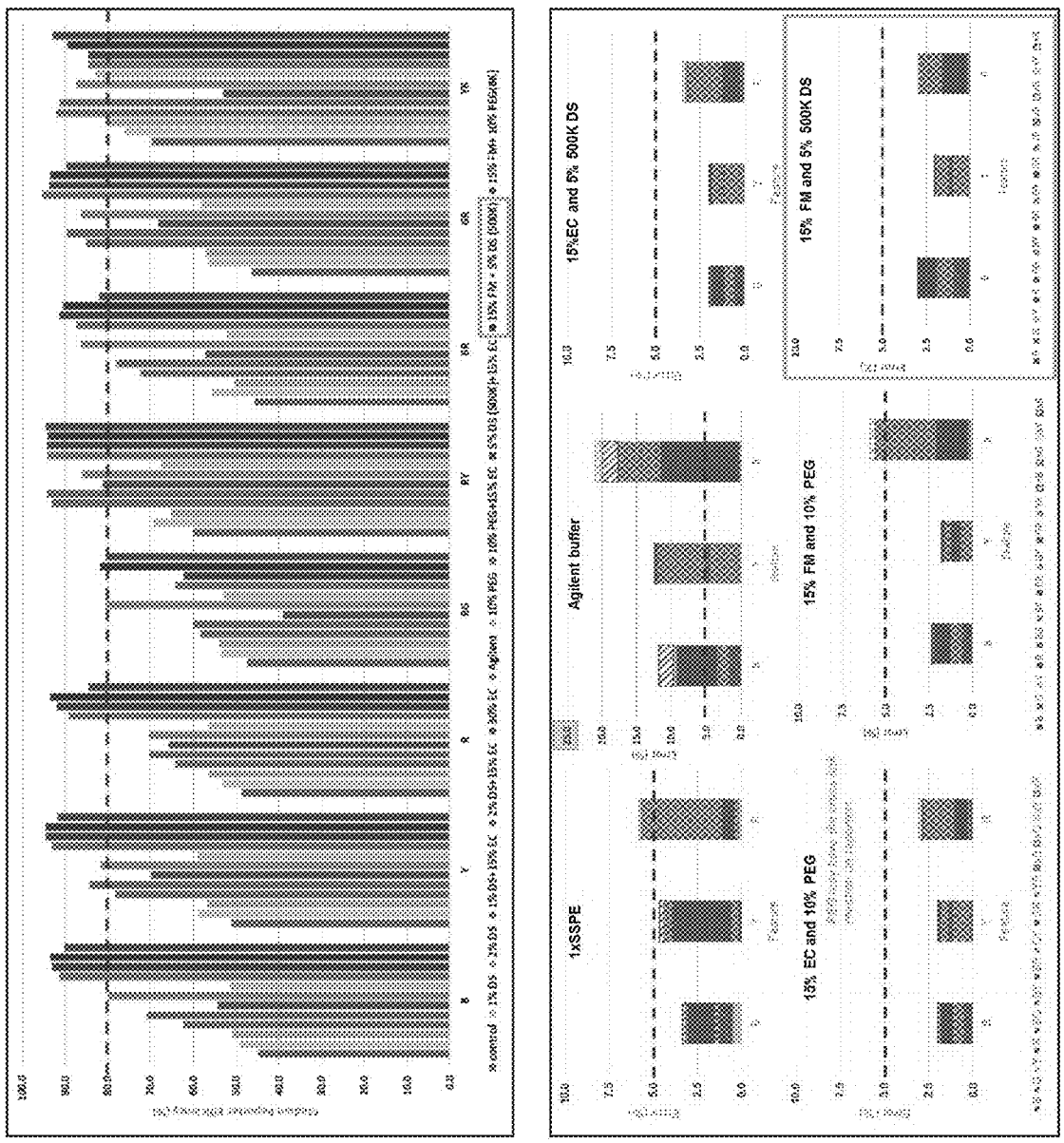
FIG. 40 shows hybridization efficiencies and accuracy of reporter probes of the present disclosure in the presence of different buffer additives.
Figure 41:
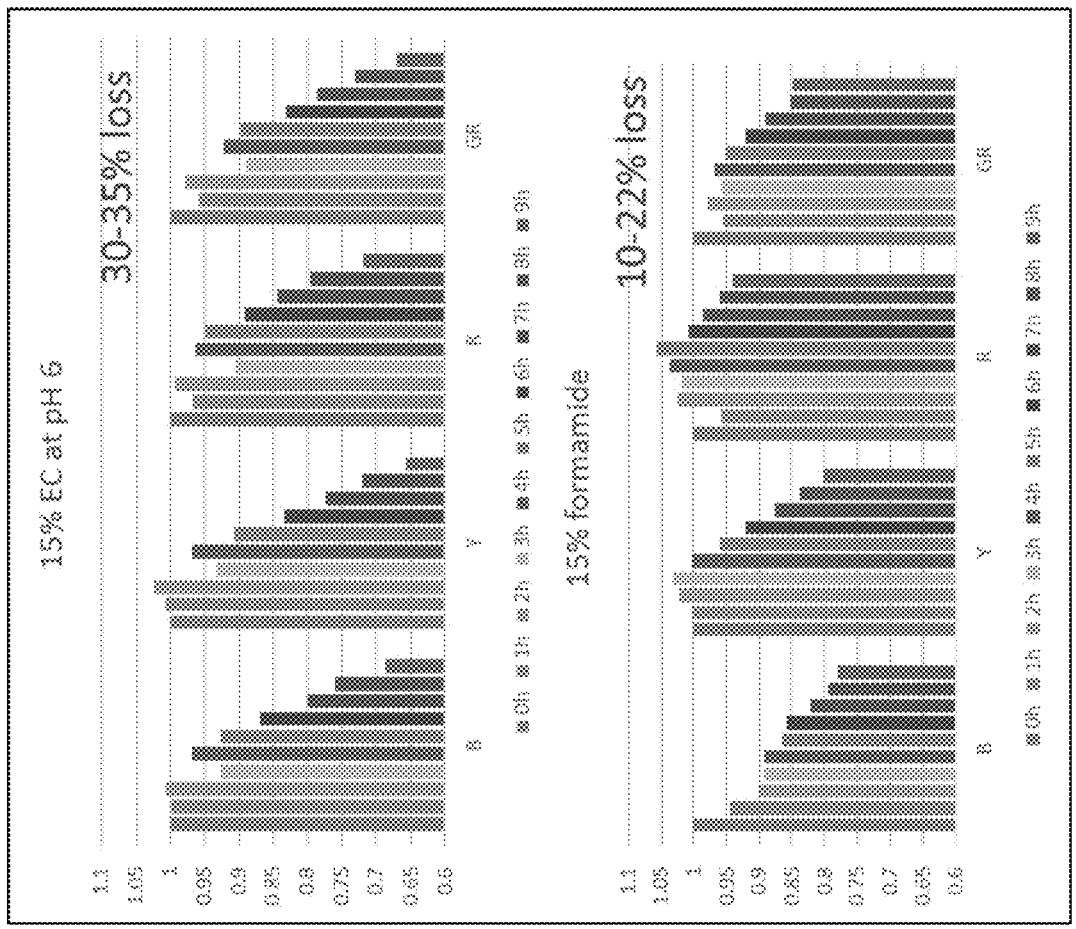
FIG. 41 shows percentage of target nucleic acid loss when the sequencing method of the present disclosure is used in the presence of different buffer additives.

To improve the efficiency and accuracy of hybridization of the reporter probes and the barcode domains of the sequencing probes, various buffer additives were tested. FIG. 40 shows results from experiments that indicate buffers containing 5% Dextran Sulfate (500K) and either 15% Formamide or 15% Ethylene Carbonate allow for the most efficient and accurate hybridization of reporter probes and sequencing probes at short hybridization times. However, FIG. 41 shows results from experiments that indicate Ethylene Carbonate has a negative impact on the surface of the sequencing slide, resulting in high loss of target nucleic acids over time. Thus, buffers containing 5% Dextran Sulfate (500K) and 15% Formamide are superior for efficient and accurate hybridization of the reporter probes and sequencing probes.

Example 11—Design and Validation of Complementary Nucleic Acid Sequences

Reporter probes contain a complementary nucleic acid that binds to a specific position (R1, R2, or R3) on the barcode domain of a sequencing probe. Complementary nucleic acids containing either 12 nucleotides (12 mer) or 14 nucleotides (14 mer) were designed and tested to determine optimal sequences for hybridization. For screening, the following criteria was used to determine optimal sequences: sequences had to display high binding efficiency as defined by reporter and sequencing probe binding at >80% efficiency in 10 sequencing cycles; sequences had to display fast hybridization kinetics occurring within 15 second to 30 seconds; and sequences had to display high specificity with <5% cross-hybridization error in the reporter pool.

Table 4 shows the twenty-four 12 mer sequences (SEQ ID NOs: 19-42) that were identified. Since each barcode domain contains three positions, the twenty-four 12 mer sequences can be divided into three groups to create an 8×8×8 12 mer reporter set.

TABLE 4

| Reporter Position | 12-mer Sequence | Reporter Name | Color | SEQ ID NO |
|---|---|---|---|---|
| 1 | AGGACAGATGAC | R1BB-07 | BB | 19 |
| 1 | GTATCGGATGAC | R1BG-07d(R1RR-06) | BG | 20 |
| 1 | AGGAGTGATGAC | R1BR-07 | BR | 21 |
| 1 | AGGGGTGAGGAG | R1GG-07c(R1YR-07) | GG | 22 |
| 1 | AGAGGGGATGAC | R1GR-07 | GR | 23 |
| 1 | AGTGGGGAGGAG | R1GY-07c(R1BY-07) | GY | 24 |
| 1 | AGCCGAGATGAC | R1RR-07 | RR | 25 |
| 1 | AGGGTGGATGAC | R1YY-07 | YY | 26 |
| 2 | TGGATGGAAAAG | R2 BB (forGRv5) | BB | 27 |

TABLE 4-continued

| Reporter Position | 12-mer Sequence | Reporter Name | Color | SEQ ID NO |
|---|---|---|---|---|
| 2 | GAAGGAGAAAAG | R2_BG (forGYv5) | BG | 28 |
| 2 | GGGGATGAAAAG | R2_BR (forGRv4) | BR | 29 |
| 2 | GTGAGGGAAAAG | R2_BY (forYYv5) | BY | 30 |
| 2 | AGCCGAGAAAAG | R2_GG | GG | 31 |
| 2 | CGAGAGGAAAAG | R2_GY (forGGv5) | GY | 32 |
| 2 | GAGGGCGAAAAG | R2_RR (forGGv4) | RR | 33 |
| 2 | AGCGTGGAAAAG | R2_YY | YY | 34 |
| 3 | TGAGAAGGGTAG | RPTR12-BG_Screen3_D2 | BG | 35 |
| 3 | GTTGTTATTGTG | RPTR12-BR_RC_D4 | BR | 36 |
| 3 | TTTGGGTTTAGG | RPTR12-BY_RC_D3 | BY | 37 |
| 3 | GTTAGTGGGAAA | RPTR12-GR_RC_D7 | GR | 38 |
| 3 | ATGGGAAAAAGT | RPTR12-GY_RC_D6 | GY | 39 |
| 3 | GAGTTGGATGAG | RPTR12-RR_RC_D10 | RR | |
| 3 | ATGTTGTGGGTA | RPTR12-YR_RC_D9 | YR | 41 |
| 3 | GAGGGTTTTAAG | RPTR12-YY_RC_D8 | YY | 42 |

The 14 mer sequences were designed in a similar manner but differ from the 12 mer sequences in three ways. First, 14 mer sequences contain a longer hybridization sequence given that 14 mer sequences contain 14 single stranded nucleotides that bind to a specific position on a barcode domain rather than the 12 single stranded nucleotides present in a 12 mer. Second, 14 mer sequences contain more sequence diversity because they were not designed to accommodate toe-holding-mediated removal. Since 14 mer sequences hybridize more strongly to sequencing probes, the efficiency of toe-holding-mediated removal is decreased. Thus, sequence independent removal strategies were explored for the 14 mer sequences, alleviating sequence constraints during screening. Sequences for screening were designed using an algorithm that includes the following set of rules: Nucleotide composition lacking either "G" or "C" (i.e. low complexity sequences); GC content between 40% to 60%; Melting temperature (Tm) between and 37° C.; Hairpin folding energy (dG)>2; and Compatibility with other sequencing probes (hamming distance >=7). To minimize the hybridization of 14 mer sequences to genomic sequences that can be present in target nucleic acids, potential sequences were filtered using the External RNA Controls Consortium sequences as a guide. Third, 14 mer sequences were designed to be removed from the barcode domains of sequencing probes by strand cleavage using cleavable linker modifications at the point where the 14 mer complementary nucleic acid is attached to the primary nucleic acid of the reporter complex. The removal of the 14 mer sequences results in the "darkening" of the reporter complex signal, allowing for the next cycle of sequencing and signal detection to occur. Various cleavable linker modifications were tested including UV-light cleavable linkers, reducing agent (such as TCEP) cleavable linkers and enzymatically cleavable linkers (such as uracil cleaved by the USER™ enzyme). All of these cleavable linker modifications were found to promote efficient reporter complex darkening. Darkening was further enhanced by the introduction of cleavable linker modifications into the secondary nucleic acids. These cleavable linker modifications were placed between the sequence that hybridizes to the primary nucleic acid and the sequence that hybridizes to the tertiary nucleic acids. FIG. 10 shows the possible positions for cleavable linker modifications within a reporter probe.

Screening of potential 14 mer sequences resulted in the identification of two groups of acceptable sequences. Table 5 shows the first group, which contained 24 sequences (SEQ ID NOs: 43-66). These 24 sequences could be split into three groups to create an 8×8×8 14 mer reporter set.

TABLE 5

| Reporter | 14-mer Sequence | Reporter Name | Color | SEQ ID |
|---|---|---|---|---|
| A | ATCTTTTCCCCACT | R14-BG_RC-Sc3_B2 | BG | 43 |
| A | CCCCACTATTTCTT | RPTR14-BY_Screen4_I2 | BY | 44 |
| A | CTACCCACAACATA | RPTR14-YR_Screen3_D9 | YR | 45 |
| A | CCATATAAACCCCA | R14-GG_RC-Sc3_B5 | GG | 46 |
| A | AAACTCCAATCTCC | R14-GR_RC-Sc3_B7 | GR | 47 |
| A | CTATTCTCAACCTA | RPTR14-YY_RS0255_H8 | YY | 48 |
| A | CCCCCTCTTTTAAA | R14-BB_RC-Sc3_B1 | BB | 49 |
| A | CCAATCTTACCTCA | RPTR14-RR_Screen3_B10 | RR | 50 |
| B | CCCTCACATAACTT | RPTR14-BG_Screen4_I1 | BG | 51 |
| B | CTCCTCTACTTTCC | RPTR14-BB_ERCC_00014.1_10 | BB | 52 |
| B | CCCTAAACCCAAAA | RPTR14-BY_Screen3_D3 | BY | 53 |
| B | CACTTTTTCCCATC | RPTR14-GY_Screen3_D6 | GY | 54 |
| B | CATCTGATTCCTCC | R14-RR_ERCC_00042.1_150RC | RR | 55 |
| B | CTAAACCCCCTACT | R14-BR_RC-Sc3_B4 | BR | 56 |

TABLE 5-continued

| Reporter | 14-mer Sequence | Reporter Name | Color | SEQ ID |
|---|---|---|---|---|
| B | CCTTTACAAACACA | RPTR14-GR_RS0247_H7 | GR | 57 |
| B | ATACCACCCTCTTT | RPTR14-YY_Screen3_B8 | YY | 58 |
| C | TATTCTTCTACCCC | RPTR14-YR_Screen4_15 | YR | 59 |
| C | TCTACCCTTCTCAT | R14-BG_RC-Sc3_D2 | BG | 60 |
| C | CCACAATAACAACC | RPTR14-BR_Screen3_D4 | BR | 61 |
| C | ACCTTAACATTCCC | R14-GG_RC-Sc3_D5 | GG | 62 |
| C | ATTTCCCACTAACC | RPTR14-GR_Screen3_D7 | GR | 63 |
| C | ACTTAAAACCCTCC | RPTR14-YY_Screen3_D8 | YY | 64 |
| C | TACCTATTCCTCCA | RPTR14-BB_Screen3_D1 | BE | 65 |
| C | CCCCTTTCTCTAAG | RPTR14-RR_ERCC_00051.1_220 | RR | 66 |

Table 6 shows the other group, which contained 30 sequences (SEQ ID NOs: 67-96). These 30 sequences could be split into three groups to create a 10×10×10 14 mer reporter set.

TABLE 6

| Reporter | 14-mer Sequence | Reporter Name | Color | SEQ ID |
|---|---|---|---|---|
| A | GATGATGGTAGGTG | R14_PC_J2_BB_v2 | BB | 67 |
| A | ATGAGAAGGGTAGA | R14_PC_D2_BG_v2 | BG | 68 |
| A | GTTTTGTTGGTGAG | R14_PC_K2_BY_v2 | BY | 69 |
| A | TTAGTGTGTTGGAG | R14_PC_K5_BR_v2 | BR | 70 |
| A | ATGTAGGAGAGAGA | R14_PC_L1_GG_v2 | GG | 71 |
| A | GGGAATGTTAAGGT | R14_PC_D5_GY_v2 | GY | 72 |
| A | GGTTAGTGGGAAAT | R14_PC_rcD7_GR_v2 | GR | 73 |
| A | GGAGGGTTTTAAGT | R14_PC_rcD8_YY_v2 | YY | 74 |
| A | GTAGTGTGGATGTT | R14_PC_J5_YR_v2 | YR | 75 |
| A | CTTAGAGAAAGGGG | R14_PC_ERCC51_RR_v2 | RR | 76 |
| B | GGAAGAGGATGAAA | R14_PC_K1_BB_v2 | BB | 77 |
| B | AAGTTATGTGAGGG | R14_PC_spB_BG_v1 | BG | 78 |
| B | GGAAAGTAGAGGAG | R14_PC_spB_BY_v1 | BY | 79 |
| B | TTTTGGGTTTAGGG | R14_PC_spB_BR_v1 | BR | 80 |
| B | AGATGTATGGGTGA | R14_PC_L2_GG_v2 | GG | 81 |
| B | GATGGGAAAAAGTG | R14_PC_spB_GY_v1 | GY | 82 |
| B | GGAGGAATCAGATG | R14_PC_spB_GR_v1 | GR | 83 |
| B | AGAGGGATTGATGA | R14_PC_J4_YY_v2 | YY | 84 |
| B | TGTGTTTGTAAAGG | R14_PC_spB_YR_v1 | YR | 85 |
| B | AAGGAGTGATAGGA | R14_PC_J1_RR_v2 | RR | 86 |
| C | TGGTGATTTAGAGG | R14_J3_BB_v2 | BB | 87 |
| C | GGGGTAGAAGAATA | R14_rc15_BG_v2 | BG | 88 |
| C | AAGAAATAGTGGGG | R14_PC_spA_BY_v1 | BY | 89 |

TABLE 6-continued

| Reporter | 14-mer Sequence | Reporter Name | Color | SEQ ID |
|---|---|---|---|---|
| C | TATGTTGTGGGTAG | R14_PC_spA_BR_v1 | BR | 90 |
| C | GTTAAAGGGAGGTT | R14_K3_GG_v2 | GG | 91 |
| C | TGGGGTTTATATGG | R14_PC_spA_GY_v1 | GY | 92 |
| C | AGGGAATATGGAGA | R14_K6_GR_v2 | GR | 93 |
| C | TAGGTTGAGAATAG | R14_PC_spA_YY_v1 | YY | 94 |
| C | TTTAAAAGAGGGGG | R14_PC_spA_YR_v1 | YR | 95 |
| C | TGAGGTAAGATTGG | R14_PC_spA_RR_v1 | RR | 96 |

After screening, the 8×8×8 12 mer, 8×8×8 14 mer, and 10×10×10 14 mer reporter sets were validated experimentally. For the 8×8×8 12 mer binding scheme, validation was performed using a Hyb & Seq prototype to record 10 sequencing cycles. Three pools of reporter probes were used in both long and short workflow methods. All 512 possible sequencing probe barcode domains were tested. Table 7 shows the experimental steps of the long and short workflow methods.

TABLE 7

| Steps in One Cycle | Long workflow: Reporter hyb without toehold | Short workflow: Reporter hyb with toehold |
|---|---|---|
| 1 | Reporter 1 for 15s, 30s, or 60s | Reporter 1 for 30s |
| 2 | Image | Image |
| 3 | Toehold 1 for 60s to dark | Reporter 2 + Toehold 1 for 15s |
| 4 | Image | Image |
| 5 | Reporter 2 for 15s, 30s, or 60s | Reporter 3 + Toehold 2 for 15s |
| 6 | Image | Image |
| 7 | Toehold 2 for 60s to dark | Wash |
| 8 | Image | Image |
| 9 | Reporter 3 for 15s, 30s, or 60s | |
| 10 | Image | |
| 11 | Wash | |
| 12 | Image | |

Figure 42:
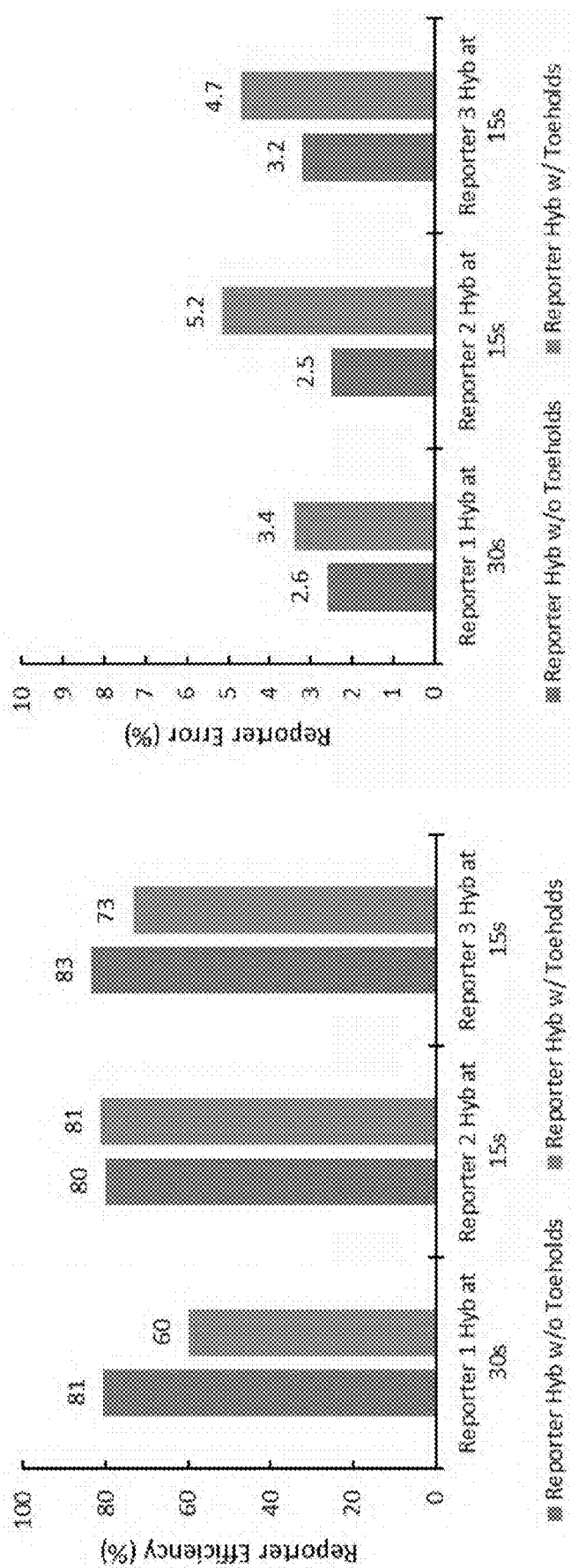
FIG. 42 shows efficiency and error of exemplary reporter probes of the present disclosure that comprise a 12 mer complementary nucleic acid.

Long workflow experiments resulted in >97% darkening efficiency. For short workflow experiments, it was assumed that darkening was about as efficient, however it was expected that a small frequency of non-darkened reporters would carry over in each image and be miscalled as a new reporter. Indeed, the highest barcode count in the short workflow experiment was YYYYYY, which was likely an artifact of non-darkening and background. FIG. 42 shows that performance of the 8×8×8 12 mer reporter set was generally lower in the short workflow compared to the long workflow. Reporter complex one (which binds to position R1 of the barcode domain) and reporter complex three (which binds to position R3 of the barcode domain) had lower efficiencies in the short workflow compared to long workflow. This is expected for reporter complex three since it includes eight additional toe-hold oligonucleotides, at a high concentrations of 2.5 uM each, which can interfere with reporter hybridizations. Reporter complex one should behave similarly between the two workflows, as no toe-holds were used to remove the first reporter complex in either the short or long workflows. Total error was also higher (1.3- to 2-fold) in the short workflow compared to long workflow for all three reporter probes.

Figure 43:
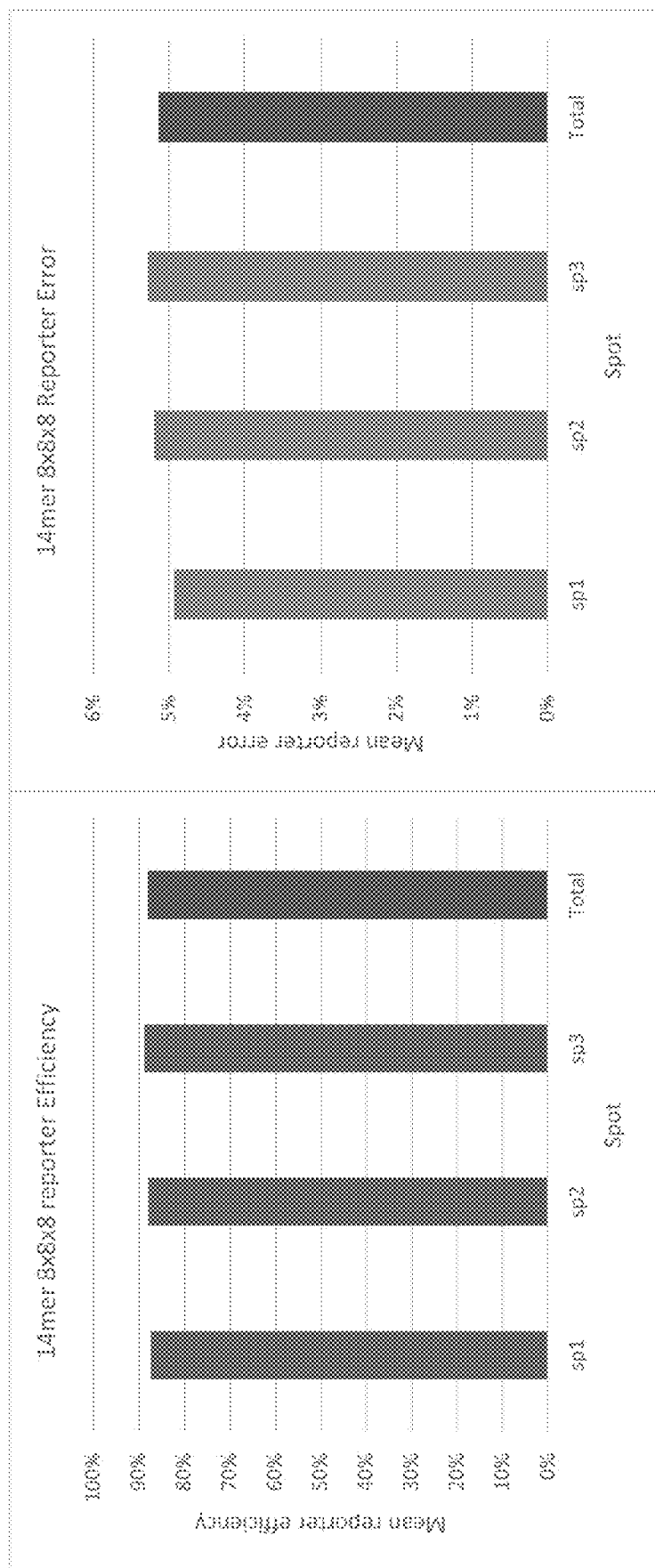
FIG. 43 shows efficiency and error of reporter probes using an exemplary 8×8×8 14 mer reporter set.

The 8×8×8 14 mer reporter set was validated by testing the efficiency, specificity, and speed of hybridization to all 512 possible sequencing probe barcode domains. The sequencing probe barcode domains were immobilized directly onto the glass of a Hyb & Seq sequencing cartridge. FIG. 43 shows that the 8×8×8 14 mer reporter probes hybridized with an average efficiency of 88% in only 15 seconds with an average error rate of 5.1%. The majority of this error is due to incorrect identification of the reporter not due to incorrect hybridization. Misclassification error of reporters remains the largest component of reporter error.

Figure 44:
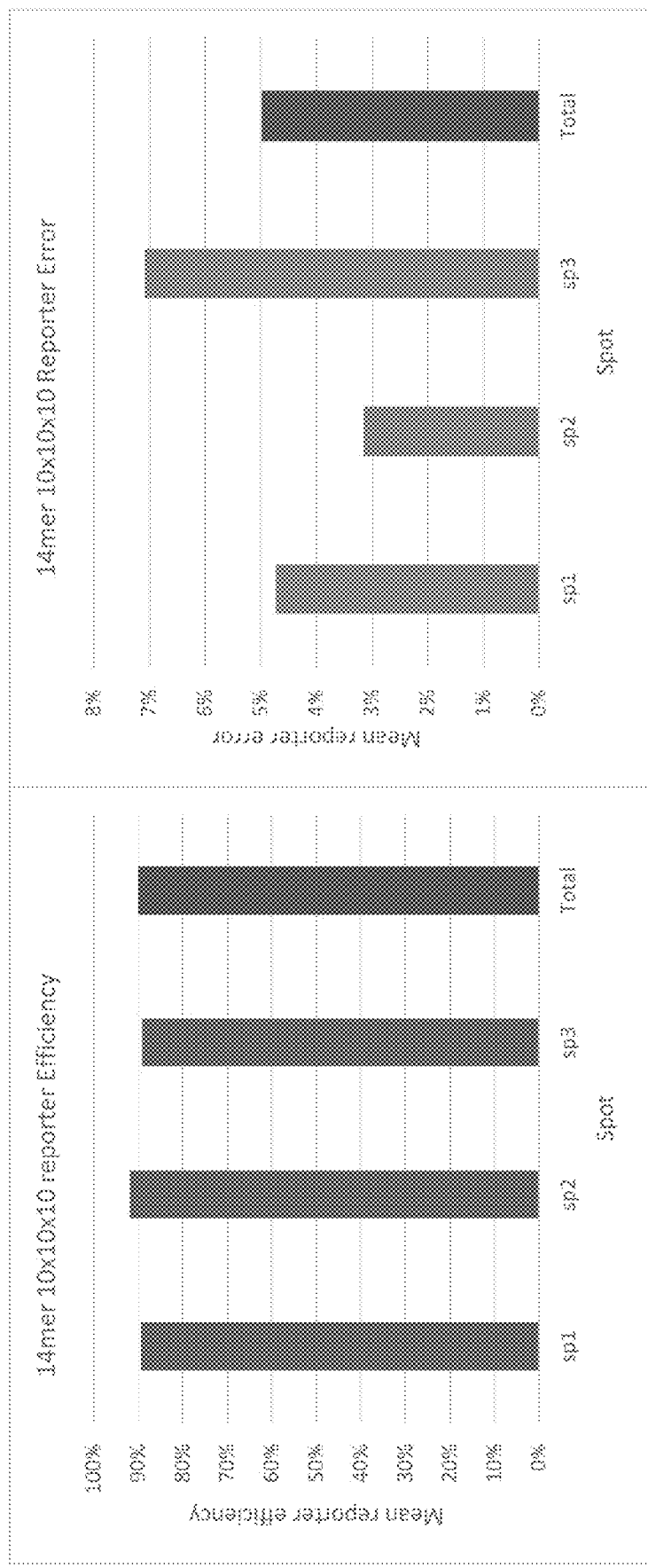
FIG. 44 shows efficiency and error of reporter probes using an exemplary 10×10×10 14 mer reporter set.

The 10×10×10 14 mer reporter set was validated by testing for efficiency, specificity, and speed of hybridization to 30 complementary, truncated sequencing probe barcode domains. Each barcode domain contained only one reporter binding site. These barcode domains were immobilized directly onto the glass of a Hyb & Seq sequencing cartridge. FIG. 44 shows that the 10×10×10 14 mer reporter set hybridized with an average efficiency of 90% in only 15 seconds with an average error rate of 5.0%. Again, the vast majority of error was due to incorrect identification of the reporter not due to incorrect hybridization.

Example 12—Design and Testing of Standard and Three-Part Sequencing Probes

The target binding and barcode domains of a sequencing probe are separated by a double-stranded "stem". FIG. 2 shows two sequencing probe architectures that were experimentally tested. On a standard sequencing probe, the target binding and barcode domains are present on the same oligonucleotide, which binds to a stem oligonucleotide to create a 36 nucleotide long double-stranded region. Using this architecture, each sequencing probes in a pool of probes use the same stem sequence. On a three-part probe, the target binding and barcode domains are separate DNA oligonucleotides that are bound together by a 36 nucleotide stem oligonucleotide. To prevent possible exchange of barcode domains, each barcode has a unique stem sequence and are hybridized separately before pooling sequencing probes.

Figure 45:
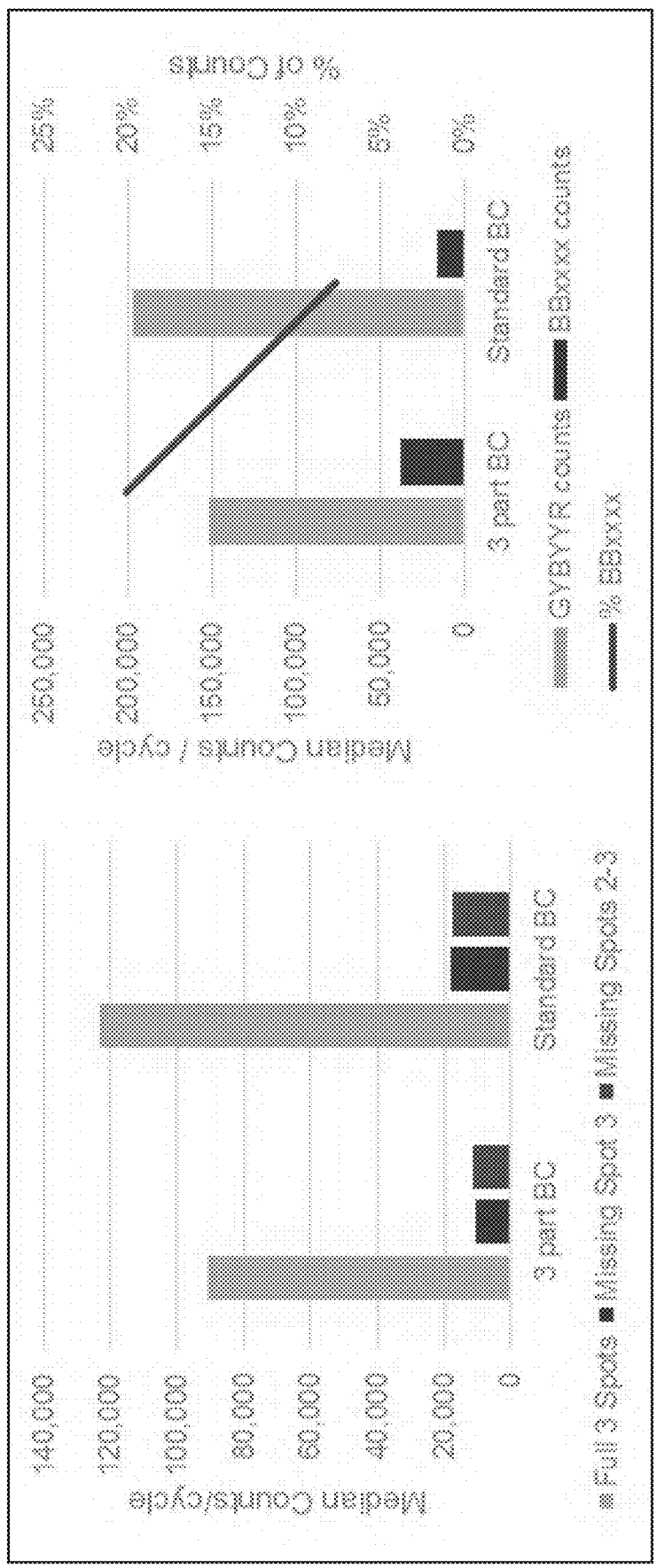
FIG. 45 shows a comparison of the performance of standard and three-part sequencing probes of the present disclosure.

FIG. 45 shows the results of a series of experiment performed to compare three-part sequencing probes to standard sequencing probes. These experiments confirmed that three-part sequencing probes survive an entire sequencing cycle with ~80% of all reads for both configurations including the detection of the third reporter probe. When compared to standard sequencing probes, three-part probes show ~12% fewer counts. To study the propensity for exchange of the barcode domain oligo, a high concentration of a short alternative oligonucleotide containing the same stem sequence was added to the reaction. The results indicated that ~13% of detected three-part sequencing probes had exchanged barcode oligoes. Oligonucleotide exchange will need to be mitigated with the incorporation of unique stem sequences. Despite the slight reduction in performance, three-part probes provide the benefits of design flexibility, speedy oligo synthesis, and reduced cost.

Example 13—Effect of Locked Nucleic Acid Substitutions in the Target Binding Domain The effect of the substitution of locked nucleic acids (LNAs) into the target binding domain of sequencing probes was tested as follows. Sequencing probes were hybridized to reporter probes in solution and properly formed sequencing probe-reporter probes were purified. The sequencing probe-reporter probes were then hybridized to synthetic target nucleic acids in solution and loaded onto a prototype sequencing cartridge. The synthetic target nucleic acid consisted of 50 nucleotides and was biotinylated. Sequencing probes were tested either individually or in a pool of nine. For the pool of nine sequencing probes, the probes were designed to bind along the length of the target nucleic acid. For analysis, the entire reaction was deposited by a breadboard instrument onto a streptavidin-coated cover slide and then flow stretched. The reporter probes were then imaged and counted using the appropriate instrument and software, for example with the NanoString nCounter® instrument and software.

Figure 46:
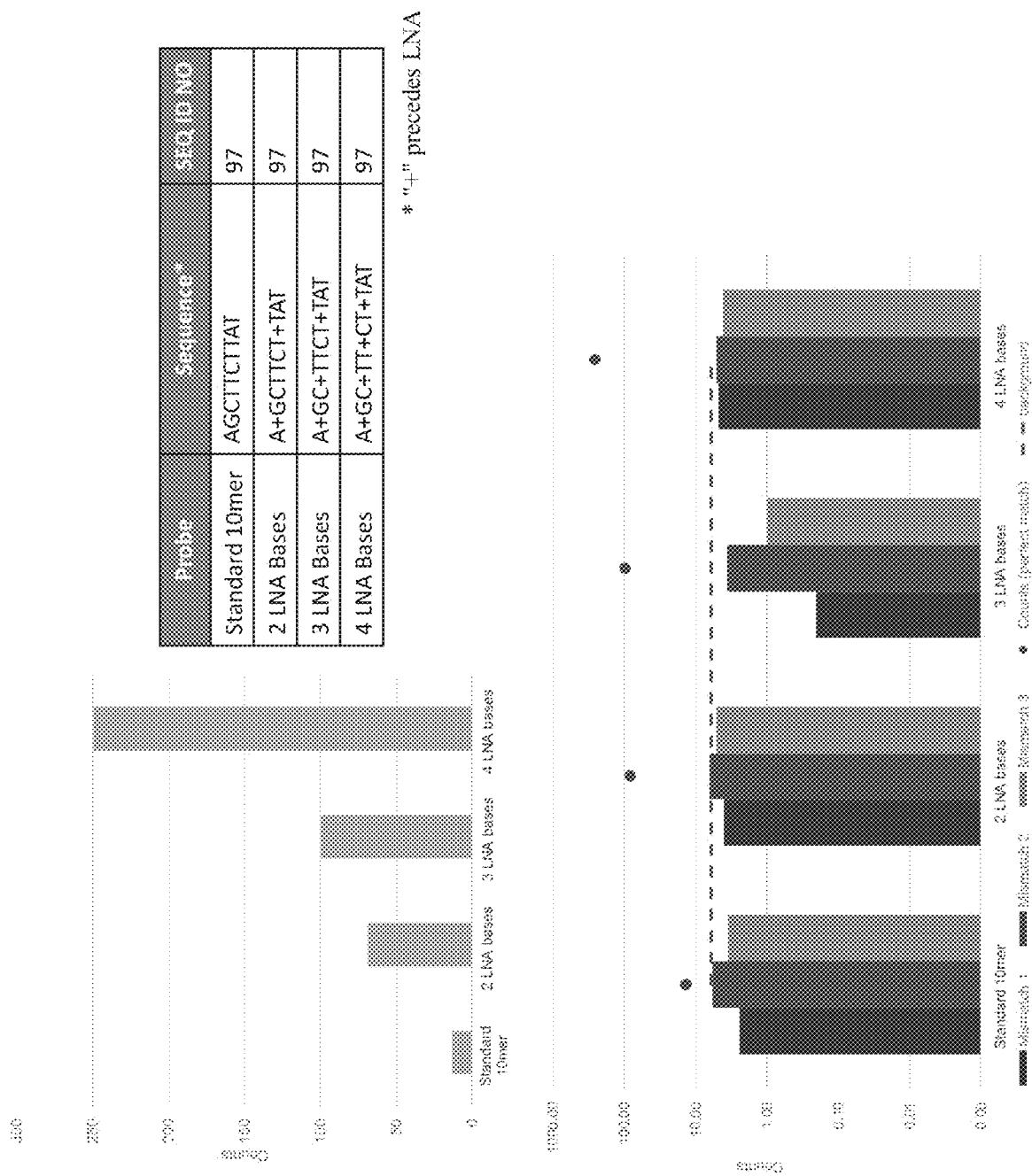
FIG. 46 shows the effect of LNA substitutions within exemplary target binding domains of the present disclosure using individual probes.
Figure 47:
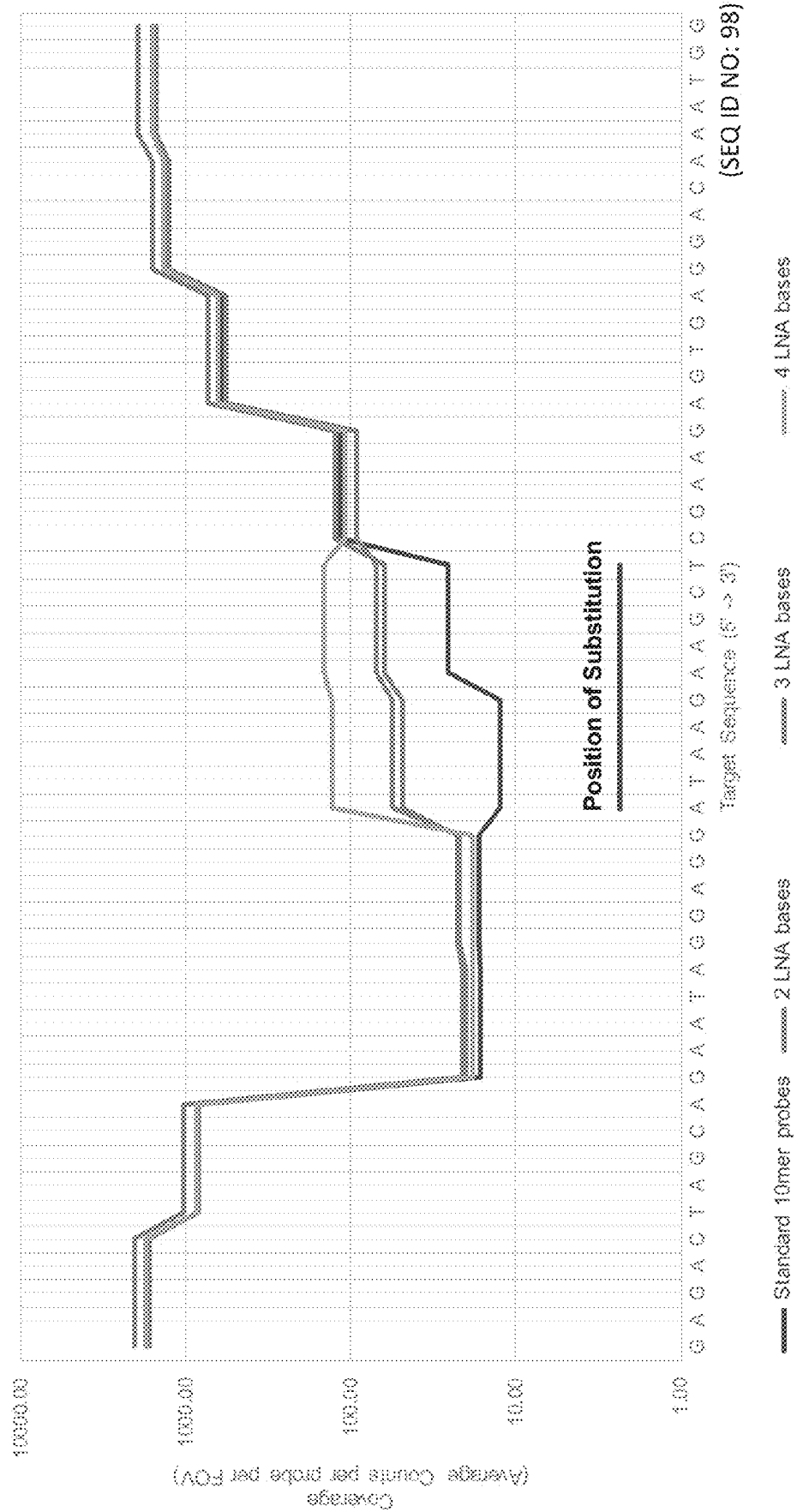
FIG. 47 shows the effect of LNA substitutions within exemplary target binding domains of the present disclosure using a pool of nine probes.

Each sequencing probe contained a target binding domain of 10 nucleotides (SEQ ID NO: 97). LNA substitutions within the target binding domains were made to include 2, 3, or 4 LNA bases at the positions shown in FIG. 46. FIG. 46 shows that the binding affinity of the individual sequencing probes for the target nucleic acid increased as the number of LNA bases increased. Importantly, FIG. 46 shows that the incorporation of LNA bases did not decrease the specificity of sequence probe binding. The pool of nine sequencing probes was tested to determine base coverage when probes could compete for target binding. FIG. 47 shows that when a single LNA probe was introduced into the pool, the coverage of the affected bases was increased with little effect on the binding of surrounding probes. These results indicated that LNA base substitutions can improve base sensitivity without reducing specificity.

Figure 48:
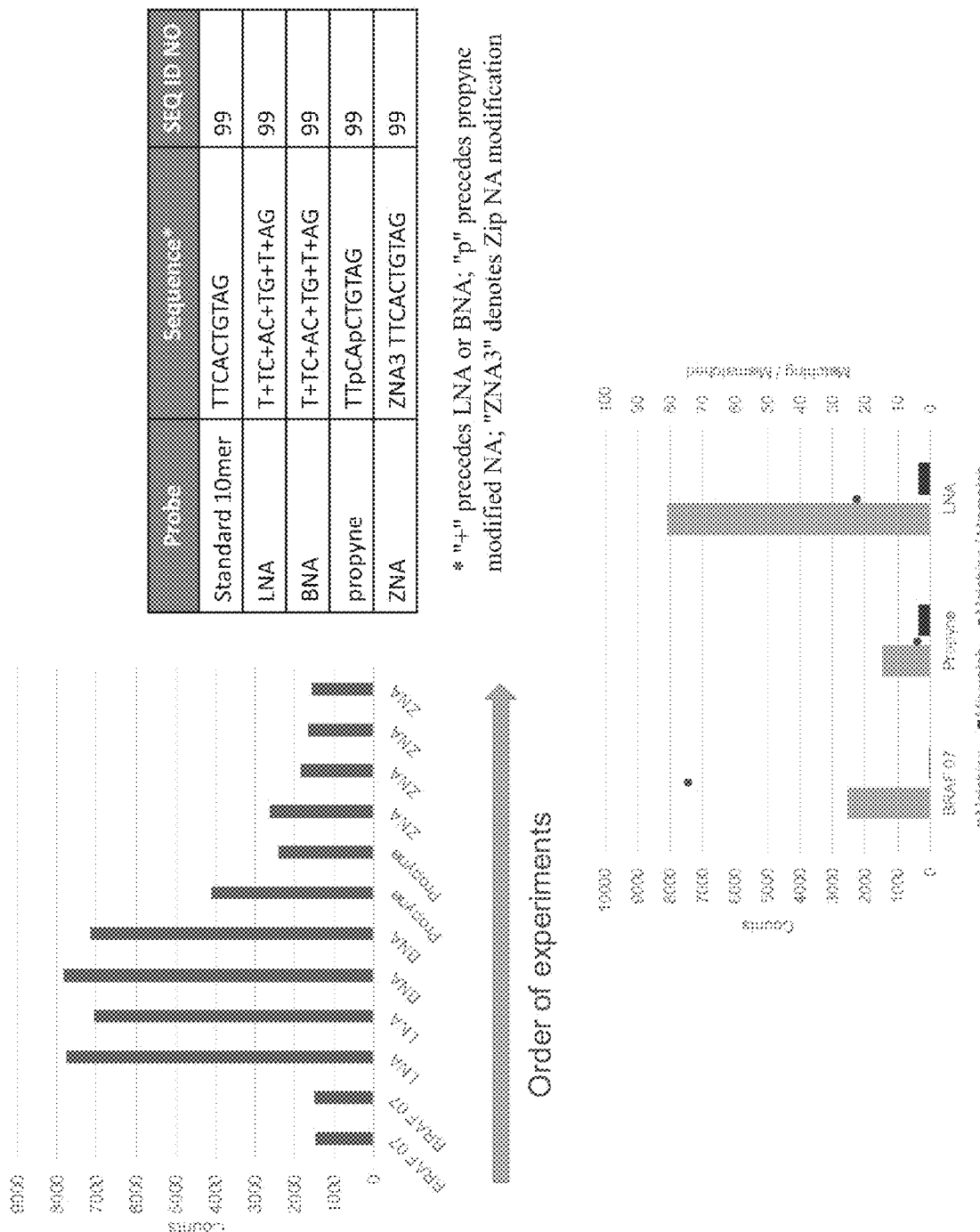
FIG. 48 shows the effect of modified nucleotides and nucleic acid analogue substitutions in exemplary target binding domains of the present disclosure.

Example 14—Effect of Modified Nucleotide and Nucleic Acid Analogue Substitutions in the Target Binding Domain The effect of the substitution of various modified nucleotides and nucleic acid analogues, including locked nucleic acids (LNA), bridged nucleic acids (BNA), propyne-modified nucleic acids, zip nucleic acids (ZNA®), isoguanine and isocytosine, into the target binding domain of sequencing probes was tested as follows. Biotinylated target nucleic acids 50 nucleotides in length were loaded onto a streptavidin cover slide of a prototype sequencing cartridge. Sequencing and reporter probes were then sequentially introduced into the sample chamber and imaged using a Hyb & Seq prototype instrument. The images were processed to compare the counts for each different sequencing probe. Substitutions in the 10 nucleotide (SEQ ID NO: 99) target binding domain of the sequencing probes were made to include LNA, BNA, propyne, and ZNA® bases at the positions shown in FIG. 48. FIG. 48 shows that probes containing LNAs and BNAs showed the largest increase in binding affinity while maintaining specificity, as indicated by the number of counts detected for matching and mismatched targets. These results indicated that LNA or BNA base substitutions can improve base sensitivity without reducing specificity.

Figure 49:
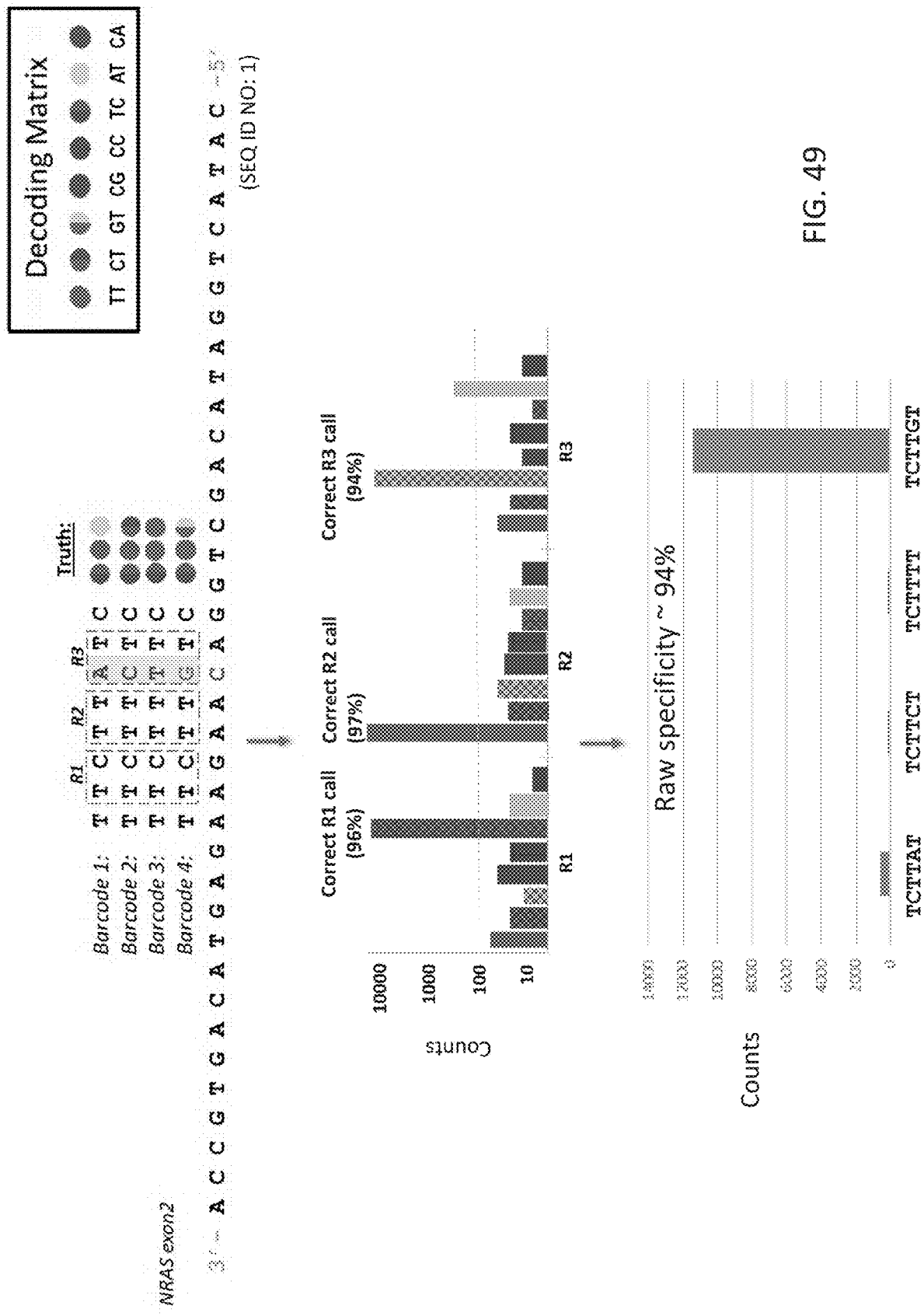
FIG. 49 shows the results from an experiment to quantify the raw accuracy of the sequencing method of the present disclosure

Example 15—Determining Accuracy of the Sequencing Method of the Present Disclosure FIG. 49 depicts the results from an experiment that quantified the raw specificity of the sequencing method of the present disclosure. In this experiment, a sequencing reaction was performed in which a pool of 4 different sequencing probes was hybridized to a target nucleic acid that included a fragment of NRAS exon2 (SEQ ID NO: 1). Each sequencing probe (barcode 1 to 4) had a target binding domain that was identical except that the hexamer of the target binding domain differed at position b5, as depicted in the top panel of FIG. 49. In this example, barcode 4 is the correct sequencing probe. After hybridization of the sequencing probes, reporter probes were sequentially hybridized to each of the three positions of the barcode domain ($R_1$, $R_2$ and $R_3$) and the corresponding fluorescence data recorded. The middle panel of FIG. 49 depicts the number of times each color combination was recorded for the three barcode domain positions and the percentage of the time that the correct combination was recorded. The color combination at $R_1$ was correctly identified 96% of the time, the color combination at $R_2$ was correctly identified 97% of the time and the correct color combination at $R_3$ was correctly identified 94% of the time. As depicted in the bottom panel of FIG. 49, this leads to an overall raw specificity of 94%. The sources of error that could explain the miscalled barcode domain positions include: (a) non-specific binding of reporter probes to the surface of the flow cell and (b) incorrect hybridization of reporter probes. The estimated amount of reporter hybridization errors was approximately 2 to 4%.

Figure 50:
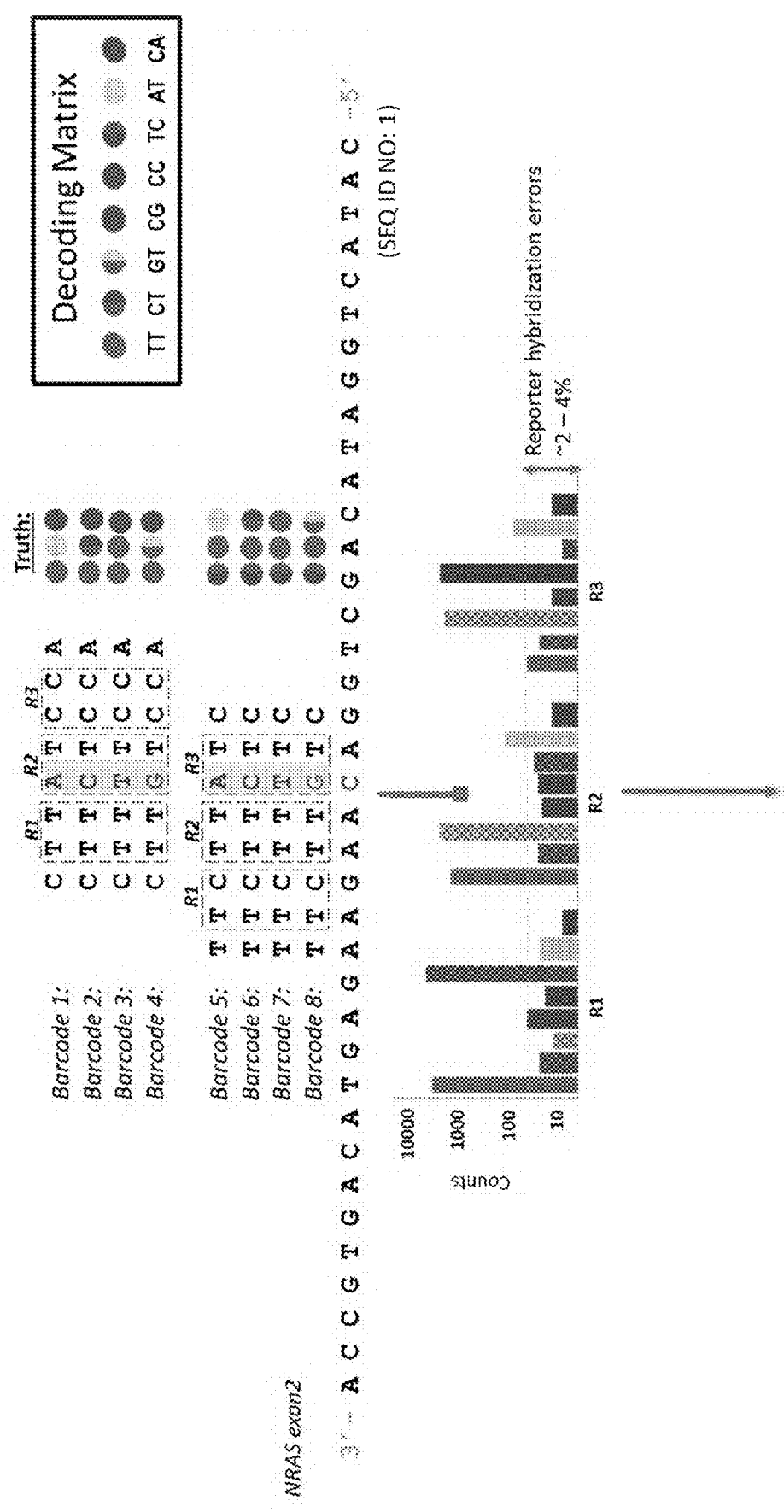
FIG. 50 shows the results from an experiment to determine the accuracy of the sequencing method of the present disclosure when nucleotides in the target nucleic acid are sequenced by more than one sequencing probe.

FIG. 50 shows the results from an experiment to determine the accuracy of the sequencing method of the present disclosure when nucleotides in the target nucleic acid are sequenced by more than one sequencing probe. As shown in the top panel of FIG. 50, the target nucleic acid in this example is a fragment of NRAS exon2 (SEQ ID NO: 1). The particular base of interest is a cytosine (C) that is highlighted in the target nucleic acid. The base of interest will be hybridized to two different sequencing probes, each with a distinct footprint of hybridization to the target nucleic acid. In this example, sequencing probes 1 to 4 (barcode 1 to 4) bind three nucleotides to the left of the base of interest, while sequencing probes 5 to 8 (barcodes 5 to 8) bind 5 nucleotides to the left of the base of interest. The middle panel of FIG. 50 shows the number of times specific color combinations were recorded at each position of the barcode domains of the sequencing probes. After image quantification and using the base calling techniques depicted in FIG. 26, an average accuracy of ~98.98% can be recorded.

What is claimed is:

1. A probe comprising a target binding domain linked to a barcode domain;
wherein the target binding domain comprises at least eight nucleotides and is capable of binding a target nucleic acid, wherein at least six nucleotides in the target binding domain are capable of identifying a target nucleic acid molecule and wherein at least two nucleotides in the target binding domain do not identify the target nucleic acid molecule;
wherein the barcode domain comprises at least one attachment position, each attachment position comprising at least one attachment region comprising at least one nucleic acid sequence capable of being bound by a complementary nucleic acid molecule, wherein the nucleic acid sequence of the at least one attachment position determines the identity of the target nucleic acid that is bound by the target binding domain.

2. The probe of claim 1, wherein said barcode domain comprises a single-stranded DNA.

3. The probe of claim 1, wherein each attachment position in the barcode domain comprises one attachment region.

4. The probe of claim 1, wherein the at least two nucleotides in the target binding domain that do not identify the target nucleic acid molecule follow the at least six nucleotides in the target binding domain that identify the target nucleic acid molecule.

5. The probe of claim 1, wherein the at least six nucleotides in the target binding domain that are capable of identifying the target nucleic acid molecule are complementary to a portion of the target nucleic acid molecule.

6. The probe of claim 1, wherein the at least two nucleotides in the target binding domain that are not capable of identifying a target nucleic acid molecule are not complementary to a portion of the target nucleic acid molecule.

7. The probe of claim 1, wherein the barcode domain comprises one attachment position.

8. The probe of claim 1, wherein each attachment position comprises between 8 nucleotides and 20 nucleotides.

9. The probe of claim 1, wherein each attachment position comprises about 20 nucleotides.

10. The probe of claim 1, further comprising: a complementary nucleic acid molecule hybridized to a first attachment region of a first attachment position of the barcode domain.

11. The probe of claim 10, wherein the complementary nucleic acid molecule comprises at least one detectable label.

12. The probe of claim 11, wherein the at least one detectable label is a fluorescent label.

13. A population of probes comprising a plurality of the probe of claim 1.

14. The probe of claim 1, wherein at least eight nucleotides in the target binding domain are capable of identifying the target nucleic acid molecule.

15. The probe of claim 1, wherein the target binding domain comprises at least ten nucleotides.

16. The probe of claim 15, wherein at least ten nucleotides in the target binding domain are capable of identifying the target nucleic acid molecule.

* * * * *

SEQUENCE LISTING

```
Sequence total quantity: 99
SEQ ID NO: 1            moltype = DNA   length = 38
FEATURE                 Location/Qualifiers
source                  1..38
                        mol_type = other DNA
                        organism = Homo sapiens
SEQUENCE: 1
accgtgacat gagaagaaca ggtcgacata ggtcatac                                 38

SEQ ID NO: 2            moltype = DNA   length = 10
FEATURE                 Location/Qualifiers
misc_feature            1..10
                        note = Example Consensus
source                  1..10
                        mol_type = other DNA
                        organism = synthetic construct
SEQUENCE: 2
aacaccacct                                                                10

SEQ ID NO: 3            moltype = DNA   length = 24
FEATURE                 Location/Qualifiers
source                  1..24
                        mol_type = other DNA
                        organism = Homo sapiens
SEQUENCE: 3
gtctagctac agtgaaatct cgat                                                24

SEQ ID NO: 4            moltype = DNA   length = 23
FEATURE                 Location/Qualifiers
source                  1..23
                        mol_type = other DNA
                        organism = Homo sapiens
SEQUENCE: 4
tcaaagtgct gggctccggt gcg                                                 23

SEQ ID NO: 5            moltype = DNA   length = 27
FEATURE                 Location/Qualifiers
source                  1..27
                        mol_type = other DNA
                        organism = Homo sapiens
SEQUENCE: 5
tagttggagc tggtggcgta ggcaaga                                             27

SEQ ID NO: 6            moltype = DNA   length = 23
FEATURE                 Location/Qualifiers
source                  1..23
                        mol_type = other DNA
                        organism = Homo sapiens
SEQUENCE: 6
gaatgatgca catcatggtg gct                                                 23

SEQ ID NO: 7            moltype = DNA   length = 23
FEATURE                 Location/Qualifiers
source                  1..23
                        mol_type = other DNA
                        organism = Homo sapiens
SEQUENCE: 7
gcagctcatc acgcagctca tgc                                                 23

SEQ ID NO: 8            moltype = DNA   length = 23
FEATURE                 Location/Qualifiers
source                  1..23
                        mol_type = other DNA
                        organism = Homo sapiens
SEQUENCE: 8
atacagctgg acaagaagag tac                                                 23

SEQ ID NO: 9            moltype = DNA   length = 25
FEATURE                 Location/Qualifiers
source                  1..25
                        mol_type = other DNA
                        organism = Homo sapiens
SEQUENCE: 9
tggctcgaga tatcatgagt gattc                                               25

SEQ ID NO: 10           moltype = DNA   length = 23
FEATURE                 Location/Qualifiers
source                  1..23
```

```
                        mol_type = other DNA
                        organism = Homo sapiens
SEQUENCE: 10
tcatcatagg tcgtcatgct tat                                              23

SEQ ID NO: 11           moltype = DNA   length = 23
FEATURE                 Location/Qualifiers
source                  1..23
                        mol_type = other DNA
                        organism = Homo sapiens
SEQUENCE: 11
atggagtatg tgtctgtgga gac                                              23

SEQ ID NO: 12           moltype = DNA   length = 23
FEATURE                 Location/Qualifiers
source                  1..23
                        mol_type = other DNA
                        organism = Homo sapiens
SEQUENCE: 12
gtgcaactct ccgtacatcg tgg                                              23

SEQ ID NO: 13           moltype = DNA   length = 23
FEATURE                 Location/Qualifiers
source                  1..23
                        mol_type = other DNA
                        organism = Homo sapiens
SEQUENCE: 13
cagccgcgtg ctgcacacca acg                                              23

SEQ ID NO: 14           moltype = RNA   length = 30
FEATURE                 Location/Qualifiers
source                  1..30
                        mol_type = other RNA
                        organism = Homo sapiens
SEQUENCE: 14
gcttcagcac cactccactc cacattctca                                       30

SEQ ID NO: 15           moltype = RNA   length = 30
FEATURE                 Location/Qualifiers
source                  1..30
                        mol_type = other RNA
                        organism = Homo sapiens
SEQUENCE: 15
tgtcctcatg tattggtctc tcatggcact                                       30

SEQ ID NO: 16           moltype = RNA   length = 30
FEATURE                 Location/Qualifiers
source                  1..30
                        mol_type = other RNA
                        organism = Homo sapiens
SEQUENCE: 16
ctttcgccaa agtggaggag accatcgccg                                       30

SEQ ID NO: 17           moltype = RNA   length = 30
FEATURE                 Location/Qualifiers
source                  1..30
                        mol_type = other RNA
                        organism = Homo sapiens
SEQUENCE: 17
gaaggtgatg tttgggtcag gtgccttagt                                       30

SEQ ID NO: 18           moltype = DNA   length = 50
FEATURE                 Location/Qualifiers
source                  1..50
                        mol_type = other DNA
                        organism = Homo sapiens
SEQUENCE: 18
caaactggtg gtggttggag caggtggtgt tgggaaaagc gcactgacaa                 50

SEQ ID NO: 19           moltype = DNA   length = 12
FEATURE                 Location/Qualifiers
misc_feature            1..12
                        note = 12-mer attachment position
source                  1..12
                        mol_type = other DNA
                        organism = synthetic construct
SEQUENCE: 19
aggacagatg ac                                                          12
```

```
SEQ ID NO: 20          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 20
gtatcggatg ac                                                              12

SEQ ID NO: 21          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 21
aggagtgatg ac                                                              12

SEQ ID NO: 22          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 22
aggggtgagg ag                                                              12

SEQ ID NO: 23          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 23
agaggggatg ac                                                              12

SEQ ID NO: 24          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 24
agtgggagg ag                                                               12

SEQ ID NO: 25          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 25
agccgagatg ac                                                              12

SEQ ID NO: 26          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 26
agggtggatg ac                                                              12

SEQ ID NO: 27          moltype = DNA   length = 12
FEATURE                Location/Qualifiers
misc_feature           1..12
                       note = 12-mer attachment position
source                 1..12
                       mol_type = other DNA
                       organism = synthetic construct
SEQUENCE: 27
tggatggaaa ag                                                              12
```

```
SEQ ID NO: 28            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 28
gaaggagaaa ag                                                              12

SEQ ID NO: 29            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 29
ggggatgaaa ag                                                              12

SEQ ID NO: 30            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 30
gtgagggaaa ag                                                              12

SEQ ID NO: 31            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 31
agccgagaaa ag                                                              12

SEQ ID NO: 32            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 32
cgagaggaaa ag                                                              12

SEQ ID NO: 33            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 33
gagggcgaaa ag                                                              12

SEQ ID NO: 34            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 34
agcgtggaaa ag                                                              12

SEQ ID NO: 35            moltype = DNA  length = 12
FEATURE                  Location/Qualifiers
misc_feature             1..12
                         note = 12-mer attachment position
source                   1..12
                         mol_type = other DNA
                         organism = synthetic construct
SEQUENCE: 35
```

```
tgagaagggt ag                                                           12

SEQ ID NO: 36        moltype = DNA  length = 12
FEATURE              Location/Qualifiers
misc_feature         1..12
                     note = 12-mer attachment position
source               1..12
                     mol_type = other DNA
                     organism = synthetic construct SEQUENCE: 36
gttgttattg tg                                                           12

SEQ ID NO: 37        moltype = DNA  length = 12
FEATURE              Location/Qualifiers
misc_feature         1..12
                     note = 12-mer attachment position
source               1..12
                     mol_type = other DNA
                     organism = synthetic construct SEQUENCE: 37
tttgggttta gg                                                           12

SEQ ID NO: 38        moltype = DNA  length = 12
FEATURE              Location/Qualifiers
misc_feature         1..12
                     note = 12-mer attachment position
source               1..12
                     mol_type = other DNA
                     organism = synthetic construct SEQUENCE: 38
gttagtggga aa                                                           12

SEQ ID NO: 39        moltype = DNA  length = 12
FEATURE              Location/Qualifiers
misc_feature         1..12
                     note = 12-mer attachment position
source               1..12
                     mol_type = other DNA
                     organism = synthetic construct SEQUENCE: 39
atgggaaaaa gt                                                           12

SEQ ID NO: 40        moltype = DNA  length = 12
FEATURE              Location/Qualifiers
misc_feature         1..12
                     note = 12-mer attachment position
source               1..12
                     mol_type = other DNA
                     organism = synthetic construct SEQUENCE: 40
gagttggatg ag                                                           12

SEQ ID NO: 41        moltype = DNA  length = 12
FEATURE              Location/Qualifiers
misc_feature         1..12
                     note = 12-mer attachment position
source               1..12
                     mol_type = other DNA
                     organism = synthetic construct SEQUENCE: 41
atgttgtggg ta                                                           12

SEQ ID NO: 42        moltype = DNA  length = 12
FEATURE              Location/Qualifiers
misc_feature         1..12
                     note = 12-mer attachment position
source               1..12
                     mol_type = other DNA
                     organism = synthetic construct SEQUENCE: 42
gagggtttta ag                                                           12
```

-continued

```
SEQ ID NO: 43          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 43
atcttttccc cact                                                           14

SEQ ID NO: 44          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 44
ccccactatt tctt                                                           14

SEQ ID NO: 45          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 45
ctacccacaa cata                                                           14

SEQ ID NO: 46          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 46
ccatataaac ccca                                                           14

SEQ ID NO: 47          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 47
aaactccaat ctcc                                                           14

SEQ ID NO: 48          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 48
ctattctcaa ccta                                                           14

SEQ ID NO: 49          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 49
ccccctcttt taaa                                                           14

SEQ ID NO: 50          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 50
ccaatcttac ctca                                                           14
```

```
SEQ ID NO: 51           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 51
ccctcacata actt                                                           14

SEQ ID NO: 52           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 52
ctcctctact ttcc                                                           14

SEQ ID NO: 53           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 53
ccctaaaccc aaaa                                                           14

SEQ ID NO: 54           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 54
cactttttcc catc                                                           14

SEQ ID NO: 55           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 55
catctgattc ctcc                                                           14

SEQ ID NO: 56           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 56
ctaaacccccc tact                                                          14

SEQ ID NO: 57           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 57
cctttacaaa caca                                                           14

SEQ ID NO: 58           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 58
```

```
ataccaccct cttt                                                                    14

SEQ ID NO: 59          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 59
tattcttcta cccc                                                                    14

SEQ ID NO: 60          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 60
tctacccttc tcat                                                                    14

SEQ ID NO: 61          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 61
ccacaataac aacc                                                                    14

SEQ ID NO: 62          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 62
accttaacat tccc                                                                    14

SEQ ID NO: 63          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 63
atttcccact aacc                                                                    14

SEQ ID NO: 64          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 64
acttaaaacc ctcc                                                                    14

SEQ ID NO: 65          moltype = DNA   length = 14
FEATURE                Location/Qualifiers
misc_feature           1..14
                       note = 14-mer attachment position
source                 1..14
                       mol_type = other DNA
                       organism = synthetic construct
SEQUENCE: 65
tacctattcc tcca                                                                    14

SEQ ID NO: 66          moltype = DNA   length = 14
FEATURE                Location/Qualifiers
misc_feature           1..14
                       note = 14-mer attachment position
source                 1..14
                       mol_type = other DNA
                       organism = synthetic construct
```

| | | |
|---|---|---|
| SEQUENCE: 66 ccccttctc taag | | 14 |
| SEQ ID NO: 67 FEATURE misc_feature source | moltype = DNA  length = 14 Location/Qualifiers 1..14 note = 14-mer attachment position 1..14 mol_type = other DNA organism = synthetic construct | |
| SEQUENCE: 67 gatgatggta ggtg | | 14 |
| SEQ ID NO: 68 FEATURE misc_feature source | moltype = DNA  length = 14 Location/Qualifiers 1..14 note = 14-mer attachment position 1..14 mol_type = other DNA organism = synthetic construct | |
| SEQUENCE: 68 atgagaaggg taga | | 14 |
| SEQ ID NO: 69 FEATURE misc_feature source | moltype = DNA  length = 14 Location/Qualifiers 1..14 note = 14-mer attachment position 1..14 mol_type = other DNA organism = synthetic construct | |
| SEQUENCE: 69 gttttgttgg tgag | | 14 |
| SEQ ID NO: 70 FEATURE misc_feature source | moltype = DNA  length = 14 Location/Qualifiers 1..14 note = 14-mer attachment position 1..14 mol_type = other DNA organism = synthetic construct | |
| SEQUENCE: 70 ttagtgtgtt ggag | | 14 |
| SEQ ID NO: 71 FEATURE misc_feature source | moltype = DNA  length = 14 Location/Qualifiers 1..14 note = 14-mer attachment position 1..14 mol_type = other DNA organism = synthetic construct | |
| SEQUENCE: 71 atgtaggaga gaga | | 14 |
| SEQ ID NO: 72 FEATURE misc_feature source | moltype = DNA  length = 14 Location/Qualifiers 1..14 note = 14-mer attachment position 1..14 mol_type = other DNA organism = synthetic construct | |
| SEQUENCE: 72 gggaatgtta aggt | | 14 |
| SEQ ID NO: 73 FEATURE misc_feature source | moltype = DNA  length = 14 Location/Qualifiers 1..14 note = 14-mer attachment position 1..14 mol_type = other DNA organism = synthetic construct | |
| SEQUENCE: 73 ggttagtggg aaat | | 14 |
| SEQ ID NO: 74 FEATURE misc_feature source | moltype = DNA  length = 14 Location/Qualifiers 1..14 note = 14-mer attachment position 1..14 mol_type = other DNA | |

```
                            organism = synthetic construct
SEQUENCE: 74
ggagggtttt aagt                                                             14

SEQ ID NO: 75           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 75
gtagtgtgga tgtt                                                             14

SEQ ID NO: 76           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 76
cttagagaaa gggg                                                             14

SEQ ID NO: 77           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 77
ggaagaggat gaaa                                                             14

SEQ ID NO: 78           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 78
aagttatgtg aggg                                                             14

SEQ ID NO: 79           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 79
ggaaagtaga ggag                                                             14

SEQ ID NO: 80           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 80
ttttgggttt aggg                                                             14

SEQ ID NO: 81           moltype = DNA  length = 14
FEATURE                 Location/Qualifiers
misc_feature            1..14
                        note = 14-mer attachment position
source                  1..14
                        mol_type = other DNA
                        organism = synthetic construct
SEQUENCE: 81
agatgtatgg gtga                                                             14

SEQ ID NO: 82           moltype = DNA  length = 14
FEATURE                 Location/Qualifiers
misc_feature            1..14
                        note = 14-mer attachment position
source                  1..14
```

```
                        mol_type = other DNA
                        organism = synthetic construct
SEQUENCE: 82
gatgggaaaa agtg                                                            14

SEQ ID NO: 83           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 83
ggaggaatca gatg                                                            14

SEQ ID NO: 84           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 84
agagggattg atga                                                            14

SEQ ID NO: 85           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 85
tgtgtttgta aagg                                                            14

SEQ ID NO: 86           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 86
aaggagtgat agga                                                            14

SEQ ID NO: 87           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 87
tggtgattta gagg                                                            14

SEQ ID NO: 88           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 88
ggggtagaag aata                                                            14

SEQ ID NO: 89           moltype = DNA   length = 14
FEATURE                 Location/Qualifiers
misc_feature            1..14
                        note = 14-mer attachment position
source                  1..14
                        mol_type = other DNA
                        organism = synthetic construct
SEQUENCE: 89
aagaaatagt gggg                                                            14

SEQ ID NO: 90           moltype = DNA   length = 14
FEATURE                 Location/Qualifiers
misc_feature            1..14
                        note = 14-mer attachment position
```

```
source                      1..14
                            mol_type = other DNA
                            organism = synthetic construct
SEQUENCE: 90
tatgttgtgg gtag                                                              14

SEQ ID NO: 91               moltype = DNA   length = 14
FEATURE                     Location/Qualifiers
misc_feature                1..14
                            note = 14-mer attachment position
source                      1..14
                            mol_type = other DNA
                            organism = synthetic construct
SEQUENCE: 91
gttaaaggga ggtt                                                              14

SEQ ID NO: 92               moltype = DNA   length = 14
FEATURE                     Location/Qualifiers
misc_feature                1..14
                            note = 14-mer attachment position
source                      1..14
                            mol_type = other DNA
                            organism = synthetic construct
SEQUENCE: 92
tggggtttat atgg                                                              14

SEQ ID NO: 93               moltype = DNA   length = 14
FEATURE                     Location/Qualifiers
misc_feature                1..14
                            note = 14-mer attachment position
source                      1..14
                            mol_type = other DNA
                            organism = synthetic construct
SEQUENCE: 93
agggaatatg gaga                                                              14

SEQ ID NO: 94               moltype = DNA   length = 14
FEATURE                     Location/Qualifiers
misc_feature                1..14
                            note = 14-mer attachment position
source                      1..14
                            mol_type = other DNA
                            organism = synthetic construct
SEQUENCE: 94
taggttgaga atag                                                              14

SEQ ID NO: 95               moltype = DNA   length = 14
FEATURE                     Location/Qualifiers
misc_feature                1..14
                            note = 14-mer attachment position
source                      1..14
                            mol_type = other DNA
                            organism = synthetic construct
SEQUENCE: 95
tttaaaagag gggg                                                              14

SEQ ID NO: 96               moltype = DNA   length = 14
FEATURE                     Location/Qualifiers
misc_feature                1..14
                            note = 14-mer attachment position
source                      1..14
                            mol_type = other DNA
                            organism = synthetic construct
SEQUENCE: 96
tgaggtaaga ttgg                                                              14

SEQ ID NO: 97               moltype = DNA   length = 10
FEATURE                     Location/Qualifiers
misc_feature                1..10
                            note = Target binding domain
source                      1..10
                            mol_type = other DNA
                            organism = synthetic construct
SEQUENCE: 97
agcttcttat                                                                   10

SEQ ID NO: 98               moltype = DNA   length = 50
FEATURE                     Location/Qualifiers
misc_feature                1..50
```

```
                        note = Target nucleic acid
source                  1..50
                        mol_type = other DNA
                        organism = synthetic construct
SEQUENCE: 98
gagactagca gaataggagg ataagaagct cgaagagtga ggacaaatgg            50

SEQ ID NO: 99           moltype = DNA  length = 10
FEATURE                 Location/Qualifiers
misc_feature            1..10
                        note = Target binding domain
source                  1..10
                        mol_type = other DNA
                        organism = synthetic construct
SEQUENCE: 99
ttcactgtag                                                        10
```